US011059876B2

(12) United States Patent
Yeung et al.

(10) Patent No.: US 11,059,876 B2
(45) Date of Patent: Jul. 13, 2021

(54) IL-15 VARIANTS AND USES THEREOF

(71) Applicant: Pfizer Inc., New York, NY (US)

(72) Inventors: Yik Andy Yeung, South San Francisco, CA (US); Reid Martin Renny Feldman, San Francisco, CA (US); Ling Hon Matthew Chu, San Jose, CA (US); Javier Fernando Chaparro Riggers, San Mateo, CA (US); Ivana Djuretic, San Bruno, CA (US); Laura Lin, Weston, MA (US); Lidia Mosyak, Newton, MA (US)

(73) Assignee: PFIZER INC., New York, NY (US)

( * ) Notice: Subject to any disclaimer, the term of this patent is extended or adjusted under 35 U.S.C. 154(b) by 59 days.

(21) Appl. No.: 16/286,158

(22) Filed: Feb. 26, 2019

(65) Prior Publication Data

US 2019/0263877 A1 Aug. 29, 2019

Related U.S. Application Data

(60) Provisional application No. 62/636,362, filed on Feb. 28, 2018, provisional application No. 62/636,371, filed on Feb. 28, 2018, provisional application No. 62/784,302, filed on Dec. 21, 2018.

(51) Int. Cl.

| | |
|---|---|
| ***C07K 14/54*** | (2006.01) |
| ***A61K 39/395*** | (2006.01) |
| ***A61K 38/17*** | (2006.01) |
| ***A61K 38/20*** | (2006.01) |
| ***A61K 35/17*** | (2015.01) |
| ***C07K 19/00*** | (2006.01) |
| ***A61P 35/00*** | (2006.01) |
| ***C07K 16/32*** | (2006.01) |
| ***C07K 16/28*** | (2006.01) |
| ***C07K 14/55*** | (2006.01) |
| ***C12N 15/62*** | (2006.01) |
| ***A61K 38/19*** | (2006.01) |
| *A61K 45/06* | (2006.01) |

(52) U.S. Cl.

CPC .......... *C07K 14/5443* (2013.01); *A61K 35/17* (2013.01); *A61K 38/1793* (2013.01); *A61K 38/19* (2013.01); *A61K 38/191* (2013.01); *A61K 38/2086* (2013.01); *A61K 39/395* (2013.01); *A61P 35/00* (2018.01); *C07K 14/55* (2013.01); *C07K 16/283* (2013.01); *C07K 16/2815* (2013.01); *C07K 16/2818* (2013.01); *C07K 16/2827* (2013.01); *C07K 16/2887* (2013.01); *C07K 16/2896* (2013.01); *C07K 16/32* (2013.01); *C07K 19/00* (2013.01); *C12N 15/62* (2013.01); *A61K 45/06* (2013.01); *C07K 2317/56* (2013.01); *C07K 2317/565* (2013.01); *C07K 2319/31* (2013.01)

(58) Field of Classification Search

None

See application file for complete search history.

(56) References Cited

U.S. PATENT DOCUMENTS

| | | | |
|---|---|---|---|
| 8,124,084 | B2 | 2/2012 | Lefrancois et al. |
| 8,507,222 | B2 | 8/2013 | Wong et al. |
| 8,940,288 | B2 | 1/2015 | Lefrancois et al. |
| 8,940,289 | B2 | 1/2015 | Wong et al. |
| 9,365,630 | B2 | 6/2016 | Lefrancois et al. |
| 9,371,368 | B2 | 6/2016 | Lefrancois et al. |
| 9,428,573 | B2 | 8/2016 | Wong et al. |
| 9,464,127 | B2 | 10/2016 | Wong et al. |
| 9,932,387 | B2 | 4/2018 | Lefrancois et al. |
| 10,150,805 | B2 | 12/2018 | Wong et al. |
| 10,407,502 | B2 | 9/2019 | Waksal et al. |
| 2016/0213750 | A1 | 7/2016 | Wong et al. |
| 2016/0340429 | A1 | 11/2016 | Waksal et al. |
| 2016/0367635 | A1 | 12/2016 | Wong et al. |
| 2018/0118828 | A1 | 5/2018 | Bernett et al. |
| 2019/0070264 | A1 | 3/2019 | Qu et al. |

FOREIGN PATENT DOCUMENTS

| | | | |
|---|---|---|---|
| EP | 3064507 | A1 | 9/2016 |
| EP | 3235830 | A1 | 10/2017 |
| WO | 2005085282 | A1 | 9/2005 |
| WO | 2006/063974 | | 6/2006 |
| WO | 2007046006 | A2 | 4/2007 |
| WO | 2012/040323 | | 3/2012 |
| WO | 2012175222 | A1 | 12/2012 |
| WO | 2013107791 | | 7/2013 |
| WO | 2014/207173 | A3 | 12/2014 |
| WO | 2015018528 | A1 | 2/2015 |
| WO | 2015018529 | A1 | 2/2015 |

(Continued)

OTHER PUBLICATIONS

Guo, Y., et al., "Immunobiology of the IL-15/IL-15R[alpha] complex as an antitumor and antiviral agent", Cytokine and Growth Factor Reviews, 2017, pp. 10-21, vol. 38.

(Continued)

*Primary Examiner* — Bridget E Bunner
*Assistant Examiner* — Fozia M Hamud
(74) *Attorney, Agent, or Firm* — Stephen E. Moyer

(57) ABSTRACT

The present invention relates to human interleukin 15 (IL-15) variants that have therapeutic and diagnostic use, and methods for making thereof. The present invention also provides fusion proteins comprising a human IL-15 variant. Also provided are methods of stimulating or suppressing immune responses in a mammal, and methods of treating a disorder (e.g., cancer) using the IL-15 variants or the fusion protein of such IL-15 variants.

36 Claims, 47 Drawing Sheets

Specification includes a Sequence Listing.

(56) References Cited

FOREIGN PATENT DOCUMENTS

| | | | |
|---|---|---|---|
| WO | 2016100375 | A2 | 6/2016 |
| WO | 2016142314 | A1 | 9/2016 |
| WO | 2018071918 | A1 | 4/2018 |
| WO | 2018071919 | A1 | 4/2018 |

OTHER PUBLICATIONS

Yang, X., et al., "Molecular Characterization and Functional Activity of an IL-15 Antagonist MutIL-15/Fc Human Fusion Protein", Molecular Pharmaceutics, 2013, pp. 717-727, vol. 10, No. 2.
International Search Report, PCT/IB2019/051539, dated Feb. 26, 2019.
Written Opinion of the International Searching Authority, PCT/IB2019/051539, dated Feb. 26, 2019.
Albertini, M., et al., "Phase II trial of hu14.18-IL2 for patients with metastatic melanoma", Cancer Immunol Immunother, 2012, 2261-2271, vol. 61.
Bernard, J., et al., "Identification of an Interleukin-15a Receptor-binding Site on Human Interleukin-15*", Journal of Biological Chemistry, 2004, Issue of Jun. 4, 24313-24322, vol. 279, No. 23.
Bessard, A., et al., "High antitumor activity of RLI, an interleukin-15 (IL-15)—IL-15 receptor α fusion protein, in metastatic melanoma and colorectal cancer", Mol. Cancer Ther, 2009, 2736-2745, vol. 8, No. 9.
Conlon, K., et al., "Redistribution, Hyperproliferation, Activation of Natural Killer Cells and CD8 T Cells, and Cytokine Production During First-in-Human Clinical Trial of Recombinant Human Interleukin-15 in Patients With Cancer", J of Clin Onc, 2015, vol. 33, No. 1.
Dubois, S., et al., "Preassociation of IL-15 with IL-15Ra-IgG1-Fc Enhances Its Activity on Proliferation of NK and CD8+/CD44high T Cells and Its Antitumor Action", J Immunol, 2008, 2099-2106, vol. 180.
Epardaud, M., et al., "Interleukin-15/Interleukin-15Ra Complexes Promote Destruction of Established Tumors by Reviving Tumor-Resident CD8+ T Cells", Cancer Res, 2008, 2972-2983, vol. 68, No. 8.
Garcin, G., et al., "High efficiency cell-specific targeting of cytokine activity", Nature Comm, 2014, 1-9, Article No. 3016, vol. 5.
Gillies , S., et al., "Antibody-targeted interleukin 2 stimulates T-cell killing of autologous tumor cells", Proc Natl Acad Sci USA, 1992, 1428-1432, vol. 89.
Hofmann, M., et al., "Generation, selection and preclinical characterization of an Fc-optimized FLT3 antibody for the treatment of myeloid leukemia", Leukemia, 2012, 1228-1237, vol. 26.
Horton, H., et al., "Potent In vitro and In vivo Activity of an Fc-Engineered Anti-CD19 Monoclonal Antibody against Lymphoma and Leukemia", Cancer Res, 2008, 8049-8057, vol. 68, No. 19.
Kaspar, M., et al., "The Antibody-Mediated Targeted Delivery of Interleukin-15 and GM-CSF to the Tumor Neovasculature Inhibits Tumor Growth and Metastasis", Cancer Res, 2007, 4940-4948, vol. 67, No. 10.
Kellner, C., et al., "Heterodimeric bispecific antibody-derivatives against CD19 and CD16 induce effective antibody-dependent cellular cytotoxicity against B-lymphoid tumor cells", Cancer Letters 303, 2011, 128-139.
Kermer, V., et al., "An Antibody Fusion Protein for Cancer Immunotherapy Mimicking IL-15 trans-Presentation at the Tumor Site", Mol Cancer Therapeutics, 2012, 1279-88, vol. 11, No. 6.
List, T., et al., "Immunocytokines: a review of molecules in clinical development for cancer therapy", Clin Pharmacol, 2013, 29-45, vol. 5, Suppl 1.
Müller, D., "Targeted cancer immunotherapy—Mimicking physiological trans-presentation of IL-15", OncoImmunology, 2012, 1213-1214, vol. 1, No. 7.
Ribas, A., et al., "Phase I/II open-label study of the biologic effects of the interleukin-2 immunocytokine EMD 273063 (hu14.18-IL2) in patients with metastatic malignant melanoma", J Transl Med, 2009, vol. 7, No. 68.
Skerra, A., "'Anticalins'; a new class of engineered ligand-binding proteins with antibody-like properties", Review in Molecular Biotechnology, 2001, 257-275, vol. 74.
Skerra, A., "Engineered protein scaffolds for molecular recognition", J of Molecular Recognition, 2000, 167-187, vol. 13.
Stoklasek, T., et al., "Combined IL-15/IL-15Ra Immunotherapy Maximizes IL-15 Activity In Vivo", J Immunol, 2006, 6072-6080, vol. 177.
Muller, Dafne, "Targeted cancer immunotherapy Mimicking physiological trans-presentation of IL-15", OncoImmunology 1:7, 1213-1214; Oct. 2012.
Ortiz-Sanchez, E., et al., "Antibody—cytokine fusion proteins: applications in cancer therapy", Expert Opin. Biol. Ther., 2008, 8(5):609-632.
Zhu, X., et al., "Novel Human Interleukin-15 Agonists", The Journal of Immunology, 2009, 183: 3598-3607.

αmPD1-IL15RaSu-IL15

αmPD-1-IL15RaSu-IL15

αmPD-1-IL15RaSu-IL15 K11S/D30N

αmPD-1-IL15RaSu-IL15 E64Q/M109A

αmPD-1-IL15RaSu-IL1 D61N

Tumor efficacy study (B16F10): Tumor growth

Tumor efficacy study (B16F10): Survival

Day6 post dose, m1 activates CD8 > NK in tumor
Peripheral blood

Day6 post dose, m2 activates CD8 > NK in tumor
Tumor

Absolute cell count
3000
2000
1000
0
PBS
0.3 mg/kg
1 mg/kg
NK
CD8
Treg

All Donors
CD8 effector memory

All Donors NK
CD8 central memory

SEQUENCE LISTING

```
<160> NUMBER OF SEQ ID NOS: 99

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 2
<211> LENGTH: 448
<212> TYPE: PRT
<213> ORGANISM: Artificial Sequence
<220> FEATURE:
<223> OTHER INFORMATION: Synthetic Construct

<400> SEQUENCE: 2
```

-continued

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

-continued 420 425 430

Leu His Asn His Tyr Thr Gln Lys Ser Leu Ser Leu Ser Pro Gly Lys
435 440 445

<210> SEQ ID NO 3
<211> LENGTH: 444
<212> TYPE: PRT
<213> ORGANISM: Artificial Sequence
<220> FEATURE:
<223> OTHER INFORMATION: Synthetic construct

<400> SEQUENCE: 3

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Asn Phe Gly Thr Gln Thr Tyr Thr Cys Asn Val Asp His Lys Pro Ser
195 200 205

Asn Thr Lys Val Asp Lys Thr Val Glu Arg Lys Cys Cys Val Glu Cys
210 215 220

Pro Pro Cys Pro Ala Pro Pro Val Ala Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser His Glu Asp Pro Glu Val Gln Phe
260 265 270

Asn Trp Tyr Val Asp Gly Val Glu Val His Asn Ala Lys Thr Lys Pro
275 280 285

Arg Glu Glu Gln Phe Asn Ser Thr Phe Arg Val Val Ser Val Leu Thr
290 295 300

Val Val His Gln Asp Trp Leu Asn Gly Lys Glu Tyr Lys Cys Lys Val
305 310 315 320

Ser Asn Lys Gly Leu Pro Ala Pro Ile Glu Lys Thr Ile Ser Lys Thr
325 330 335

Lys Gly Gln Pro Arg Glu Pro Gln Val Tyr Thr Leu Pro Pro Ser Arg

```
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 4
<211> LENGTH: 445
<212> TYPE: PRT
<213> ORGANISM: Artificial Sequence
<220> FEATURE:
<223> OTHER INFORMATION: Synthetic construct

<400> SEQUENCE: 4

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
```

```
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 5
<211> LENGTH: 162
<212> TYPE: PRT
<213> ORGANISM: Homo sapiens

<400> SEQUENCE: 5

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser


<210> SEQ ID NO 6
<211> LENGTH: 14
<212> TYPE: PRT
```

<213> ORGANISM: Artificial Sequence
<220> FEATURE:
<223> OTHER INFORMATION: Synthetic Construct

<400> SEQUENCE: 6

Gly Gly Gly Gly Gly Thr Ser Ala Thr Ala Thr Pro Gly Ala
1 5 10

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Gly Leu Asn Asp Ile Phe Glu Ala Gln Lys Ile Glu Trp His Glu
1 5 10 15

<210> SEQ ID NO 8
<211> LENGTH: 241
<212> TYPE: PRT
<213> ORGANISM: Artificial Sequence
<220> FEATURE:
<223> OTHER INFORMATION: Synthetic Construct

<400> SEQUENCE: 8

Ile Thr Cys Pro Pro Pro Met Ser Val Glu His Ala Asp Ile Trp Val
1 5 10 15

Lys Ser Tyr Ser Leu Tyr Ser Arg Glu Arg Tyr Ile Cys Asn Ser Gly
20 25 30

Phe Lys Arg Lys Ala Gly Thr Ser Ser Leu Thr Glu Cys Val Leu Asn
35 40 45

Lys Ala Thr Asn Val Ala His Trp Thr Thr Pro Ser Leu Lys Cys Ile
50 55 60

Arg Asp Pro Ala Leu Val His Gln Arg Pro Ala Pro Pro Ser Gly Gly
65 70 75 80

Ser Gly Gly Gly Gly Ser Gly Gly Gly Ser Gly Gly Gly Gly Ser Gly
85 90 95

Gly Asn Trp Val Asn Val Ile Ser Asp Leu Lys Lys Ile Glu Asp Leu
100 105 110

Ile Gln Ser Met His Ile Asp Ala Thr Leu Tyr Thr Glu Ser Asp Val
115 120 125

His Pro Ser Cys Lys Val Thr Ala Met Lys Cys Phe Leu Leu Glu Leu
130 135 140

Gln Val Ile Ser Leu Glu Ser Gly Asp Ala Ser Ile His Asp Thr Val
145 150 155 160

Glu Asn Leu Ile Ile Leu Ala Asn Asn Ser Leu Ser Ser Asn Gly Asn
165 170 175

Val Thr Glu Ser Gly Cys Lys Glu Cys Glu Glu Leu Glu Glu Lys Asn
180 185 190

Ile Lys Glu Phe Leu Gln Ser Phe Val His Ile Val Gln Met Phe Ile
195 200 205

Asn Thr Gly Gly Gly Gly Ser Gly His His His His His His His His
210 215 220

Gly Gly Gly Leu Asn Asp Ile Phe Glu Ala Gln Lys Ile Glu Trp His
225 230 235 240

Glu

<210> SEQ ID NO 9
<211> LENGTH: 144
<212> TYPE: PRT
<213> ORGANISM: Artificial Sequence
<220> FEATURE:
<223> OTHER INFORMATION: Synthetic Construct

<400> SEQUENCE: 9

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Arg Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Gly Gly Gly Gly Ser Gly His His His His His His His His Gly
        115                 120                 125

Gly Gly Leu Asn Asp Ile Phe Glu Ala Gln Lys Ile Glu Trp His Glu
    130                 135                 140
```

<210> SEQ ID NO 10
<211> LENGTH: 144
<212> TYPE: PRT
<213> ORGANISM: Artificial Sequence
<220> FEATURE:
<223> OTHER INFORMATION: Synthetic Construct

<400> SEQUENCE: 10

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Asn Ala Thr Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Gly Gly Gly Gly Ser Gly His His His His His His His His Gly
        115                 120                 125

Gly Gly Leu Asn Asp Ile Phe Glu Ala Gln Lys Ile Glu Trp His Glu
    130                 135                 140
```

<210> SEQ ID NO 11
<211> LENGTH: 144
<212> TYPE: PRT
<213> ORGANISM: Artificial Sequence
<220> FEATURE:
<223> OTHER INFORMATION: Synthetic Construct

<400> SEQUENCE: 11

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Asn Ala Thr Leu Glu Ser Gly Asp Ala Ser Ile His Asp Thr Val Glu
    50                  55                  60

Asn Leu Ile Ile Leu Ala Asn Asn Ser Leu Ser Ser Asn Gly Gln Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Gly Gly Gly Gly Ser Gly His His His His His His His His Gly
        115                 120                 125

Gly Gly Leu Asn Asp Ile Phe Glu Ala Gln Lys Ile Glu Trp His Glu
    130                 135                 140
```

<210> SEQ ID NO 12
<211> LENGTH: 118
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser
        115
```

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

```
Asp Ile Val Met Thr Gln Ser Pro Ser Ser Leu Ser Val Ser Ala Gly
1               5                   10                  15
```

```
Asp Lys Val Thr Met Ser Cys Arg Ala Ser Gln Gly Ile Ser Ser Trp
            20                  25                  30

Leu Ala Trp Tyr Gln Gln Lys Pro Trp Gln Pro Pro Lys Leu Leu Ile
        35                  40                  45

Tyr Lys Ala Ser Thr Leu Glu Ser Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Glu Asp Leu Ala Val Tyr Tyr Cys Gln Gln Ser Tyr Ser Thr Pro Trp
                85                  90                  95

Thr Phe Gly Gly Gly Thr Lys Leu Glu Ile Lys
            100                 105


<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Gly Phe Thr Phe Ser Ser Tyr
1               5


<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Ser Tyr Trp Met Ser
1               5


<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Ser Pro Ser Gly Gly Ser
1               5


<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Ala Ile Ser Pro Ser Gly Gly Ser Thr Tyr Tyr Ala Asp Ser Val Lys
1               5                   10                  15

Gly


<210> SEQ ID NO 18
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 18

Glu Ser Trp Gly Ala Tyr Tyr Asp Leu
1 5

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Arg Ala Ser Gln Gly Ile Ser Ser Trp Leu Ala
1 5 10

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Lys Ala Ser Thr Leu Glu Ser
1 5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln Ser Tyr Ser Thr Pro Trp Thr
1 5

<210> SEQ ID NO 22
<211> LENGTH: 668
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

-continued

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Asn Val
```

```
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asp Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Glu Asn Leu Ile Ile Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Met Phe Ile Asn Thr
            660                 665


<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gly Gly Gly Gly Ser Gly Ser Gly Gly
1               5


<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Gly Gly Gly Gly Gly Thr Ser Ala Thr Ala Thr Pro Gly Ala
1               5                   10


<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25

Gly Gly Ser Gly Gly Gly Gly Ser Gly Gly Gly Ser Gly Gly Gly Gly
1               5                   10                  15

Ser Gly Gly


<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

His His His His His His His His
1               5


<210> SEQ ID NO 27
```

<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

His His His His His His
1               5

<210> SEQ ID NO 28
<211> LENGTH: 461
<212> TYPE: PRT
<213> ORGANISM: Artificial Sequence
<220> FEATURE:
<223> OTHER INFORMATION: Synthetic Construct

<400> SEQUENCE: 28

```
His His His His His His His His Gly Gly Gly Gly Ser Gly Ser Gly
1               5                   10                  15

Gly Glu Val Gln Leu Val Glu Ser Gly Gly Gly Leu Val Lys Pro Gly
            20                  25                  30

Gly Ser Leu Glu Leu Ser Cys Ala Ala Ser Gly Phe Thr Phe Ser Ser
        35                  40                  45

Tyr Trp Met Ser Trp Val Arg Gln Ala Pro Glu Lys Gly Leu Glu Trp
    50                  55                  60

Val Ala Ala Ile Ser Pro Ser Gly Gly Ser Thr Tyr Tyr Ala Asp Ser
65                  70                  75                  80

Val Lys Gly Arg Phe Thr Ile Ser Arg Asp Asn Ala Lys Asn Thr Leu
                85                  90                  95

Phe Leu Gln Met Thr Ser Leu Arg Ser Glu Asp Thr Ala Met Tyr Tyr
            100                 105                 110

Cys Ala Lys Glu Ser Trp Gly Ala Tyr Tyr Asp Leu Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Arg Val Arg
225                 230                 235                 240

Cys Pro Arg Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Ala Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
```

```
305                 310                 315                 320

Thr Val Val His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Arg Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210> SEQ ID NO 29
<211> LENGTH: 570
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
```

-continued

```
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ala Thr Ala Thr Pro Gly Ala Asn Trp Val Asn Val Ile Ser
    450                 455                 460

Asp Leu Lys Lys Ile Glu Asp Leu Ile Gln Ser Met His Ile Asn Ala
465                 470                 475                 480

Thr Leu Phe Thr Glu Ser Asp Val His Pro Ser Cys Lys Val Thr Ala
                485                 490                 495

Met Lys Cys Phe Leu Leu Gln Leu Gln Val Ile Ser Leu Gln Ser Gly
            500                 505                 510

Asp Ala Ser Ile His Asp Thr Val Glu Asn Leu Ile Ile Leu Ala Asn
        515                 520                 525

Asn Ser Leu Ser Ser Asn Gly Asn Val Thr Glu Ser Gly Cys Lys Glu
    530                 535                 540

Cys Gln Glu Leu Glu Gln Lys Asn Ile Lys Glu Phe Leu Gln Ser Phe
545                 550                 555                 560

Val His Ile Val Gln Met Phe Ile Asn Thr
                565                 570


<210> SEQ ID NO 30
<211> LENGTH: 214
<212> TYPE: PRT
<213> ORGANISM: Artificial Sequence
<220> FEATURE:
<223> OTHER INFORMATION: Synthetic Construct

<400> SEQUENCE: 30

Asp Ile Val Met Thr Gln Ser Pro Ser Ser Leu Ser Val Ser Ala Gly
```

```
1               5                   10                  15

Asp Lys Val Thr Met Ser Cys Arg Ala Ser Gln Gly Ile Ser Ser Trp
            20                  25                  30

Leu Ala Trp Tyr Gln Gln Lys Pro Trp Gln Pro Pro Lys Leu Leu Ile
        35                  40                  45

Tyr Lys Ala Ser Thr Leu Glu Ser Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Glu Asp Leu Ala Val Tyr Tyr Cys Gln Gln Ser Tyr Ser Thr Pro Trp
                85                  90                  95

Thr Phe Gly Gly Gly Thr Lys Leu Glu Ile Lys Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Lys Ser Ser Gln Ser Leu Trp Asp Ser Gly Asn Gln Lys Asn Phe Leu
1               5                   10                  15

Thr


<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Trp Thr Ser Tyr Arg Glu Ser
1               5


<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33
```

```
Gln Asn Asp Tyr Phe Tyr Pro Leu Thr
1               5


<210> SEQ ID NO 34
<211> LENGTH: 117
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser
        115


<210> SEQ ID NO 35
<211> LENGTH: 113
<212> TYPE: PRT
<213> ORGANISM: Artificial Sequence
<220> FEATURE:
<223> OTHER INFORMATION: Synthetic Construct

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gly Gly Thr Lys Val Glu Ile
            100                 105                 110

Lys


<210> SEQ ID NO 36
<211> LENGTH: 117
<212> TYPE: PRT
<213> ORGANISM: Artificial Sequence
<220> FEATURE:
<223> OTHER INFORMATION: Synthetic Construct

<400> SEQUENCE: 36
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser
        115


<210> SEQ ID NO 37
<211> LENGTH: 113
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Trp Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Thr Ser Tyr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asp Tyr Phe Tyr Pro Leu Thr Phe Gly Gly Gly Thr Lys Val Glu Ile
            100                 105                 110

Lys


<210> SEQ ID NO 38
<211> LENGTH: 571
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60
```

```
Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480
```

```
Ala Thr Leu Tyr Thr Glu Ser Asp Val His Pro Ser Cys Lys Val Thr
                485                 490                 495

Ala Met Lys Cys Phe Leu Leu Gly Leu Gln Arg Ile Ser Leu Glu Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570


<210> SEQ ID NO 39
<211> LENGTH: 571
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270
```

-continued

Asn Trp Tyr Val Asp Gly Val Glu Val His Asn Ala Lys Thr Lys Pro
275 280 285

Arg Glu Glu Gln Phe Asn Ser Thr Phe Arg Val Val Ser Val Leu Thr
290 295 300

Val Val His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Thr
325 330 335

Lys Gly Gln Pro Arg Glu Pro Gln Val Tyr Thr Leu Pro Pro Ser Arg
340 345 350

Glu Glu Met Thr Lys Asn Gln Val Ser Leu Thr Cys Glu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Met Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly Ser Gly Gly Gly Gly
435 440 445

Gly Thr Ser Ala Thr Ala Thr Pro Gly Ala Asn Trp Val Asn Val Ile
450 455 460

Ser Asp Leu Lys Lys Ile Glu Asp Leu Ile Gln Ser Met His Ile Asp
465 470 475 480

Ala Thr Leu Tyr Thr Glu Ser Asn Val His Pro Ser Cys Lys Val Thr
485 490 495

Ala Met Lys Cys Phe Leu Leu Gly Leu Gln Arg Ile Ser Leu Glu Ser
500 505 510

Gly Asp Ala Ser Ile His Asp Thr Val Gln Asn Leu Ile Ile Leu Ala
515 520 525

Asn Asn Ser Leu Ser Ser Asn Gly Asn Val Thr Glu Ser Gly Cys Lys
530 535 540

Glu Cys Glu Glu Leu Glu Glu Lys Asn Ile Lys Glu Phe Leu Gln Ser
545 550 555 560

Phe Val His Ile Val Gln Met Phe Ile Asn Thr
565 570

<210> SEQ ID NO 40
<211> LENGTH: 571
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

-continued

```
Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asn Val His Pro Ser Cys Lys Val Thr
```

```
                485                 490                 495

Ala Met Lys Cys Phe Leu Leu Gly Leu Gln Arg Ile Ser Leu Glu Ser
            500                 505                 510

Gly Asp Ala Ser Ile His Asp Thr Val Gln Asn Leu Ile Ser Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570


<210> SEQ ID NO 41
<211> LENGTH: 571
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
```

```
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Lys Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asn Val His Pro Ser Cys Lys Val Thr
                485                 490                 495

Ala Met Lys Cys Phe Leu Leu Gly Leu Gln Arg Ile Ser Leu Glu Ser
            500                 505                 510

Gly Asp Ala Ser Ile His Asp Thr Val Gln Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570


<210> SEQ ID NO 42
<211> LENGTH: 571
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
```

-continued

```
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asn Val His Pro Ser Cys Lys Val Thr
                485                 490                 495
```

```
Ala Met Lys Cys Phe Leu Leu Gly Leu Gln Arg Ile Ser Leu Glu Ser
            500                 505                 510

Gly Asp Ala Ser Ile His Asp Thr Val Gln Asn Leu Ile Ser Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Ala Phe Ile Asn Thr
                565                 570


<210> SEQ ID NO 43
<211> LENGTH: 571
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285
```

```
Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Lys Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asn Val His Pro Ser Cys Lys Val Thr
                485                 490                 495

Ala Met Lys Cys Phe Leu Leu Gly Leu Gln Arg Ile Ser Leu Glu Ser
            500                 505                 510

Gly Asp Ala Ser Ile His Asp Thr Val Gln Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Ala Phe Ile Asn Thr
                565                 570
```

```
<210> SEQ ID NO 44
<211> LENGTH: 571
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80
```

```
Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asn Val His Pro Ser Cys Lys Val Thr
                485                 490                 495
```

```
Ala Met Lys Cys Phe Leu Leu Gly Leu Gln Arg Ile Ser Leu Glu Ser
            500                 505                 510

Gly Asp Ala Ser Ile His Asp Thr Val Gln Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Ala Phe Ile Asn Thr
                565                 570


<210> SEQ ID NO 45
<211> LENGTH: 571
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285
```

Arg Glu Glu Gln Phe Asn Ser Thr Phe Arg Val Val Ser Val Leu Thr
290 295 300

Val Val His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Thr
325 330 335

Lys Gly Gln Pro Arg Glu Pro Gln Val Tyr Thr Leu Pro Pro Ser Arg
340 345 350

Glu Glu Met Thr Lys Asn Gln Val Ser Leu Thr Cys Glu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Met Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly Ser Gly Gly Gly Gly
435 440 445

Gly Thr Ser Ala Thr Ala Thr Pro Gly Ala Asn Trp Val Asn Val Ile
450 455 460

Ser Asp Leu Lys Lys Ile Glu Asp Leu Ile Gln Ser Met His Ile Asp
465 470 475 480

Ala Thr Leu Lys Thr Glu Ser Asp Val His Pro Ser Cys Lys Val Thr
485 490 495

Ala Met Lys Cys Phe Leu Leu Glu Leu Gln Arg Ile Ser Leu Glu Ser
500 505 510

Gly Asp Ala Ser Ile His Asp Thr Val Glu Asn Leu Ile Ile Leu Ala
515 520 525

Asn Asn Ser Leu Ser Ser Asn Gly Asn Val Thr Glu Ser Gly Cys Lys
530 535 540

Glu Cys Glu Glu Leu Glu Glu Lys Asn Ile Lys Glu Phe Leu Gln Ser
545 550 555 560

Phe Val His Ile Val Gln Met Phe Ile Asn Thr
565 570

<210> SEQ ID NO 46
<211> LENGTH: 571
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

```
Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Lys Thr Glu Ser Asn Val His Pro Ser Cys Lys Val Thr
                485                 490                 495

Ala Met Lys Cys Phe Leu Leu Glu Leu Gln Arg Ile Ser Leu Glu Ser
```

```
            500                 505                 510

Gly Asp Ala Ser Ile His Asp Thr Val Gln Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570


<210> SEQ ID NO 47
<211> LENGTH: 571
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
```

```
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Lys Thr Glu Ser Asp Val His Pro Ser Cys Lys Val Thr
                485                 490                 495

Ala Met Lys Cys Phe Leu Leu Glu Leu Gln Lys Ile Ser Leu Glu Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570
```

<210> SEQ ID NO 48
<211> LENGTH: 571
<212> TYPE: PRT
<213> ORGANISM: Artificial Sequence
<220> FEATURE:
<223> OTHER INFORMATION: Synthetic Construct

<400> SEQUENCE: 48

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
```

-continued

```
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Gly Leu Gln Lys Ile Ser Leu Glu Ser
            500                 505                 510
```

```
Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570


<210> SEQ ID NO 49
<211> LENGTH: 668
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300
```

```
Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Asn Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ile Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Met Phe Ile Asn Thr
            660                 665
```

<210> SEQ ID NO 50
<211> LENGTH: 668
<212> TYPE: PRT
<213> ORGANISM: Artificial Sequence
<220> FEATURE:
<223> OTHER INFORMATION: Synthetic Construct

<400> SEQUENCE: 50

-continued

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Asn Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ser Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Met Phe Ile Asn Thr
            660                 665


<210> SEQ ID NO 51
<211> LENGTH: 668
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110
```

-continued

```
Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
```

```
    530                 535                 540

Gly Gly Gly Ser Gly Gly Gly Gly Ser Gly Gly Asn Trp Val Lys Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ile Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Met Phe Ile Asn Thr
            660                 665


<210> SEQ ID NO 52
<211> LENGTH: 668
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
```

-continued

```
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Asn Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ile Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655
```

Ser Phe Val His Ile Val Gln Ala Phe Ile Asn Thr
660 665

<210> SEQ ID NO 53
<211> LENGTH: 668
<212> TYPE: PRT
<213> ORGANISM: Artificial Sequence
<220> FEATURE:
<223> OTHER INFORMATION: Synthetic Construct

<400> SEQUENCE: 53

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Asn Phe Gly Thr Gln Thr Tyr Thr Cys Asn Val Asp His Lys Pro Ser
195 200 205

Asn Thr Lys Val Asp Lys Thr Val Glu Arg Lys Cys Glu Val Glu Cys
210 215 220

Pro Glu Cys Pro Ala Pro Pro Val Ala Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Ala Val Ser His Glu Asp Pro Glu Val Gln Phe
260 265 270

Asn Trp Tyr Val Asp Gly Val Glu Val His Asn Ala Lys Thr Lys Pro
275 280 285

Arg Glu Glu Gln Phe Asn Ser Thr Phe Arg Val Val Ser Val Leu Thr
290 295 300

Val Val His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Thr
325 330 335

Lys Gly Gln Pro Arg Glu Pro Gln Val Tyr Thr Leu Pro Pro Ser Arg
340 345 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460

Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Asn Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ser Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Ala Phe Ile Asn Thr
            660                 665

<210> SEQ ID NO 54
<211> LENGTH: 668
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

```
Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Ile Thr Cys Pro Pro Pro
    450                 455                 460
```

```
Met Ser Val Glu His Ala Asp Ile Trp Val Lys Ser Tyr Ser Leu Tyr
465                 470                 475                 480

Ser Arg Glu Arg Tyr Ile Cys Asn Ser Gly Phe Lys Arg Lys Ala Gly
                485                 490                 495

Thr Ser Ser Leu Thr Glu Cys Val Leu Asn Lys Ala Thr Asn Val Ala
            500                 505                 510

His Trp Thr Thr Pro Ser Leu Lys Cys Ile Arg Asp Pro Ala Leu Val
        515                 520                 525

His Gln Arg Pro Ala Pro Pro Ser Gly Gly Ser Gly Gly Gly Gly Ser
    530                 535                 540

Gly Gly Gly Ser Gly Gly Gly Gly Ser Gly Gly Asn Trp Val Lys Val
545                 550                 555                 560

Ile Ser Asp Leu Lys Lys Ile Glu Asp Leu Ile Gln Ser Met His Ile
                565                 570                 575

Asp Ala Thr Leu Tyr Thr Glu Ser Asn Val His Pro Ser Cys Lys Val
            580                 585                 590

Thr Ala Met Lys Cys Phe Leu Leu Glu Leu Gln Val Ile Ser Leu Glu
        595                 600                 605

Ser Gly Asp Ala Ser Ile His Asp Thr Val Gln Asn Leu Ile Ile Leu
    610                 615                 620

Ala Asn Asn Ser Leu Ser Ser Asn Gly Asn Val Thr Glu Ser Gly Cys
625                 630                 635                 640

Lys Glu Cys Glu Glu Leu Glu Glu Lys Asn Ile Lys Glu Phe Leu Gln
                645                 650                 655

Ser Phe Val His Ile Val Gln Ala Phe Ile Asn Thr
            660                 665
```

<210> SEQ ID NO 55
<211> LENGTH: 571
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Gln Leu Gln Arg Ile Ser Leu Glu Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570
```

<210> SEQ ID NO 56
<211> LENGTH: 571
<212> TYPE: PRT
<213> ORGANISM: Artificial Sequence
<220> FEATURE:
<223> OTHER INFORMATION: Synthetic Construct

<400> SEQUENCE: 56

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
```

370 375 380

Glu Asn Asn Tyr Lys Thr Thr Pro Pro Met Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly Ser Gly Gly Gly Gly
435 440 445

Gly Thr Ser Ala Thr Ala Thr Pro Gly Ala Asn Trp Val Asn Val Ile
450 455 460

Ser Asp Leu Lys Lys Ile Glu Asp Leu Ile Gln Ser Met His Ile Asp
465 470 475 480

Ala Thr Leu Tyr Thr Glu Ser Asp Val His Pro Ser Cys Lys Val Thr
485 490 495

Ala Met Lys Cys Phe Leu Leu Glu Leu Gln Arg Ile Ser Leu Gln Ser
500 505 510

Gly Asp Ala Ser Ile His Asp Thr Val Glu Asn Leu Ile Ile Leu Ala
515 520 525

Asn Asn Ser Leu Ser Ser Asn Gly Asn Val Thr Glu Ser Gly Cys Lys
530 535 540

Glu Cys Glu Glu Leu Glu Glu Lys Asn Ile Lys Glu Phe Leu Gln Ser
545 550 555 560

Phe Val His Ile Val Gln Met Phe Ile Asn Thr
565 570

<210> SEQ ID NO 57
<211> LENGTH: 571
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln

-continued

```
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Glu Leu Gln Arg Ile Ser Leu Glu Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Gln Lys Asn Ile Lys Glu Phe Leu Gln Ser
545                 550                 555                 560

Phe Val His Ile Val Gln Met Phe Ile Asn Thr
                565                 570
```

<210> SEQ ID NO 58

<211> LENGTH: 571
<212> TYPE: PRT
<213> ORGANISM: Artificial Sequence
<220> FEATURE:
<223> OTHER INFORMATION: Synthetic Construct

<400> SEQUENCE: 58

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380
```

Glu Asn Asn Tyr Lys Thr Thr Pro Pro Met Leu Asp Ser Asp Gly Ser
385 390 395 400

Phe Phe Leu Tyr Ser Lys Leu Thr Val Asp Lys Ser Arg Trp Gln Gln
405 410 415

Gly Asn Val Phe Ser Cys Ser Val Met His Glu Ala Leu His Asn His
420 425 430

Tyr Thr Gln Lys Ser Leu Ser Leu Ser Pro Gly Ser Gly Gly Gly Gly
435 440 445

Gly Thr Ser Ala Thr Ala Thr Pro Gly Ala Asn Trp Val Asn Val Ile
450 455 460

Ser Asp Leu Lys Lys Ile Glu Asp Leu Ile Gln Ser Met His Ile Asp
465 470 475 480

Ala Thr Leu Tyr Thr Glu Ser Asp Val His Pro Ser Cys Lys Val Thr
485 490 495

Ala Met Lys Cys Phe Leu Leu Gln Leu Gln Val Ile Ser Leu Glu Ser
500 505 510

Gly Asp Ala Ser Ile His Asp Thr Val Glu Asn Leu Ile Ile Leu Ala
515 520 525

Asn Asn Ser Leu Ser Ser Asn Gly Asn Val Thr Glu Ser Gly Cys Lys
530 535 540

Glu Cys Glu Glu Leu Glu Gln Lys Asn Ile Lys Glu Phe Leu Gln Ser
545 550 555 560

Phe Val His Ile Val Gln Met Phe Ile Asn Thr
565 570

<210> SEQ ID NO 59
<211> LENGTH: 571
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Leu Val Lys Pro Gly Gly
1 5 10 15

Ser Leu Glu Leu Ser Cys Ala Ala Ser Gly Phe Thr Phe Ser Ser Tyr
20 25 30

Trp Met Ser Trp Val Arg Gln Ala Pro Glu Lys Gly Leu Glu Trp Val
35 40 45

Ala Ala Ile Ser Pro Ser Gly Gly Ser Thr Tyr Tyr Ala Asp Ser Val
50 55 60

Lys Gly Arg Phe Thr Ile Ser Arg Asp Asn Ala Lys Asn Thr Leu Phe
65 70 75 80

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

```
Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Gln Leu Gln Val Ile Ser Leu Gln Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570
```

<210> SEQ ID NO 60
<211> LENGTH: 571

<212> TYPE: PRT
<213> ORGANISM: Artificial Sequence
<220> FEATURE:
<223> OTHER INFORMATION: Synthetic Construct

<400> SEQUENCE: 60

```
Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380
```

```
Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Glu Leu Gln Val Ile Ser Leu Gln Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Gln Lys Asn Ile Lys Glu Phe Leu Gln Ser
545                 550                 555                 560

Phe Val His Ile Val Gln Met Phe Ile Asn Thr
                565                 570


<210> SEQ ID NO 61
<211> LENGTH: 571
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Gly Gly Gly Gly
        435                 440                 445

Gly Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Gln Leu Gln Val Ile Ser Leu Gln Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Gln Lys Asn Ile Lys Glu Phe Leu Gln Ser
545                 550                 555                 560

Phe Val His Ile Val Gln Met Phe Ile Asn Thr
                565                 570
```

<210> SEQ ID NO 62
<211> LENGTH: 8
<212> TYPE: PRT

<213> ORGANISM: Artificial Sequence
<220> FEATURE:
<223> OTHER INFORMATION: Synthetic Construct

<400> SEQUENCE: 62

Leu Thr Thr Gly Thr Phe Ala Tyr
1               5

<210> SEQ ID NO 63
<211> LENGTH: 571
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Glu Val Glu Cys
    210                 215                 220

Pro Glu Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

```
Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Glu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys Gly Gly Gly Gly
        435                 440                 445

Arg Thr Ser Ala Thr Ala Thr Pro Gly Ala Asn Trp Val Asn Val Ile
    450                 455                 460

Ser Asp Leu Lys Lys Ile Glu Asp Leu Ile Gln Ser Met His Ile Asp
465                 470                 475                 480

Ala Thr Leu Tyr Thr Glu Ser Asp Val His Pro Ser Cys Lys Val Thr
                485                 490                 495

Ala Met Lys Cys Phe Leu Leu Glu Leu Gln Arg Ile Ser Leu Glu Ser
            500                 505                 510

Gly Asp Ala Ser Ile His Asp Thr Val Glu Asn Leu Ile Ile Leu Ala
        515                 520                 525

Asn Asn Ser Leu Ser Ser Asn Gly Asn Val Thr Glu Ser Gly Cys Lys
    530                 535                 540

Glu Cys Glu Glu Leu Glu Glu Lys Asn Ile Lys Glu Phe Leu Gln Ser
545                 550                 555                 560

Phe Val His Ile Val Gln Met Phe Ile Asn Thr
                565                 570
```

<210> SEQ ID NO 64
<211> LENGTH: 326
<212> TYPE: PRT
<213> ORGANISM: Artificial Sequence
<220> FEATURE:
<223> OTHER INFORMATION: Synthetic Construct

<400> SEQUENCE: 64

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Ala
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ser Ser Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 65
<211> LENGTH: 220
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Trp Asp Ser
20 25 30

Gly Asn Gln Lys Asn Phe Leu Thr Trp Tyr Gln Gln Lys Pro Gly Lys
35 40 45

Ala Pro Lys Leu Leu Ile Tyr Trp Thr Ser Tyr Arg Glu Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Asn
85 90 95

Asp Tyr Phe Tyr Pro Leu Thr Phe Gly Gly Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 66
<211> LENGTH: 447
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Met
35 40 45

Gly Asn Ile Tyr Pro Gly Ser Ser Ile Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Thr Thr Gly Thr Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Arg Lys Thr His
210 215 220

Thr Cys Pro Arg Cys Pro Ala Pro Glu Ala Ala Gly Ala Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 67
<211> LENGTH: 671
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

-continued

```
Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ile Thr Cys Pro
    450                 455                 460

Pro Pro Met Ser Val Glu His Ala Asp Ile Trp Val Lys Ser Tyr Ser
465                 470                 475                 480

Leu Tyr Ser Arg Glu Arg Tyr Ile Cys Asn Ser Gly Phe Lys Arg Lys
                485                 490                 495

Ala Gly Thr Ser Ser Leu Thr Glu Cys Val Leu Asn Lys Ala Thr Asn
            500                 505                 510

Val Ala His Trp Thr Thr Pro Ser Leu Lys Cys Ile Arg Asp Pro Ala
        515                 520                 525

Leu Val His Gln Arg Pro Ala Pro Pro Ser Gly Gly Ser Gly Gly Gly
    530                 535                 540

Gly Ser Gly Gly Gly Ser Gly Gly Gly Gly Ser Gly Gly Asn Trp Val
545                 550                 555                 560

Asn Val Ile Ser Asp Leu Lys Lys Ile Glu Asp Leu Ile Gln Ser Met
                565                 570                 575

His Ile Asp Ala Thr Leu Tyr Thr Glu Ser Asp Val His Pro Ser Cys
            580                 585                 590

Lys Val Thr Ala Met Lys Cys Phe Leu Leu Glu Leu Gln Val Ile Ser
        595                 600                 605

Leu Glu Ser Gly Asp Ala Ser Ile His Asp Thr Val Glu Asn Leu Ile
    610                 615                 620

Ile Leu Ala Asn Asn Ser Leu Ser Ser Asn Gly Asn Val Thr Glu Ser
```

```
625                 630                 635                 640

Gly Cys Lys Glu Cys Glu Glu Leu Glu Glu Lys Asn Ile Lys Glu Phe
                645                 650                 655

Leu Gln Ser Phe Val His Ile Val Gln Met Phe Ile Asn Thr Ser
            660                 665                 670


<210> SEQ ID NO 68
<211> LENGTH: 574
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
```

```
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Asn
    450                 455                 460

Val Ile Ser Asp Leu Lys Lys Ile Glu Asp Leu Ile Gln Ser Met His
465                 470                 475                 480

Ile Asn Ala Thr Leu Phe Thr Glu Ser Asp Val His Pro Ser Cys Lys
                485                 490                 495

Val Thr Ala Met Lys Cys Phe Leu Leu Gln Leu Gln Val Ile Ser Leu
            500                 505                 510

Gln Ser Gly Asp Ala Ser Ile His Asp Thr Val Glu Asn Leu Ile Ile
        515                 520                 525

Leu Ala Asn Asn Ser Leu Ser Ser Asn Gly Asn Val Thr Glu Ser Gly
    530                 535                 540

Cys Lys Glu Cys Gln Glu Leu Glu Gln Lys Asn Ile Lys Glu Phe Leu
545                 550                 555                 560

Gln Ser Phe Val His Ile Val Gln Met Phe Ile Asn Thr Ser
                565                 570


<210> SEQ ID NO 69
<211> LENGTH: 574
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
```

```
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Asn
    450                 455                 460

Val Ile Ser Asp Leu Lys Lys Ile Glu Asp Leu Ile Gln Ser Met His
465                 470                 475                 480

Ile Asp Ala Thr Leu Tyr Thr Glu Ser Asp Val His Pro Ser Cys Lys
                485                 490                 495

Val Thr Ala Met Lys Cys Phe Leu Leu Gly Leu Gln Arg Ile Ser Leu
            500                 505                 510

Glu Ser Gly Asp Ala Ser Ile His Asp Thr Val Gln Asn Leu Ile Ile
        515                 520                 525

Leu Ala Asn Asn Ser Leu Ser Ser Asn Gly Asn Val Thr Glu Ser Gly
    530                 535                 540
```

Cys Lys Glu Cys Glu Glu Leu Glu Glu Lys Asn Ile Lys Glu Phe Leu
545 550 555 560

Gln Ser Phe Val His Ile Val Gln Met Phe Ile Asn Thr Ser
565 570

<210> SEQ ID NO 70
<211> LENGTH: 574
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Met
35 40 45

Gly Asn Ile Tyr Pro Gly Ser Ser Ile Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Thr Thr Gly Thr Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Glu Lys Thr His
210 215 220

Thr Cys Pro Glu Cys Pro Ala Pro Glu Ala Ala Gly Ala Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Asn
    450                 455                 460

Val Ile Ser Asp Leu Lys Lys Ile Glu Asp Leu Ile Gln Ser Met His
465                 470                 475                 480

Ile Asp Ala Thr Leu Tyr Thr Glu Ser Asn Val His Pro Ser Cys Lys
                485                 490                 495

Val Thr Ala Met Lys Cys Phe Leu Leu Gly Leu Gln Arg Ile Ser Leu
            500                 505                 510

Glu Ser Gly Asp Ala Ser Ile His Asp Thr Val Gln Asn Leu Ile Ile
        515                 520                 525

Leu Ala Asn Asn Ser Leu Ser Ser Asn Gly Asn Val Thr Glu Ser Gly
    530                 535                 540

Cys Lys Glu Cys Glu Glu Leu Glu Glu Lys Asn Ile Lys Glu Phe Leu
545                 550                 555                 560

Gln Ser Phe Val His Ile Val Gln Met Phe Ile Asn Thr Ser
                565                 570


<210> SEQ ID NO 71
<211> LENGTH: 574
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125
```

-continued

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Gln
    450                 455                 460

Val Ile Ser Asp Leu Lys Lys Ile Glu Asp Leu Ile Gln Ser Met His
465                 470                 475                 480

Ile Asp Ala Thr Leu Tyr Thr Glu Ser Asn Val His Pro Ser Cys Lys
                485                 490                 495

Val Thr Ala Met Lys Cys Phe Leu Leu Gly Leu Gln Arg Ile Ser Leu
            500                 505                 510

Glu Ser Gly Asp Ala Ser Ile His Asp Thr Val Glu Asn Leu Ile Ile
        515                 520                 525

Leu Ala Asn Asn Ser Leu Ser Ser Asn Gly Asn Val Thr Glu Ser Gly
    530                 535                 540
```

```
Cys Lys Glu Cys Glu Glu Leu Glu Glu Lys Asn Ile Lys Glu Phe Leu
545                 550                 555                 560

Gln Ser Phe Val His Ile Val Gln Met Phe Ile Asn Thr Ser
                565                 570


<210> SEQ ID NO 72
<211> LENGTH: 574
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Glu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Gly Gly
435 440 445

Gly Gly Ser Gly Gly Gly Gly Ser Gly Gly Gly Gly Lys Trp Val Asn
450 455 460

Val Ile Ser Asp Leu Lys Lys Ile Glu Asp Leu Ile Gln Ser Met His
465 470 475 480

Ile Asp Ala Thr Leu Tyr Thr Glu Ser Asn Val His Pro Ser Cys Lys
485 490 495

Val Thr Ala Met Lys Cys Phe Leu Leu Gly Leu Gln Arg Ile Ser Leu
500 505 510

Glu Ser Gly Asp Ala Ser Ile His Asp Thr Val Glu Asn Leu Ile Ile
515 520 525

Leu Ala Asn Asn Ser Leu Ser Ser Asn Gly Asn Val Thr Glu Ser Gly
530 535 540

Cys Lys Glu Cys Glu Glu Leu Glu Glu Lys Asn Ile Lys Glu Phe Leu
545 550 555 560

Gln Ser Phe Val His Ile Val Gln Met Phe Ile Asn Thr Ser
565 570

<210> SEQ ID NO 73
<211> LENGTH: 574
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Met
35 40 45

Gly Asn Ile Tyr Pro Gly Ser Ser Ile Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Thr Thr Gly Thr Phe Ala Tyr Trp Gly Gln Gly Thr Leu
100 105 110

Val Thr Val Ser Ser Ala Ser Thr Lys Gly Pro Ser Val Phe Pro Leu
115 120 125

-continued

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Glu Lys Thr His
    210                 215                 220

Thr Cys Pro Glu Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Glu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Asn
    450                 455                 460

Val Ile Thr Asp Leu Lys Lys Ile Glu Asp Leu Ile Gln Ser Met His
465                 470                 475                 480

Ile Asp Ala Thr Leu Tyr Thr Glu Ser Asn Val His Pro Ser Cys Lys
                485                 490                 495

Val Thr Ala Met Lys Cys Phe Leu Leu Gly Leu Gln Arg Ile Ser Leu
            500                 505                 510

Glu Ser Gly Asp Ala Ser Ile His Asp Thr Val Glu Asn Leu Ile Ile
        515                 520                 525

Leu Ala Asn Asn Ser Leu Ser Ser Asn Gly Asn Val Thr Glu Ser Gly
    530                 535                 540

Cys Lys Glu Cys Glu Glu Leu Glu Glu Lys Asn Ile Lys Glu Phe Leu
```

545 550 555 560

Gln Ser Phe Val His Ile Val Gln Met Phe Ile Asn Thr Ser
565 570

<210> SEQ ID NO 74
<211> LENGTH: 447
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Met
35 40 45

Gly Asn Ile Tyr Pro Gly Ser Ser Ile Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Thr Thr Gly Thr Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Ala Ala Gly Ala Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Cys Thr Leu Pro

```
            340                 345                 350

Pro Ser Arg Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 75
<211> LENGTH: 574
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Asn Trp Val Asn
    450                 455                 460

Val Ile Ser Asp Leu Lys Lys Ile Glu Asp Leu Ile Gln Ser Met His
465                 470                 475                 480

Ile Asp Ala Thr Leu Tyr Thr Glu Ser Asn Val His Pro Ser Cys Lys
                485                 490                 495

Val Thr Ala Met Lys Cys Phe Leu Leu Gly Leu Gln Arg Ile Ser Leu
            500                 505                 510

Glu Ser Gly Asp Ala Ser Ile His Asp Thr Val Gln Asn Leu Ile Ile
        515                 520                 525

Leu Ala Asn Asn Ser Leu Ser Ser Asn Gly Asn Val Thr Glu Ser Gly
    530                 535                 540

Cys Lys Glu Cys Glu Glu Leu Glu Glu Lys Asn Ile Lys Glu Phe Leu
545                 550                 555                 560

Gln Ser Phe Val His Ile Val Gln Met Phe Ile Asn Thr Ser
                565                 570
```

<210> SEQ ID NO 76
<211> LENGTH: 114
<212> TYPE: PRT
<213> ORGANISM: Artificial Sequence
<220> FEATURE:
<223> OTHER INFORMATION: Synthetic construct

<400> SEQUENCE: 76

```
Asn Trp Val Asn Val Ile Ser Asp Leu Lys Lys Ile Glu Asp Leu Ile
1               5                   10                  15

Gln Ser Met His Ile Asn Ala Thr Leu Phe Thr Glu Ser Asp Val His
            20                  25                  30

Pro Ser Cys Lys Val Thr Ala Met Lys Cys Phe Leu Leu Gln Leu Gln
        35                  40                  45

Val Ile Ser Leu Gln Ser Gly Asp Ala Ser Ile His Asp Thr Val Glu
```

50 55 60

Asn Leu Ile Ile Leu Ala Asn Asn Ser Leu Ser Ser Asn Gly Asn Val
65 70 75 80

Thr Glu Ser Gly Cys Lys Glu Cys Gln Glu Leu Glu Gln Lys Asn Ile
85 90 95

Lys Glu Phe Leu Gln Ser Phe Val His Ile Val Gln Met Phe Ile Asn
100 105 110

Thr Ser

<210> SEQ ID NO 77
<211> LENGTH: 15
<212> TYPE: PRT
<213> ORGANISM: Artificial Sequence
<220> FEATURE:
<223> OTHER INFORMATION: Synthetic construct

<400> SEQUENCE: 77

Ser Gly Gly Gly Gly Ser Gly Gly Gly Gly Ser Gly Gly Gly Gly
1 5 10 15

<210> SEQ ID NO 78
<211> LENGTH: 117
<212> TYPE: PRT
<213> ORGANISM: Artificial Sequence
<220> FEATURE:
<223> OTHER INFORMATION: Synthetic construct

<400> SEQUENCE: 78

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Met
35 40 45

Gly Asn Ile Tyr Pro Gly Ser Ser Leu Thr Asn Tyr Asn Glu Lys Phe
50 55 60

Lys Asn Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Leu Ser Thr Gly Thr Phe Ala Tyr Trp Gly Gln Gly Thr Leu
100 105 110

Val Thr Val Ser Ser
115

<210> SEQ ID NO 79
<211> LENGTH: 113
<212> TYPE: PRT
<213> ORGANISM: Artificial Sequence
<220> FEATURE:
<223> OTHER INFORMATION: Synthetic construct

<400> SEQUENCE: 79

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Trp Asp Ser
20 25 30

Gly Asn Gln Lys Asn Phe Leu Thr Trp Tyr Gln Gln Lys Pro Gly Gln
35 40 45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
            100                 105                 110

Lys

<210> SEQ ID NO 80
<211> LENGTH: 5
<212> TYPE: PRT
<213> ORGANISM: Artificial Sequence
<220> FEATURE:
<223> OTHER INFORMATION: Synthetic construct

<400> SEQUENCE: 80

Ser Tyr Trp Ile Asn
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic construct

<400> SEQUENCE: 81

Gly Tyr Thr Phe Thr Ser Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: Synthetic construct

<400> SEQUENCE: 82

Asn Ile Tyr Pro Gly Ser Ser Ile Thr Asn Tyr Ala Gln Lys Phe Gln
1               5                   10                  15

Gly

<210> SEQ ID NO 83
<211> LENGTH: 6
<212> TYPE: PRT
<213> ORGANISM: Artificial Sequence
<220> FEATURE:
<223> OTHER INFORMATION: Synthetic construct

<400> SEQUENCE: 83

Tyr Pro Gly Ser Ser Ile
1               5

<210> SEQ ID NO 84
<211> LENGTH: 114
<212> TYPE: PRT
<213> ORGANISM: Artificial Sequence
<220> FEATURE:
<223> OTHER INFORMATION: Synthetic Construct

<400> SEQUENCE: 84

Ala Trp Val Asn Val Ile Ser Asp Leu Lys Lys Ile Glu Asp Leu Ile

```
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Gly Leu Gln
        35                  40                  45

Arg Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 85
<211> LENGTH: 114
<212> TYPE: PRT
<213> ORGANISM: Artificial Sequence
<220> FEATURE:
<223> OTHER INFORMATION: Synthetic Construct

<400> SEQUENCE: 85

Gly Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Gly Leu Gln
        35                  40                  45

Arg Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 86
<211> LENGTH: 576
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80
```

```
Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ser
        435                 440                 445

Gly Gly Gly Gly Ser Gly Gly Gly Gly Ser Gly Gly Gly Gly Ala Trp
    450                 455                 460

Val Asn Val Ile Ser Asp Leu Lys Lys Ile Glu Asp Leu Ile Gln Ser
465                 470                 475                 480

Met His Ile Asp Ala Thr Leu Tyr Thr Glu Ser Asn Val His Pro Ser
                485                 490                 495
```

```
Cys Lys Val Thr Ala Met Lys Cys Phe Leu Leu Gly Leu Gln Arg Ile
            500                 505                 510

Ser Leu Glu Ser Gly Asp Ala Ser Ile His Asp Thr Val Glu Asn Leu
        515                 520                 525

Ile Ile Leu Ala Asn Asn Ser Leu Ser Ser Asn Gly Asn Val Thr Glu
    530                 535                 540

Ser Gly Cys Lys Glu Cys Glu Glu Leu Glu Glu Lys Asn Ile Lys Glu
545                 550                 555                 560

Phe Leu Gln Ser Phe Val His Ile Val Gln Met Phe Ile Asn Thr Ser
                565                 570                 575


<210> SEQ ID NO 87
<211> LENGTH: 576
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Ser Trp Gly Ala Tyr Tyr Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ser
        435                 440                 445

Gly Gly Gly Gly Ser Gly Gly Gly Gly Ser Gly Gly Gly Gly Gly Trp
    450                 455                 460

Val Asn Val Ile Ser Asp Leu Lys Lys Ile Glu Asp Leu Ile Gln Ser
465                 470                 475                 480

Met His Ile Asp Ala Thr Leu Tyr Thr Glu Ser Asn Val His Pro Ser
                485                 490                 495

Cys Lys Val Thr Ala Met Lys Cys Phe Leu Leu Gly Leu Gln Arg Ile
            500                 505                 510

Ser Leu Glu Ser Gly Asp Ala Ser Ile His Asp Thr Val Gln Asn Leu
        515                 520                 525

Ile Ile Leu Ala Asn Asn Ser Leu Ser Ser Asn Gly Asn Val Thr Glu
    530                 535                 540

Ser Gly Cys Lys Glu Cys Glu Glu Leu Glu Glu Lys Asn Ile Lys Glu
545                 550                 555                 560

Phe Leu Gln Ser Phe Val His Ile Val Gln Met Phe Ile Asn Thr Ser
                565                 570                 575


<210> SEQ ID NO 88
<211> LENGTH: 448
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Lys Pro Gly Gly
1               5                   10                  15

Ser Leu Glu Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ala Ala Ile Ser Pro Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Phe
65                  70                  75                  80
```

Leu Gln Met Thr Ser Leu Arg Ser Glu Asp Thr Ala Met Tyr Tyr Cys
85 90 95

Ala Lys Glu Ser Trp Gly Ala Tyr Tyr Asp Leu Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Ala Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Cys Thr Leu
340 345 350

Pro Pro Ser Arg Glu Glu Met Thr Lys Asn Gln Val Ser Leu Trp Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 89
<211> LENGTH: 575
<212> TYPE: PRT
<213> ORGANISM: Artificial Sequence
<220> FEATURE:
<223> OTHER INFORMATION: Synthetic Construct

<400> SEQUENCE: 89

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
```

```
            420                 425                 430

His Asn His Tyr Thr Gln Lys Ser Leu Ser Leu Ser Pro Gly Ser Gly
        435                 440                 445

Gly Gly Gly Ser Gly Gly Gly Gly Ser Gly Gly Gly Gly Ala Trp Val
    450                 455                 460

Asn Val Ile Ser Asp Leu Lys Lys Ile Glu Asp Leu Ile Gln Ser Met
465                 470                 475                 480

His Ile Asp Ala Thr Leu Tyr Thr Glu Ser Asn Val His Pro Ser Cys
                485                 490                 495

Lys Val Thr Ala Met Lys Cys Phe Leu Leu Gly Leu Gln Arg Ile Ser
            500                 505                 510

Leu Glu Ser Gly Asp Ala Ser Ile His Asp Thr Val Glu Asn Leu Ile
        515                 520                 525

Ile Leu Ala Asn Asn Ser Leu Ser Ser Asn Gly Asn Val Thr Glu Ser
    530                 535                 540

Gly Cys Lys Glu Cys Glu Glu Leu Glu Glu Lys Asn Ile Lys Glu Phe
545                 550                 555                 560

Leu Gln Ser Phe Val His Ile Val Gln Met Phe Ile Asn Thr Ser
                565                 570                 575


<210> SEQ ID NO 90
<211> LENGTH: 575
<212> TYPE: PRT
<213> ORGANISM: Artificial Sequence
<220> FEATURE:
<223> OTHER INFORMATION: Synthetic Construct

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
```

-continued

```
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Ser Gly
        435                 440                 445

Gly Gly Gly Ser Gly Gly Gly Gly Ser Gly Gly Gly Gly Gly Trp Val
    450                 455                 460

Asn Val Ile Ser Asp Leu Lys Lys Ile Glu Asp Leu Ile Gln Ser Met
465                 470                 475                 480

His Ile Asp Ala Thr Leu Tyr Thr Glu Ser Asn Val His Pro Ser Cys
                485                 490                 495

Lys Val Thr Ala Met Lys Cys Phe Leu Leu Gly Leu Gln Arg Ile Ser
            500                 505                 510

Leu Glu Ser Gly Asp Ala Ser Ile His Asp Thr Val Gln Asn Leu Ile
        515                 520                 525

Ile Leu Ala Asn Asn Ser Leu Ser Ser Asn Gly Asn Val Thr Glu Ser
    530                 535                 540

Gly Cys Lys Glu Cys Glu Glu Leu Glu Glu Lys Asn Ile Lys Glu Phe
545                 550                 555                 560

Leu Gln Ser Phe Val His Ile Val Gln Met Phe Ile Asn Thr Ser
                565                 570                 575


<210> SEQ ID NO 91
<211> LENGTH: 10
<212> TYPE: PRT
<213> ORGANISM: Artificial Sequence
<220> FEATURE:
<223> OTHER INFORMATION: Synthetic Construct

<400> SEQUENCE: 91

Gly Tyr Thr Phe Thr Ser Tyr Trp Ile Asn
```

1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

Gly Phe Thr Phe Ser Ser Tyr Trp Met Ser
1               5                   10

<210> SEQ ID NO 93
<211> LENGTH: 114
<212> TYPE: PRT
<213> ORGANISM: Artificial Sequence
<220> FEATURE:
<223> OTHER INFORMATION: Synthetic Construct

<400> SEQUENCE: 93

Asn Trp Val Asn Val Ile Ser Asp Leu Lys Lys Ile Glu Asp Leu Ile
1               5                   10                  15

Gln Ser Met His Ile Asn Ala Thr Leu Phe Thr Glu Ser Asp Val His
            20                  25                  30

Pro Ser Cys Lys Val Thr Ala Met Lys Cys Phe Leu Leu Gln Leu Gln
        35                  40                  45

Val Ile Ser Leu Gln Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Gln Glu Leu Glu Gln Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 94
<211> LENGTH: 117
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Trp Val Ser
        35                  40                  45

Ala Ile Ser Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Thr His Leu Tyr Leu Phe Asp Tyr Trp Gly Gln Gly Thr Leu
            100                 105                 110

Val Thr Val Ser Ser
        115

<210> SEQ ID NO 95
<211> LENGTH: 5
<212> TYPE: PRT
<213> ORGANISM: Artificial Sequence
<220> FEATURE:
<223> OTHER INFORMATION: Synthetic Construct

<400> SEQUENCE: 95

Gly Gly Ser Gly Gly
1               5

<210> SEQ ID NO 96
<211> LENGTH: 108
<212> TYPE: PRT
<213> ORGANISM: Artificial Sequence
<220> FEATURE:
<223> OTHER INFORMATION: Synthetic Construct

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 97
<211> LENGTH: 15
<212> TYPE: PRT
<213> ORGANISM: Artificial Sequence
<220> FEATURE:
<223> OTHER INFORMATION: Synthetic Construct

<400> SEQUENCE: 97

Ser Ser Ser Ser Gly Ser Ser Ser Ser Gly Ser Ser Ser Ser Gly
1               5                   10                  15

<210> SEQ ID NO 98
<211> LENGTH: 160
<212> TYPE: PRT
<213> ORGANISM: Artificial Sequence
<220> FEATURE:
<223> OTHER INFORMATION: Synthetic Construct

<400> SEQUENCE: 98

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

```
Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 99
<211> LENGTH: 406
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
        115                 120                 125

Gln Ser Pro Gly Thr Leu Ser Leu Ser Pro Gly Glu Arg Ala Thr Leu
    130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Met Arg Gly Arg Pro Pro Thr Phe Gly Gln
    210                 215                 220

Gly Thr Lys Val Glu Ile Lys Ser Ser Ser Ser Gly Ser Ser Ser Ser
225                 230                 235                 240

Gly Ser Ser Ser Ser Gly Ser Pro Gly Gln Gly Thr Gln Ser Glu Asn
                245                 250                 255
```

-continued

```
Ser Cys Thr His Phe Pro Gly Asn Leu Pro Asn Met Leu Arg Asp Leu
            260                 265                 270

Arg Asp Ala Phe Ser Arg Val Lys Thr Phe Phe Gln Met Lys Asp Gln
        275                 280                 285

Leu Asp Asn Leu Leu Leu Lys Glu Ser Leu Leu Glu Asp Phe Lys Gly
    290                 295                 300

Tyr Leu Gly Cys Gln Ala Leu Ser Glu Met Ile Gln Phe Tyr Leu Glu
305                 310                 315                 320

Glu Val Met Pro Gln Ala Glu Asn Gln Asp Pro Asp Ile Lys Ala His
                325                 330                 335

Val Asn Ser Leu Gly Glu Asn Leu Lys Thr Leu Arg Leu Arg Leu Arg
            340                 345                 350

Arg Cys His Arg Phe Leu Pro Cys Glu Asn Lys Ser Lys Ala Val Glu
        355                 360                 365

Gln Val Lys Asn Ala Phe Asn Lys Leu Gln Glu Lys Gly Ile Tyr Lys
    370                 375                 380

Ala Met Ser Glu Phe Asp Ile Phe Ile Asn Tyr Ile Glu Ala Tyr Met
385                 390                 395                 400

Thr Met Lys Ile Arg Asn
                405
```

IL-15 VARIANTS AND USES THEREOF

This application claims the benefit of U.S. Provisional Application No. 62/636,362 filed Feb. 28, 2018, U.S. Provisional Application No. 62/636,371 filed Feb. 28, 2018, and U.S. Provisional Application No. 62/784,302 filed Dec. 21, 2018, the contents of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72383A_SequenceListing_ST25.txt" created on Feb. 25, 2019 and having a size of 264 KB. The sequence listing contained in this .txt file is part of the specification and is herein incorporated by reference in its entirety.

FIELD

The present invention relates to interleukin 15 (IL-15) variants that have therapeutic and diagnostic use, and methods for making thereof. The present invention also provides fusion proteins comprising such IL-15 variants. Also provided are methods of stimulating or suppressing immune responses in a mammal, and methods of treating a disorder (e.g., cancer) using the IL-15 variants or the fusion proteins of such IL-15 variants.

BACKGROUND

Cytokines are powerful modulators of the immune response and hold the potential to dramatically affect outcomes to immune-oncology therapeutic approaches.

However, previous efforts to utilize cytokines in human subjects have yielded only modest efficacies and significant toxicities. Recent studies have suggested that a "targeted cytokine", such as an antibody-cytokine fusion protein, may deliver cytokines to a desired cell type while minimizing peripheral exposure and thus toxicities. See, e.g., Guo et al., Cytokine Growth Factor Rev. 38:10-21 (2017); Jakobisiak M, et al., Cytokine Growth Factor Rev. 22(2):99-108 (2011); Robinson, T. & Schluns, K. S., Immunol. Lett. 190:159-168 (2017); Rhode et al., Cancer Immunol. Res. 4(1): 49-60 (2016); Conlon et al., J Clin. Oncol. 33(1): 74-82 (2015). Accordingly, development of a therapeutic agent based on a targeted cytokine would be of great value in treatments of various diseases such as cancer.

SUMMARY

The invention disclosed herein is directed to human interleukin 15 (IL-15) variants and fusion proteins comprising thereof. It is demonstrated that the IL-15 variants of the present invention have decreased or no binding to the IL-15 receptor alpha (CD215), and/or have reduced interaction between IL-15 and its signaling receptor, comprised of IL-2 receptor beta (CD122) and the common gamma chain (CD132) as compared to the wild-type human IL-15 polypeptide or a wild-type IL-15 receptor alpha-IL-15 fusion polypeptide. In a second aspect of the invention, these reduced affinity IL-15 variants, when presented as an antibody fusion chimeric protein, are targeted selectively to desired cell types (those cells expressing the antibody target). Cell types that express the IL-15 receptor complex, but not the antibody target, are activated less, or not activated, compared to those cells which express both components. Accordingly, the IL-15 variants and the IL-15 fusion proteins of the present invention selectively modulate the activation of cell subsets to promote biological activity, such as an anti-tumor activity, efficaciously and safely. In a third aspect of this invention, these reduced affinity IL-15 variants and the IL-15 fusion proteins, when expressed as polynucleotides in CAR (Chimeric Antigen Receptor) T cells, either as secreted or membrane-tethered versions, are used to enhance CAR T function, including activity and proliferation.

Accordingly, in one aspect, the invention provides an isolated human interleukin 15 (IL-15) variant comprising amino acid substitution at positions a) V49 and I51 or b) V49, I50, and S51 of SEQ ID NO: 1, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant has decreased or no binding to the human IL-15 receptor alpha (IL-15Rα) and the human IL-2 receptor beta/gamma (IL-2Rβγ) as compared to the wild-type human IL-15 polypeptide or a wild-type IL-15 receptor alpha-IL-15 fusion polypeptide, and wherein the amino acid substitution at position V49 is glycosylated.

In another aspect, provided is an isolated fusion protein comprising: 1) an antibody comprising a Fc domain; and b) a human interleukin 15 (IL-15) variant comprising amino acid substitution at positions a) V49 and I51 or b) V49, I50, and S51 of SEQ ID NO: 1, wherein the amino acid substitution at position V49 of SEQ ID NO: 1 is glycosylated, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

In some embodiments, the IL-15 variant comprises amino acid substitution at V49N, wherein V49N is glycosylated. In some embodiments, the amino acid substitution(s) at E53 and/or E89 of SEQ ID NO: 1 are also glycosylated.

In some embodiments, the IL-15 variant comprises amino acid substitutions of SEQ ID NO: 1 at positions selected from the group consisting of: a) V49, I50, S51, N4, D30, and E64; b) V49, I50, S51, N4, D30, E64, and 168; c) V49, I50, S51, N4, D30, E64, M109; d) V49, I50, S51, N4, D30, E64, I68, and M109; e) V49, I50, S51, D30, E64, and 168; f) V49, I50, S51, D30, E64, M109; g) V49, I50, S51, D30, E64, I68, and M109; h) N1, V49, I50, and S51; i) N4, V49, I50, and S51; j) S7, V49, I50, and S51; k) K10, V49, I50, and S51; l) K11, V49, I50, and S51; m) S29, V49, I50, and S51; n) V31, V49, I50, and S51; o) H32, V49, I50, and S51; p) V49, I50, S51, and E64; q) V49, I50, S51, and 168; r) V49, I50, S51, and L69; s) V49, I50, S51, and I111; t) N4, V49, I50, S51, and E64; u) N1, D30, V49, I50, and S51; v) N4, D30, V49, I50, and S51; w) S7 D30, V49, I50, and S51; x) K10, D30, V49, I50, and S51; y) K11, D30, V49, I50, and S51; z) S29, D30, V49, I50, and S51; aa) D30, V49, I50, S51, and E64; bb) D30, V49, I150, S51, and 168; cc) D30, V49, I50, S51, and L69; and dd) D30, V49, I50, S51, and I111.

In some embodiments, the IL-15 variant comprises amino acid substitutions comprising one or more specific substitutions at: a) V49N, V49K, V49E, V49H, V49Q or V49R; b) I50A or I50G; c) S51T; d) N1K, N1G, N1Q, N1R, N1E, N1A, or N1D; e) N4K, N4G, N4A, N4S, N4D, N4E, N4L, N4R, N4T, or N4Q; f) S7E, S7G, S7D, S7K, S7N, S7R, S7H, or S7T; g) K10A, K10S, K10E, K10L, K10M, K10D, or K10G; h) K11D, K11S, or K11W; i) D30N; j) E64Q, E64K, E64A, E64S, E64N, E64H, E64T, or E64R; k) E53N; l) G55S or G55T; m) E89N; n) L91S or L91T; o) Y26K, Y26R, or Y26H; p) S29N; q) V31S, V31D, or V31K; r) H32G; s) I68S, I68A, I68R, I68T, I68K, I68N, I68M, I68F, I68Y, 168E, or I68H; t) L69A, L69S, L69D, L69T, L69M, L69G, L69Q, L69I, L69E, or L69V; u) M109A, M109S, M109D, or M109K; and/or v) I111A, I111K, I111S, or I111D. In some embodiments, the IL-15 variant comprises amino acid substitutions at positions selected from the group consisting of: a) N4K, D30N, V49N, I50A, S51T, and E64Q; b) N4Q, D30N, V49N, I50A, and S51T; c) D30N, V49N, I50A, S51T, and E64Q; d) N4Q, D30N, V49N, I50A, S51T, and E64Q; e) N4Q, V49N, I50A, and S51T; f) V49N, I50A, S51T, and E64Q; and g) N4Q, V49N, I50A, S51T, and E64Q.

In another aspect, provided is an isolated human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant has no binding to the human IL-15 receptor alpha (IL-15Rα) and decreased binding to the human IL-2 receptor beta/gamma (IL-2Rβγ) as compared to the wild-type human IL-15 polypeptide or a wild-type IL-15 receptor alpha-IL-15 fusion polypeptide.

In another aspect, provided is an isolated fusion protein comprising: 1) an antibody comprising a Fc domain; and b) a human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

In some embodiments, the IL-15 variant comprises amino acid substitutions in SEQ ID NO: 1 at positions selected from the group consisting of: a) N1, E46, and V49; b) N4, E46, and V49; c) S7, E46, and V49; d) K10, E46, and V49; e) K11, E46, and V49; f) S29, E46, and V49; g) V31, E46, and V49; h) H32, E46, and V49; i) E46, V49, and E64; j) E46, V49, and 168; k) E46, V49, and L69; l) E46, V49, and I111; m) N4, E46, V49, and E64; n) E46, V49, N4, D30, and E64; o) E46, V49, N4, D30, E64, and 168; p) E46, V49, N4, D30, E64, and M109; q) E46, V49, N4, D30, E64, I68, and M109; r) N1, D30, E46, and V49; s) N4, D30, E46, and V49; t) S7, D30, E46, and V49; u) K10, D30, E46, and V49; v) K11, D30, E46, and V49; w) S29, D30, E46, and V49; x) D30, E46, V49, and E64; y) D30, E46, V49R, and 168; z) D30, E46, V49R, and L69; aa) D30, E46, V49R, and I111; bb) N1, D30, E46, V49, and M109; cc) N4, D30, E46, V49, and M109; dd) S7, D30, E46, V49, and M109; ee) K10, D30, E46, V49, and M109; ff) K11, D30, E46, V49, and M109; gg) D30, E46, V49, E64, and M109; hh) D30, E46, V49, 168, and M109; ii) D30, E46, V49, L69 and M109; jj) D30, E46, V49, M109, and I111; kk) D30, E46, V49, E64, I68, and M109; ll) E46, V49, D30, E64, and 168; mm) E46, V49, E64, and M109; nn) E46, V49, D30, E64, I68, and M109; oo) D22, Y26, V49, E46, E53, E89, and E93; and pp) N1, D30, E46, V49, and E64.

In some embodiments, the IL-15 variant comprises amino acid substitutions comprising one or more specific substitutions at: a) N1Q, N1K, N1R, N1E, N1A, N1D, or N1G; b) N4K, N4G, N4A, N4S, N4D, N4E, N4R, N4T, N4I, N4L, N4W, or N4Q; c) S7E, S7G, S7D, S7K, S7N, S7R, S7H, or S7T; d) K10D, K10A, K10S, K10E, K10L, K10M, K10D, or K10G; e) K11D, K11S, or K11W; f) D22N; g) Y26K, Y26R, or Y26H; h) S29N; i) D30N; j) V31S, V31D, or V31K; k) H32G; l) E46G or E46Q; m) V49N, V49K, or V49R V49E, V49H, or V49Q; n) E53Q; o) G55S or G55T; p) E64Q, E64K, E64A, E64S, E64N, E64H, E64T, or E64R; q) I68S, I68A, I68R, I68T, I68K, I68N, I68M, I68F, I68Y, 168E, or I68H; r) L69S, L69A, L69D, L69T, L69M, L69G, L69Q, L69I, L69E, or L69V; s) E89Q; t) E93Q; u) M109A, M109S, M109D, or M109K; and/or v) I111A, I111K, I111S, or I111D. In some embodiments, the IL-15 variant comprises amino acid substitutions at positions selected from the group consisting of a) N1K, E46G, and V49R; b) N4K, E46G, and V49R; c) N4Q, E46G, and V49R; d) S7T, E46G, and V49R; e) V31S, E46G, and V49R; f) V31K, E46G, and V49R; g) E46G, V49R, and E64Q; h) E46G, V49R, and E64K; i) N4Q, E46G, V49R, and E64Q; j) N1G, D30N, E46G, and V49R; k) N1K, D30N, E46G, and V49R; l) N1Q, D30N, E46G, and V49R; m) N4G, D30N, E46G, and V49R; n) N4K, D30N, E46G, and V49R; o) N4Q, D30N, E46G, and V49R; p) S7E, D30N, E46G, and V49R; q) S7G, D30N, E46G, and V49R; r) S7T, D30N, E46G, and V49R; s) K10D, D30N, E46G, and V49R; t) D30N, E46G, V49R, and E64A; u) D30N, E46G, V49R, and E64Q; v) D30N, E46G, V49R, and E64K; w) D30N, E46G, V49R, and I68S; x) D30N, E46G, V49R, and I68K; y) N4K, D30N, E46G, V49R, and E64K; z) N4Q, D30N, E46G, V49R, and E64K; aa) N4K, D30N, E46G, V49R, and E64Q; bb) N4Q, D30N, E46G, V49R, and E64Q; cc) N4K, D30N, E46G, V49R, and I68S; dd) D30N, E46G, V49R, E64Q, and I68S; ee) N1A, D30N, E46G, and V49R; and ff) N1G, D30N, E46G, V49R, and E64Q.

In another aspect, provided is an isolated human IL-15 variant comprising one or more amino acid substitution(s) at position(s) N1, N4, S7, K10, K11, D22, Y26, S29, D30, V31, H32, E46, E53, E64, I68, L69, E89, E93, M109, and/or I111 of SEQ ID NO: 1, wherein the IL-15 variant has decreased or no binding to the human IL-15 receptor alpha (IL-15Rα) and/or the human IL-2 receptor beta (IL-2Rβ) and/or IL-2 receptor gamma (IL-2Rγ) as compared to the wild-type human IL-15 polypeptide or a wild-type IL-15 receptor alpha-IL-15 fusion polypeptide.

In another aspect, provided is an isolated human IL-15 variant comprising the amino acid sequence shown in SEQ ID NO: 93. In some embodiments, the IL-15 variant further comprises a transmembrane domain.

In another aspect, provided is an isolated fusion protein comprising: 1) an antibody comprising a Fc domain; and b) a human interleukin 15 (IL-15) variant comprising one or more amino acid substitutions at positions N1, N4, S7, K10, K11, D22, Y26, S29, D30, V31, H32, E46, E53, E64, I68, L69, E89, E93, M109, and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

In another aspect, provided is an isolated fusion protein comprising: 1) an IL-15 antibody comprising a Fc domain; and b) a human interleukin 15 (IL-15) protein of SEQ ID NO: 1, wherein the IL-15 is covalently linked to the Fc domain of the antibody.

In some embodiments, the antibody in the IL-15 fusion protein of the present invention can be a human antibody, a humanized antibody, a chimeric antibody, or a bispecific antibody.

In some embodiments, the antibody in the IL-15 fusion protein of the present invention is of the human $IgG_1$, $IgG_2$, $IgG_{2\Delta a}$, $IgG_3$, $IgG_4$, $IgG_{4\Delta b}$, $IgG_{4\Delta c}$, $IgG_4$ S228P, $IgG_{4\Delta b}$ S228P, and $IgG_{4\Delta c}$ S228P subclass.

In some embodiments, the antibody of the IL-15 fusion protein of the present invention is a) an IgG2, and the antibody variable domain comprises amino acid modifications at positions 223, 225, and 228 in the hinge region and at position 409 or 368 (EU numbering scheme) in the CH3 region of the human IgG2 (SEQ ID NO: 3); b) an IgG1, and the antibody variable domain comprises amino acid modifications at positions 221 and 228 in the hinge region and at position 409 or 368 (EU numbering scheme) in the CH3 region of the human IgG1 (SEQ ID NO: 2); or c) an IgG1, and the antibody variable domain comprise amino acid modifications at positions 349, 354, 366, 368, and/or 407 (EU numbering scheme) in the CH3 region of the human IgG1 (SEQ ID NO: 2). In some embodiments, the antibody further comprises an amino acid modification at a) one or more positions 265, 330, and/or 331 of the human IgG2 (SEQ ID NO: 3); or b) one or more positions 234, 235, 237, and/or 322 of the human IgG1 (SEQ ID NO: 2). In some embodiments, the antibody further comprises an amino acid modification at one or more positions 234, 235, 237, 349, 354, 366, 368 and/or 407 of the human IgG1 (SEQ ID NO: 74 and 75).

In some embodiments, the antibody for the IL-15 fusion protein is selected from the group consisting of an anti-CTLA-4 antibody, an anti-CD3 antibody, an anti-CD4 antibody, an anti-CD8 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-IL-8 antibody, an anti-IL-15 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-MARCO antibody, an anti-CXCR4 antibodies, an anti-VEGF antibody, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-FLT3 antibody, an anti-B7-H4 antibody, an anti-B7-H3 antibody, an KLRG1 antibody, and an anti-GITR antibody.

In some embodiments, the IL-15 fusion protein of the present invention is covalently linked to the antibody via a polypeptide linker and/or a polypeptide tag.

In another aspect, the invention provides a pharmaceutical composition comprising a therapeutically effective amount of an IL-15 variant or an IL-15 fusion protein as described herein and a pharmaceutically acceptable carrier.

In another aspect, the invention provides an isolated polynucleotide comprising a nucleotide sequence encoding an IL-15 variant or an IL-15 fusion protein as described herein. In another aspect, the invention provides a vector comprising the polynucleotide.

In another aspect, the invention provides an isolated host cell or cell line that recombinantly produces an IL-15 variant or an IL-15 fusion protein as described herein. In some embodiments, the host cell or cell line is an engineered immune cell, wherein the engineered immune cell comprises a chimeric antigen receptor (CAR). In some embodiments, the CAR expressing cells are T cells, and the T cells express the IL-15 variant or the IL-15 fusion proteins as described herein in a secreted form or a membrane-tethered form.

In another aspect, the invention provides a method of producing an IL-15 variant or an IL-15 fusion protein, the method comprising: culturing a cell line that recombinantly produces the IL-15 variant or the IL-15 fusion protein as described herein under conditions wherein the protein variant or the fusion protein is produced; and recovering the protein variant or the fusion protein.

In another aspect, the invention provides a method for treating a condition in a subject comprising administering to the subject in need thereof an effective amount of the pharmaceutical composition as described herein. In some embodiments, the condition is a cancer. In some embodiments, the cancer is a liquid cancer or a solid cancer. In some embodiments, the cancer is relapsed, refractory, or metastatic.

In another aspect, the invention provides a method of inhibiting tumor growth or progression in a subject who has a tumor, comprising administering to the subject an effective amount of the pharmaceutical composition as described herein.

In another aspect, the invention provides a method of inhibiting or preventing metastasis of cancer cells in a subject, comprising administering to the subject in need thereof an effective amount of the pharmaceutical composition as described herein.

In another aspect, the invention provides a method of inducing tumor regression in a subject in need thereof, comprising administering to the subject an effective amount of the pharmaceutical composition as described herein.

In some embodiments, the IL-15 variants and the IL-15 fusion proteins described herein can be administered parenterally in a subject. In some embodiments, the subject is a human.

In some embodiments, the method can further comprise administering an effective amount of a second therapeutic agent. In some embodiments, the second therapeutic agent is a biotherapeutic agent.

In some embodiments, the second therapeutic agent is a cytokine, an immunocytokine (e.g. anti-EDA-IL10 fusion protein), a TNFα, a PAP inhibitor, an oncolytic virus, a kinase inhibitor, an ALK inhibitor (e.g., sunitinib or crizotinib), a MEK inhibitor, an IDO inhibitor, a GLS1 inhibitor, a tyrosine kinase inhibitor (e.g., axitinib or palbociclib), a CAR (Chimeric Antigen Receptor)-T cell or T cell therapy, a PRR (Pattern Recognition Receptor) agonist such as a TLR (Toll-Like Receptor) Agonist (e.g., TLR3, TLR4, TLR5, TLR7, TLR9), or a tumor vaccine.

Also provided is the use of any of the IL-15 variants or the IL-15 fusion proteins provided herein in the manufacture of a medicament for the treatment of cancer or for inhibiting tumor growth or progression in a subject in need thereof.

In one aspect, the invention provides for a method for treating cancer in a subject comprising administering to the subject a combination therapy which comprises a first therapeutic agent and a second therapeutic agent, wherein the first therapeutic agent is an IL-15 variant or IL-15 fusion protein.

In some embodiments, the first therapeutic agent is an IL-15 variant. In some embodiments, the first therapeutic agent is an IL-15 fusion protein. In some embodiments, the first therapeutic agent is any IL-15 variant or IL-15 fusion protein of the present invention. In some embodiments, the first therapeutic agent comprises the amino acid sequence shown in SEQ ID NO: 84, 85, 86, 87, 89, or 90.

In some embodiments, the second therapeutic agent is an immunocytokine. In some embodiments, the second therapeutic agent is an immunocytokine comprising an antibody, or fragment thereof, conjugated or fused to a cytokine (e.g. fusion protein). In some embodiments, the antibody, or fragment thereof, binds the Extra Domain-A (EDA) isoform of fibronectin (e.g. anti-EDA antibody). In some embodiments, the anti-EDA antibody, or fragment thereof, comprises a CDR1, a CDR2 and CDR3 of the heavy chain variable (VH) region shown in SEQ ID NO: 94 and/or a CDR1, a CDR2 and CDR3 of the light chain variable (VL) region shown in SEQ ID NO: 96. In some embodiments, the anti-EDA antibody, or fragment thereof, comprises a VH region having the amino acid sequence of SEQ ID NO: 94 and/or a VL region having the amino acid sequence of SEQ ID NO: 96. In some embodiments, the cytokine is IL-10. In some embodiments, IL-10 comprises the amino acid sequence of SEQ ID NO: 98. In some embodiments, the immunocytokine comprises at least one linker. In some embodiments, the linker(s) comprises SEQ ID NO: 95 and/or 97. In some embodiments, the immunocytokine is an anti-EDA-IL-10 fusion protein comprising the amino acid sequence shown in SEQ ID NO: 99.

In some embodiments, the invention provides for a method for treating cancer in a subject comprising administering to the subject a combination therapy which comprises a first therapeutic agent and a second therapeutic agent, wherein the first therapeutic agent is an IL-15 fusion protein, and wherein the second agent is an anti-EDA-IL-10 fusion protein. In some embodiments, the IL-15 fusion protein comprises the amino acid sequence shown in SEQ ID NO: 84, 85, 86, 87, 89, or 90 and the anti-EDA-IL-10 fusion protein comprises the amino acid sequence shown in SEQ ID NO: 99.

In some embodiments, the combination therapy may further comprise 1, 2, 3, 4 or 5 additional therapeutic agents. In some embodiments, the combination therapy further comprises an anti-PD-1 or anti-PD-L1 antibody. In some embodiments, the anti-PD-1 antibody is BCD-100, camrelizumab (SHR-1210), cemiplimab (REGN2810), genolimzurnab (CBT-501). MEDIO680, nivolumab (OPDIVO®), pembrolizumab (KEYTRUDA®), PF-06801591 (RN888), sintilimab (IBI-308), spartalizumab (PDR-001), STI-A1110, tisleizumab (BGB-A317), or TSR-042 In some embodiments, the anti-PD-L1 antibody is atezolizumab (TECENTRIQ®), durvalumab (IMFINZI®), BMS-936559 (MDX-1105), or LY3300054.

In some embodiments, each therapeutic agent in a combination therapy may be administered simultaneously, (e.g., in the same medicament or at the same time), concurrently (i.e., in separate medicaments administered one right after the other in any order, or sequentially in any order.

BRIEF DESCRIPTION OF THE FIGURES/DRAWINGS

FIG. 1A is a schematic drawing depicting an anti-mouse PD1 antibody-IL-15 fusion protein construct comprising the full human hIgG2Δa with bivalent Fab at the N-terminus as the targeting antibody arms; heterodimeric Fc with mutations that abolish FcγR binding at CH2 and CH3 (D265A, A330S, P331S), bispecific mutations on the hinge (C223R/E, E225R/E, and P228R/E) and CH3 (K409R or L368E) for the monovalent linking of an IL-15 mutein molecule at the C-terminus through a flexible glycine-serine (GS)-linker. The mutations in the IL-15 protein include N4K, D30N, V49N, I50A, S51T and E64Q (of SEQ ID NO: 1); V49N-I50A-S51T are the N-linked glycosylation sites (as shown with a schematic carbohydrate motif sticking out of the V49N position.

FIG. 1B depicts another anti-mouse PD1 antibody-IL-15 mutant fusion protein construct with the same mutations on the antibody as shown in FIG. 1A, and the difference in the mutations in the IL-15 protein including N4K, D30N, E46G (or Y26K), V49R (or V49K) and E64Q.

FIG. 1C is a schematic drawing depicting an anti-mouse PD1 antibody-IL-15 fusion protein construct ("M2") comprising the full human IgG1 with bivalent Fab at the N-terminus as the targeting antibody arms; bispecific mutations on the hinge (L234A, L235A, and G237A) and CH3 (Y349C, T366W, S354C, T366S, L368A, and Y407V) for the monovalent linking of an IL-15 mutein molecule at the C-terminus through a flexible glycine-serine (GS)-linker. The mutations in the IL-15 protein include E46G, V49R, E64Q, D30N, and N1G (of SEQ ID NO: 1).

FIG. 1D depicts another anti-mouse PD1 antibody-IL-15 mutant fusion protein construct ("M1") with the same mutations on the antibody as shown in FIG. 1C, and difference is in the mutations in the IL-15 protein including E46G, V49R, D30N, and N1A (of SEQ ID NO: 1).

FIG. 2A, FIG. 2B, FIG. 2C, and FIG. 2D show the direct binding of antibody or antibody-cytokine fusion molecules to cells expressing the IL-15 receptor (CD122 plus CD132), and in some cases, PD-1 as well. The molecules include: anti-mouse PD-1 antibody (FIG. 2A); isotype control antibody (Ab8.8)-aSu-IL-15 (FIG. 2B); anti-mouse PD-1-IL-15RaSu-IL15 (FIG. 2C); and anti-mouse PD-1-IL-15 NQ (FIG. 2D).

FIG. 3A, FIG. 3B, and FIG. 3C show the comparison of untargeted IL-15, xmPD-1-IL-15RaSu-IL15 (wild-type IL-15), and xmPD-1-IL15 NQ variant in a reporter assay, by plotting the percentage of cells that are either PD-1+ or PD-1(low) in a given assay that also stained as positive for pSTAT5 by flow cytometric analysis.

FIGS. 4A, 4B, 4C, 4D, 4E, 4F, 4G, and 4H show plots of a range of muteins (mutants or variants, used interchangeably), all of which are based on the xmPD-1-IL15RaSu-IL15. The specific molecules assayed are indicated in each plot.

FIGS. 5A, 5B, 5C, 5D, 5E, 5F, and 5G show plots of a range of muteins, all of which lack the IL-15RaSu domain and contain mutations to reduce or eliminate binding to IL-15Ra. The specific molecules assayed are indicated in each plot.

FIGS. 6A, 6B, 6C, 6D, 6E, 6F, and 6G show plots of a range of muteins which have altered activities (pSTAT5 activation) relative to IL-15 wildtype. The specific molecules assayed are indicated in each plot.

FIGS. 7A, 7B, 7C, 7D, 7E, 7F, 7G, and 7H show plots of a range of muteins which have altered activities (pSTAT5 activation) relative to IL-15 wild-type. The specific molecules assayed are indicated in each plot.

FIGS. 8A, 8B, 8C, and 8D show the effects on survival and body weight of mice treated with either xmPD-1-IL15RaSu-IL15 or xmPD1-IL15 NQ. More specifically, FIG. 8A shows the changes in body weight for animals dosed with 2, 1, or 0.2 mg/kg xmPD1-IL15RaSu-IL15 on days indicated with arrows (d0, 4, 7). FIG. 8B shows overall survival of these same animals. FIG. 8C shows the changes in body weight for animals dosed on days 0, 3, and 6 with 1, 0.8, or 0.5 mg/kg xmPD1-IL15RaSu-IL15. FIG. 8D shows the changes in body weight for animals dosed on days 0, 3, and 6 with 3, 2, or 1 mg/kg xmPD1-IL15 NQ.

FIGS. 9A and 9B plot the percentage of splenocytes or tumor-infiltrating lymphocytes that were gated as being CD4+ or CD8+ cells or NK cells and that scored as PD-1+(FIG. 9A); FIG. 9B shows the same study plotted as actual mean fluorescence intensities.

FIGS. 10A, 10B, and 10C show data from an in vivo B16F10 tumor efficacy study, with mice treated with 5, 3, 1, or 0.3 mg/kg xmPD1-IL15 NQ, or 0.3 mg/kg xmPD1-IL15RaSu-IL15 and compared to a control (PBS-treated) group. More specifically, in FIG. 10A, primary tumor volume is plotted for all groups. In FIG. 10B, overall survival of animals in the study groups is plotted. In FIG. 10C, body weight changes (relative to study start body weight) are plotted for each group.

FIGS. 11I, 11J, 11K and 11L show data from an in vivo MC38 tumor efficacy study, with mice treated with either anti-PD1-IL15 M1 or M2, each at either 0.1, 0.3, 1 or 5 mg/kg. FIGS. 11A, 11C, 11E, 11G, 11I and 11K plot the volume of the primary tumor mass over time for each group; arrows below the X-axis indicated the dosing schedule. FIGS. 11B, 11D, 11F, 11H, 11J and 11L plot the averaged changes in body weight from baseline (at beginning of dosing, d=0) for each group.

Figure 12A:
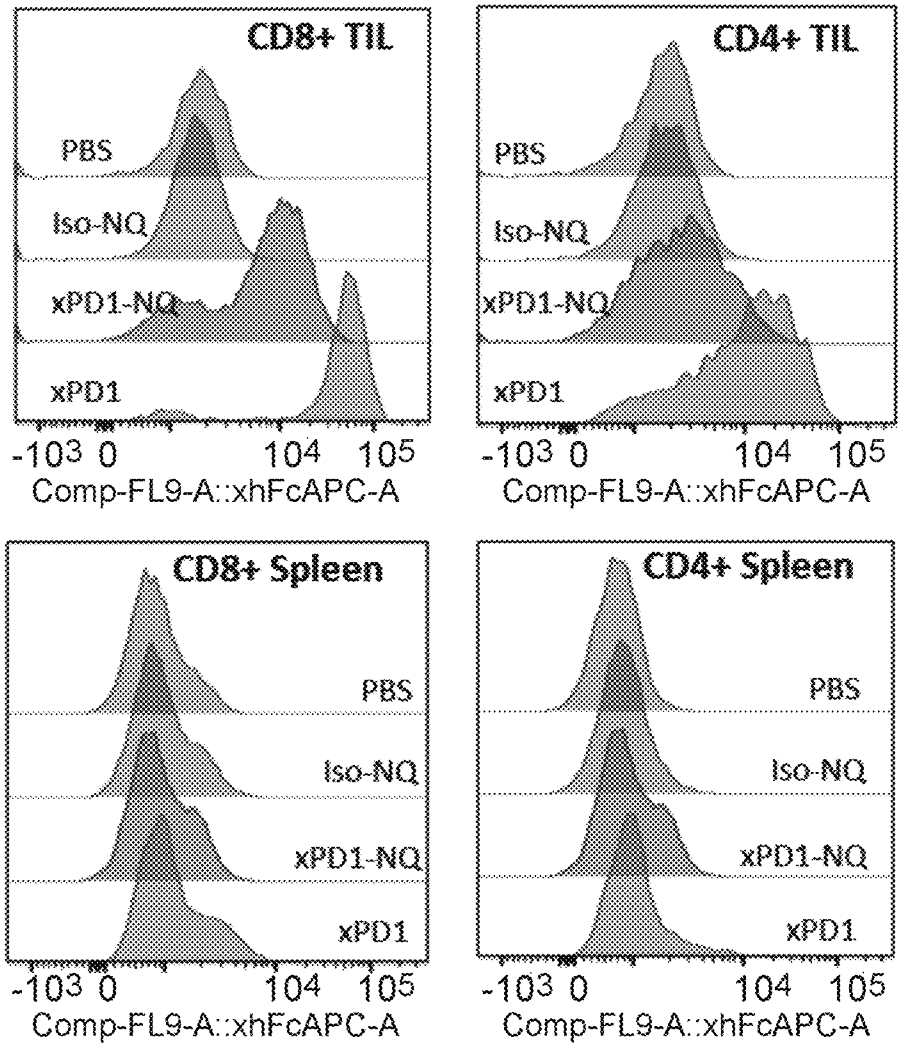
Figure 12B:
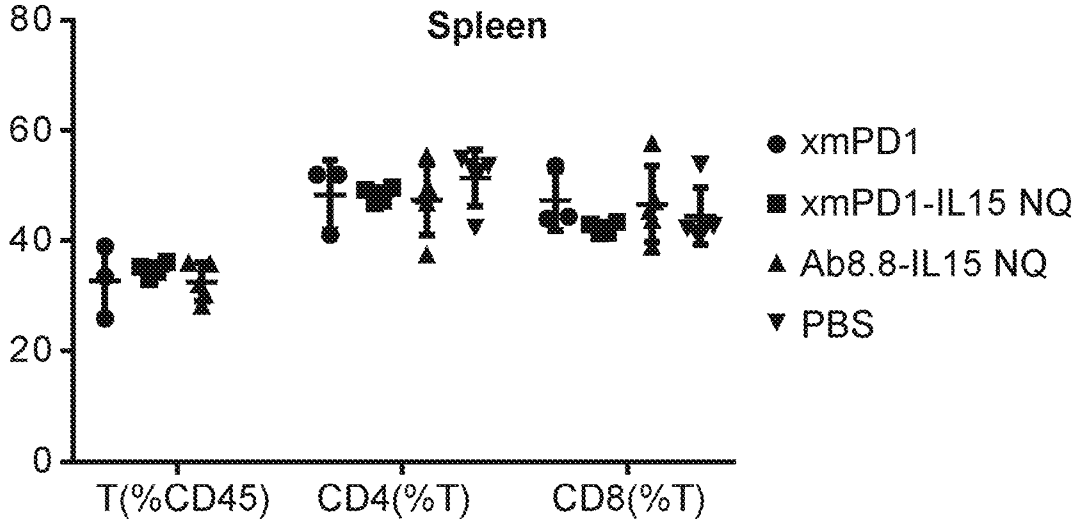
Figure 12C:
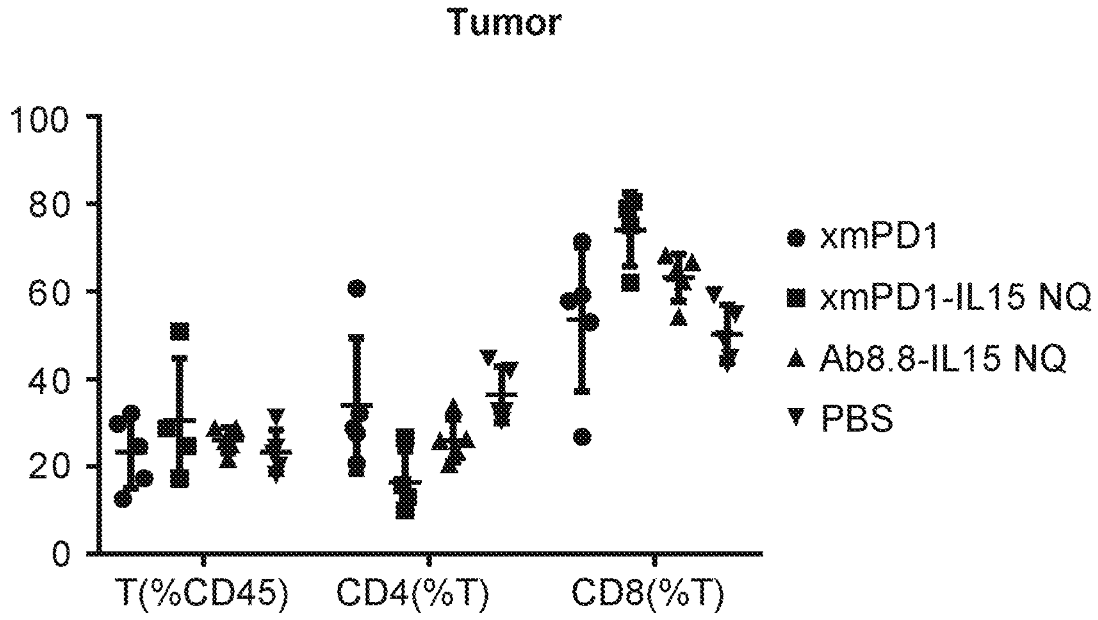
Figure 12D:
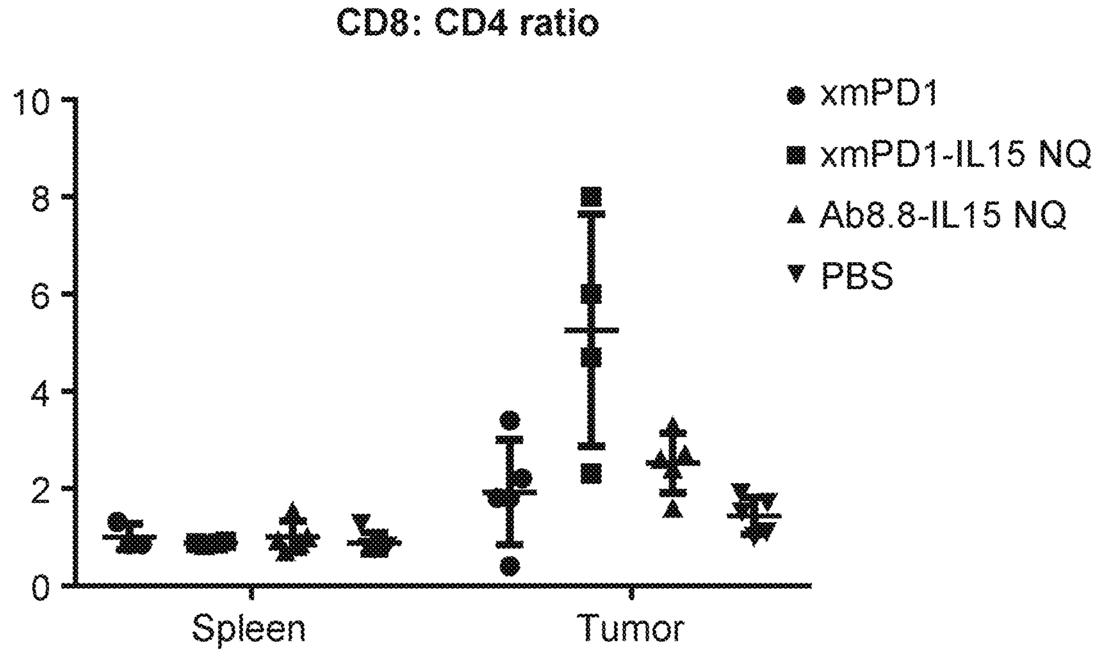

FIGS. 12A, 12B, 12C, and 12D show results from an experiment to analyze changes in splenic and TIL lymphocytes due to IL-15 drug administration. FIG. 12A shows the detection, via anti-human Fc, of anti-PD-1, Ab8.8-IL15 NQ, or xmPD1-IL15 NQ on the cells from animals treated with the aforementioned molecules. Upper row: histograms from TIL CD8+ (left) or CD4+ (right) cells as indicated. Bottom row: histograms from splenic CD8+ (left) or CD4+ (right) cells as indicated. FIG. 12B shows percentages of splenic T cells, CD4+ T cells, and CD8+ T cells, as indicated, from animals sampled 1 day after 3 doses of the indicated compound. FIG. 12C shows percentages of TIL T cells, CD4+ T cells, and CD8+ T cells, as indicated, from animals sampled 1 day after 3 doses of the indicated compound. FIG. 12D plots the ratios of CD8 to CD4 T cells from spleen and tumor as calculated from FIGS. 12B and 12C.

Figure 13A:
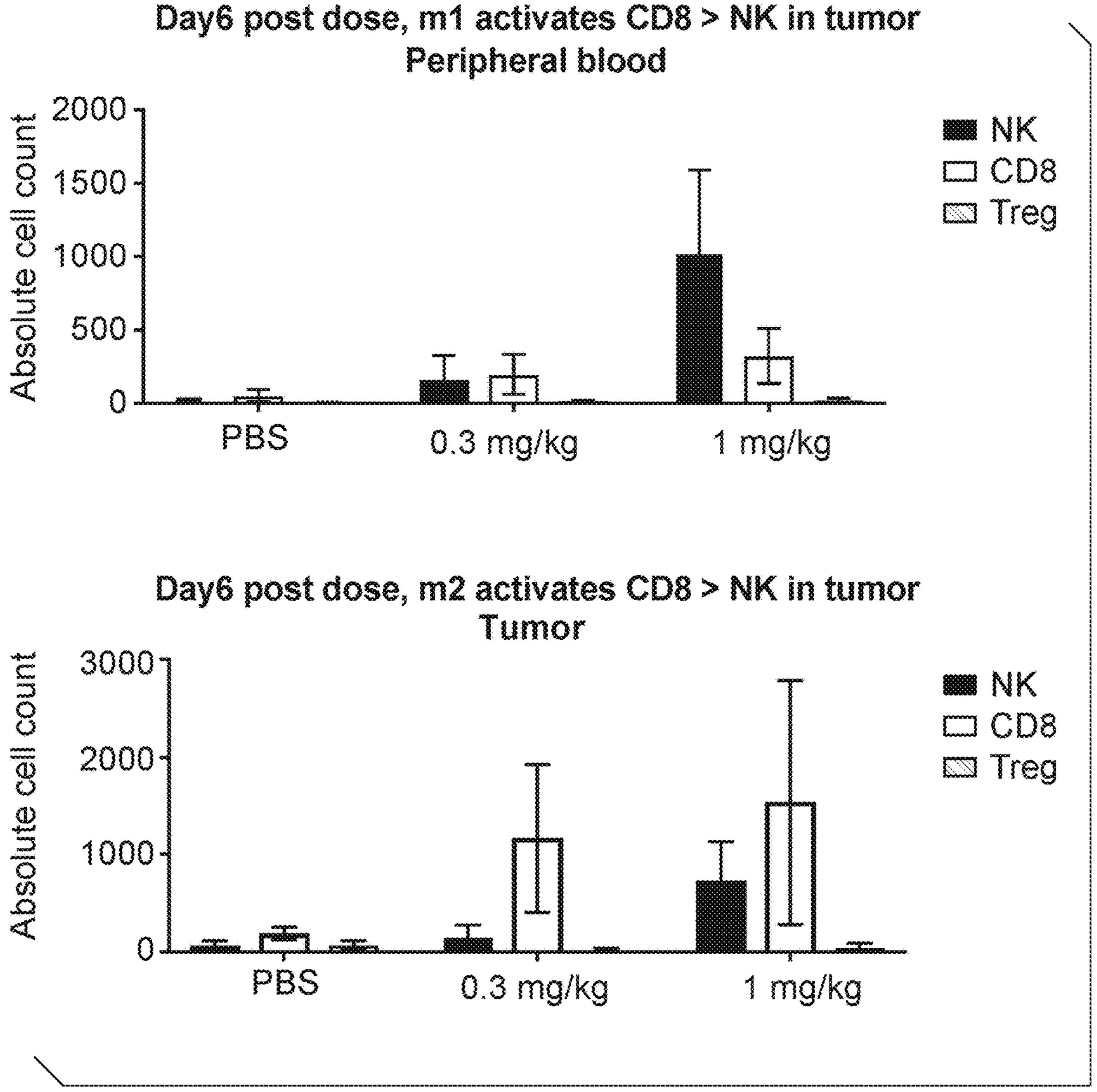
Figure 13B:
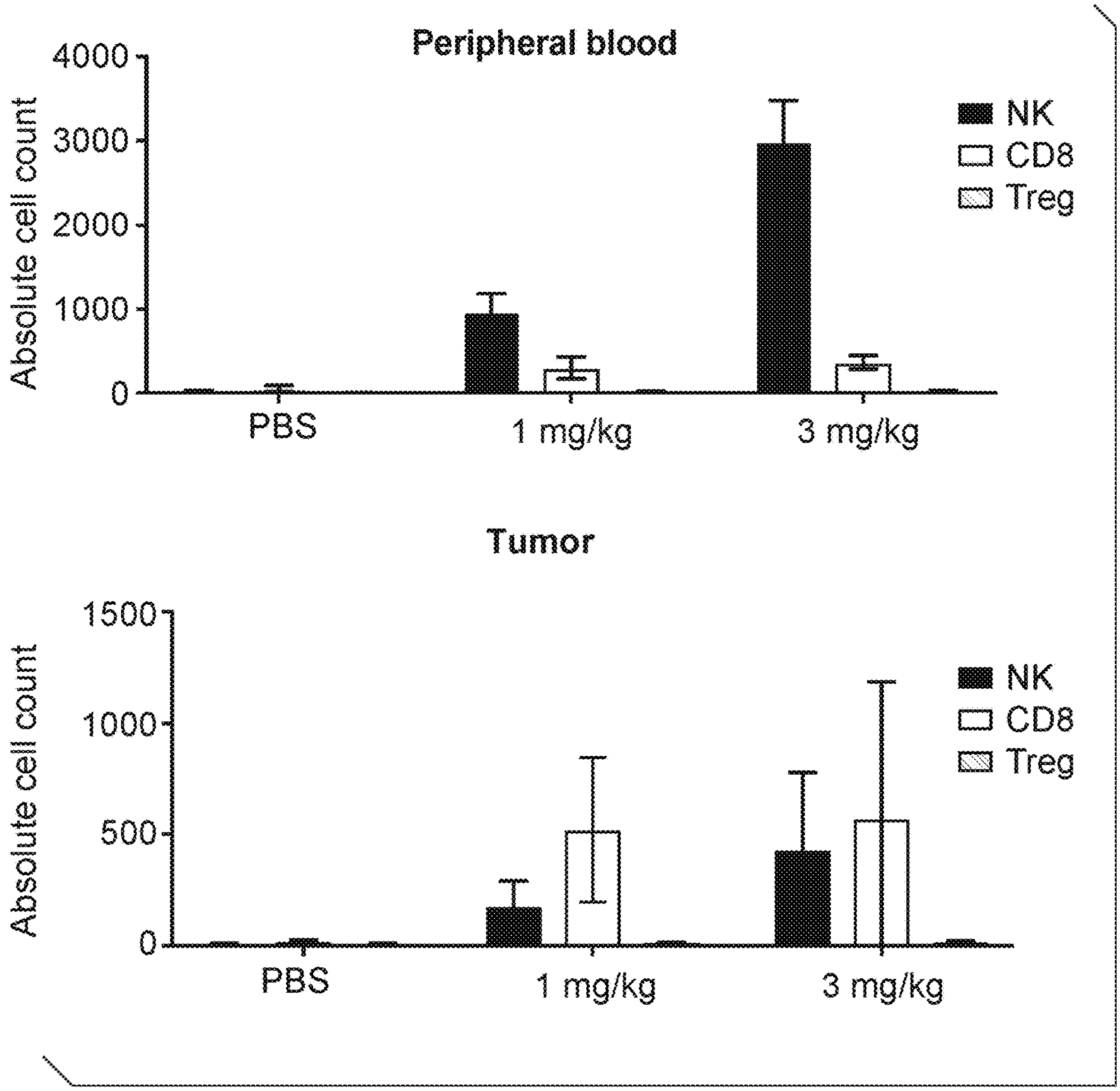

FIGS. 13A and 13B show the absolute counts of NK, CD8+ T and Treg cells in peripheral blood or tumor-infiltrating lymphocytes at Day 6, which showed to have the maximum effect by xmPD1-IL15 M1 and xmPD1-IL15 m2, respectively.

Figure 13C:
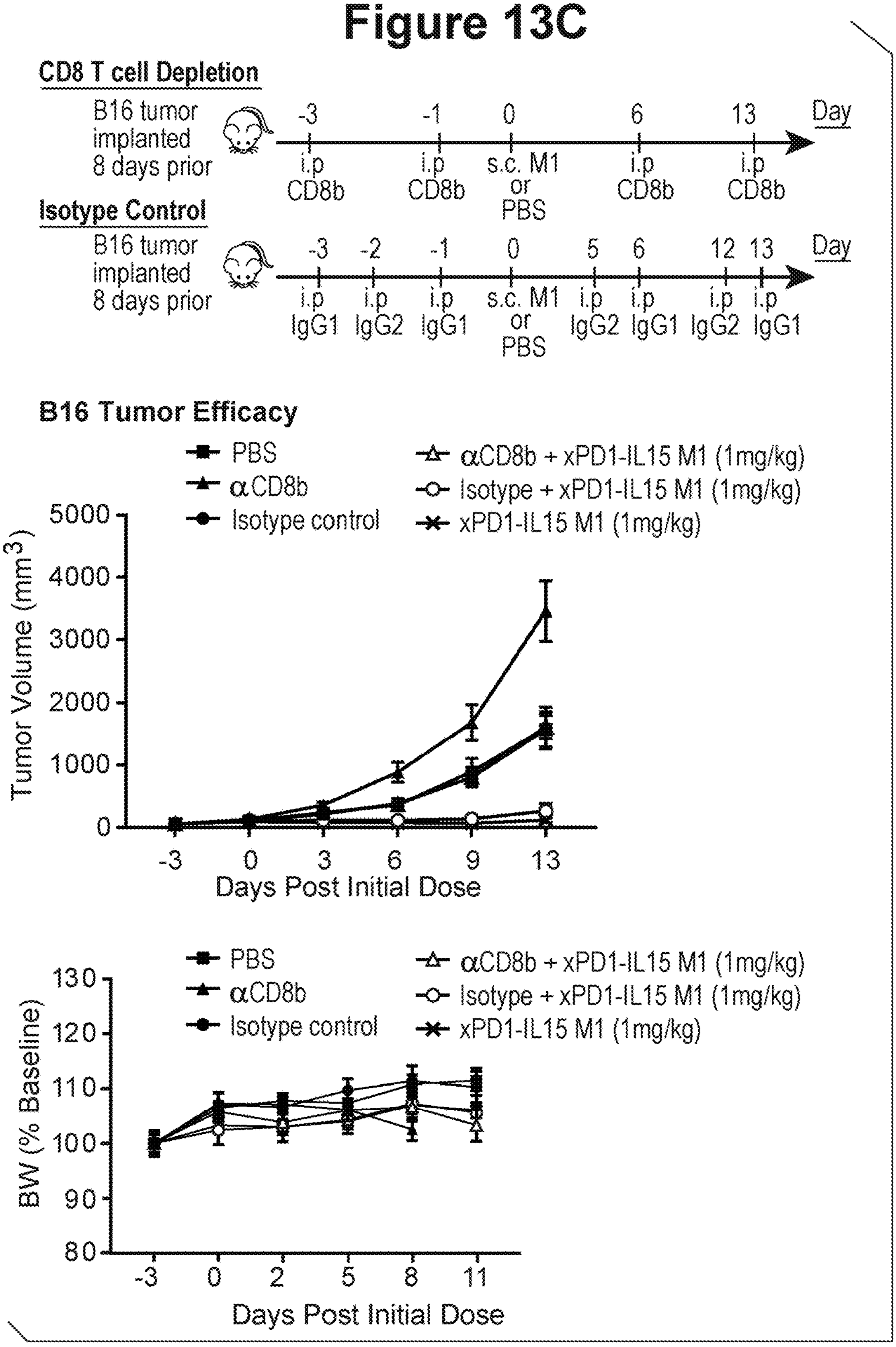
Figure 13D:
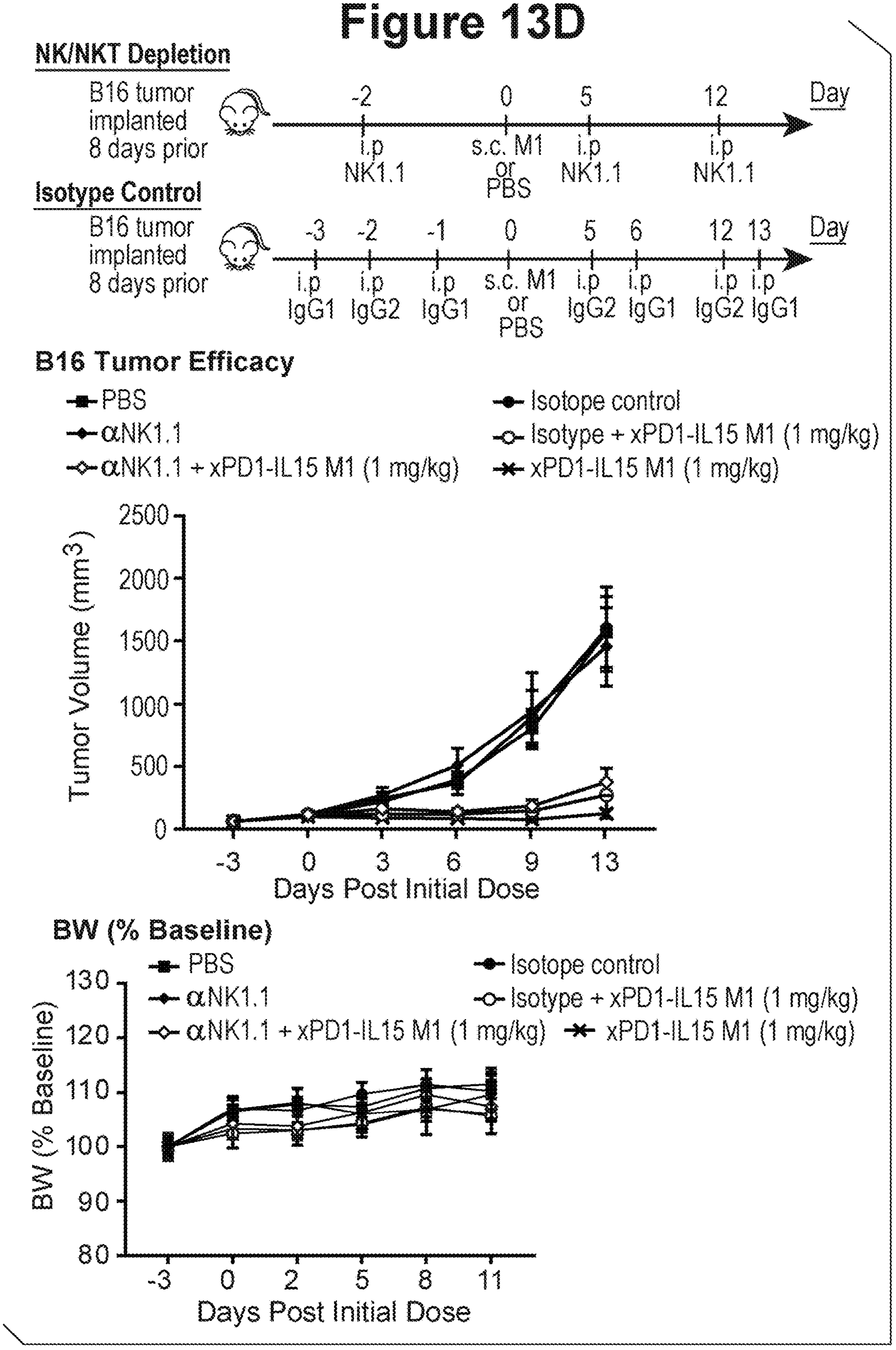

FIGS. 13C and 13D show the respective effects of depleting CD8 T and NK1.1+ cells on B16F10 tumor efficacy model. Treatment regimen and average weights of mice during the studies are also shown.

Figure 13E:
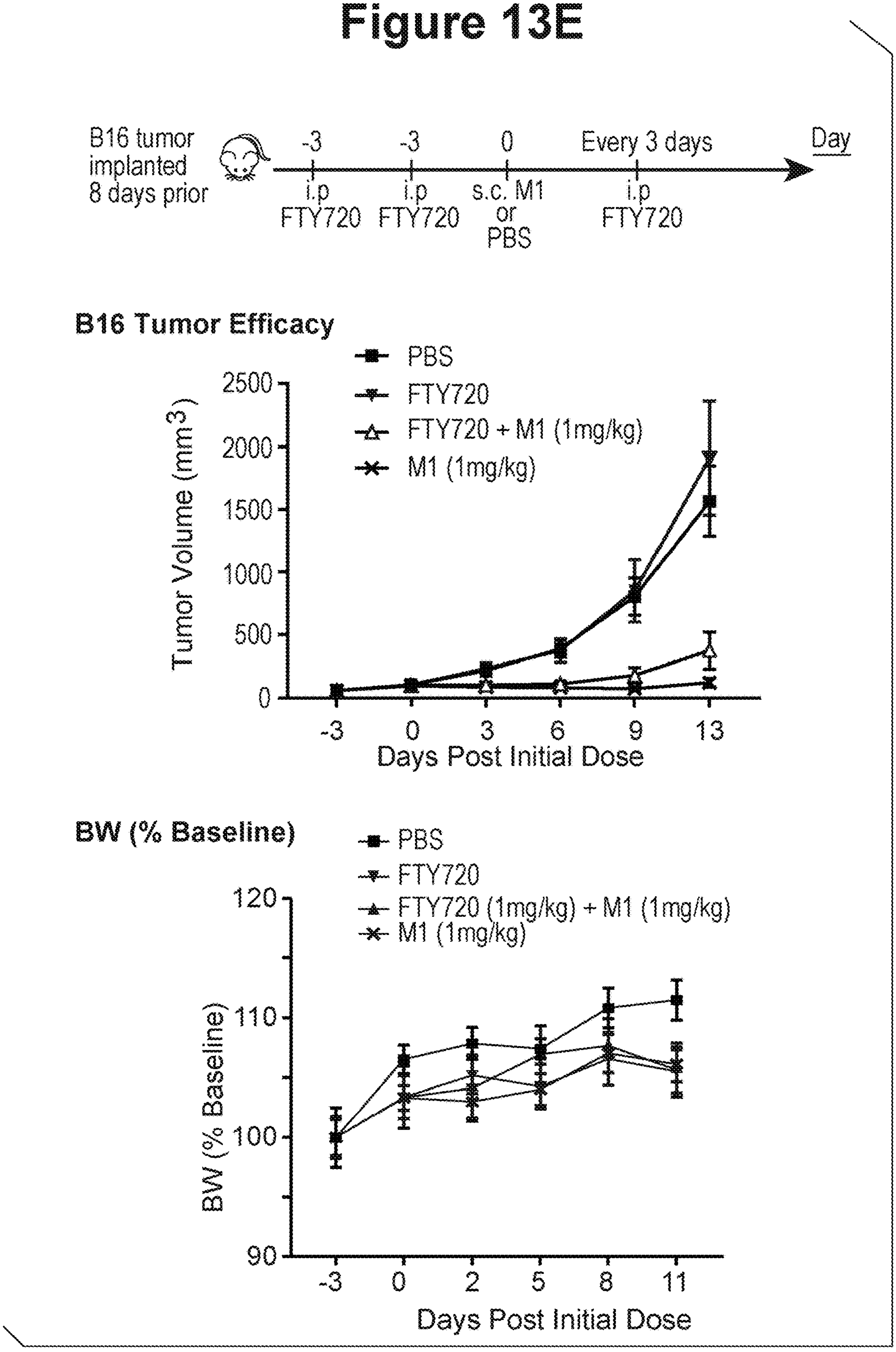

FIG. 13E shows the effect of FTY420 treatment, which inhibits T cell egress, on B16F10 tumor efficacy model. Treatment regimen and average weights of mice during the studies are also shown.

Figure 14A:
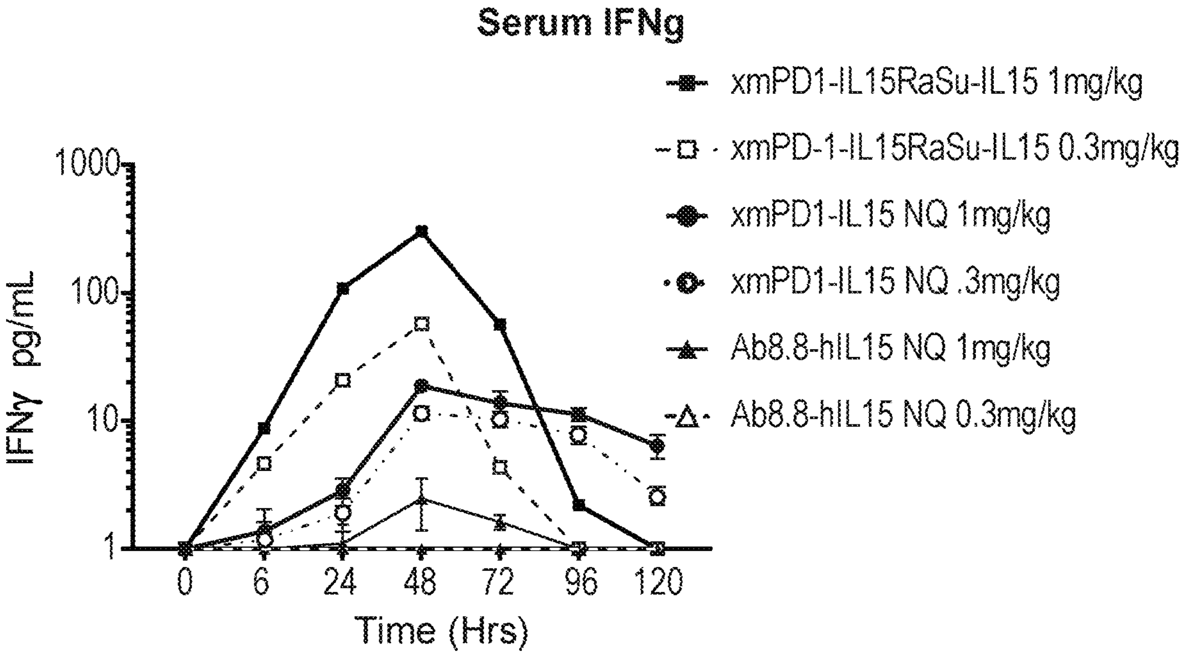
Figure 14B:
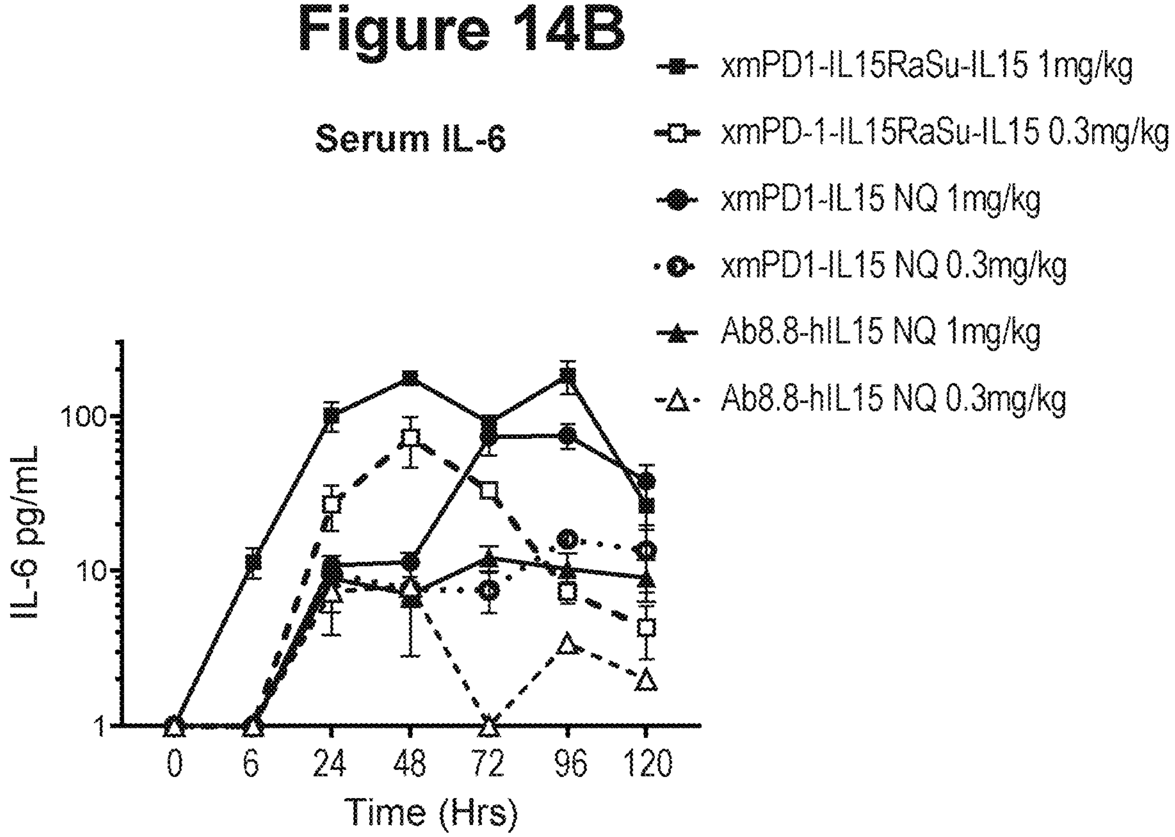
Figure 15A:
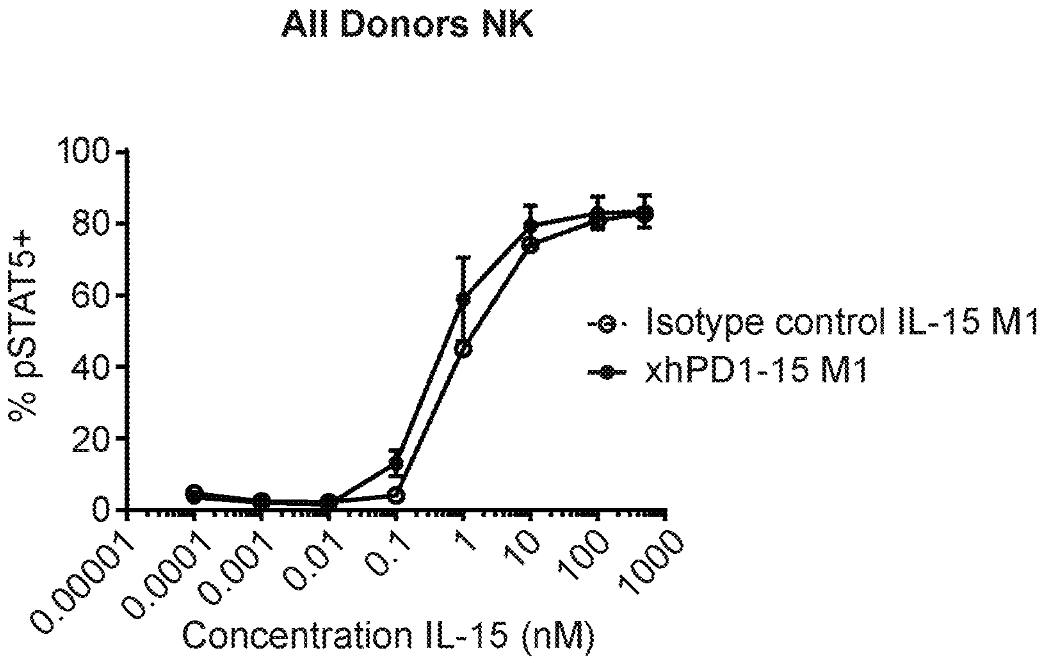
Figure 15B:
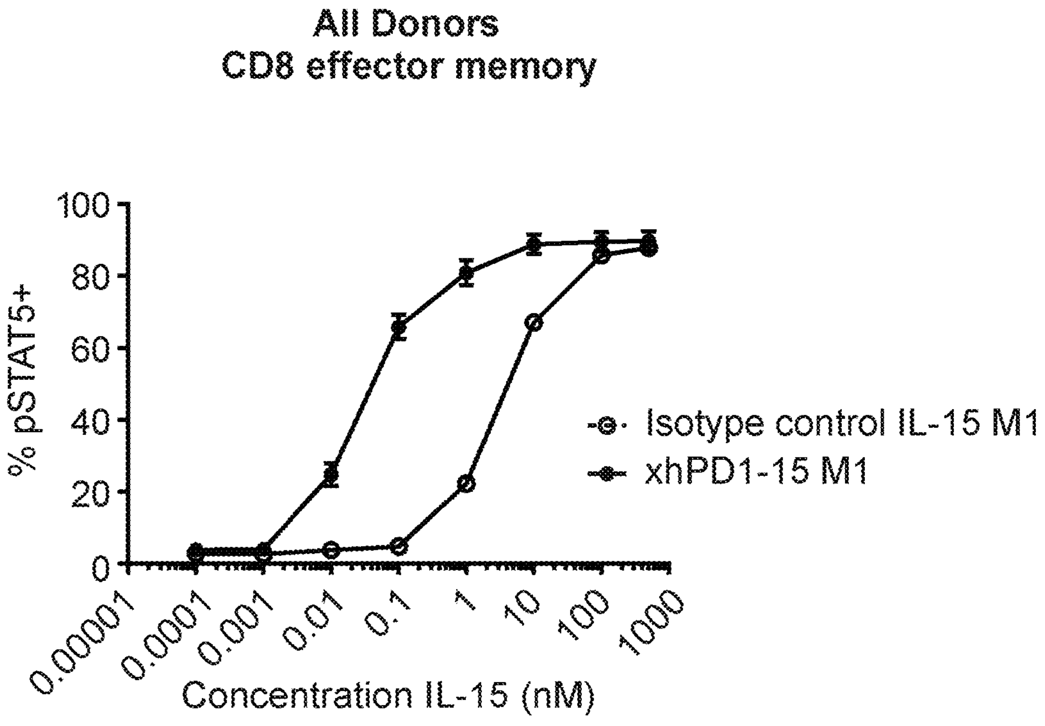
Figure 15C:
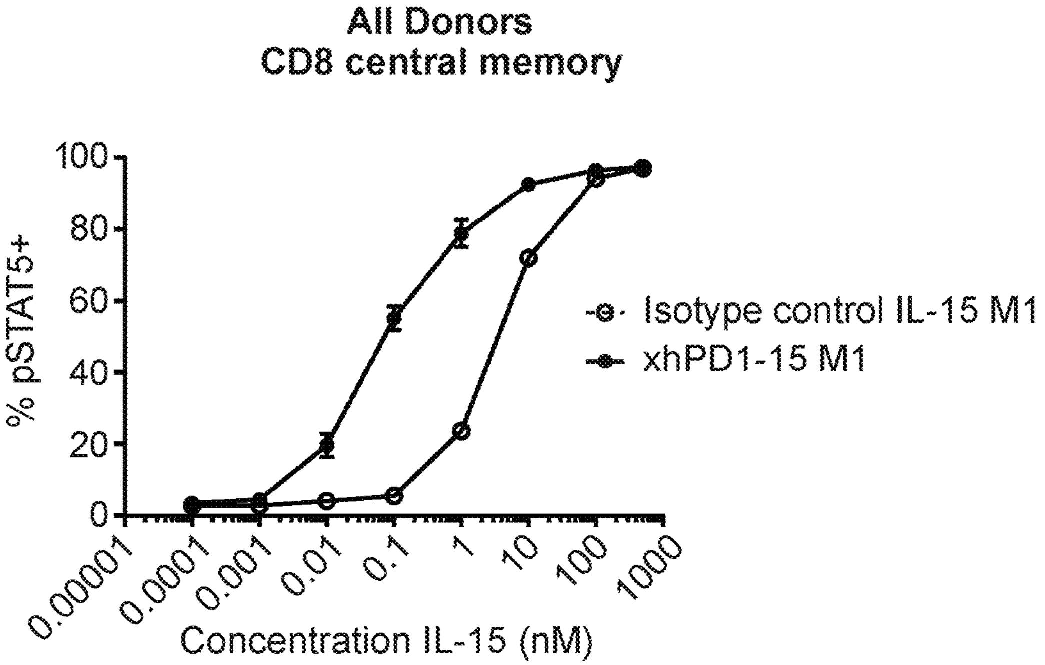
Figure 15D:
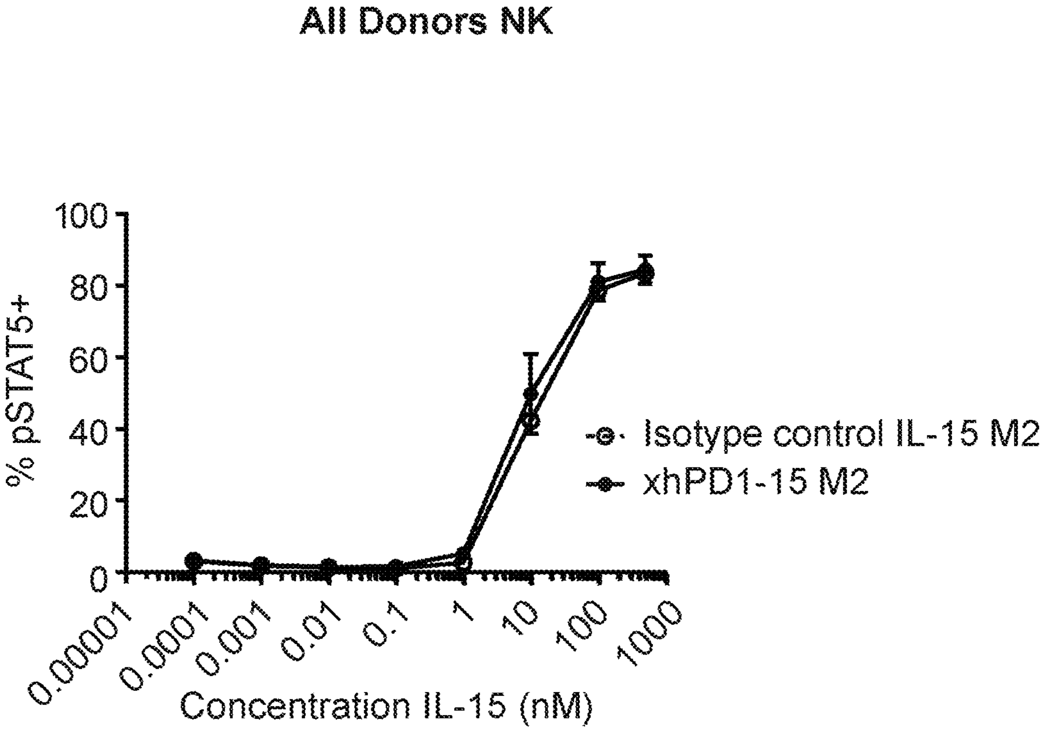
Figure 15E:
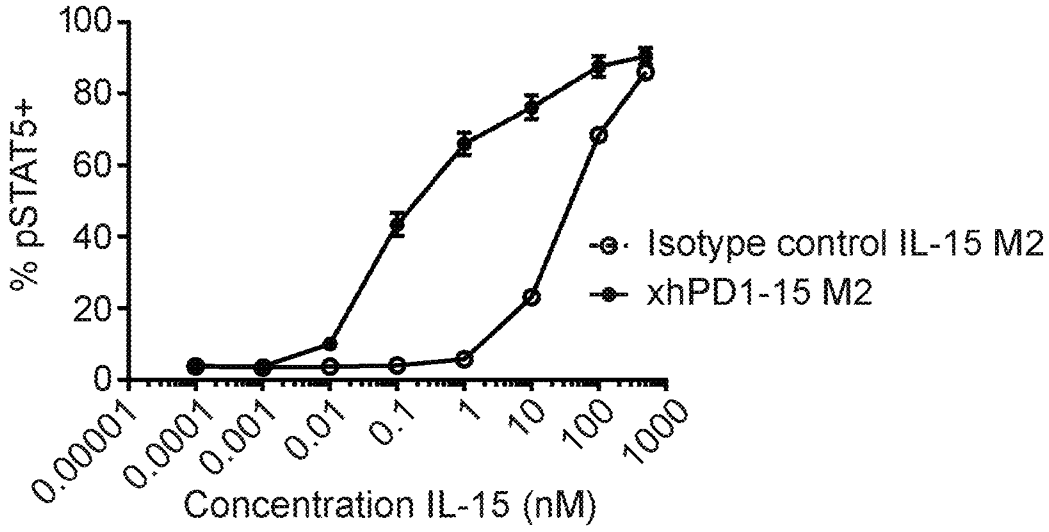
Figure 15F:
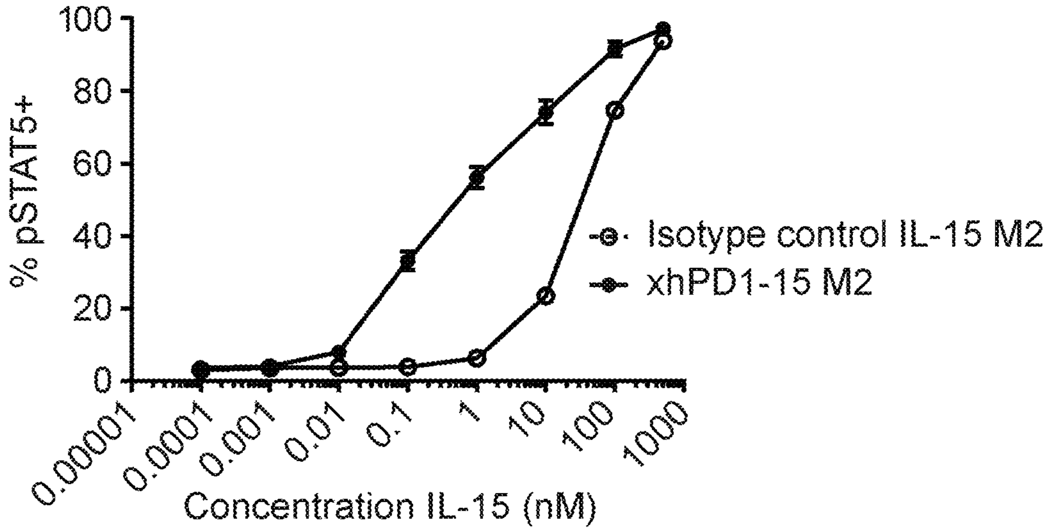

FIGS. 14A and 14B show the effects on in vivo cytokine production from mice given an IL-15-containing compound. FIG. 14A shows averaged IFNg levels (n=3 animals) at 6, 24, 48, 72, 96, and 120 hours following a single dose of the indicated IL-15 compound. FIG. 14B shows averaged IL-6 levels (n=3 animals) at 6, 24, 48, 72, 96, and 120 hours following a single dose of the indicated IL-15 compound.

FIGS. 15A, 15B, 15C, 15D, 15E and 15F show the effects of adding targeted anti-human PD-1 (xhPD1)-IL15 M1 or M2 or untargeted isotype control-antibody-IL15 chimeric molecules to the human peripheral blood mononuclear cells, where they cause different pSTAT5 activation on human NK cells, $CD8^+$ effector memory T cells and $CD8^+$ central memory T cells, respectively.

Figure 16A:
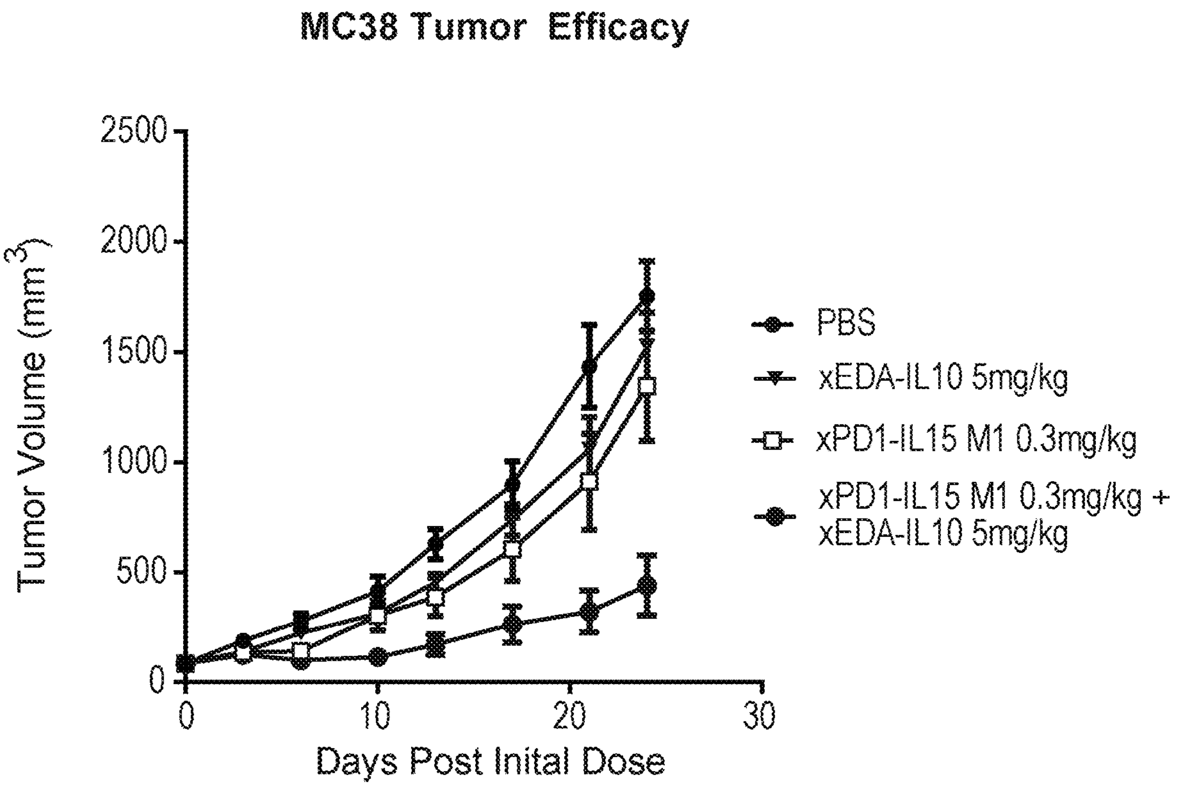
Figure 16B:
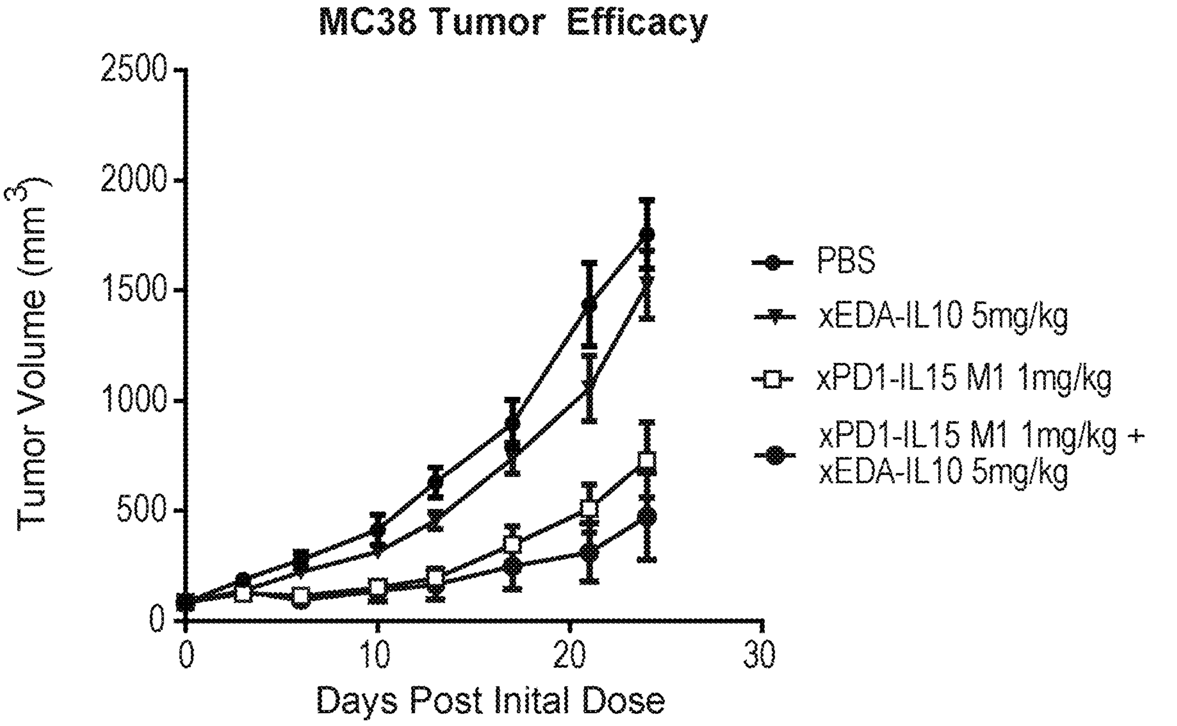
Figure 16C:
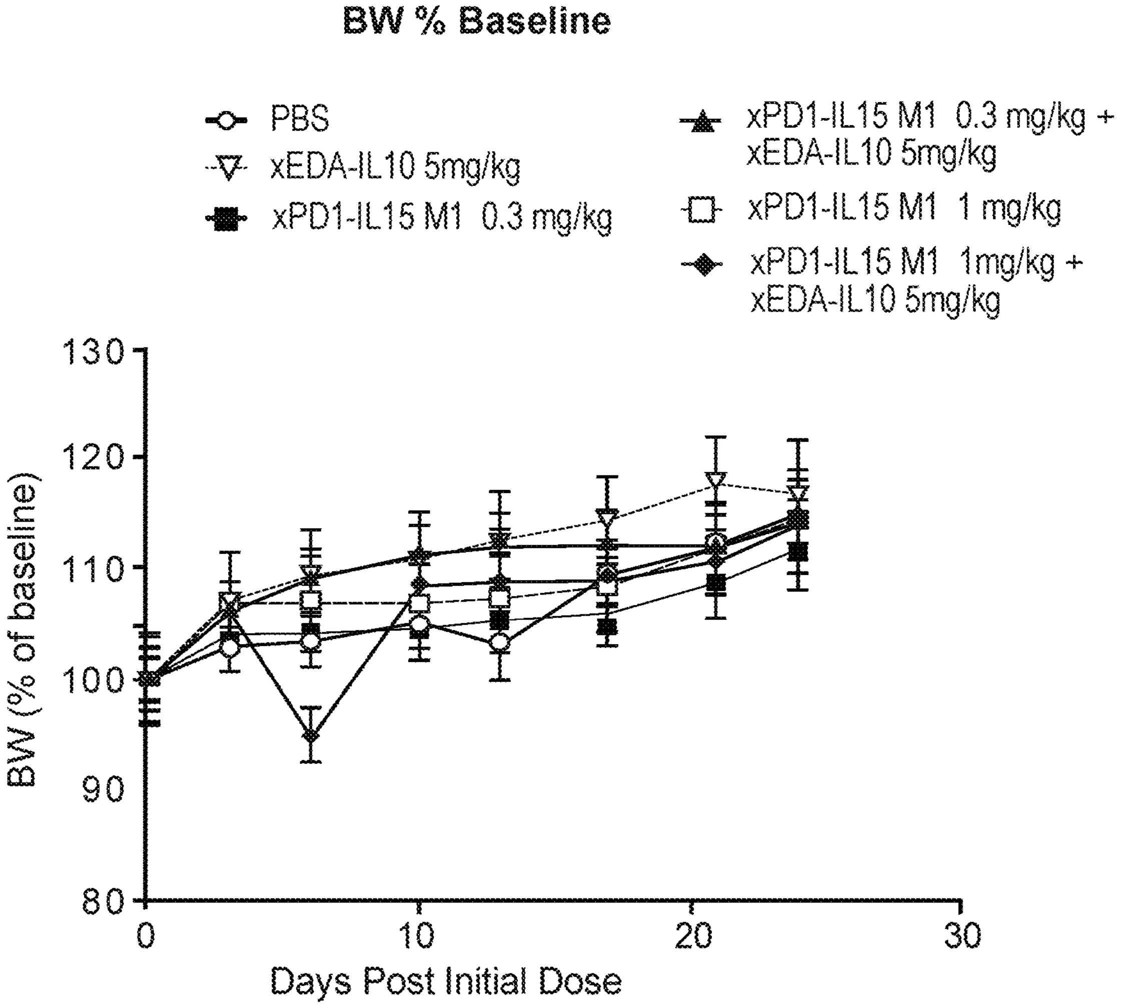

FIGS. 16A, 16B and 16C show an in vivo efficacy study of a PD-1-targeted IL-15 molecule (xPD1-IL15 M1) in combination with an anti-EDA-IL-10 fusion protein. FIG. 16A shows the anti-tumor efficacy of 0.3 mg/kg xPD1-IL15 M1 and 5 mg/kg anti-EDA-IL-10 fusion protein (xEDA-IL 10). FIG. 16B shows the anti-tumor efficacy of 1 mg/kg xPD1-IL15 M1 and 5 mg/kg anti-EDA-IL-10 fusion protein (xEDA-IL 10). FIG. 16C plots the averaged body weight changes (from baseline, at day 0) of animals in each treatment group throughout the study.

DETAILED DESCRIPTION

The invention disclosed herein is directed to human interleukin 15 (IL-15) variants and fusion proteins comprising thereof. It is demonstrated that the IL-15 variants of the present invention have decreased or no binding to the IL-15 receptor alpha (CD215), and have reduced interaction between IL-15 and its signaling receptor, comprised of IL-2 receptor beta (CD122) and the common gamma chain (CD132), as compared to the wild-type human IL-15 polypeptide or a wild-type IL-15 receptor alpha-IL-15 fusion polypeptide. In a second aspect of the invention, these reduced affinity IL-15 variants, when presented as an antibody fusion chimeric protein, are targeted selectively to desired cell types (those cells expressing the antibody target). Cell types that express the IL-15 receptor complex, but not the antibody target, are activated less, or not activated, compared to those cells which express both components. Further, it is also demonstrated that the IL-15 fusion proteins of the present invention preferentially activate downstream biomarker pSTAT5 in human peripheral CD8 T cells over natural killer (NK) cells, and have potent and preferential activation of human CD8 tumor infiltrating T lymphocytes (TILs). Accordingly, the IL-15 variants and the IL-15 fusion proteins of the present invention selectively modulate the activation of cell subsets to promote biological activity, such as an anti-tumor activity, efficaciously and safely. In a third aspect of this invention, these reduced affinity IL-15 variants and the IL-15 fusion proteins, when expressed as polynucleotides in CAR T cells, either as secreted or membrane-tethered versions, are used to enhance CAR T function, including activity and proliferation.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "IL-15" refers to any form of IL-15 and variants thereof that retain at least part of the activity of IL-15. Unless indicated differently, such as by specific reference to human IL-15, IL-15 includes all mammalian species of native sequence IL-15, e.g., human, canine, feline, equine, and bovine. One exemplary wild-type human IL-15 is found as Uniprot Accession Number P40933 (SEQ ID NO: 5).

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', $F(ab')_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "ABM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a target (e.g., PD-1) epitope is an antibody that binds this epitope with greater affinity, avidity, more readily, and/or with greater duration than it binds to other target epitopes or non-target epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of a tumor, remission of cancer, decreasing symptoms resulting from cancer, increasing the quality of life of those suffering from cancer, decreasing the dose of other medications required to treat cancer, delaying the progression of cancer, curing a cancer, and/or prolong survival of patients having cancer.

"Ameliorating" means a lessening or improvement of one or more symptoms as compared to not administering an IL-15 variant or the IL-15 fusion protein as described herein. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, solid cancer and liquid cancer including, for example without limitation, gastric cancer, small intestine cancer, sarcoma, head and neck cancer, thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer (e.g., renal cell carcinoma), bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer, decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS* (*USA*), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods,* 202: 163 (1996), may be performed.

The term "$k_{on}$" or "$k_a$", as used herein, refers to the rate constant for association of an antibody to an antigen. Specifically, the rate constants ($k_{on}$ or $k_a$ and $k_{off}$ or $k_d$) and equilibrium dissociation constants are measured using whole antibody (i.e. bivalent) and monomeric proteins.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD4 T cells, NK cells, and B cells.

The term "immune modulator" refers to a substance capable of altering (e.g., inhibiting, decreasing, increasing, enhancing, or stimulating) the immune response (as defined herein) or the working of any component of the innate, humoral or cellular immune system of a host mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids).

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("Treg"), myeloid-derived suppressor cells, and tumor-associated macrophages.

The term "intradermal administration," or "administered intradermally," in the context of administering a substance to a mammal including a human, refers to the delivery of the substance into the dermis layer of the skin of the mammal. The skin of a mammal is composed of an epidermis layer, a dermis layer, and a subcutaneous layer. The epidermis is the outer layer of the skin. The dermis, which is the middle layer of the skin, contains nerve endings, sweat glands and oil (sebaceous) glands, hair follicles, and blood vessels. The subcutaneous layer is made up of fat and connective tissue that houses larger blood vessels and nerves. In contrast in intradermal administration, "subcutaneous administration" refers to the administration of a substance into the subcutaneous layer and "topical administration" refers to the administration of a substance onto the surface of the skin.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "preventing" or "prevent" refers to (a) keeping a disorder from occurring or (b) delaying the onset of a disorder or onset of symptoms of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen in the mammal. A vaccine typically contains an agent (known as "antigen" or "immunogen") that resembles, or is derived from, the target of the immune response, such as a disease-causing microorganism or tumor cells. A vaccine intended for the treatment of a tumor, such as a cancer, typically contains an antigen that is derived from a TAA found on the target tumor and is able to elicit immunogenicity against the TAA on the target tumor.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

IL-15 Variants

Provided herein are IL-15 variants (e.g., human IL-15 variants) that have decreased or no binding to the IL-15 receptor alpha (CD215), and/or reduced interaction between IL-15 and its signaling receptor, comprised of IL-2 receptor beta (CD122) and the common gamma chain (CD132), as compared to the wild-type human IL-15 polypeptide or a wild-type IL-15 receptor alpha-IL-15 fusion polypeptide, as illustrated in Tables 1-2 under the Example section.

In one aspect, the invention provides an isolated human interleukin 15 (IL-15) variant comprising amino acid substitution at positions a) V49 and I51 or b) V49, I50, and S51 of SEQ ID NO: 1, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant has decreased or no binding to the human IL-15 receptor alpha (IL-15Rα) and the human IL-2 receptor beta/gamma (IL-2Rβγ) as compared to the wild-type human IL-15 polypeptide or a wild-type IL-15 receptor alpha-IL-15 fusion polypeptide, and wherein the amino acid substitution at position V49 is glycosylated.

Glycosylation of the IL-15 variant is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Accordingly, in some embodiments, the IL-15 variant comprises amino acid substitution at V49N, wherein V49N is glycosylated. In some embodiments, the amino acid substitution(s) at E53 and/or E89 of SEQ ID NO: 1 are also glycosylated. In some embodiments, the IL-15 variant comprises amino acid substitutions of SEQ ID NO: 1 at positions selected from the group consisting of: a) V49, I50, S51, N4, D30, and E64; b) V49, I50, S51, N4, D30, E64, and 168; c) V49, I50, S51, N4, D30, E64, M109; d) V49, I50, S51, N4, D30, E64, I68, and M109; e) V49, I50, S51, D30, E64, and 168; f) V49, I50, S51, D30, E64, M109; g) V49, I50, S51, D30, E64, I68, and M109; h) N1, V49, I50, and S51; i) N4, V49, I50, and S51; j) S7, V49, I50, and S51; k) K10, V49, I50, and S51; l) K11, V49, I50, and S51; m) S29, V49, I50, and S51; n) V31, V49, I50, and S51; o) H32, V49, I50, and S51; p) V49, I50, S51, and E64; q) V49, I50, S51, and 168; r) V49, I50, S51, and L69; s) V49, I50, S51, and I111; t) N4, V49, I50, S51, and E64; u) N1, D30, V49, I50, and S51; v) N4, D30, V49, I50, and S51; w) S7 D30, V49, I50, and S51; x) K10, D30, V49, I50, and S51; y) K11, D30, V49, I50, and S51; z) S29, D30, V49, I50, and S51; aa) D30, V49, I50, S51, and E64; bb) D30, V49, I150, S51, and 168; cc) D30, V49, I50, S51, and L69; and dd) D30, V49, I50, S51, and I111.

In some embodiments, the IL-15 variant comprises amino acid substitutions comprising one or more specific substitutions at: a) V49N, V49K, V49E, V49H, V49Q or V49R; b) I50A or I50G; c) S51T; d) N1K, N1G, N1Q, N1R, N1E, N1A, or N1D; e) N4K, N4G, N4A, N4S, N4D, N4E, N4I, N4L, N4R, N4T, N4W, or N4Q; f) S7E, S7G, S7D, S7K, S7N, S7R, S7H, or S7T; g) K10A, K10S, K10E, K10L, K10M, K10D, or K10G; h) K11D, K11S, or K11W; i) D30N; j) E64Q, E64K, E64A, E64S, E64N, E64H, E64T, or E64R; k) E53N; l) G55S or G55T; m) E89N; n) L91S or L91T; o) Y26K, Y26R, or Y26H; p) S29N; q) V31S, V31D, or V31K; r) H32G; s) I68S, I68A, I68R, I68T, I68K, I68N, I68M, I68F, I68Y, 168E, or I68H; t) L69A, L69S, L69D, L69T, L69M, L69G, L69Q, L69I, L69E, or L69V; u)

M109A, M109S, M109D, or M109K; and/or v) I111A, I111K, I111S, or I111D. In some embodiments, the IL-15 variant comprises amino acid substitutions at positions selected from the group consisting of: a) N4K, D30N, V49N, I50A, S51T, and E64Q; b) N4Q, D30N, V49N, I50A, and S51T; c) D30N, V49N, I50A, S51T, and E64Q; d) N4Q, D30N, V49N, I50A, S51T, and E64Q; e) N4Q, V49N, I50A, and S51T; f) V49N, I50A, S51T, and E64Q; and g) N4Q, V49N, I50A, S51T, and E64Q.

In another aspect, provided is an isolated human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant has no binding to the human IL-15 receptor alpha (IL-15Rα) and decreased binding to the human IL-2 receptor beta/gamma (IL-2Rβγ) as compared to the wild-type human IL-15 polypeptide or a wild-type IL-15 receptor alpha-IL-15 fusion polypeptide.

In some embodiments, the IL-15 variant comprises amino acid substitutions in SEQ ID NO: 1 at positions selected from the group consisting of: a) N1, E46, and V49; b) N4, E46, and V49; c) S7, E46, and V49; d) K10, E46, and V49; e) K11, E46, and V49; f) S29, E46, and V49; g) V31, E46, and V49; h) H32, E46, and V49; i) E46, V49, and E64; j) E46, V49, and 168; k) E46, V49, and L69; l) E46, V49, and I111; m) N4, E46, V49, and E64; n) E46, V49, N4, D30, and E64; o) E46, V49, N4, D30, E64, and 168; p) E46, V49, N4, D30, E64, and M109; q) E46, V49, N4, D30, E64, I68, and M109; r) N1, D30, E46, and V49; s) N4, D30, E46, and V49; t) S7, D30, E46, and V49; u) K10, D30, E46, and V49; v) K11, D30, E46, and V49; w) S29, D30, E46, and V49; x) D30, E46, V49, and E64; y) D30, E46, V49R, and 168; z) D30, E46, V49R, and L69; aa) D30, E46, V49R, and I111; bb) N1, D30, E46, V49, and M109; cc) N4, D30, E46, V49, and M109; dd) S7, D30, E46, V49, and M109; ee) K10, D30, E46, V49, and M109; ff) K11, D30, E46, V49, and M109; gg) D30, E46, V49, E64, and M109; hh) D30, E46, V49, 168, and M109; ii) D30, E46, V49, L69 and M109; jj) D30, E46, V49, M109, and I111; kk) D30, E46, V49, E64, I68, and M109; ll) E46, V49, D30, E64, and 168; mm) E46, V49, E64, and M109; nn) E46, V49, D30, E64, I68, and M109; oo) D22, Y26, V49, E46, E53, E89, and E93; and pp) N1, D30, E46, V49, and E64.

In some embodiments, the IL-15 variant comprises amino acid substitutions comprising one or more specific substitutions at: a) N1Q, N1K, N1R, N1E, N1A, N1D, or N1G; b) N4K, N4G, N4A, N4S, N4D, N4E, N4R, N4T, N4I, N4L, N4W, or N4Q; c) S7E, S7G, S7D, S7K, S7N, S7R, S7H, or S7T; d) K10D, K10A, K10S, K10E, K10L, K10M, K10D, or K10G; e) K11D, K11S, or K11W; f) D22N; g) Y26K, Y26R, or Y26H; h) S29N; i) D30N; j) V31S, V31D, or V31K; k) H32G; l) E46G or E46Q; m) V49N, V49K, or V49R V49E, V49H, or V49Q; n) E53Q; o) G55S or G55T; p) E64Q, E64K, E64A, E64S, E64N, E64H, E64T, or E64R; q) I68S, I68A, I68R, I68T, I68K, I68N, I68M, I68F, I68Y, 168E, or I68H; r) L695, L69A, L69D, L69T, L69M, L69G, L69Q, L69I, L69E, or L69V; s) E89Q; t) E93Q; u) M109A, M109S, M109S, or M109K; and/or v) I111A, I111K, I111S, or I111D. In some embodiments, the IL-15 variant comprises amino acid substitutions at positions selected from the group consisting of: a) N1K, E46G, and V49R; b) N4K, E46G, and V49R; c) N4Q, E46G, and V49R; d) S7T, E46G, and V49R; e) V31S, E46G, and V49R; f) V31K, E46G, and V49R; g) E46G, V49R, and E64Q; h) E46G, V49R, and E64K; i) N4Q, E46G, V49R, and E64Q; j) N1G, D30N, E46G, and V49R; k) N1K, D30N, E46G, and V49R; l) N1Q, D30N, E46G, and V49R; m) N4G, D30N, E46G, and V49R; n) N4K, D30N, E46G, and V49R; o) N4Q, D30N, E46G, and V49R; p) S7E, D30N, E46G, and V49R; q) S7G, D30N, E46G, and V49R; r) S7T, D30N, E46G, and V49R; s) K10D, D30N, E46G, and V49R; t) D30N, E46G, V49R, and E64A; u) D30N, E46G, V49R, and E64Q; v) D30N, E46G, V49R, and E64K; w) D30N, E46G, V49R, and I68S; x) D30N, E46G, V49R, and I68K; y) N4K, D30N, E46G, V49R, and E64K; z) N4Q, D30N, E46G, V49R, and E64K; aa) N4K, D30N, E46G, V49R, and E64Q; bb) N4Q, D30N, E46G, V49R, and E64Q; cc) N4K, D30N, E46G, V49R, and I68S; dd) D30N, E46G, V49R, E64Q, and I68S; ee) N1A, D30N, E46G, and V49R; and ff) N1G, D30N, E46G, V49R, and E64Q.

In some embodiments, the IL-15 variant comprises an amino acid sequence of SEQ ID NO: 84 or 85.

In another aspect, provided is an isolated human IL-15 variant comprising one or more amino acid substitution(s) at position(s) N1, N4, S7, K10, K11, D22, Y26, S29, D30, V31, H32, E46, E53, E64, I68, L69, E89, E93, M109, and/or I111 of SEQ ID NO: 1, wherein the IL-15 variant has decreased or no binding to the human IL-15 receptor alpha (IL-15Rα) and/or the human IL-2 receptor beta (IL-2Rβ) and/or IL-2 receptor gamma (IL-2Rγ) as compared to the wild-type human IL-15 polypeptide or a wild-type IL-15 receptor alpha-IL-15 fusion polypeptide. For example, the specific substitutions may include, but not limited to, N1K, N4K, N4Q, S7T, K10S, K11S, D22N, Y26F, D30N, V31S, H32G, M109A, and/or I111A.

In some embodiments, the isolated human IL-15 variant comprises amino acid substitutions at positions D22N, Y26F, E46Q, E53Q, E89Q, and E93Q (e.g., see SEQ ID NO: 76), wherein the IL-15 variant has decreased or no binding to the human IL-15 receptor alpha (IL-15Rα) and/or the human IL-2 receptor beta (IL-2Rβ) and/or IL-2 receptor gamma (IL-2Rγ) as compared to the wild-type human IL-15 polypeptide.

In another aspect, provided is an isolated human IL-15 variant comprising the amino acid sequence shown in SEQ ID NO: 93. In some embodiments, the IL-15 variant further comprises a transmembrane domain.

IL-15 Fusion Proteins

Provided herein are IL-15 fusion proteins (e.g., antibody-IL-15 fusion proteins) that have decreased or no binding to the IL-15 receptor alpha (CD215), and reduced interaction between IL-15 and its signaling receptor, comprised of IL-2 receptor beta (CD122) and the common gamma chain (CD132). Such IL-15 fusion proteins can deliver cytokines to a desired cell type while minimizing peripheral exposure (e.g., NK cells which are a major site of action) and thus toxicities. Further, the IL-15 fusion proteins of the present invention preferentially activate downstream biomarker pSTAT5 in human peripheral CD8 T cells over natural killer (NK) cells, and have potent and preferential activation of human CD8 tumor infiltrating T lymphocytes (TILs). Accordingly, in some embodiments, an IL-15 variant can be coupled to a PD-1 antibody, which acts as a marker to antigen-specific tumor-resident CD8+ cells, thereby maximizing anti-tumor efficacy and minimizing exposure to peripheral immune cell subsets.

In one aspect, provided is an isolated fusion protein comprising: 1) an antibody comprising a Fc domain; and b) any one of the IL-15 variants as described herein, wherein the IL-15 variant is covalently linked to the Fc domain of the antibody.

In some embodiments, provided is an isolated fusion protein comprising: 1) an antibody comprising a Fc domain; and b) a human interleukin 15 (IL-15) variant comprising amino acid substitution at positions a) V49 and I51 or b) V49, I50, and S51 of SEQ ID NO: 1, wherein the amino acid substitution at position V49 of SEQ ID NO: 1 is glycosylated, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc. In some embodiments, the IL-15 variant comprises amino acid substitution at V49N, wherein V49N is glycosylated. In some embodiments, the amino acid substitution(s) at E53 and/or E89 of SEQ ID NO: 1 are also glycosylated.

In some embodiments, the IL-15 fusion protein comprises an antibody comprising a Fc domain and an IL-15 variant comprises amino acid substitutions of SEQ ID NO: 1 at positions selected from the group consisting of: a) V49, I50, S51, N4, D30, and E64; b) V49, I50, S51, N4, D30, E64, and 168; c) V49, I50, S51, N4, D30, E64, M109; d) V49, I50, S51, N4, D30, E64, I68, and M109; e) V49, I50, S51, D30, E64, and 168; f) V49, I50, S51, D30, E64, M109; g) V49, I50, S51, D30, E64, I68, and M109; h) N1, V49, I50, and S51; i) N4, V49, I50, and S51; j) S7, V49, I50, and S51; k) K10, V49, I50, and S51; l) K11, V49, I50, and S51; m) S29, V49, I50, and S51; n) V31, V49, I50, and S51; o) H32, V49, I50, and S51; p) V49, I50, S51, and E64; q) V49, I50, S51, and 168; r) V49, I50, S51, and L69; s) V49, I50, S51, and I111; t) N4, V49, I50, S51, and E64; u) N1, D30, V49, I50, and S51; v) N4, D30, V49, I50, and S51; w) S7 D30, V49, I50, and S51; x) K10, D30, V49, I50, and S51; y) K11, D30, V49, I50, and S51; z) S29, D30, V49, I50, and S51; aa) D30, V49, I50, S51, and E64; bb) D30, V49, I150, S51, and 168; cc) D30, V49, I50, S51, and L69; and dd) D30, V49, I50, S51, and I111. In some embodiments, the IL-15 variant comprises amino acid substitutions comprising one or more specific substitutions at: a) V49N, V49K, V49E, V49H, V49Q or V49R; b) I50A or I50G; c) S51T; d) N1K, N1G, N1Q, N1R, N1E, N1A, or N1D; e) N4K, N4G, N4A, N4S, N4D, N4E, N4I, N4L, N4R, N4W, N4T, or N4Q; f) S7E, S7G, S7D, S7K, S7N, S7R, S7H, or S7T; g) K10A, K10S, K10E, K10L, K10M, K10D, or K10G; h) K11D, K11S, or K11W; i) D30N; j) E64Q, E64K, E64A, E64S, E64N, E64H, E64T, or E64R; k) E53N; l) G55S or G55T; m) E89N; n) L91S or L91T; o) Y26K, Y26R, or Y26H; p) S29N; q) V31S, V31D, or V31K; r) H32G; s) I68S, I68A, I68R, I68T, I68K, I68N, I68M, I68F, I68Y, 168E, or I68H; t) L69A, L695, L69D, L69T, L69M, L69G, L69Q, L69I, L69E, or L69V; u) M109A, M109S, M109D, or M109K; and/or v) I111A, I111K, I111S, or I111D.

In some embodiments, provided is an isolated fusion protein comprising: 1) an antibody comprising a Fc domain; and b) an IL-15 variant covalently linked to the Fc domain of the antibody, wherein the IL-15 variant comprises amino acid substitutions at positions selected from the group consisting of: a) N4K, D30N, V49N, I50A, S51T, and E64Q; b) N4Q, D30N, V49N, I50A, and S51T; c) D30N, V49N, I50A, S51T, and E64Q; d) N4Q, D30N, V49N, I50A, S51T, and E64Q; e) N4Q, V49N, I50A, and S51T; f) V49N, I50A, S51T, and E64Q; and g) N4Q, V49N, I50A, S51T, and E64Q.

In another aspect, provided is an isolated fusion protein comprising: 1) an antibody comprising a Fc domain; and b) a human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

In some embodiments, the IL-15 fusion protein comprises an antibody comprising a Fc domain and an IL-15 variant comprises amino acid substitutions of SEQ ID NO: 1 at positions selected from the group consisting of: a) N1, E46, and V49; b) N4, E46, and V49; c) S7, E46, and V49; d) K10, E46, and V49; e) K11, E46, and V49; f) S29, E46, and V49; g) V31, E46, and V49; h) H32, E46, and V49; i) E46, V49, and E64; j) E46, V49, and 168; k) E46, V49, and L69; l) E46, V49, and I111; m) N4, E46, V49, and E64; n) E46, V49, N4, D30, and E64; o) E46, V49, N4, D30, E64, and 168; p) E46, V49, N4, D30, E64, and M109; q) E46, V49, N4, D30, E64, I68, and M109; r) N1, D30, E46, and V49; s) N4, D30, E46, and V49; t) S7, D30, E46, and V49; u) K10, D30, E46, and V49; v) K11, D30, E46, and V49; w) S29, D30, E46, and V49; x) D30, E46, V49, and E64; y) D30, E46, V49R, and 168; z) D30, E46, V49R, and L69; aa) D30, E46, V49R, and I111; bb) N1, D30, E46, V49, and M109; cc) N4, D30, E46, V49, and M109; dd) S7, D30, E46, V49, and M109; ee) K10, D30, E46, V49, and M109; ff) K11, D30, E46, V49, and M109; gg) D30, E46, V49, E64, and M109; hh) D30, E46, V49, 168, and M109; ii) D30, E46, V49, L69 and M109; jj) D30, E46, V49, M109, and I111; kk) D30, E46, V49, E64, I68, and M109; ll) E46, V49, D30, E64, and 168; mm) E46, V49, E64, and M109; nn) E46, V49, D30, E64, I68, and M109; oo) D22, Y26, V49, E46, E53, E89, and E93; and pp) N1, D30, E46, V49, and E64. In some embodiments, the IL-15 variant comprises amino acid substitutions comprising one or more specific substitutions at: a) N1Q, N1K, N1R, N1E, N1A, N1D, or N1G; b) N4K, N4G, N4A, N4S, N4D, N4E, N4L, N4I, N4R, N4T, N4W, or N4Q; c) S7E, S7G, S7D, S7K, S7N, S7R, S7H, or 57T; d) K10D, K10A, K10S, K10E, K10L, K10M, K10D, or K10G; e) K11D, K11S, or K11W; f) D22N; g) Y26K, Y26R, or Y26H; h) S29N; i) D30N; j) V31S, V31D, or V31K; k) H32G; l) E46G or E46Q; m) V49N, V49K, or V49R V49E, V49H, or V49Q; n) E53Q; o) G55S or G55T; p) E64Q, E64K, E64A, E64S, E64N, E64H, E64T, or E64R; q) I68S, I68A, I68R, I68T, I68K, I68N, I68M, I68F, I68Y, 168E, or I68H; r) L695, L69A, L69D, L69T, L69M, L69G, L69Q, L69I, L69E, or L69V; s) E89Q; t) E93Q; u) M109A, M109S, M109D, or M109K; and/or v) I111A, I111K, I111S, or I111D.

In some embodiments, provided is an isolated fusion protein comprising: 1) an antibody comprising a Fc domain; and b) an IL-15 variant covalently linked to the Fc domain of the antibody, wherein the IL-15 variant comprises amino acid substitutions at positions selected from the group consisting of: a) N1K, E46G, and V49R; b) N4K, E46G, and V49R; c) N4Q, E46G, and V49R; d) S7T, E46G, and V49R; e) V31S, E46G, and V49R; f) V31K, E46G, and V49R; g) E46G, V49R, and E64Q; h) E46G, V49R, and E64K; i) N4Q, E46G, V49R, and E64Q; j) N1G, D30N, E46G, and V49R; k) N1K, D30N, E46G, and V49R; l) N1Q, D30N, E46G, and V49R; m) N4G, D30N, E46G, and V49R; n) N4K, D30N, E46G, and V49R; o) N4Q, D30N, E46G, and V49R; p) S7E, D30N, E46G, and V49R; q) S7G, D30N, E46G, and V49R; r) S7T, D30N, E46G, and V49R; s) K10D, D30N, E46G, and V49R; t) D30N, E46G, V49R, and E64A;

u) D30N, E46G, V49R, and E64Q; v) D30N, E46G, V49R, and E64K; w) D30N, E46G, V49R, and I68S; x) D30N, E46G, V49R, and I68K; y) N4K, D30N, E46G, V49R, and E64K; z) N4Q, D30N, E46G, V49R, and E64K; aa) N4K, D30N, E46G, V49R, and E64Q; bb) N4Q, D30N, E46G, V49R, and E64Q; cc) N4K, D30N, E46G, V49R, and I68S; dd) D30N, E46G, V49R, E64Q, and I68S; ee) N1A, D30N, E46G, and V49R; and ff) N1G, D30N, E46G, V49R, and E64Q.

In some embodiments, the isolated fusion protein comprises an amino acid sequence of SEQ ID NO: 86, 87, 89, or 90.

In another aspect, provided is an isolated fusion protein comprising: 1) an antibody comprising a Fc domain; and b) a human IL-15 variant comprising one or more amino acid substitution(s) at position(s) N1, N4, S7, K10, K11, D22, Y26, S29, D30, V31, H32, E46, E53, E64, I68, L69, E89, E93, M109, and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc. In some embodiments, the human IL-15 variant comprises amino acid substitutions at positions D22N, Y26F, E46Q, E53Q, E89Q, and E93Q (e.g., see SEQ ID NO: 76), and the antibody is an anti-PD-1 antibody.

In another aspect, provided is an isolated fusion protein comprising: 1) an IL-15 antibody comprising a Fc domain; and b) a human interleukin 15 (IL-15) protein of SEQ ID NO: 1, wherein the IL-15 is covalently linked to the Fc domain of the antibody.

In some embodiments, one or more polypeptides (e.g., heterologous or homologous sequence) can be inserted between the antibody and the IL-15 variant of the IL-15 fusion proteins as described herein. In some embodiments, the polypeptide can be inserted or conjugated at the amino terminus, at the carboxyl terminus, or both the amino and carboxyl termini of the antibody. In some embodiments, the polypeptide comprises a polypeptide linker conjugating the antibody and the IL-15 variant, as depicted in FIGS. 1A, 1B, 1C, and 1D. For example, the polypeptide linker is a glycine-serine (GS)-linker as shown in SEQ ID NO: 6, 23, 24, 25, or 77.

In some embodiments, the polypeptide comprises one or more linker(s) and tag(s). Examples of a polypeptide tag include, but not are not limited to a FLAG tag, a 6His tag (i.e., SEQ ID NO: 27), a 8His tag (i.e., SEQ ID NO: 26), or an AVI tag (e.g., SEQ ID NO: 7).

Exemplary human IL-15 (hIL-15) variants with a polypeptide linker and polypeptide tags are provided below.

The underlined sequence represents the linker, 8×His, and AVI tags; The bolded letters represent the amino acid mutations on the hIL-15 protein sequence.

The antibodies useful in the IL-15 fusion proteins of the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies.

In some embodiments, the antibodies described herein have an isotype that is selected from the group consisting of $IgG_1$, $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P, and $IgG_{4\Delta c}$ S228P.

In some embodiments, the antibodies of the IL-15 fusion proteins as described comprise a Fc domain. In some embodiments, the Fc domain can be a human IgG1, IgG2, or IgG4.

In some embodiments, the antibodies as described herein comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 3). In some embodiments, the antibodies described herein are bispecific antibodies.

In some embodiments, the antibodies as described herein comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1 (SEQ ID NO: 2). In some embodiments, the antibodies described herein are bispecific antibodies.

In some embodiments, the antibodies as described herein comprise amino acid modifications at positions 349, 354, 366, 368, and/or 407 (EU numbering scheme) in the CH3 region of the human IgG1 (SEQ ID NO: 2). For example, the amino acid modifications comprise Y349C, S354C, T366W, T366S, L368A, and/or Y407V. In some embodiments, the antibodies described herein are bispecific antibodies.

In some embodiments, the antibodies as described herein comprise amino acid modifications at positions 228 (e.g., (S228D, S228E, S228R, or S228K)) in the hinge region and hIL-15 V49R GS-linker-8xHis-tags
(SEQ ID NO: 9)
NWVNVISDLK KIEDLIQSMH IDATLYTESD VHPSCKVTAM KCFLLELQRISLESGDASI
H DTVENLIILA NNSLSSNGNV TESGCKECEE LEEKNIKEFL QSFVHIVQMF INTGGG
GSGH HHHHHHHGGG LNDIFEAQKI EWHE hIL-15 V49N/I50A/S51T-GS-linker-8xHis-tags
(SEQ ID NO: 10)
NWVNVISDLK KIEDLIQSMH IDATLYTESD VHPSCKVTAM KCFLLELQNATLESGDAS
IH DTVENLIILA NNSLSSNGNV TESGCKECEE LEEKNIKEFL QSFVHIVQMF INTGGG
GSGH HHHHHHHGGG LNDIFEAQKI EWHE hIL-15 V49N/I50A/S51T/N79Q-GS-linker-8xHis-tags
(SEQ ID NO: 11)
NWVNVISDLK KIEDLIQSMH IDATLYTESD VHPSCKVTAM KCFLLELQNATLESGDAS
IH DTVENLIILA NNSLSSNGQV TESGCKECEE LEEKNIKEFL QSFVHIVQMF INTGGG
GSGH HHHHHHHGGG LNDIFEAQKI EWHE at position 409 or 368 (e.g., R409K, R409, or L368E (EU numbering scheme)) in the CH3 region of human IgG4 (SEQ ID NO: 4). In some embodiments, the antibodies described herein are bispecific antibodies.

In some embodiments, the antibodies as described herein comprise amino acid modifications at one or more of positions 265 (e.g., D265A), 330 (e.g., A330S), and 331 (e.g., P331S) of the human IgG2 (SEQ ID NO: 3); or one or more positions 234, 235, 237, and/or 322 of the human IgG1 (SEQ ID NO: 2). In some embodiments, the antibodies as described herein comprise amino acid modifications at each of positions 265 (e.g., D265A), 330 (e.g., A330S), and 331 (e.g., P331S) of the human IgG2.

In some embodiments, the antibodies as described herein comprise amino acid modifications at one or more of positions 234 (e.g., L234A), 235 (e.g., L235A), and 237 (e.g., G237A) of the human IgG1 (SEQ ID NO: 2). In some embodiments, the antibodies as described herein comprise amino acid modifications at each of positions 234 (e.g., L234A), 235 (e.g., L235A), and 237 (e.g., G237A) of the human IgG1 (SEQ ID NO: 2). For example, the antibody as described herein comprises an amino acid sequence of SEQ ID NO: 88.

In some embodiments, the antibodies as described herein comprise amino acid modifications E233F234L235 to P233V234A235 ($IgG_{4\Delta c}$) of the human IgG4 (SEQ ID NO: 4). In yet another embodiment, the amino acid modifications are E233F234L235 to P233V234A235 with deletion G236 ($IgG_{4\Delta b}$) of human IgG4 (SEQ ID NO: 4).

Exemplary antibodies used for the present invention include, but are not limited to, the sequences listed below.

TABLE 1.1

| SEQ ID NO:/ | Sequence |
|---|---|
| 64/<br>CH1-<br>hinge-<br>CH2-<br>CH3 of<br>hIgG2Δa-<br>D265A<br>(underlined:<br>hinge) | ASTKGPSVFPLAPCSRSTSESTAALGCLVKDYFPEPVTVSWNSGALTSGV<br>HTFPAVLCISSGLYSLSSVVTVPSSNFGTQTYTCNVDFIKPSNTKVDKTVER<br>KCCVECPPCPAPPVAGPSVFLFPPKPKDTLMISRTPEVTCVVVAVSHEDPE<br>VQFNWYVDGVEVHNAKTKPREEQFNSTFRVVSVLTVVHQDWLNGKEYKC<br>KVSNKGLPSSIEKTISKTKGQPREPQVYTLPPSREEMTKNQVSLTCLVKGF<br>YPSDIAVEWESNGQPENNYKTTPPMLDSDGSFFLYSKLTVDKSRWQQGN<br>VFSCSVMHEALHNHYTQKSLSLSPGK |
| 65/<br>xhPD1<br>(VK1-39)-<br>Light<br>chain<br>(bolded:<br>V-kappa;<br>underlined:<br>C-<br>kappa) | **DIQMTQSPSSLSASVGDRVTITCKSSQSLWDSGNQKNFLTWYQQKPGKA**<br>**PKLLIYWTSYRESGVPSRFSGSGSGTDFTLTISSLQPEDFATYYCQNDYFY**<br>**PLTFGGGTKVEIK**RTVAAPSVFIFPPSDEQLKSGTASVVCLLNNFYPREAK<br>VQWKVDNALQSGNSQESVTEQDSKDSTYSLSSTLTLSKADYEKHKVYACE<br>VTHQGLSSPVTKSFNRGEC |
| 66/<br>xhPD1<br>(VH1-69b)-<br>hIgG1-<br>AAA-<br>Bsp-R-<br>arm | QVQLVQSGAEVKKPGSSVKVSCKASGYTFTSYWINWVRQAPGQGLEVVM<br>GNIYPGSSITNY<br>AQKFQGRVTITADESTSTAYMELSSLRSEDTAVYYCARLTTGTFAYWGQG<br>TLVTVSSAST<br>KGPSVFPLAPSSKSTSGGTAALGCLVKDYFPEPVTVSWNSGALTSGVHTF<br>PAVLQSSGLY<br>SLSSVVTVPSSSLGTQTYICNVNHKPSNTKVDKKVEPKSCRKTHTCPRCPA<br>PEAAGAPSV<br>FLFPPKPKDTLMISRTPEVTCVVVDVSHEDPEVKFNWYVDGVEVHNAKTK<br>PREEQYNSTY<br>RVVSVLTVLHQDWLNGKEYKCKVSNKALPAPIEKTISKAKGQPREPQVYTL<br>PPSREEMTK<br>NQVSLTCLVKGFYPSDIAVEWESNGQPENNYKTTPPVLDSDGSFFLYSRLT<br>VDKSRWQQG<br>NVFSCSVMHEALHNHYTQKSLSLSPGK |
| 74/<br>xhPD1<br>(VH1-69b)-<br>hIgG1-<br>AAA-<br>'knob' | QVQLVQSGAEVKKPGSSVKVSCKASGYTFTSYWINWVRQAPGQGLEVVM<br>GNIYPGSSITNY<br>AQKFQGRVTITADESTSTAYMELSSLRSEDTAVYYCARLTTGTFAYWGQG<br>TLVTVSSAST<br>KGPSVFPLAPSSKSTSGGTAALGCLVKDYFPEPVTVSWNSGALTSGVHTF<br>PAVLQSSGLY<br>SLSSVVTVPSSSLGTQTYICNVNHKPSNTKVDKKVEPKSCDKTHTCPPCPA<br>PEAAGAPSV<br>FLFPPKPKDTLMISRTPEVTCVVVDVSHEDPEVKFNWYVDGVEVHNAKTK<br>PREEQYNSTY<br>RVVSVLTVLHQDWLNGKEYKCKVSNKALPAPIEKTISKAKGQPREPQVCTL<br>PPSREEMTK<br>NQVSLWCLVKGFYPSDIAVEWESNGQPENNYKTTPPVLDSDGSFFLYSKL<br>TVDKSRWQQG<br>NVFSCSVMHEALHNHYTQKSLSLSPGK |

In some embodiments, the antibodies described herein comprise a modified constant region that have increased or decreased binding affinity to a human Fc gamma receptor, are immunologically inert or partially inert, e.g., do not trigger complement mediated lysis, do not stimulate antibody-dependent cell mediated cytotoxicity (ADCC), or do not activate microglia; or have reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Publication No. WO99/058572.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

The antibodies used in the IL-15 fusion proteins of the present invention include, but are not limited to, an anti-CTLA-4 antibody, an anti-CD3 antibody, an anti-CD4 antibody, an anti-CD8 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-IL-8 antibody, an anti-IL-15 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-MARCO antibody, an anti-CXCR4 antibodies, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-FLT3 antibody, an anti-B7-H4 antibody, an anti-B7-H3 antibody, an KLRG1 antibody, an anti-BTN1A1 antibody, and an anti-GITR antibody.

In some embodiments, the antibody in the IL-15 fusion protein is a PD-1 antibody. For example, the PD-1 antibody comprises a heavy chain variable (VH) region comprising (i) a VH complementarity determining region one (CDR1) comprising the amino acid sequence of SEQ ID NO: 14, 15, 80, 81, or 91, a VH CDR2 comprising the amino acid sequence of SEQ ID NO: 16, 17, 82, or 83, and a VH CDR3 comprising the amino acid sequence shown in SEQ ID NO: 18 or 62; and/or a VL CDR1 comprising the amino acid sequence shown in SEQ ID NO: 19 or 31, a VL CDR2 comprising the amino acid sequence shown in SEQ ID NO: 20 or 32, and a VL CDR3 comprising the amino acid sequence shown in SEQ ID NO: 21 or 33. In some embodiments, the PD-1 antibody comprises a VH region comprising a CDR1, CDR2, and CDR3 of the VH having an amino acid sequence of SEQ ID NO: 12, 34, 78, or 36 and/or a VL region comprising a CDR1, CDR2, and CDR3 of the VL having an amino acid sequence of SEQ ID NO: 13, 35, 79, or 37.

Exemplary IL-15 fusion proteins include, but are not limited to, the sequences listed below. The IL-15 variants are in bold; and the linkers are underlined.

TABLE 1.2

| SEQ ID NO:/name | SEQUENCE |
|---|---|
| 29/ xmPD1- hIL-15 NQ mutant (E arm) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTATATPGA**NWVNVISDLKKIEDLIQSMHINATLFTESDVHPSCKVTAMKC** |

TABLE 1.2-continued

| SEQ ID NO:/name | SEQUENCE |
| --- | --- |
| | **FLLQLQVISLQSGDASIHDTVENLIILANNSLSSNGNVTESGCKECQELEQ**<br>**KNIKEFLQSFVHIVQMFINT**<br>(Mutations of NQ are in italics) |
| 38/<br>xmPD1-<br>hIL15_<br>V49R-<br>E46G | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLGLQRISLESGDASIHDTVENLIILANNSLSSNGNVTESGCKECEELEE**<br>**KNIKEFLQSFVHIVQMFINT** |
| 39/<br>xmPD1-<br>hIL15_<br>V49R-<br>E46G-<br>E64Q-<br>D30N | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESNVHPSCKVTAMK**<br>**CFLLGLQRISLESGDASIHDTVQNLIILANNSLSSNGNVTESGCKECEELEE**<br>**KNIKEFLQSFVHIVQMFINT** |
| 40/<br>xmPD1-<br>hIL15_<br>V49R-<br>E46G-<br>E64Q-<br>I68S-<br>D30N | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGANWV NVISDLKKIE DLIQSMHIDA TLYTESNVHP SCKVTA<br>MKCF LLGLQRISLE SGDASIHDTV QNLISLANNS LSSNGNVTES GCKE<br>CEELEE KNIKEFLQSF VHIVQMANT |
| 41/<br>xmPD1-<br>hIL15_<br>V49R-<br>E46G-<br>N4K-<br>E64Q-<br>D30N | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGANWV KVISDLKKIE DLIQSMHIDA TLYTESNVHP SCKVTA<br>MKCF LLGLQRISLE SGDASIHDTV QNLIILANNS LSSNGNVTES GCKEC<br>EELEE KNIKEFLQSF VHIVQMANT |
| 42/<br>xmPD1-<br>hIL15_<br>V49R-<br>E46G-<br>E64Q-<br>I68S-<br>D30N-<br>M109A | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGANWV NVISDLKKIE DLIQSMHIDA TLYTESNVHP SCKVTA<br>MKCF LLGLQRISLE SGDASIHDTV QNLISLANNS LSSNGNVTES GCKE<br>CEELEE KNIKEFLQSF VHIVQAFINT |
| 43/<br>xmPD1-<br>hIL15_<br>V49R-<br>E46G-<br>E64Q-<br>N4K-<br>D30N- | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG |

TABLE 1.2-continued

| SEQ ID NO:/name | SEQUENCE |
|---|---|
| M109A | SFFLYSKLTVDKSRWQQGNVFSCSVMHEALHNHYTQKSLSLSPGSGGGG<br>GTSATATPGANWV KVISDLKKIE DLIQSMHIDA TLYTESNVHP SCKVTA<br>MKCF LLGLQRISLE SGDASIHDTV QNLIILANNS LSSNGNVTES GCKEC<br>EELEE KNIKEFLQSF VHIVQAFINT |
| 44/<br>xmPD1-<br>hIL15_<br>V49R-<br>E46G-<br>E64Q-<br>D30N-<br>M109A | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGANWV NVISDLKKIE DLIQSMHIDA TLYTESNVHP SCKVTA<br>MKCF LLGLQRISLE SGDASIHDTV QNLIILANNS LSSNGNVTES GCKEC<br>EELEE KNIKEFLQSF VHIVQAFINT |
| 45/<br>xmPD1-<br>hIL15_<br>V49R-<br>Y26K | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLKTESDVHPSCKVTAMK**<br>**CFLLELQRISLESGDASIHDTVENLIILANNSLSSNGNVTESGCKECEELEE**<br>**KNIKEFLQSFVHIVQMFINT** |
| 46/<br>xmPD1-<br>hIL15_<br>V49R-<br>Y26K-<br>E64Q-<br>D30N | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLKTESNVHPSCKVTAMK**<br>**CFLLELQRISLESGDASIHDTVQNLIILANNSLSSNGNVTESGCKECEELEE**<br>**KNIKEFLQSFVHIVQMFINT** |
| 47<br>xmPD1-<br>hIL15_<br>V49K-<br>Y26K | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLKTESDVHPSCKVTAMK**<br>**CFLLELQKISLESGDASIHDTVENLIILANNSLSSNGNVTESGCKECEELEE**<br>**KNIKEFLQSFVHIVQMFINT** |
| 48/<br>xmPD1-<br>hIL15_<br>V49K-<br>E46G | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLGLQKISLESGDASIHDTVENLIILANNSLSSNGNVTESGCKECEELEE**<br>**KNIKEFLQSFVHIVQMFINT** |
| 49/<br>xmPD1-<br>hIL15Ra<br>su-hIL15<br>(E64Q/<br>D30N) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP |

TABLE 1.2-continued

| SEQ ID NO:/name | SEQUENCE |
|---|---|
| | SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGAITCPPPMSVE HADIWVKSYS LYSRERYICN SGFKRKAGT<br>S SLTECVLNKA TNVAHWTTPS LKCIRDPALV HQRPAPPSGG SGGGGS<br>GGGS GGGGSGGNWV NVISDLKKIE DLIQSMHIDA TLYTESNVHP SCKV<br>TAMKCF LLELQVISLE SGDASIHDTV QNLIILANNS LSSNGNVTES GCK<br>ECEELEE KNIKEFLQSF VHIVQMFINT |
| 50/<br>xmPD1-<br>hIL15Ra<br>su-<br>hIL15<br>(E64Q/<br>I68S/D30N) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGAITCPPPMSVE HADIWVKSYS LYSRERYICN SGFKRKAGT<br>S SLTECVLNKA TNVAHWTTPS LKCIRDPALV HQRPAPPSGG SGGGGS<br>GGGS GGGGSGGNWV NVISDLKKIE DLIQSMHIDA TLYTESNVHP SCKV<br>TAMKCF LLELQVISLE SGDASIHDTV QNLISLANNS LSSNGNVTES GCK<br>ECEELEE KNIKEFLQSF VHIVQMFINT |
| 51/<br>xmPD1-<br>hIL15Ra<br>su-hIL15<br>(E64Q/<br>N4K/D30N) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGAITCPPPMSVE HADIWVKSYS LYSRERYICN SGFKRKAGT<br>S SLTECVLNKA TNVAHWTTPS LKCIRDPALV HQRPAPPSGG SGGGGS<br>GGGS GGGGSGGNWV KVISDLKKIE DLIQSMHIDA TLYTESNVHP SCKV<br>TAMKCF LLELQVISLE SGDASIHDTV QNLIILANNS LSSNGNVTES GCK<br>ECEELEE KNIKEFLQSF VHIVQMFINT |
| 52/<br>xmPD1-<br>hIL15Ra<br>su-hIL15<br>(E64Q/<br>D30N/<br>M109A) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGAITCPPPMSVE HADRWKSYS LYSRERYICN SGFKRKAGT<br>S SLTECVLNKA TNVAHWTTPS LKCIRDPALV HQRPAPPSGG SGGGGS<br>GGGS GGGGSGGNWV NVISDLKKIE DLIQSMHIDA TLYTESNVHP SCKV<br>TAMKCF LLELQVISLE SGDASIHDTV QNLIILANNS LSSNGNVTES GCK<br>ECEELEE KNIKEFLQSF VHIVQAFINT |
| 53/<br>xmPD1-<br>hIL15Ra<br>su-hIL15<br>(E64Q/<br>I68S/<br>D30N/<br>M109A) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGAITCPPPMSVE HADIWVKSYS LYSRERYICN SGFKRKAGT<br>S SLTECVLNKA TNVAHWTTPS LKCIRDPALV HQRPAPPSGG SGGGGS<br>GGGS GGGGSGGNWV NVISDLKKIE DLIOSMHIDA TLYTESNVHP SCKV<br>TAMKCF LLELQVISLE SGDASIHDTV QNLISLANNS LSSNGNVTES GCK<br>ECEELEE KNIKEFLQSF VHIVQAFINT |
| 54/<br>xmPD1-<br>hIL15Ra<br>su-<br>hIL15(E<br>64Q/N4<br>K/D30N/<br>M109A) | EVQLVESGGGLVKPGGSLELSCAASGFTFSSYWMSWVRQAPEKGLEWV<br>AAISPSGGSTYYADSVKGRFTISRDNAKNTLFLQMTSLRS EDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG |

TABLE 1.2-continued

| SEQ ID NO:/name | SEQUENCE |
|---|---|
| | GTSATATPGAITCPPPMSVE HADIWVKSYS LYSRERYICN SGFKRKAGT<br>S SLTECVLNKA TNVAHWTTPS LKCIRDPALV HQRPAPPSGG SGGGGS<br>GGGS GGGGSGGNWV KVISDLKKIE DLIQSMHIDA TLYTESNVHP SCKV<br>TAMKCF LLELQVISLE SGDASIHDTV QNLIILANNS LSSNGNVTES GCK<br>ECEELEE KNIKEFLQSF VHIVQAFINT |
| 55/<br>xmPD1-<br>hIL15_<br>V49R-<br>E46Q | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLQLQRISLESGDASIHDTVENLIILANNSLSSNGNVTESGCKECEELEE**<br>**KNIKEFLQSFVHIVQMFINT** |
| 56/<br>xmPD1-<br>hIL15_<br>V49R-<br>E53Q | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLELQRISLQSGDASIHDTVENLIILANNSLSSNGNVTESGCKECEELEE**<br>**KNIKEFLQSFVHIVQMFINT** |
| 57/<br>xmPD1-<br>hIL15_<br>V49R-<br>E93Q | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLELQRISLESGDASIHDTVENLIILANNSLSSNGNVTESGCKECEELEQ**<br>**KNIKEFLQSFVHIVQMFINT** |
| 58/<br>xmPD1-<br>hIL15<br>NQ-2a<br>(E46Q/<br>E93Q) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLQLQVISLESGDASIHDTVENLIILANNSLSSNGNVTESGCKECEELEQ**<br>**KNIKEFLQSFVHIVQMFINT** |
| 59/<br>xmPD1-<br>hIL15<br>NQ-2b<br>(E46Q/<br>E53Q) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLQLQVISLQSGDASIHDTVENLIILANNSLSSNGNVTESGCKECEELEE**<br>**KNIKEFLQSFVHIVQMFINT** |
| 60/<br>xmPD1-<br>hIL15<br>NQ-2c<br>(E53Q/<br>E93Q) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVWSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV |

TABLE 1.2-continued

| SEQ ID NO:/name | SEQUENCE |
|---|---|
| | VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLELQVISLQSGDASIHDTVENLIILANNSLSSNGNVTESGCKECEELEQ**<br>**KNIKEFLQSFVHIVQMFINT** |
| 61/<br>xmPD1-<br>hIL15<br>NQ-3d<br>(E46Q/<br>E53Q/<br>E93Q) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVIVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGSGGGG<br>GTSATATPGA**NWVNVISDLKKIEDLIQSMHIDATLYTESDVHPSCKVTAMK**<br>**CFLLQLQVISLQSGDASIHDTVENLIILANNSLSSNGNVTESGCKECEELE**<br>**QKNIKEFLQSFVHIVQMFINT** |
| 63/<br>xmPD-1-<br>hIL-15<br>V49R<br>fusion | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVIVSSASTKGPSVFPLAPCSRSTSESTAALGCLVKD<br>YFPEPVTVSWNSGALTSGVHTFPAVLQSSGLYSLSSVVTVPSSNFGTQTY<br>TCNVDHKPSNTKVDKTVERKCEVECPECPAPPVAGPSVFLFPPKPKDTLMI<br>SRTPEVTCVVVAVSHEDPEVQFNWYVDGVEVHNAKTKPREEQFNSTFRV<br>VSVLTVVHQDWLNGKEYKCKVSNKGLPSSIEKTISKTKGQPREPQVYTLPP<br>SREEMTKNQVSLTCEVKGFYPSDIAVEWESNGQPENNYKTTPPMLDSDG<br>SFFLYSKLTVDKSRWQQGNVFSCSVMHEALHNHYTQKSLSLSPGKGGGG<br>RTSATATPGA**NWVNVISDLKKIEDLIQSMHIDATLYTESDVHPSCKVTAMK**<br>**CFLLELQRISLESGDASIHDTVENLIILANNSLSSNGNVTESGCKECEELEE**<br>**KNIKEFLQSFVHIVQMFINT** |
| 67/<br>xhPD1<br>(VH1-69b)-<br>hIgG1-<br>AAA-<br>Bsp-E-<br>arm-<br>3GS-<br>hIL15Ra<br>su-hIL15 | QVQLVQSGAEVKKPGSSVKVSCKASGYTFTSYWINWVRQAPGQGLEVVM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCEKTHTCPECPAPEAAGAPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PSREEMTKNQVSLTCEVKGFYPSDIAVEWESNGQPENNYKTTPPVLDSDG<br>SFFLYSKLTVDKSRWQQGNVFSCSVMHEALHNHYTQKSLSLSPGGGGGS<br>GGGGSGGGGITCPPPMSVEHADIINVKSYSLYSRERYICNSGFKRKAGTS<br>SLTECVLNKATNVAHWTTPSLKCIRDPALVHQRPAPPSGGSGGGGSGG<br>GSGGGGSGG**NWVNVISDLKKIEDLIQSMHIDATLYTESDVHPSCKVTAMK**<br>**CFLLELQVISLESGDASIHDTVENLIILANNSLSSNGNVTESGCKECEELEE**<br>**KNIKEFLQSFVHIVQMFINTS** |
| 68/<br>xhPD1<br>(VH1-69b)-<br>hIgG1-<br>AAA-<br>Bsp-E-<br>arm-<br>3GS-<br>hIL15<br>NQ | QVQLVQSGAEVKKPGSSVKVSCKASGYTFTSYWINWVRQAPGQGLEVVM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCEKTHTCPECPAPEAAGAPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PSREEMTKNQVSLTCEVKGFYPSDIAVEWESNGQPENNYKTTPPVLDSDG<br>SFFLYSKLTVDKSRWQQGNVFSCSVMHEALHNHYTQKSLSLSPGGGGGS<br>GGGGSGGGG**NWVNVISDLKKIEDLIQSMHINATLFTESDVHPSCKVTAMK**<br>**CFLLQLQVISLQSGDASIHDTVENLIILANNSLSSNGNVTESGCKECQELE**<br>**QKNIKEFLQSFVHIVQMFINTS** |
| 69/<br>xhPD1<br>(VH1-69b)-<br>hIgG1-<br>AAA-<br>Bsp-E-<br>arm-<br>3GS-<br>hIL15<br>V49R-<br>E46G-<br>E64Q | QVQLVQSGAEVKKPGSSVKVSCKASGYTFTSYWINWVRQAPGQGLEVVM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCEKTHTCPECPAPEAAGAPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PSREEMTKNQVSLTCEVKGFYPSDIAVEWESNGQPENNYKTTPPVLDSDG<br>SFFLYSKLTVDKSRWQQGNVFSCSVMHEALHNHYTQKSLSLSPGGGGGS<br>GGGGSGGGG**NWVNVISDLKKIEDLIQSMHIDATLYTESDVHPSCKVTAMK**<br>**CFLLGLQRISLESGDASIHDTVQNLIILANNSLSSNGNVTESGCKECEELEE**<br>**KNIKEFLQSFVHIVQMFINTS** |
| 70/<br>xhPD1<br>(VH1-69b)- | QVQLVQSGAEVKKPGSSVKVSCKASGYTFTSYWINWVRQAPGQGLEVVM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF |

TABLE 1.2-continued

| SEQ ID NO:/name | SEQUENCE |
|---|---|
| hIgG1- | PEPVTVSWNSGALTSGVHTFPAVLQSSGLYSLSSVVTVPSSSLGTQTYICN |
| AAA- | VNHKPSNTKVDKKVEPKSCEKTHTCPECPAPEAAGAPSVFLFPPKPKDTL |
| Bsp-E- | MISRTPEVTCVVVDVSHEDPEVKFNWYVDGVEVHNAKTKPREEQYNSTYR |
| arm- | VVSVLTVLHQDWLNGKEYKCKVSNKALPAPIEKTISKAKGQPREPQVYTLP |
| 3GS- | PSREEMTKNQVSLTCEVKGFYPSDIAVEWESNGQPENNYKTTPPVLDSDG |
| hIL15 | SFFLYSKLTVDKSRWQQGNVFSCSVMHEALHNHYTQKSLSLSPGGGGGS |
| V49R- | GGGGSGGGG**NWVNVISDLKKIEDLIQSMHIDATLYTESNVHPSCKVTAMK** |
| E46G- | **CFLLGLQRISLESGDASIHDTVQNLIILANNSLSSNGNVTESGCKECEELEE** |
| E64Q- | **KNIKEFLQSFVHIVQMFINTS** |
| D30N | |
| | |
| 71/ | QVQLVQSGAEVKKPGSSVKVSCKASGYTFTSYWINWVRQAPGQGLEVVM |
| xhPD1 | GNIYPGSSITNYAQKFQGRVTITADESTSTAYMELSSLRSEDTAVYYCARLT |
| (VH1-69b)- | TGTFAYWGQGTLVTVSSASTKGPSVFPLAPSSKSTSGGTAALGCLVKDYF |
| hIgG1- | PEPVTVSWNSGALTSGVHTFPAVLQSSGLYSLSSVVTVPSSSLGTQTYICN |
| AAA- | VNHKPSNTKVDKKVEPKSCEKTHTCPECPAPEAAGAPSVFLFPPKPKDTL |
| Bsp-E- | MISRTPEVTCVVVDVSHEDPEVKFNWYVDGVEVHNAKTKPREEQYNSTYR |
| arm- | VVSVLTVLHQDWLNGKEYKCKVSNKALPAPIEKTISKAKGQPREPQVYTLP |
| 3GS- | PSREEMTKNQVSLTCEVKGFYPSDIAVEWESNGQPENNYKTTPPVLDSDG |
| hIL15 | SFFLYSKLTVDKSRWQQGNVFSCSVMHEALHNHYTQKSLSLSPGGGGGS |
| V49R- | GGGGSGGGGNWV QVISDLKKIE DLIQSMHIDA TLYTESNVHP SCKVTA |
| E46G- | MKCF LLGLQRISLE SGDASHADTV ENLILANNS LSSNGNVTES GCKEC |
| N4Q- | EELEE KNIKEFLQSF VHIVQMFINTS |
| D30N | |
| | |
| 72 | QVQLVQSGAEVKKPGSSVKVSCKASGYTFTSYWINWVRQAPGQGLEVVM |
| xhPD1 | GNIYPGSSITNYAQKFQGRVTITADESTSTAYMELSSLRSEDTAVYYCARLT |
| (VH1-69b)- | TGTFAYWGQGTLVTVSSASTKGPSVFPLAPSSKSTSGGTAALGCLVKDYF |
| hIgG1- | PEPVTVSWNSGALTSGVHTFPAVLQSSGLYSLSSVVTVPSSSLGTQTYICN |
| AAA- | VNHKPSNTKVDKKVEPKSCEKTHTCPECPAPEAAGAPSVFLFPPKPKDTL |
| Bsp-E- | MISRTPEVTCVVVDVSHEDPEVKFNWYVDGVEVHNAKTKPREEQYNSTYR |
| arm- | VVSVLTVLHQDWLNGKEYKCKVSNKALPAPIEKTISKAKGQPREPQVYTLP |
| 3GS- | PSREEMTKNQVSLTCEVKGFYPSDIAVEWESNGQPENNYKTTPPVLDSDG |
| hIL15 | SFFLYSKLTVDKSRWQQGNVFSCSVMHEALHNHYTQKSLSLSPGGGGGS |
| V49R- | GGGGSGGGGKWV NVISDLKKIE DLIQSMHIDA TLYTESNVHP SCKVTA |
| E46G- | MKCF LLGLQRISLE SGDASIHDTV ENLIILANNS LSSNGNVTES GCKEC |
| N1K- | EELEE KNIKEFLQSF VHIVQMANTS |
| D30N | |
| | |
| 73 | QVQLVQSGAEVKKPGSSVKVSCKASGYTFTSYWINWVRQAPGQGLEVVM |
| xhPD1 | GNIYPGSSITNYAQKFQGRVTITADESTSTAYMELSSLRSEDTAVYYCARLT |
| (VH1-69b)- | TGTFAYWGQGTLVTVSSASTKGPSVFPLAPSSKSTSGGTAALGCLVKDYF |
| hIgG1- | PEPVTVSWNSGALTSGVHTFPAVLQSSGLYSLSSVVTVPSSSLGTQTYICN |
| AAA- | VNHKPSNTKVDKKVEPKSCEKTHTCPECPAPEAAGAPSVFLFPPKPKDTL |
| Bsp-E- | MISRTPEVTCVVVDVSHEDPEVKFNWYVDGVEVHNAKTKPREEQYNSTYR |
| arm- | VVSVLTVLHQDWLNGKEYKCKVSNKALPAPIEKTISKAKGQPREPQVYTLP |
| 3GS- | PSREEMTKNQVSLTCEVKGFYPSDIAVEWESNGQPENNYKTTPPVLDSDG |
| hIL15 | SFFLYSKLTVDKSRWQQGNVFSCSVMHEALHNHYTQKSLSLSPGGGGGS |
| V49R- | GGGGSGGGGNWV NVITDLKKIE DLIQSMHIDA TLYTESNVHP SCKVTA |
| E46G- | MKCF LLGLQRISLE SGDASIHDTV ENLIILANNS LSSNGNVTES GCKEC |
| S7T- | EELEE KNIKEFLQSF VHIVQMANTS |
| D30N | |
| | |
| 75/ | QVQLVQSGAEVKKPGSSVKVSCKASGYTFTSYWINWVRQAPGQGLEVVM |
| xhPD1 | GNIYPGSSITNYAQKFQGRVTITADESTSTAYMELSSLRSEDTAVYYCARLT |
| (VH1-69b)- | TGTFAYWGQGTLVTVSSASTKGPSVFPLAPSSKSTSGGTAALGCLVKDYF |
| hIgG1- | PEPVTVSWNSGALTSGVHTFPAVLQSSGLYSLSSVVTVPSSSLGTQTYICN |
| AAA- | VNHKPSNTKVDKKVEPKSCDKTHTCPPCPAPEAAGAPSVFLFPPKPKDTL |
| 'hole'- | MISRTPEVTCVVVDVSHEDPEVKFNWYVDGVEVHNAKTKPREEQYNSTYR |
| 3GS- | VVSVLTVLHQDWLNGKEYKCKVSNKALPAPIEKTISKAKGQPREPQVYTLP |
| hIL15 | PCREEMTKNQVSLSCAVKGFYPSDIAVEWESNGQPENNYKTTPPVLDSD |
| V49R- | GSFFLVSKLTVDKSRWQQGNVFSCSVMHEALHNHYTQKSLSLSPGGGGG |
| E46G- | SGGGGSGGGG**NWVNVISDLKKIEDLIQSMHIDATLYTESNVHPSCKVTAM** |
| E64Q- | **KCFLLGLQRISLESGDASIHDTVQNLIILANNSLSSNGNVTESGCKECEEL** |
| D30N | **EEKNIKEFLQSFVHIVQMFINTS** |
| | |
| 86 | EVQLVESGGGLVKPGGSLELSCAASGFTFSSYWMSWVRQAPEKGLEWV |
| xmPD1- | AAISPSGGSTYYADSVKGRFTISRDNAKNTLFLQMTSLRSEDTAMYYCAKE |
| hIgG1- | SWGAYYDLWGQGTTVWSSASTKGPSVFPLAPSSKSTSGGTAALGCLVK |
| AAA- | DYFPEPVTVSWNSGALTSGVHTFPAVLQSSGLYSLSSVVTVPSSSLGTQT |
| 'hole'- | YICNVNHKPSNTKVDKKVEPKSCDKTHTCPPCPAPEAAGAPSVFLFPPKPK |
| 3GS- | DTLMISRTPEVTCVVVDVSHEDPEVKFNWYVDGVEVHNAKTKPREEQYNS |
| hIL15 | TYRVVSVLTVLHQDWLNGKEYKCKVSNKALPAPIEKTISKAKGQPREPQVY |
| V49R- | TLPPCREEMTKNQVSLSCAVKGFYPSDIAVEWESNGQPENNYKTTPPVLD |
| E46G- | SDGSFFLVSKLTVDKSRWQQGNVFSCSVMHEALHNHYTQKSLSLSPGSG |

TABLE 1.2-continued

| SEQ ID NO:/name | SEQUENCE |
|---|---|
| N1A-<br>D30N<br>(m1) | GGGSGGGGSGGGG**AWVNVISDLKKIEDLIQSMHIDATLYTESNVHPSCKV**<br>**TAMKCFLLGLQRISLESGDASIHDTVENLIILANNSLSSNGNVTESGCKEC**<br>**EELEEKNIKEFLQSFVHIVQMFINTS** |
| 87<br>xmPD1-<br>hIgG1-<br>AAA-<br>'hole'-<br>3GS-<br>hIL15<br>V49R-<br>E46G-<br>N1G-<br>E64Q-<br>D30N<br>(m2) | EVQLVESGGGLVKPGGSLELSCAASGFTFSSYWMSWVRQAPEKGLEWV<br>AAISPSGGSTYYADSVKGRFTISRDNAKNTLFLQMTSLRSEDTAMYYCAKE<br>SWGAYYDLWGQGTTVTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPEAAGAPSVFLFPPKPK<br>DTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVY<br>TLPPCREEMTKNQVSLSCAVKGFYPSDIAVEWESNGQPENNYKTTPPVLD<br>SDGSFFLVSKLTVDKSRWQQGNVFSCSVMHEALHNHYTQKSLSLSPGSG<br>GGGSGGGGSGGGGG**WVNVISDLKKIEDLIQSMHIDATLYTESNVHPSCK**<br>**VTAMKCFLLGLQRISLESGDASIHDTVQNLIILANNSLSSNGNVTESGCKE**<br>**CEELEEKNIKEFLQSFVHIVQMFINTS** |
| 89<br>xhPD1<br>(VH1-69b)-<br>hIgG1-<br>AAA-<br>'hole'-<br>3GS-<br>hIL15<br>V49R-<br>E46G-<br>N1A-<br>D30N<br>(m1) | QVQLVQSGAEVKKPGSSVKVSCKASGYTFTSYWINWVRQAPGQGLEWM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPEAAGAPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PCREEMTKNQVSLSCAVKGFYPSDIAVEWESNGQPENNYKTTPPVLDSD<br>GSFFLVSKLTVDKSRWQQGNVFSCSVMHEALHNHYTQKSLSLSPGSGGG<br>GSGGGGSGGGG**AWVNVISDLKKIEDLIQSMHIDATLYTESNVHPSCKVTA**<br>**MKCFLLGLQRISLESGDASIHDTVENLIILANNSLSSNGNVTESGCKECEE**<br>**LEEKNIKEFLQSFVHIVQMFINTS** |
| 90<br>xhPD1<br>(VH1-69b)-<br>hIgG1-<br>AAA-<br>'hole'-<br>3G5-<br>hIL15<br>V49R-<br>E46G-<br>N1G-<br>E64Q-<br>D30N<br>(m2) | QVQLVQSGAEVKKPGSSVKVSCKASGYTFTSYWINWVRQAPGQGLEWM<br>GNIYPGSSITNYAQKFQGRVTITADESTSTAYMELSSLRSEDTAVYYCARLT<br>TGTFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPEAAGAPSVFLFPPKPKDTL<br>MISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PCREEMTKNQVSLSCAVKGFYPSDIAVEWESNGQPENNYKTTPPVLDSD<br>GSFFLVSKLTVDKSRWQQGNVFSCSVMHEALHNHYTQKSLSLSPGSGGG<br>GSGGGGSGGGGG**WVNVISDLKKIEDLIQSMHIDATLYTESNVHPSCKVTA**<br>**MKCFLLGLQRISLESGDASIHDTVQNLIILANNSLSSNGNVTESGCKECEE**<br>**LEEKNIKEFLQSFVHIVQMFINTS** |

The IL-15 fusion protein as described herein can be created by methods known in the art, for example, synthetically or recombinantly. Typically, the fusion proteins of this invention are made by preparing and expressing a polynucleotide encoding them using recombinant methods described herein, although they may also be prepared by other means known in the art, including, for example, chemical synthesis.

The antibodies as described herein can also be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies.

Hybridomas that produce antibodies used for the present invention may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with cells expressing the antibody target (e.g., PD-1), a human target protein (e.g., PD-1), or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups, can yield a population of antibodies (e.g., monoclonal antibodies).

If desired, the antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

In some embodiments, antibodies as described herein are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

The IL-15 fusion proteins or the 11-15 variants of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the IL-15 variant and IL-15 fusion proteins as described herein. In one aspect, the invention provides a method of making any of the polynucleotides described herein. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding any of the IL-15 variant and IL-15 fusion proteins described herein.

In another aspect, provided is an isolated cell line that produces the IL-15 variants and the IL-15 fusion proteins as described herein. In some embodiments, the cell line is an engineered immune cell, wherein the engineered immune cell comprises a chimeric antigen receptor (CAR). In some embodiments, the IL-15 variants and the IL-15 fusion proteins, when expressed as polynucleotides in CAR T cells, either as secreted or membrane-tethered versions, are used to enhance CAR T function, including activity and proliferation. In some embodiments, the Il-15 variants or the IL-15 fusion proteins comprising thereof comprise amino acid substitutions at positions D22N, Y26F, E46Q, E53Q, E89Q, and E93Q (e.g., see SEQ ID NO: 76).

Immune cells producing the IL-15 variants and the IL-15 fusion proteins as described herein may be made by introducing a CAR into immune cells, and expanding the cells. For example, the immune cells can be engineered by: providing a cell and expressing at the surface of the cell at least one CAR and at least one IL-15 variant or IL-15 fusion protein as described herein. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the cell can be transformed with at least one polynucleotide encoding a CAR, one polynucleotide encoding the IL-15 variant or IL-15 fusion protein as described herein, followed by expressing the polynucleotides in the cell.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to IL-15 or a IL-15 domain is effected by an immunoassay or FACS. A cell overexpressing the antibody or protein of interest can be identified.

An expression vector can be used to direct expression of an IL-15 variant or an IL-15 fusion protein. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics:

Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of an IL-15 variant or an IL-15 fusion protein as described herein. Examples of such compositions, as well as how to formulate, are also described herein. In some embodiments, the composition comprises one or more IL-15 variant or IL-15 fusion protein. In some embodiments, the composition comprises an IL-15 fusion protein comprising an PD-1 antibody and a human IL-15 variant comprising amino acid substitutions at positions V49, I50, S51, N4, D30, and E64 (e.g., V49N, I50A, S51T, N4K, D30N, and E64Q), wherein the human IL-15 variant is covalently linked to the Fc domain of the antibody. In some embodiments, the composition comprises a human IL-15 fusion protein comprising an PD-1 antibody and a human IL-15 variant comprising amino acid substitutions at positions E46, V49, E64, D30, and N4 (e.g., E46G, V49R, E64Q, D30N, and N4K), wherein the IL-15 variant is covalently linked to the Fc domain of the antibody. In some embodiments, the composition comprises a human IL-15 fusion protein comprising an PD-1 antibody and a human IL-15 variant comprising amino acid substitutions at positions N1, D30, E46, and V49 (e.g., N1A, D30N, E46G, and V49R), wherein the IL-15 variant is covalently linked to the Fc domain of the antibody. In some embodiments, the composition comprises a human IL-15 fusion protein comprising an PD-1 antibody and a human IL-15 variant comprising amino acid substitutions at positions N1, D30, E46, V49, and E64 (e.g., N1G, D30N, E46G, V49R, and E64Q), wherein the IL-15 variant is covalently linked to the Fc domain of the antibody.

It is understood that the compositions can comprise more than one IL-15 variant or IL-15 fusion protein (e.g., a mixture of IL-15 variants or IL-15 fusions comprising different IL-15 variants and/or different antibodies). For example, the composition comprises 1) a human IL-15 fusion protein comprising a PD-1 antibody and a human IL-15 variant comprising amino acid substitutions at positions E46G, V49R, E64Q, D30N, and N4K; and 2) an IL-15 fusion protein comprising a PD-1 antibody and a human IL-15 variant comprising amino acid substitutions at positions V49N, I50A, S51T, N4K, D30N, and E64Q. In another example, the composition comprises 1) a human IL-15 fusion protein comprising a PD-1 antibody and a human IL-15 variant comprising amino acid substitutions at positions N1A, D30N, E46G, and V49R; and 2) an IL-15 fusion protein comprising a PD-1 antibody and a human IL-15 variant comprising amino acid substitutions at positions N1G, D30N, E46G, V49R, and E64Q.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The IL-15 variants, IL-15 fusion proteins, and compositions thereof can also be used in conjunction with, or administered separately, simultaneously, or sequentially with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the IL-15 variants and IL-15 fusion proteins as described herein. In other embodiment, the composition comprises an expression vector comprising a polynucleotide encoding any of the IL-15 variants and IL-15 fusion proteins described herein.

Methods for Preventing or Treating Conditions Using IL-15 Variants and IL-15 Fusion Proteins The IL-15 variants and the IL-15 fusion proteins of the present invention are useful in various applications including, but are not limited to, therapeutic treatment methods and diagnostic treatment methods.

In one aspect, the invention provides a method for treating a cancer. In some embodiments, the method of treating a cancer in a subject comprises administering to the subject in need thereof an effective amount of a composition (e.g., pharmaceutical composition) comprising any of the IL-15 variants and the IL-15 fusion proteins as described herein. As used herein, a cancer can be a solid cancer or a liquid cancer. Solid cancers include, but are not limited to, gastric cancer, small intestine cancer, sarcoma, head and neck cancer (e.g., squamous cell head and neck cancer), thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer (e.g., renal cell carcinoma), bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma.

Liquid cancers include, but not limited to, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer.

In some embodiments, the cancer is relapsed, refractory, or metastatic.

In some embodiments, provided is a method of inhibiting tumor growth or progression in a subject, comprising administering to the subject in need thereof an effective amount of a composition comprising the IL-15 variants or IL-15 fusion proteins as described herein. In some embodiments, provided is a method of inhibiting metastasis of cancer cells in a subject, comprising administering to the subject in need thereof an effective amount of a composition comprising any of the IL-15 variants or IL-15 fusion proteins as described herein. In other embodiments, provided is a method of inducing regression of a tumor in a subject, comprising administering to the subject in need thereof an effective amount of a composition comprising any of the IL-15 variants or IL-15 fusion proteins as described herein.

In another aspect, provided is a method of detecting, diagnosing, and/or monitoring a cancer. For example, the IL-15 variants or IL-15 fusion proteins as described herein can be labeled with a detectable moiety such as an imaging agent and an enzyme-substrate label. The IL-15 variants or IL-15 fusion proteins as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

With respect to all methods described herein, reference to IL-15 variants or IL-15 fusion proteins also includes compositions comprising one or more additional agents. These compositions may further comprise suitable excipients, such as pharmaceutically acceptable excipients including buffers, which are well known in the art. The present invention can be used alone or in combination with other methods of treatment.

The IL-15 variants or IL-15 fusion proteins as described herein can be administered to a subject via any suitable route. It should be apparent to a person skilled in the art that the examples described herein are not intended to be limiting but to be illustrative of the techniques available. Accordingly, in some embodiments, the IL-15 variant or IL-15 fusion protein is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the IL-15 variants or IL-15 fusion proteins can be aerosolized using a fluorocarbon formulation and a metered dose inhaler, or inhaled as a lyophilized and milled powder.

In some embodiments, an IL-15 variant or IL-15 fusion protein is administered via site-specific or targeted local delivery techniques. Examples of site-specific or targeted local delivery techniques include various implantable depot sources of the IL-15 variants or IL-15 fusion proteins or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an IL-15 variant or IL-15 fusion protein may be used for administration. In some embodiments, the IL-15 variant or IL-15 fusion protein may be administered neat. In some embodiments, the IL-15 variant or IL-15 fusion protein and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

The IL-15 variants or IL-15 fusion proteins described herein can be administered using any suitable method, including by injection (e.g., intraperitoneally, intravenously, subcutaneously, intramuscularly, etc.). The IL-15 variants or IL-15 fusion proteins can also be administered topically or via inhalation, as described herein. Generally, for administration of IL-15 variants or IL-15 fusion proteins, the candidate dosage can be administered daily, every week, every other week, every three weeks, every four weeks, every five weeks, every six weeks, every seven weeks, every eight weeks, every ten weeks, every twelve weeks, or more than every twelve weeks. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the specific IL-15 variants or IL-15 fusion proteins used) can vary over time.

In some embodiments, the candidate dosage is administered daily with the dosage ranging from about any of 1 μg/kg to 30 μg/kg to 300 μg/kg to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 μg/kg to 30 μg/kg to 300 μg/kg to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 μg/kg to 30 μg/kg to 300 μg/kg to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 μg/kg to 30 μg/kg to 300 μg/kg to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 μg/kg to 30 μg/kg to 300 μg/kg to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500, about 2600 mg, about 2700 mg, about 2800 mg, about 2900 mg, or about 3000 mg may be used.

In some embodiments, a therapeutic of the present invention is administered at a dose ranging from about 1 μg/kg to about 600 μg/kg or more, about 6 μg/kg to about 600 μg/kg, about 6 μg/kg to about 300 μg/kg, about 30 μg/kg to about 600 μg/kg or about 30 μg/kg to about 300 μg/kg. For example, the dose is administered at about 1 μg/kg, about 2 μg/kg, about 3 μg/kg, about 4 μg/kg, about 5 μg/kg, about 6 μg/kg, about 7 μg/kg, about 8 μg/kg, about 9 μg/kg, about 10 μg/kg, about 15 μg/kg, about 20 μg/kg, about 25 μg/kg, about 30 μg/kg, about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg, about 110 μg/kg, about 120 μg/kg, about 130 μg/kg, about 140 μg/kg, about 150 μg/kg, about 160 μg/kg, about 170 μg/kg, about 180 μg/kg, about 190 μg/kg, about 200 μg/kg, about 210 μg/kg, about 220 μg/kg, about 230 μg/kg, about 240 μg/kg, about 250 μg/kg, about 260 μg/kg, about 270 μg/kg, about 280 μg/kg, about 290 μg/kg, about 300 μg/kg, about 350 μg/kg, about 400 μg/kg, about 450 μg/kg, about 500 μg/kg, about 550 μg/kg or about 600 μg/kg may be used.

For the purpose of the present invention, the appropriate dosage of an IL-15 variant or an IL-15 fusion protein will depend on the IL-15 variant or an IL-15 fusion protein (or compositions thereof) employed, the type and severity of symptoms to be treated, whether the agent is administered for preventive or therapeutic purposes, previous therapy, the patient's clinical history and response to the agent, the patient's clearance rate for the administered agent, and the discretion of the attending physician. Typically the clinician will administer an IL-15 variant or an IL-15 fusion protein until a dosage is reached that achieves the desired result. Dose and/or frequency can vary over course of treatment. Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of symptoms. Alternatively, sustained continuous release formulations of IL-15 variants or IL-15 fusion proteins may be appropriate. Various formulations and devices for achieving sustained release are known in the art.

In one embodiment, dosages for an IL-15 variant or an IL-15 fusion protein may be determined empirically in individuals who have been given one or more administration (s) of an IL-15 variant or an IL-15 fusion protein. For example, individuals are given incremental dosages of an IL-15 variant or an IL-15 fusion protein. To assess efficacy, an indicator of the disease can be followed.

Administration of an IL-15 variant or an IL-15 fusion protein as described herein in accordance with the method in the present invention can be continuous or intermittent, depending, for example, upon the recipient's physiological condition, whether the purpose of the administration is therapeutic or prophylactic, and other factors known to skilled practitioners. The administration of an IL-15 variant or an IL-15 fusion protein may be essentially continuous over a preselected period of time or may be in a series of spaced doses.

In some embodiments, more than one IL-15 variant or IL-15 fusion protein may be present. At least one, at least two, at least three, at least four, at least five different, or more IL-15 variants or an IL-15 fusion proteins can be present. Generally, those IL-15 variants or IL-15 fusion proteins may have complementary activities that do not adversely affect each other.

In some embodiments, the IL-15 variant or the IL-15 fusion protein may be administered in combination with the administration of one or more additional therapeutic agents. These include, but are not limited to, the administration of a biotherapeutic agent, a chemotherapeutic agent, a vaccine, a CAR-T cell-based therapy, radiotherapy, another cytokine therapy (e.g., immunostimulatory cytokines including various signaling proteins that stimulate immune response, such as interferons, interleukins, and hematopoietic growth factors), a vaccine, an inhibitor of other immunosuppressive pathways, an inhibitors of angiogenesis, a T cell activator, an inhibitor of a metabolic pathway, an mTOR (mechanistic target of rapamycin) inhibitor (e.g., rapamycin, rapamycin derivatives, sirolimus, temsirolimus, everolimus, and deforolimus), an inhibitor of an adenosine pathway, a tyrosine kinase inhibitor including but not limited to inlyta, ALK (anaplastic lymphoma kinase) inhibitors (e.g., crizotinib, ceritinib, alectinib, and sunitinib), a BRAF inhibitor (e.g., vemurafenib and dabrafenib), an epigenetic modifier, an inhibitors or depletor of Treg cells and/or of myeloid-derived suppressor cells, a JAK (Janus Kinase) inhibitor (e.g., ruxolitinib and tofacitinb, varicitinib, filgotinib, gandotinib, lestaurtinib, momelotinib, pacritinib, and upadacitinib), a STAT (Signal Transducers and Activators of Transcription) inhibitor (e.g., STAT1, STAT3, and STAT5 inhibitors such as fludarabine), a cyclin-dependent kinase inhibitor, an immunogenic agent (for example, attenuated cancerous cells, tumor antigens, antigen presenting cells such as dendritic cells pulsed with tumor derived antigen or nucleic acids, a MEK inhibitor (e.g., trametinib, cobimetinib, binimetinib, and selumetinib), a GLS1 inhibitor, a PAP inhibitor, an oncolytic virus, an IDO (Indoleamine-pyrrole 2,3-dioxygenase) inhibitor, a PRR (Pattern Recognition Receptors) agonist, and cells transfected with genes encoding immune stimulating cytokines such as but not limited to GM-CSF).

In some embodiments, exemplary immunostimulatory cytokines include, but are not limited to, GM-CSF, G-CSF, IFNγ, IFNα; IL-2 (e.g. denileukin difitox), IL-6, IL-7, IL-10, IL-11, IL-12, IL-15, IL-18, IL-21, and TNFα. In some embodiments, the cytokines are pegylated (e.g., pegylated IL-2, IL-10, IFNγ, and IFNα).

Pattern recognition receptors (PRRs) are receptors that are expressed by cells of the immune system and that recognize a variety of molecules associated with pathogens and/or cell damage or death. PRRs are involved in both the innate immune response and the adaptive immune response. PRR agonists may be used to stimulate the immune response in a subject. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein.

The terms "TLR" and "toll-like receptor" refer to any toll-like receptor. Toll-like receptors are receptors involved in activating immune responses. TLRs recognize, for example, pathogen-associated molecular patterns (PAMPs) expressed in microbes, as well as endogenous damage-associated molecular patterns (DAMPs), which are released from dead or dying cells.

Molecules which activate TLRs (and thereby activate immune responses) are referred to herein as "TLR agonists". TLR agonists can include, for example, small molecules (e.g. organic molecule having a molecular weight under about 1000 Daltons), as well as large molecules (e.g. oligonucleotides and proteins). Some TLR agonists are specific for a single type of TLR (e.g. TLR3 or TLR9), while some TLR agonists activate two or more types of TLR (e.g. both TLR7 and TLR8).

Exemplary TLR agonists provided herein include agonists of TLR2, TLR3, TLR4, TLR5, TLR6, TLR7, TLR8, and TLR9.

Exemplary small molecule TLR agonists include those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091,214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852.

Additional examples of small molecule TLR agonists include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-.beta.-D-ribofuranosylthiazolo [4,5-d]pyrimidine derivatives (such as those described in U.S. Publication No. 2003/0199461), and certain small molecule immuno-potentiator compounds such as those described, for example, in U.S. Patent Publication No. 2005/0136065.

Exemplary large molecule TLR agonists include as oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529, Mar. 5, 2004.

Other TLR agonists include biological molecules such as aminoalkyl glucosaminide phosphates (AGPs) and are described, for example, in U.S. Pat. Nos. 6,113,918; 6,303,347; 6,525,028; and 6,649,172.

TLR agonists also include inactivated pathogens or fractions thereof, which may activate multiple different types of TLR receptor. Exemplary pathogen-derived TLR agonists include BCG, *Mycobacterium obuense* extract, Talimogene laherparepvec (T-Vec) (derived from HSV-1), and Pexa-Vec (derived from vaccina virus).

In some embodiments, a TLR agonist may be an agonist antibody that binds specifically to the TLR.

In some embodiments, the biotherapeutic agent is an antibody, including but not limited to, an anti-CTLA-4 antibody, an anti-CD3 antibody, an anti-CD4 antibody, an anti-CD8 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-IL-8 antibody, an anti-IL-15 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-IL-7R antibody, an anti-MARCO antibody, an anti-CXCR4 antibodies, an anti-VEGF antibody, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-FLT3 antibody, an anti-B7-H4 antibody, an anti-B7-H3 antibody, an KLRG1 antibody, a BTN1A1 antibody, a BCMA antibody, or an anti-GITR antibody.

In some embodiments, an IL-15 variant or an IL-15 fusion protein is used in combination with an immunocytokine. In some embodiments, the immunocytokine comprises an antibody, or fragment thereof, conjugated or fused to a cytokine (e.g. fusion protein). In some embodiments, the antibody, or fragment thereof, binds the Extra Domain-A (EDA) isoform of fibronectin (e.g. anti-EDA antibody). For example, the anti-EDA antibody, or fragment thereof, comprises a CDR1, a CDR2 and CDR3 of the heavy chain variable (VH) region shown in SEQ ID NO: 94 and/or a CDR1, a CDR2 and CDR3 of the light chain variable (VL) region shown in SEQ ID NO: 96. In some embodiments, the anti-EDA antibody, or fragment thereof, comprises a VH region having the amino acid sequence of SEQ ID NO: 94 and/or a VL region having the amino acid sequence of SEQ ID NO: 96. In some embodiments the cytokine is IL-10. For example, IL-10 may comprise the amino acid sequence of SEQ ID NO: 98. In some embodiments, the immunocytokine comprises at least one linker. For example, the linker(s) may comprise SEQ ID NO: 95 and/or 97. In some embodiments, the immunocytokine is an anti-EDA-IL-10 fusion protein comprising the amino acid sequence of SEQ ID NO: 99 (Table 1.3, CDRs underlined).

TABLE 1.3

| SEQ ID NO: | SEQUENCE |
|---|---|
| 94<br>Anti-EDA<br>Ab VH | EVQLLESGGGLVQPGGSLRLSCAASGFTFS**LFT**MSWVRQAPGKGLWV<br>SAI**SGSGGS**TYYADSVKGRFTISRDNSKNTLYLQMNSLRAEDTAVYYC<br>AK**STHLYL**FDYWGQGTLVTVSS |
| 95<br>Linker | *ggsgg* |
| 96<br>Anti-EDA<br>Ab VL | EIVLTQSPGTLSLSPGERATLSCRASQSVS**MPF**LAWYQQKPGQAPRLLI<br>Y**GASSRAT**GIPDRFSGSGSGTDFTLTISRLEPEDFAVYYCQQ**MRGRPP**<br>TFGQGTKVEIK |
| 97<br>Linker | *ssssgssssgssssg* |
| 98<br>IL-10 | SPGQGTQSENSCTHFPGNLPNMLRDLRDAFSRVKTFFQMKDQLDNLL<br>LKESLLEDFKGYLGCQALSEMIQFYLEEVMPQAENQDPDIKAHVNSLGE<br>NLKTLRLRLRRCHRFLPCENKSKAVEQVKNAFNKLQEKGIYKAMSEFDI<br>FINYIEAYMTMKIRN |
| 99<br>Anti-EDA-<br>IL-10<br>Fusion<br>Protein | EVQLLESGGGLVQPGGSLRLSCAASGFTFS**LFT**MSWVRQAPGKGLEW<br>VSAI**SGSGGS**TYYADSVKGRFTISRDNSKNTLYLQMNSLRAEDTAVYY<br>CAK**STHLYL**FDYWGQGTLVTVSS*ggsw*EIVLTQSPGTLSLSPGERATLS<br>CRASQSVS**MPF**LAWYQQKPGQAPRLLIY**GASSRAT**GIPDRFSGSGSG<br>TDFTLTISRLEPEDFAVYYCQQ**MRGRPP**TFGQGTKVEIK*ssssgssssgsss*<br>*sg*SPGQGTQSENSCTHFPGNLPNMLRDLRDAFSRVKTFFQMKDQLDN<br>LLLKESLLEDFKGYLGCQALSEMIQFYLEEVMPQAENQDPDIKAHVNSL<br>GENLKTLRLRLRRCHRFLPCENKSKAVEQVKNAFNKLQEKGIYKAMSE<br>FDIFINYIEAYMTMKIRN |

Accordingly, in some embodiments, an IL-15 variant or an IL-15 fusion protein is used in conjunction with, for example, an anti-PD-L1 antagonist antibody; an anti-PD-1 antagonist antibody such as for example, nivolumab (OPDIVO®), pembrolizumab (KEYTRUDA®), mAb7 (e.g., as described in US Pub. No. US20160159905, hereby incorporated by reference), and pidilizumab; an anti-CTLA-4 antagonist antibody such as for example ipilimumab (YERVOY®); an anti-LAG-3 antagonist antibody such as BMS-986016 and IMP701; an anti-TIM-3 antagonist antibody; an anti-B7-H3 antagonist antibody such as for example MGA271; an-anti-VISTA antagonist antibody; an anti-TIGIT antagonist antibody; an anti-CD28 antagonist antibody; an anti-CD80 antibody; an anti-CD86 antibody; an anti-B7-H4 antagonist antibody; an anti-ICOS agonist antibody; an anti-CD28 agonist antibody; an innate immune response modulator (e.g., TLRs, KIR, NKG2A), and an IDO inhibitor. In some embodiments, an IL-15 variant or an IL-15 fusion protein is used in conjunction with a 4-1BB (CD137) agonist such as, for example, PF-05082566 or urelumab (BMS-663513). In some embodiments, an IL-15 variant or an IL-15 fusion protein is used in conjunction with an OX40 agonist such as, for example, an anti-OX-40 agonist antibody. In some embodiments, an IL-15 variant or an IL-15 fusion protein is used in conjunction with a GITR agonist such as, for example, TRX518. In some embodiments, an IL-15 variant or an IL-15 fusion protein is used in conjunction with an IDO inhibitor. In some embodiments, an IL-15 variant or an IL-15 fusion protein is used in conjunction with a cytokine therapy such as, for example without limitation, (pegylated or non-pegylated) IL-2, IL-10, IL-12, IL-7, IL-15, IL-21, IL-33, CSF-1, MCSF-1, etc.

In some embodiments, other examples of the antibody for the combination use with the IL-15 variant or the IL-15 fusion protein of the present invention can be directed to, 5T4; A33; alpha-folate receptor 1 (e.g. mirvetuximab soravtansine); Alk-1; CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), PF-06671008 (CD3/P-cadherin bispecific), PF-06863135 (CD3/BCMA bispecific), CD25; CD28; CD30 (e.g. brentuximab vedotin); CD33 (e.g. gemtuzumab ozogamicin); CD38 (e.g. daratumumab, isatuximab), CD44v6; CD63; CD79 (e.g. polatuzumab vedotin); CD80; CD123; CD276/B7-H3 (e.g. omburtamab); CDH17; CEA; ClhCG; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GloboH; GM1; GM2; HER2/neu [e.g. margetuximab, pertuzumab, trastuzumab; ado-trastuzumab emtansine, trastuzumab duocarmazine, PF-06804103 (see U.S. Pat. No. 8,828,401)]; HER3; HER4; ICOS; IL-10; ITG-AvB6; LAG-3 (e.g. relatlimab); Lewis-Y; LG; Ly-6; M-CSF [e.g. PD-0360324 (see U.S. Pat. No. 7,326,414)]; MCSP; mesothelin; MUC1; MUC2; MUC3; MUC4; MUCSAC; MUCSB; MUC7; MUC16; Notch1; Notch3; Nectin-4 (e.g. enfortumab vedotin); P-Cadherein [e.g. PF-06671008 (see WO2016/001810)]; PCDHB2; PDGFRA (e.g. olaratumab); Plasma Cell Antigen; PolySA; PSCA; PSMA; PTK7 [e.g. PF-06647020 (see U.S. Pat. No. 9,409,995)]; Ror1; SAS; SCRx6; SLAMF7 (e.g. elotuzumab); SHH; SIRPa (e.g.

ED9, Effi-DEM); STEAP; TGF-beta; TIGIT; TMPRSS3; TNF-alpha precursor; TROP-2 (e.g., sacituzumab govitecan); TSPAN8; and Wue-1.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, fluridil, apalutamide, enzalutamide, cimetidine and goserelin; KRAS inhibitors; MCT4 inhibitors; MAT2a inhibitors; tyrosine kinase inhibitors such as sunitinib, axitinib; alk/c-Met/ROS inhibitors such as crizotinib, lorlatinib; mTOR inhibitors such as temsirolimus, gedatolisib; src/abl inhibitors such as bosutinib; cyclin-dependent kinase (CDK) inhibitors such as palbociclib, PF-06873600; erb inhibitors such as dacomitinib; PARP inhibitors such as talazoparib; SMO inhibitors such as glasdegib, PF-5274857; EGFR T790M inhibitors such as PF-06747775; EZH2 inhibitors such as PF-06821497; PRMT5 inhibitors such as PF-06939999; TGFRβr1 inhibitors such as PF-06952229; and pharmaceutically acceptable salts, acids or derivatives of any of the above.

In some embodiments, an IL-15 variant or an IL-15 fusion protein is used in conjunction with one or more other therapeutic agents targeting an immune checkpoint modulator, such as, for example without limitation, an agent targeting PD-1, PD-L1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1(CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator.

In some embodiments, an IL-15 variant or an IL-15 fusion protein is used in conjunction with a biotherapeutic agent and a chemotherapeutic agent. For example, provided is a method for treating cancer in a subject in need thereof comprising administering to the subject an effective amount of the IL-15 variant or IL-15 fusion protein as described wherein, an anti-PD-L1 antagonist antibody, and a chemotherapeutic agent (e.g., gemcitabine, methotrexate, or a platinum analog). In some embodiments, provided is a method for treating cancer in a subject in need thereof comprising administering to the subject an effective amount of the IL-15 variant or IL-15 fusion protein as described wherein, an anti-PD-1 antagonist antibody (e.g., nivolumab (OPDIVO®), mAb7 (e.g., as described in US Pub. No. US20160159905, hereby incorporated by reference), or pembrolizumab (KEYTRUDA®), and a chemotherapeutic agent (e.g., gemcitabine, methotrexate, or a platinum analog). In some embodiments, provided is a method for treating cancer in a subject in need thereof comprising administering to the subject an effective amount of the IL-15 variant or IL-15 fusion protein as described wherein, an anti-CTLA-4 antagonist antibody (e.g., ipilimumab (YERVOY®)), and a chemotherapeutic agent (e.g., gemcitabine, methotrexate, or a platinum analog).

In some embodiments, the IL-15 variant or IL-15 fusion protein therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an IL-15 variant or an IL-15 fusion protein composition comprises a second agent selected from crizotinib, palbociclib, gemcitabine, cyclophosphamide, fluorouracil, FOLFOX, folinic acid, oxaliplatin, axitinib, sunitinib malate, tofacitinib, bevacizumab, rituximab, and trastuzumab.

In some embodiments, an IL-15 variant or IL-15 fusion protein composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Formulations

Therapeutic formulations of the IL-15 variant or IL-15 fusion protein used in accordance with the present invention are prepared for storage by mixing the protein having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the IL-15 variant or IL-15 fusion protein are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic IL-15 variant or IL-15 fusion protein compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an IL-15 variant or IL-15 fusion protein with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the IL-15 variants or IL-15 fusion proteins described herein. Kits of the invention include one or more containers comprising an IL-15 variant or IL-15 fusion protein described herein and instructions for use in accordance with any of the methods of the invention described herein. Generally, these instructions comprise a description of administration of the IL-15 variant or IL-15 fusion protein for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of an IL-15 variant or an IL-15 fusion protein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). A t least one active agent in the composition is an IL-15 variant or an IL-15 fusion protein. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801 University Boulevard, Manassas, Va. 20110-2209, USA, on Jan. 23, 2019. Vector VK1-39 having ATCC Accession No. PTA-125686 is a polynucleotide encoding the antibody VK1-39 light chain variable region, and vector VH1-69b-hole-m2 having ATCC Accession No. PTA-125685 is a polynucleotide encoding the VH1-69 heavy chain variable region and the IL-15 variant M2. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Preparation of Human IL-15 Variants in Condition Media and the Purification of Antibody-IL-15 Fusion Proteins This example illustrates the production of human IL-15 variants in condition media and the purification of various IL-15 fusion proteins as described herein.

Four micrograms of DNA of each carboxyl-terminal 8-histidine-AVI-tagged IL-15 mutants having the mutations of as showing in Tables 1-2 were transiently transfected into Expi-293 cells at a density of about $3\times10^6$ cells per mL in each well of 24-well blocks. After five days of post-transfection, condition media supernatant of the cells that contain the secreted IL-15 mutants was harvested by centrifugation, transferred to a 96-well block and subsequently filtered and ready for kinetics and affinity determination.

Antibody-IL-15 fusion proteins (e.g., PD-1 antibody with IL-15 mutations as shown in Tables 1-2) were produced by transient transfection with the DNA plasmids of antibody heavy chain-IL-15 chimera, antibody heavy chain and antibody light chain in Expi-293 cells at a density of about $3\times10^6$ cells per mL. After five days of post-transfection, supernatant of the cells that contained the secreted antibody-IL-15 fusion proteins was harvested by centrifugation and subsequently filtered. The antibody-IL-15 fusion proteins were then purified from the cell supernatant using Protein A affinity chromatography on a MabSelectSuRe column (GE Lifesciences, Marlborough, Mass.), nickel affinity chromatography, ion-exchange chromatography on a Mono S 5/50 GL or Mono S 10/100 GL column (GE Lifesciences, Marlborough, Mass.) and size exclusion chromatography on a HiLoad 16/600 Superdex 200 prep grade or HiLoad 26/600 Superdex 200 prep grade column (GE Lifesciences, Marlborough, Mass.).

Example 2: Determination of Kinetics and Affinity of Human IL-15 Variants or Anti-PD-1-hIL-15 Fusion Proteins/IL-15Rα and IL-2Rβ Interactions at 37° C.

This example illustrates the kinetics and affinities of various human IL-15 variants binding to human IL-15Rα and human IL-2Rβ at 37° C.

All experiments were performed on a Biacore 8K or Biacore 4000 Surface Plasmon Resonance based biosensor (GE Lifesciences, Marlborough, Mass.). The anti-AVI tag sensor chips were prepared at 25° C. with a running buffer of 10 mM HEPES, 150 mM NaCl, 0.05% (v/v) Tween-20, pH 7.4. All surfaces of a Biacore CM4 sensor chip were activated with a 1:1 (v/v) mixture of 400 mM EDC and 100 mM NHS for 7 minutes, at a flow rate of 10 μL/min. An anti-Avi reagent (Rabbit Anti-Avi-tag, Genscript Catalog #A00674-200) was diluted to 30 μg/mL in 10 mM sodium acetate (pH 4.5) and injected on all flow cells for 7 minutes at 20 μL/min. All flow cells were blocked with 100 mM ethylenediamine in 200 mM Borate buffer pH 8.5 for 7 minutes at 10 μL/min.

All protein interaction experiments were performed at 37° C. using a running buffer of 10 mM HEPES, 150 mM NaCl, 0.05% (v/v) Tween-20, pH 7.4, 1 mg/mL BSA. For experiments performed on a Biacore 4000, Avi-tagged IL-15 variants were captured from undiluted supernatants onto spots 1 and 5 on flow cells 1, 2, 3 and 4 at a flow rate of 10 μL/min for 2 minutes. Different mutants were captured on each spot. Spots 2 and 4 on flow cells 1, 2, 3 and 4 were used as reference surfaces. Following capture of IL15 variants, analyte (buffer, 12.3 nM, 37 nM, 111 nM, 333 nM and 1 μM concentrations of human IL-15Rα or human IL-2Rβ) was injected at a flow rate of 30 μL/min in all flow cells for two minutes. After each analyte injection, dissociation was monitored for 5 minutes, followed by regeneration of all flow cells with three 30-second injections of 75 mM phosphoric acid. Buffer cycles were collected for each captured IL-15V49R mutant for double-referencing purposes (double-referencing as described in Myszka, D. G., Improving biosensor analysis. *J. Mol. Recognit.* 12, 279-284 (1999)). For kinetic analysis, the double-referenced sensorgrams were fit globally to a simple 1:1 Langmuir with mass transport binding model using Biacore 4000 Evaluation Software version 1.1 For steady-state affinity analysis, the double-referenced equilibrium binding responses were fit with a 1:1 Langmuir steady-state model using Biacore 4000 Evaluation Software version 1.1.

For experiments performed on a Biacore 8K, Avi-tagged IL-15 variants were captured from undiluted supernatants for 2 minutes at 10 μL/min on flow cell 2 in each channel, while flow cell 1 was used as a reference surface. A different IL-15 variants was captured in each channel. Following the capture of IL-15V49R mutants, analyte (buffer, 3.2 nM, 16 nM, 80 nM, 400 nM, 1840 nM human IL-15Rα and 0.8 nM, 4 nM, 20 nM, 100 nM, 500 nM human IL-2Rβ) was injected over both flow cells for 2 minutes at a flow rate of 30 μL/min. After each analyte injection, dissociation was monitored for 10 minutes followed by regeneration of all flow cells with three 30-second injections of 75 mM phosphoric acid. Buffer cycles were collected for each captured IL-15 variants for double-referencing purposes (double-referencing as described in Myszka, D. G. Improving biosensor analysis. *J. Mol. Recognit.* 12, 279-284 (1999)). For kinetic analysis, the double-referenced sensorgrams were fit globally to a simple 1:1 Langmuir with mass transport binding model using Biacore 8K Evaluation Software version 1.1.1.7442. For steady-state affinity analysis, the double-referenced equilibrium binding responses were fit with a 1:1 Langmuir steady-state model using Biacore 8K Evaluation Software version 1.1.1.7442.

The kinetics and affinity parameters for tested IL-15 variants are shown in Tables 1-2. The term "IL-15Rasu" refers to IL-15R alpha sushi domain.

The below example determines the kinetics and affinity of various anti-PD-1-hIL-15 fusion proteins binding to human IL-15Rα and human IL-2Rβ at 37° C. Experiments were performed on a Biacore T200 Surface Plasmon Resonance based biosensor (GE Lifesciences, Marlborough, Mass.).

Anti-human Fc sensor chips were prepared at 25° C. with a running buffer of 10 mM HEPES, 150 mM NaCl, 0.05% (v/v) Tween-20, pH 7.4. All surfaces of a Biacore CM4 sensor chip were activated with a 1:1 (v/v) mixture of 400 mM EDC and 100 mM NHS for 7 minutes, at a flow rate of 10 μL/min. An anti-human Fc reagent (Goat anti-human IgG Fc-γ specific, SouthernBiotech, Birmingham, Ala., Catalog #2014-01) was diluted to 50 μg/mL in 10 mM sodium acetate (pH 4.5) and injected on all flow cells for 7 minutes at 20 μL/min. All flow cells were blocked with 100 mM ethylenediamine in 200 mM Borate buffer pH 8.5 for 7 minutes at 10 μL/min.

All protein interaction experiments were performed at 37° C. using a running buffer of 10 mM HEPES, 150 mM NaCl, 0.05% (v/v) Tween-20, pH 7.4, 1 mg/mL BSA. Anti-PD-1-hIL-15 fusion proteins were captured at 10 μg/mL at a flow rate of 10 μL/min for 2 minutes. Different fusion proteins were captured in flow cells 2, 3 and 4. No protein was captured onto flow cell 1 which was used as a reference surface. Following capture of fusion proteins, analyte (buffer, 12.3 nM, 37 nM, 111 nM, 333 nM, 1000 nM and 3000 nM concentrations of human IL-15Rα or human IL-2Rβ) was injected at a flow rate of 30 μL/min in all flow cells for two minutes. After each analyte injection, dissociation was monitored for 5 minutes followed by regeneration of all flow cells with three 60-second injections of 75 mM phosphoric acid. Buffer cycles were collected for each captured fusion protein for double-referencing purposes (double-referencing as described in Myszka, D. G. Improving biosensor analysis. *J. Mol. Recognit.* 12, 279-284 (1999)). For kinetic analysis, the double-referenced sensorgrams were fit globally to a simple 1:1 Langmuir with mass transport binding model using Biacore T200 Evaluation Software version 2.0. For steady-state affinity analysis, the double-referenced equilibrium binding responses were fit with a 1:1 Langmuir steady-state model using Biacore T200 Evaluation Software version 2.0.

The kinetics and affinity parameters for anti-PD-1-hIL-15 variant fusion proteins are shown in Tables 3-5.

TABLE 1

Kinetics and affinity parameters for non-fusion human IL-15 variants that reduced human IL-15α binding:

| Mutants | hIL-15α kinetics $k_a$ (1/Ms) | $k_d$ (1/s) | $t_{1/2}$ (min) | hIL-15Rα $K_D$ (nM) | hIL-2Rβ $K_D$ (nM) | Lower hIL-15Rα affinity than V49R? |
|---|---|---|---|---|---|---|
| IL-15Rasu-IL-15 | N/A | N/A | N/A | No binding | 69.6* | — |
| IL-15 (wild-type) | 9.0E+06 | 2.1E−04 | 55.85 | 0.023 | 31 | — |
| V49R | N/A | N/A | N/A | 91.9* | 109* | — |
| V49A | 1.27E+06 | 1.11E−03 | 10.42 | 0.874 | N/A | No |
| V49E | N/A | N/A | N/A | 43.4* | N/A | No |
| V49G | 1.69E+06 | 7.33E−03 | 1.58 | 4.32 | N/A | No |
| V49H | N/A | N/A | N/A | 28.5* | N/A | No |
| V49K | N/A | N/A | N/A | 241* | 86.6* | Yes |
| V49N | 2.07E+06 | 3.85E−03 | 3.00 | 1.86 | N/A | No |
| V49Q | 1.56E+06 | 1.28E−02 | 0.91 | 8.17 | N/A | No |
| V49S | 2.06E+06 | 2.77E−03 | 4.17 | 1.34 | N/A | No |
| Y26H | N/A | N/A | N/A | 10.9* | 87* | No |
| Y26K | N/A | N/A | N/A | 146* | 75.7* | Yes |
| Y26R | N/A | N/A | N/A | 96.8* | 57.9* | Yes |
| E46G | N/A | N/A | N/A | 267* | 141* | Yes |

*A steady state affinity analysis was used due to fast kinetics

TABLE 2

Affinity parameters for non-fusion human IL-15 variants in the background of V49R mutation that reduced human IL-2Rβ binding:

| Position | Mutations | hIL-2Rβ $K_D$ (nM) | hIL-15Rα $K_D$ (nM) | Reduced hIL-2Rβ $K_D$ to >300 nM |
|---|---|---|---|---|
| IL-15^ | WT | 21.6 | 0.023 | N/A |
| IL-15Rasu-IL15^ | WT | 54.4 | N/A | N/A |
| V49 | R | 97.5 | 94.2 | No |
| N1 | A | 398 | 175 | Yes |
| N1 | D | 311 | 105 | Yes |
| N1 | K | >500 | 264 | Yes |
| N1 | S | 194 | 140 | No |
| N1 | H | 235 | 151 | No |
| N1 | R | 479* | 243 | Yes |
| N1 | E | 340 | 171 | Yes |
| N1 | T | 249 | 104 | No |
| N1 | Q | >500 | 115 | Yes |
| N1 | G | >500 | 160 | Yes |
| N1 | P | Ambiguous (LC) | Binds# (LC) | N/A |
| N1 | I | Ambiguous (LC) | Ambiguous (LC) | N/A |
| N1 | L | Binds# (LC) | Binds# (LC) | N/A |
| N1 | M | Binds# (LC) | Binds# (LC) | N/A |
| N1 | F | Binds# (LC) | Binds# (LC) | N/A |
| N1 | Y | Binds# | Binds# | N/A |
| N1 | W | Ambiguous (LC) | Ambiguous (LC) | N/A |
| N1 | V | Binds# (LC) | Binds# (LC) | N/A |
| N4 | A | >500 | 98 | Yes |
| N4 | D | 365 | 103 | Yes |
| N4 | K | No binding | 73.1 | Yes |
| N4 | S | No binding | 94.7 | Yes |
| N4 | H | 96.4 | 81.5 | No |
| N4 | R | Binds# | 56.1 | N/A |
| N4 | E | 311 | 79.8 | Yes |
| N4 | T | Ambiguous | 88.6 (approx.) | No |
| N4 | Q | >500 | 59.5 | Yes |
| N4 | G | >500 | 105 | Yes |
| N4 | P | Binds# | 356 | N/A |
| N4 | I | No binding | Binds# | Yes |
| N4 | L | 429 | 98.6 | Yes |

TABLE 2-continued

Affinity parameters for non-fusion human IL-15 variants in the background of V49R mutation that reduced human IL-2Rβ binding:

| Position | Mutations | hIL-2Rβ $K_D$ (nM) | hIL-15Rα $K_D$ (nM) | Reduced hIL-2Rβ $K_D$ to >300 nM |
|---|---|---|---|---|
| N4 | M | 233 | 88.1 | No |
| N4 | F | 247 | Binds# | No |
| N4 | Y | 117* | Binds# | Yes |
| N4 | W | 438 | 143 | No |
| N4 | V | Binds# | Binds# | N/A |
| S7 | A | 220 | 84 | No |
| S7 | D | >500 | 121 | Yes |
| S7 | K | >500 | 103 | Yes |
| S7 | N | >500 | 93.2 | Yes |
| S7 | H | 354 | 75.6 | Yes |
| S7 | R | >500 | 77 | Yes |
| S7 | E | >500 | 87.6 | Yes |
| S7 | T | >500 | 93.9 | Yes |
| S7 | Q | 215 | 88.1 | No |
| S7 | G | >500 | 147 | Yes |
| S7 | P | Binds# | >500 | N/A |
| S7 | I | Ambiguous (LC) | Ambiguous (LC) | N/A |
| S7 | L | Ambiguous (LC) | Ambiguous (LC) | N/A |
| S7 | M | Ambiguous (LC) | Ambiguous (LC) | N/A |
| S7 | F | Ambiguous (LC) | Ambiguous (LC) | N/A |
| S7 | Y | Ambiguous (LC) | Ambiguous (LC) | N/A |
| S7 | W | Ambiguous (LC) | Ambiguous (LC) | N/A |
| S7 | V | Ambiguous (LC) | Ambiguous (LC) | N/A |
| D8 | A | No binding | 102 | Yes |
| D8 | K | No binding | 101 | Yes |
| D8 | S | No binding | 124 | Yes |
| D8 | N | No binding | 119 | Yes |
| K10 | A | 321 | 150 | Yes |

TABLE 2-continued

Affinity parameters for non-fusion human IL-15 variants in the background of V49R mutation that reduced human IL-2Rβ binding:

| Position | Mutations | hIL-2Rβ $K_D$ (nM) | hIL-15Rα $K_D$ (nM) | Reduced hIL-2Rβ $K_D$ to >300 nM |
|---|---|---|---|---|
| K10 | D | >500 | 270 | Yes |
| K10 | S | 496 | 195 | Yes |
| K10 | N | 230 | 128 | No |
| K10 | H | 114 | 85.6 | No |
| K10 | R | 146 | 94.5 | No |
| K10 | E | 360 | 126 | Yes |
| K10 | T | Ambiguous (LC) | Ambiguous (LC) | N/A |
| K10 | Q | 250 | 100 | No |
| K10 | G | >500 | 209 | Yes |
| K10 | P | No binding | Binds# | Yes |
| K10 | I | Ambiguous | Binds# | N/A |
| K10 | L | 348 | 124 | Yes |
| K10 | M | 391 | 122 | Yes |
| K10 | F | Binds# (LC) | Binds# (LC) | N/A |
| K10 | Y | Ambiguous (LC) | Ambiguous (LC) | N/A |
| K10 | W | 185 | 101 | No |
| K10 | V | Binds# | Binds# | N/A |
| K11 | A | 206 | 191 | No |
| K11 | D | >500 | 242 | Yes |
| K11 | S | 453 | 194 | Yes |
| K11 | N | 291 | 217 | No |
| K11 | H | 104 | 147 | No |
| K11 | R | 138 | 140 | No |
| K11 | E | 160 | 159 | No |
| K11 | T | 225 | 169 | No |
| K11 | Q | 107 | 156 | No |
| K11 | G | Binds# | Binds# | N/A |
| K11 | P | No binding | Binds# | N/A |
| K11 | I | 76 | 95.8 | No |
| K11 | L | 92.2 | 142 | No |
| K11 | M | 180 | Binds# | No |
| K11 | F | 162 | Binds# | No |
| K11 | Y | 143 | 219 | No |
| K11 | W | 346* | 361 | Yes |
| K11 | V | 110 | 142 | No |
| S29 | A | 274 | 154 | No |
| S29 | D | 238 | 121 | No |
| S29 | K | 248 | 261 | No |
| S29 | N | 322 | 154 | Yes |
| D30 | A | 273 | 151 | No |
| D30 | K | 351 | 158 | Yes |
| D30 | S | 249 | 146 | No |
| D30 | N | 163 | 94 | No |
| D30 | H | 149 | 121 | No |
| D30 | R | 290 | 155 | No |
| D30 | E | 165 | 124 | No |
| D30 | T | 269 | 184 | No |
| D30 | Q | 197 | 111 | No |
| D30 | G | 513* | Binds# | Yes |
| D30 | P | Binds# | No binding | N/A |
| D30 | I | 201 | 197 | No |
| D30 | L | 277 | 237 | No |
| D30 | M | 238 | 142 | No |
| D30 | F | 213 | 166 | No |
| D30 | Y | 231 | 159 | No |
| D30 | W | 321 | Binds# | Yes |
| D30 | V | 258 | 153 | No |
| V31 | A | 269 | 129 | No |
| V31 | K | >500 | No binding | Yes |
| V31 | S | >500 | 265 | Yes |
| V31 | D | >500 | >500 | Yes |
| H32 | A | 218 | 152 | No |
| H32 | K | 149 | 92.8 | No |
| H32 | S | 176 | 110 | No |
| H32 | D | 123 | 85.5 | No |
| H32 | N | 124 | 85.9 | No |
| H32 | R | 156 | 131 (approx.) | No |
| H32 | E | 130 | 108 | No |
| H32 | T | 186 | Binds# | No |

TABLE 2-continued

Affinity parameters for non-fusion human IL-15 variants in the background of V49R mutation that reduced human IL-2Rβ binding:

| Position | Mutations | hIL-2Rβ $K_D$ (nM) | hIL-15Rα $K_D$ (nM) | Reduced hIL-2Rβ $K_D$ to >300 nM |
|---|---|---|---|---|
| H32 | Q | 147 | 64 | No |
| H32 | G | 459 | 249 | Yes |
| H32 | P | 146 | 162 | No |
| H32 | I | 110 | 113 | No |
| H32 | L | 159 | 189 | No |
| H32 | M | 161 | 134 | No |
| H32 | F | 315* | Binds# | Yes |
| H32 | Y | Binds# | Binds# | N/A |
| H32 | W | 376 | Binds# | Yes |
| H32 | V | 247 | 99.8 | No |
| D61 | A | >500 | 78.2 | Yes |
| D61 | K | No binding | 116 | Yes |
| D61 | S | No binding | 102 | Yes |
| D61 | N | No binding | 121 | Yes |
| E64 | A | >500 | 130 | Yes |
| E64 | K | No binding | 164 | Yes |
| E64 | N/S | >500 | 130 | Yes |
| E64 | N | >500 | 115 | Yes |
| E64 | D | 291 | 108 | No |
| E64 | H | >1000 | 112 | Yes |
| E64 | R | Binds# | Binds# | N/A |
| E64 | T | >500 | 141 | Yes |
| E64 | Q | >500 | 127 | Yes |
| E64 | G | Binds# | Binds# | N/A |
| E64 | P | Ambiguous (LC) | Ambiguous (LC) | N/A |
| E64 | I | Ambiguous (LC) | Ambiguous (LC) | N/A |
| E64 | L | Ambiguous (LC) | Ambiguous (LC) | N/A |
| E64 | M | Ambiguous (LC) | Ambiguous (LC) | N/A |
| E64 | F | Ambiguous (LC) | Ambiguous (LC) | N/A |
| E64 | Y | Ambiguous (LC) | Ambiguous (LC) | N/A |
| E64 | W | Ambiguous (LC) | Ambiguous (LC) | N/A |
| E64 | V | Ambiguous (LC) | Binds# | N/A |
| N65 | A | No binding | 202 | Yes |
| N65 | K | 193 | 201 | No |
| N65 | S | No binding | 158 | Yes |
| N65 | D | >500 | 121 | Yes |
| 168 | A | >500 | 113 | Yes |
| 168 | K | No binding | 94.2 | Yes |
| 168 | S | No binding | 104 | Yes |
| 168 | D | No binding | 106 | Yes |
| 168 | H | >1000 | 87.6 | Yes |
| 168 | R | >500 | 102 | Yes |
| 168 | T | >500 | 76.3 | Yes |
| 168 | Q | Ambiguous | 132 | N/A |
| 168 | G | Binds# | 101 | N/A |
| 168 | P | No binding | No binding | Yes |
| 168 | N | >1000 | 85 | Yes |
| 168 | L | 245 | 73.6 | No |
| 168 | M | 1000 | 96.2 | Yes |
| 168 | F | >1000 | 78.5 | Yes |
| 168 | Y | >1000 | 92.9 | Yes |
| 168 | W | Binds# | 93.7 | N/A |
| 168 | V | 296 | 104 | No |
| 168 | E | Binds# | 122 | N/A |
| L69 | A | >500 | 82.9 | Yes |
| L69 | K | No binding | No binding | Yes |
| L69 | S | >500 | 78.2 | Yes |
| L69 | D | >500 | 65.6 | Yes |
| L69 | H | Binds# | 54.5 | N/A |
| L69 | R | Ambiguous | 111 | N/A |
| L69 | T | >1000 | 63.6 | Yes |
| L69 | Q | Binds# | 43.3 (approx.) | N/A |
| L69 | G | Binds# | Binds# | N/A |

TABLE 2-continued

Affinity parameters for non-fusion human IL-15 variants in the background of V49R mutation that reduced human IL-2Rβ binding:

| Position | Mutations | hIL-2Rβ $K_D$ (nM) | hIL-15Rα $K_D$ (nM) | Reduced hIL-2Rβ $K_D$ to >300 nM |
|---|---|---|---|---|
| L69 | P | No binding | No binding | Yes |
| L69 | I | 306 | 93.1 | Yes |
| L69 | N | Binds# | 44 | N/A |
| L69 | M | ≥1000 | 74.5 | Yes |
| L69 | F | Ambiguous | 106 | N/A |
| L69 | Y | Ambiguous | 137 | N/A |
| L69 | W | Ambiguous (LC) | Ambiguous (LC) | N/A |
| L69 | V | >1000 | 85.5 | Yes |
| L69 | E | >1000 | 47.8 | Yes |
| N72 | A | 148 | 117 | No |
| N72 | D | 101 | 105 | No |
| N72 | K | >500 | 101 | Yes |
| N72 | S | 182 | 118 | No |
| Q108 | A | 462 | 161 | Yes |
| Q108 | D | 215 | 125 | No |
| Q108 | K | 249 | 85.4 | No |
| Q108 | S | 290 | 144 | No |
| M109 | A | >500 | 198 | Yes |
| M109 | K | >500 | 215 | Yes |
| M109 | S | 362 | 190 | Yes |
| M109 | D | 339 | 288 | Yes |
| I111 | A | 375 | 173 | Yes |
| I111 | K | 397 | 199 | Yes |
| I111 | S | >500 | 223 | Yes |
| I111 | D | >500 | 214 | Yes |

^Wild-type IL-15 and IL-15Rasu-IL15 do not contain the V49R mutation

*Affinities reported are from kinetic fits (all other $K_D$ values mentioned are steady state $K_D$ values)

#Fits could not be obtained because of low responses

LC Low Capture of supernatant

TABLE 3

Affinity parameters for anti-PD-1-hIL-15 variant fusion proteins to human IL-2Rβ binding:

| Mutants | hIL-2Rβ kinetics | | | |
|---|---|---|---|---|
| | $k_a$ (1/Ms) | $k_d$ (1/s) | $t_{1/2}$ (s) | $K_D$ (nM) |
| xmPD-1-hIL15Rasu-hIL15 | 2.36E+06 | 9.88E−02 | 7.00 | 41.8 |
| xmPD-1-hIL15Rasu-hIL15(E64Q/D30N) | N/A | N/A | N/A | 271* |
| xmPD-1-hIL15Rasu-hIL15(E64Q/D30N/I68S) | N/A | N/A | N/A | >3000 |
| xmPD-1-hIL15Rasu-hIL15(E64Q/D30N N4K) | N/A | N/A | N/A | 767* |
| xmPD-1-hIL15Rasu-hIL15(E64Q/D30N/M109A) | N/A | N/A | N/A | 315* |
| xmPD-1-hIL15Rasu-hIL15(E64Q/D30N/I68S/M109A) | N/A | N/A | N/A | >1500 |
| xmPD-1-hIL15Rasu-hIL15(E64Q/D30N/N4K/M109A) | N/A | N/A | N/A | >3000 |
| Ab8.8-hIL15Raus-hIL15 | 2.62E+06 | 9.71E−02 | 7.14 | 37.1 |
| xmPD-1-hIL15(wild-type) | N/A | N/A | N/A | 561 |
| xmPD-1-hIL15 V49R | N/A | N/A | N/A | 494* |
| xmPD-1-hIL15 V49R/E46G | N/A | N/A | N/A | 437* |
| xmPD-1-hIL15 V49R/E46G/N1A/D30N | N/A | N/A | N/A | 433* |
| xmPD-1-hIL15 V49R/E46G/N1G/E64Q/D30N | N/A | N/A | N/A | >1500 |
| xmPD-1-hIL15 V49R/E46G/N1G/N4Q/D30N | N/A | N/A | N/A | >1500 |
| xmPD-1-hIL15 V49R/E46G/E64Q/D30N | N/A | N/A | N/A | >3000 |
| xmPD-1-hIL15 V49R/Y26K/E64Q/D30N | N/A | N/A | N/A | >1500 |
| xmPD-1-hIL15 V49R/E46G/E64Q/D30N/I68S | N/A | N/A | N/A | No binding |
| xmPD-1-hIL15 V49R/E46G/E64Q/D30N/N4K | N/A | N/A | N/A | No binding |
| xmPD-1-hIL15 V49R/E46G/E64Q/D30N/M109A | N/A | N/A | N/A | >3000 |
| xmPD-1-hIL15 V49R/E46G/E64Q/D30N/I68S/M109A | N/A | N/A | N/A | No binding |
| xmPD-1-hIL15 V49R/E46G/E64Q/D30N/N4K/M109A | N/A | N/A | N/A | No binding |
| xmPD-1-hIL15 V49R/E46Q | N/A | N/A | N/A | 560* |
| xmPD-1-hIL15 V49R/E53Q | N/A | N/A | N/A | 590* |
| xmPD-1-hIL15 V49R/E93Q | N/A | N/A | N/A | 451* |
| xmPD-1-hIL15 NQ mutant | N/A | N/A | N/A | 518* |
| xmPD-1-hIL15 NQ-3d | N/A | N/A | N/A | 446* |
| xmPD-1-hIL15 NQ-2a | N/A | N/A | N/A | 514* |
| xmPD-1-hIL15 NQ-2b | N/A | N/A | N/A | 724* |
| xmPD-1-hIL15 NQ-2c | N/A | N/A | N/A | 262* |
| Ab8.8-hIL15 NQ mutant | N/A | N/A | N/A | 506* |

*A steady state affinity analysis was used due to fast kinetics

TABLE 4

Affinity parameters for anti-PD-1-hIL-15 variant fusion proteins to human IL-15Rα binding:

| Mutants | hIL-15Rα kinetics $k_a$ (1/Ms) | $k_d$ (1/s) | $t_{1/2}$ (s) | $K_D$ (nM) |
|---|---|---|---|---|
| xmPD-1-hIL15Rasu-hIL15 | | No binding | | |
| xmPD-1-hIL15Rasu-hIL15(E64Q/D30N) | | No binding | | |
| xmPD-1-hIL15Rasu-hIL15(E64Q/D30N/I68S) | | No binding | | |
| xmPD-1-hIL15Rasu-hIL15(E64Q/D30N N4K) | | No binding | | |
| xmPD-1-hIL15Rasu-hIL15(E64Q/D30N/M109A) | | No binding | | |
| xmPD-1-hIL15Rasu-hIL15(E64Q/D30N/I68S/M109A) | | No binding | | |
| xmPD-1-hIL15Rasu-hIL15(E64Q/D30N/N4K/M109A) | | No binding | | |
| Ab8.8-hIL15Raus-hIL15 | | No binding | | |
| xmPD-1-hIL15(wild-type) | 4.31E+06 | 3.63E−04 | N/A | 0.084 |
| xmPD-1-hIL15 V49R | N/A | N/A | N/A | 119* |
| xmPD-1-hIL15 V49R/E46G | | No binding | | |
| xmPD-1-hIL15 V49R/E46G/N1A/D30N | | No binding | | |
| xmPD-1-hIL15 V49R/E46G/N1G/E64Q/D30N | | No binding | | |
| xmPD-1-hIL15 V49R/E46G/N1G/N4Q/D30N | | No binding | | |
| xmPD-1-hIL15 V49R/E46G/E64Q/D30N | | No binding | | |
| xmPD-1-hIL15 V49R/Y26K/E64Q/D30N | | No binding | | |
| xmPD-1-hIL15 V49R/E46G/E64Q/D30N/I68S | | No binding | | |
| xmPD-1-hIL15 V49R/E46G/E64Q/D30N/N4K | | No binding | | |
| xmPD-1-hIL15 V49R/E46G/E64Q/D30N/M109A | | No binding | | |
| xmPD-1-hIL15 V49R/E46G/E64Q/D30N/I68S/M109A | | No binding | | |
| xmPD-1-hIL15 Vs49R/E46G/E64Q/D30N/N4K/M109A | | No binding | | |
| xmPD-1-hIL15 V49R/E46Q | | No binding | | |
| xmPD-1-hIL15 V49R/E53Q | N/A | N/A | N/A | >1500 |
| xmPD-1-hIL15 V49R/E93Q | N/A | N/A | N/A | 943* |
| xmPD-1-hIL15 NQ mutant | | No binding | | |
| xmPD-1-hIL15 NQ-3d | | No binding | | |
| xmPD-1-hIL15 NQ-2a | N/A | N/A | N/A | >3000 |
| xmPD-1-hIL15 NQ-2b | | No binding | | |
| xmPD-1-hIL15 NQ-2c | 1.06E+06 | 2.84E−02 | 24.4 | 26.8 |
| Ab8.8-hIL15 NQ mutant | | No binding | | |

*A steady state affinity analysis was used due to fast kinetics

TABLE 5

Affinity parameters for anti-human PD-1-hIL-15 variant fusion proteins to human PD-1 binding:

| Mutants | hPD-1 kinetics $k_a$ (1/Ms) | $k_d$ (1/s) | $t_{1/2}$ (s) | $K_D$ (nM) |
|---|---|---|---|---|
| Ab8.8-hIL15Raus-IL15 | N/A | N/A | N/A | No binding |
| xhPD1-hIL15Rasu-IL15 | 1.63E+05 | 5.41E−04 | 1281.2 | 3.32 |
| xhPD1-hIL15 NQ mutant | 1.73E+05 | 5.96E−04 | 1163.8 | 3.44 |

Example 3: Construction of Reporter Cell Lines with Constitutive Expression of the IL-15 Receptor and Inducible Expression of PD-1

This example demonstrates a method for establishing useful reporter cell lines to evaluate the bioactivity of IL-15-based molecules.

To assay the IL-15-based molecules described herein, a reporter cell line that has a functional response to IL-15 was generated and was used to assay the effect of PD-1-target-driven activity. To this end, reporter cell lines were constructed with the following properties: (1) constitutive expression of functional IL-15 signaling receptors: IL-2Rβ (also known as CD122), and common gamma chain (also known as CD132); and (2) inducible expression of either human or mouse PD-1.

A lentiviral system was used as described previously by Metzger, T., et al., Cancer Res. July 1; 76 (13):3684-9. (2016)). To express full-length human IL-2Rβ, plasmid pRF791 was also generated. Briefly, cDNA sequences encoding the TurboGFP fluorescent protein followed by a short glycine-serine linker sequence, the viral T2A sequence, and the full length human CD122 (IL-2Rβ) sequence were cloned into a lentiviral transfer vector so that they were expressed under the control of the EF1alpha promoter. pRF791 was used to generate lentiviral particles as described in Metzger, T., et al. (2016), and the resulting virus was used to transduce the murine 32D cell line, which is normally grown in media as described by American Type Culture Collection (ATCC). This cell line was chosen because it expresses only the common gamma chain, and not mouse IL2Rb or mouse IL-15Ralpha, and has also been used as a host to assay IL-15 bioactivity previously. (See, e.g., Zhu, X., et. al., J Immunol. 2009 Sep. 15; 183(6):3598-607. Transduced cells were identified by resistance to 100 μg/mL blasticidin and by GFP fluorescence. A blasticidin-resistant, GFP-expressing population of cells were selected and maintained as line polyclonal line 32D[pRF791].

To express human or mouse PD-1 under the control of the doxycycline-inducible TetOn3G promoter, cDNA sequences encoding the mCherry fluorescent protein followed by a short glycine-serine linker sequence, the viral T2A sequence, and full-length human or mouse PD-1 were cloned into the lentiviral transfer vector pLVX-SFFV-Puro-P2A-TetOn3G (see, e.g., Metzger et al. (2016)). The resulting vectors, pRF768 (expressing human PD-1) and pRF770 (expressing mouse PD-1) were each used to generate lentiviral particles as described in Metzger, T., et al. (2016), and the resulting viruses were used to transduce the 32D [pRF791] cell line. Transduced cells were identified by resistance to 100 μg/mL blasticidin plus 10 ug/mL Puromycin, and by GFP and mCherry fluorescence. Blasticidin-resistant, puromycin-resistant, GFP-expressing population of cells were selected and maintained as polyclonal line 32D[pRF768+pRF791] or 32D[pRF770+[pRF791], depending on whether they were transduced with virus from pRF768 or pRF770, respectively.

Inducible expression of mCherry-PD-1 was confirmed in 32D[pRF768+pRF791] and 32D[pRF770+pRF791] by addition of doxycycline (to 1 ug/mL final concentration) for 12-16 hours, followed by analysis of mCherry expression by flow cytometry. Expression of IL-2Rb and PD-1 were also confirmed by staining with antibodies specific for CD122 (IL-2Rβ) or PD-1, respectively.

To establish clonal cell lines, 32D[pRF768+pRF791] or 32D[pRF770+pRF791] cells were induced with 1 ug/mL doxycycline for 12-16 hours, and then analyzed by flow cytometry for GFP and mCherry fluorescence. Single cells of each cell line that fell within the top decile of fluorescence intensity were sorted into unique wells of a 96-well plate and cultured for 2 weeks until small colonies of cells appeared. These colonies were expanded to generate single cell cloned lines, which were confirmed by flow cytometry for transgene expression.

Example 4: Binding Assay of Antibody-IL15 Chimeric Molecules to a Reporter Cell Line This Example describes a method to assay the direct binding of antibody-cytokine fusion molecules to cells expressing the IL-15 receptor (CD122 plus CD132), either with or without expression of the antibody binding target.

To detect the binding of antibody-IL-15 molecules to cells, approximately 200 micrograms of each of the purified, recombinant molecules were labeled with Alexa647 fluorophore using a the Click-IT Alexa Fluor 647 sDIBO Alkyne kit and following the manufacturer's protocol. The antibodies and the chimeric molecules described in this and all subsequent Examples are summarized in Table 6, below:

TABLE 6

List of molecules utilized in all following Examples:

| Name | Relevant SEQ IDs | Brief description |
|---|---|---|
| xmPD-1 | 12 (VH) + 64 (CH1-hinge-IgG2dA-D265A-CH2—CH3) + 30 (LC: VK-CK) | Anti-mouse PD-1 (clone F12.3) with human IgG2dA constant regions |
| xmPD-1-IL15RaSu-IL15* | 28 (R-arm) + 22 (E-arm) + 30 | Anti-mouse PD-1 (clone F12.3) IgG fusion with human IL15Ra Sushi domain—human IL15 (wildtype mature protein sequence) |
| xmPD-1-IL15 NQ* | 28 + 29 + 30 | Anti-mouse PD-1 (clone F12.3) IgG fusion with human IL15 NQ variant (6 mutations D22N/Y26F/E46Q/E53Q/E89Q/E93Q of SEQ ID NO: 1, eliminate binding to IL-15Ralpha) |
| xmPD-1-IL15 NQ-2a | 28 + 30 + 58 | Anti-mouse PD-1 (clone F12.3) IgG fusion with human IL15 NQ-2a variant (reduce binding to IL-15Ralpha) |
| xmPD-1-IL15 NQ-2b | 28 + 30 + 59 | Anti-mouse PD-1 (clone F12.3) IgG fusion with human IL15 NQ variant (reduce binding to IL-15Ralpha) |
| xmPD-1-IL15 NQ-3d | 28 + 30 + 61 | Anti-mouse PD-1 (clone F12.3) IgG fusion with human IL15 NQ variant (reduce binding to IL-15Ralpha) |
| xmPD-1-IL15 m1 | 86 + 30 + 88 | Anti-mouse PD-1 (clone F12.3) IgG fusion with human IL15 m1 variant (4 mutations V49R/E46G/N1A/D30N of SEQ ID NO: 1, eliminate binding to IL-15Ralpha, reduce binding to IL-2Rbeta-gamma) |
| xmPD-1-IL15 m2 | 87 + 30 + 88 | Anti-mouse PD-1 (clone F12.3) IgG fusion with human IL15 m2 variant (5 mutations V49R/E46G/N1G/E64Q/D30N of SEQ ID NO: 1, eliminate binding to IL-15Ralpha, reduce binding to IL-2Rbeta-gamma) |
| xhPD-1-IL15 m1 | 74 + 65 + 89 | Anti-human PD-1 (VH1-69b/VK1-39) IgG fusion with human IL15 m1 variant (4 mutations V49R/E46G/N1A/D30N of SEQ ID NO: 1, eliminate binding to IL-15Ralpha, reduce binding to IL-2Rbeta-gamma) |

TABLE 6-continued

| List of molecules utilized in all following Examples: | | |
|---|---|---|
| Name | Relevant SEQ IDs | Brief description |
| xhPD-1-IL15 m2 | 74 + 65 + 90 | Anti-human PD-1 (VH1-69b/VK1-39) IgG fusion with human IL15 m2 variant (5 mutations V49R/E46G/N1G/E64Q/D30N of SEQ ID NO: 1, eliminate binding to IL-15Ralpha, reduce binding to IL-2Rbeta-gamma) |

*Mutant versions of these proteins are indicated in the text with the format "original amino acid-residue number-new amino acid", where residue number corresponds to the amino acid sequence listing of human IL-15 as shown in SEQ ID 1.

The following cell lines were suspended in growth medium to 0.7*10^6 cells/mL and, cultured for 16 hrs: 1) untransduced 32D (parental line); 2) 32D[pRF770+pRF791]; and 3) 32D[pRF770+pRF791] grown in the presence of 1 ug/mL doxycycline, to induce PD-1 expression. Cultures were then resuspended to a final concentration of 1.0*10^6 cells/mL, and 0.1 mL of each suspension was plated into separate wells of a 96-well round-bottom plate, of sufficient number required for the experiment. Each Alexa647-labeled antibody or antibody-cytokine chimeric proteins were then added to a unique well to obtain a final concentration of 500 nM, 100 nM, 10 mM, 1 nM, 0.1 nM, 0.01 nM, or 0.001 nM in a given well. Plates were incubated at 4° C. for 30', and then the cells were pelleted by centrifugation (300×g, 5') and resuspended in 0.2 mL of PBS. This wash step was repeated twice. Upon final resuspension, the cells were analyzed on an LSRII flow cytometer. Data were analyzed using FlowJo version 10. Cells that exhibited a fluorescence in the Alexa647 channel above background (as defined by cells to which no labeled antibody-cytokine chimera had been added) were scored as positive for binding. The percent of Alexa647-positive cells as a function of added labeled protein concentration is shown in FIGS. 2A-2D.

Figure 1A:
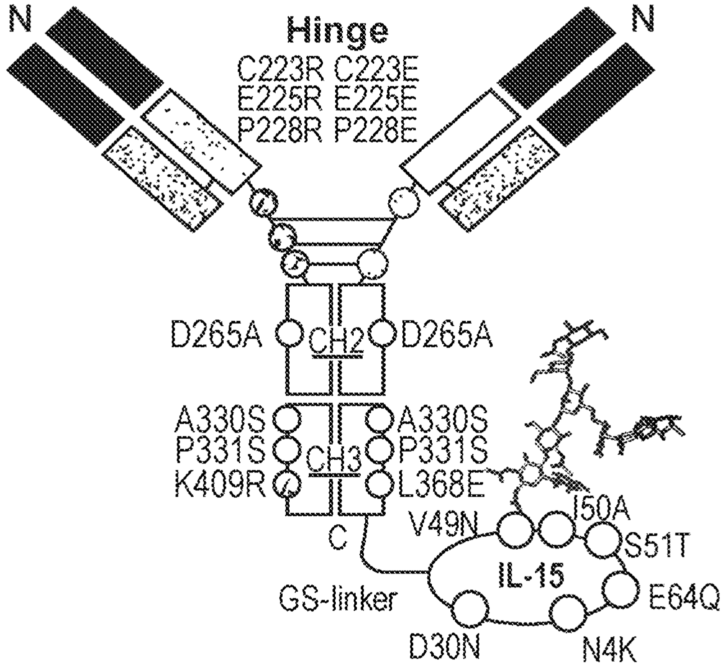
Figure 1B:
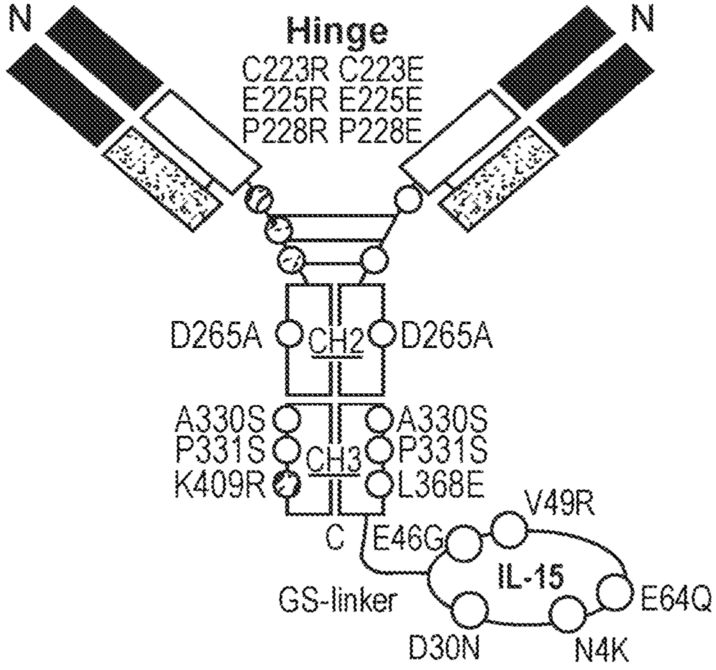
Figure 1C:
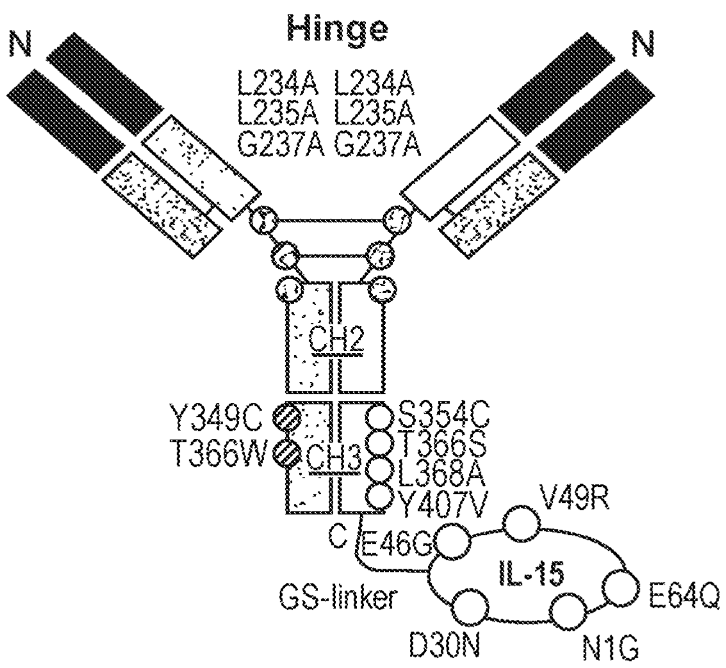
Figure 1D:
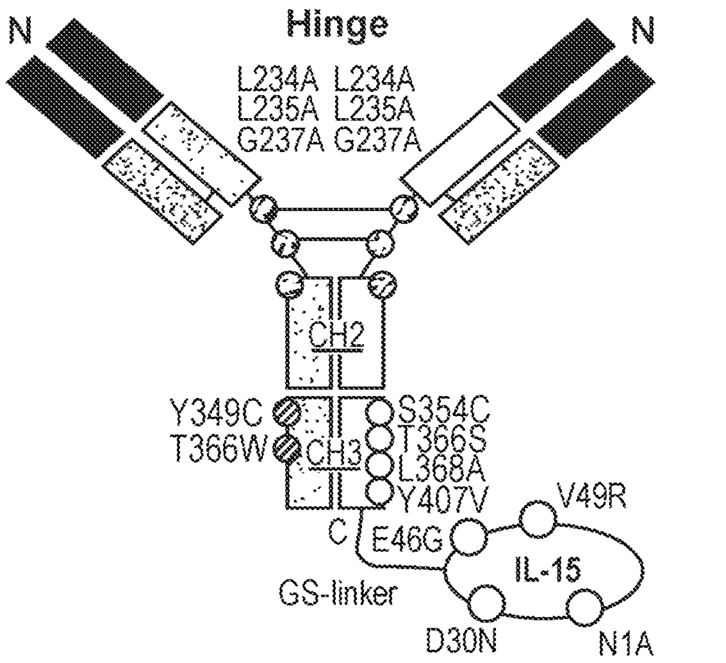
Figure 2A:
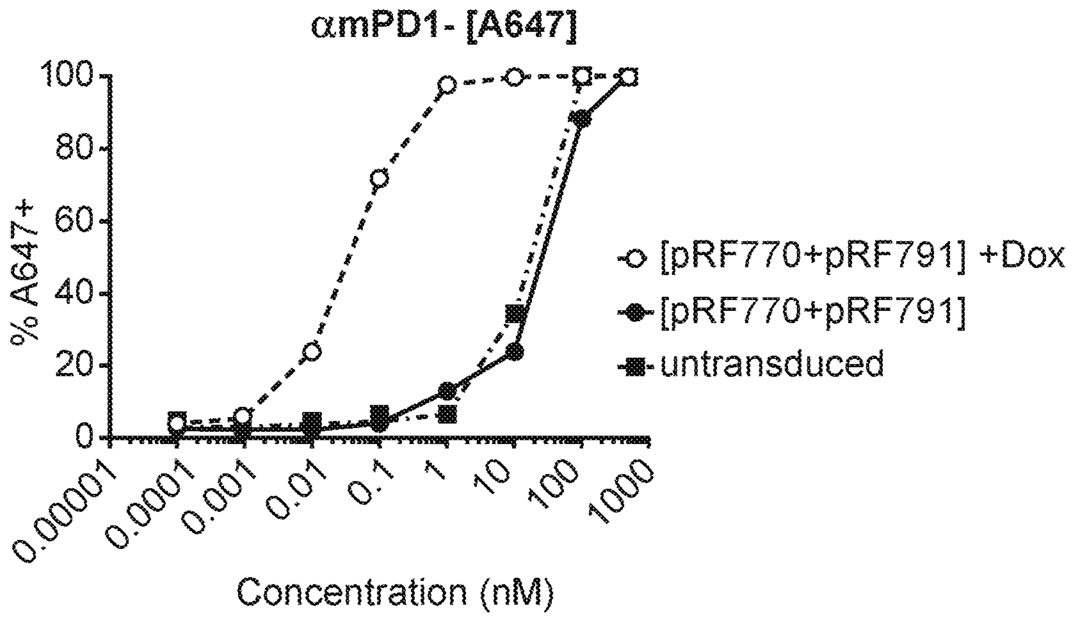
Figure 2B:
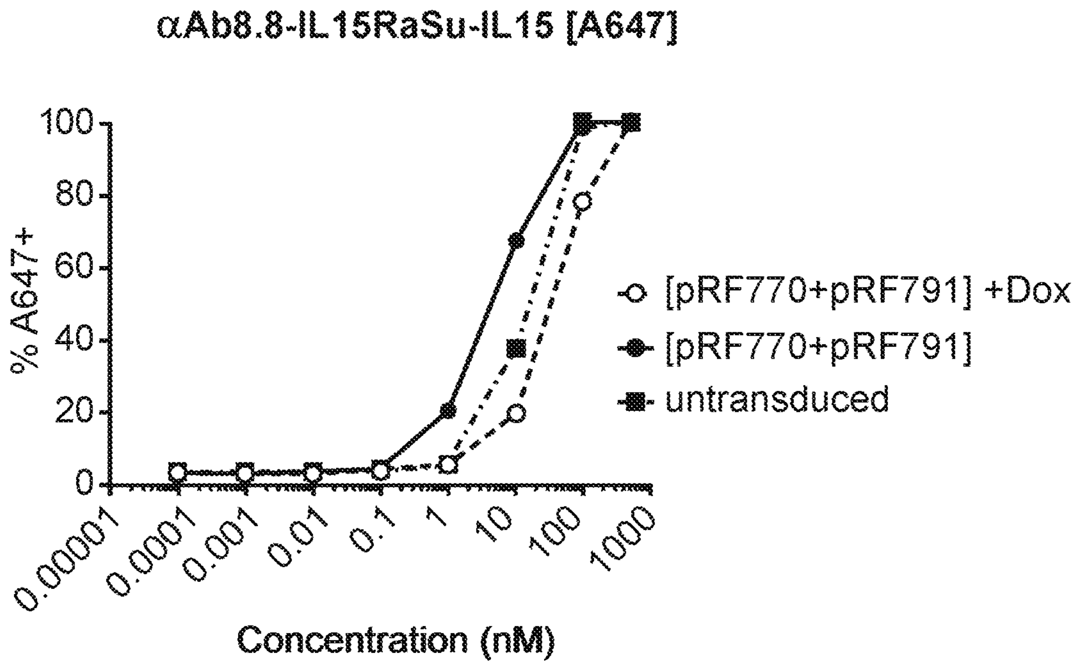
Figure 2C:
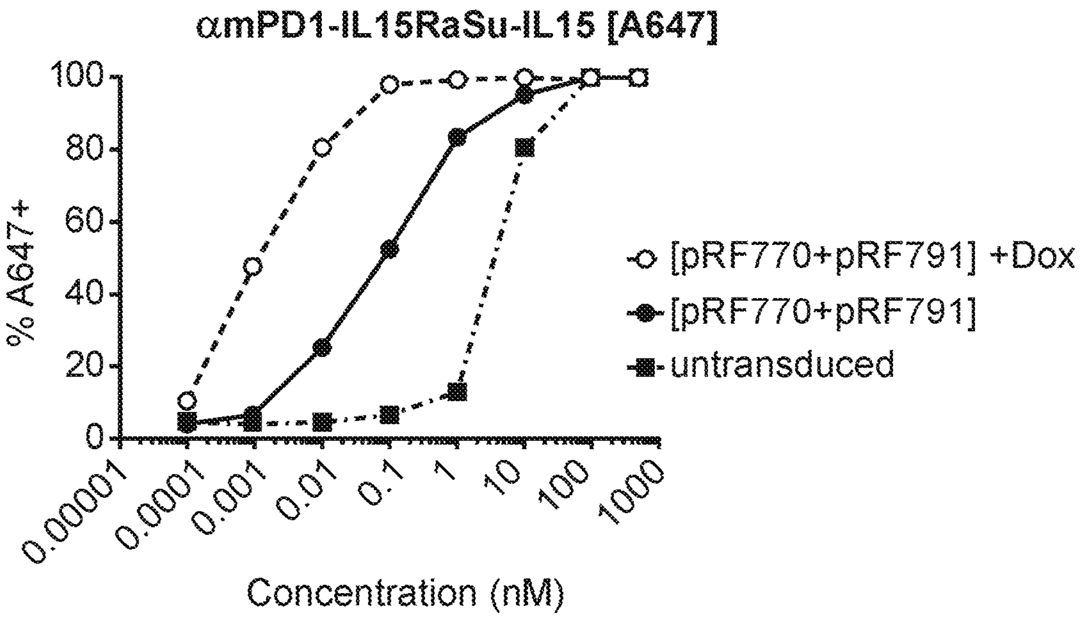
Figure 2D:
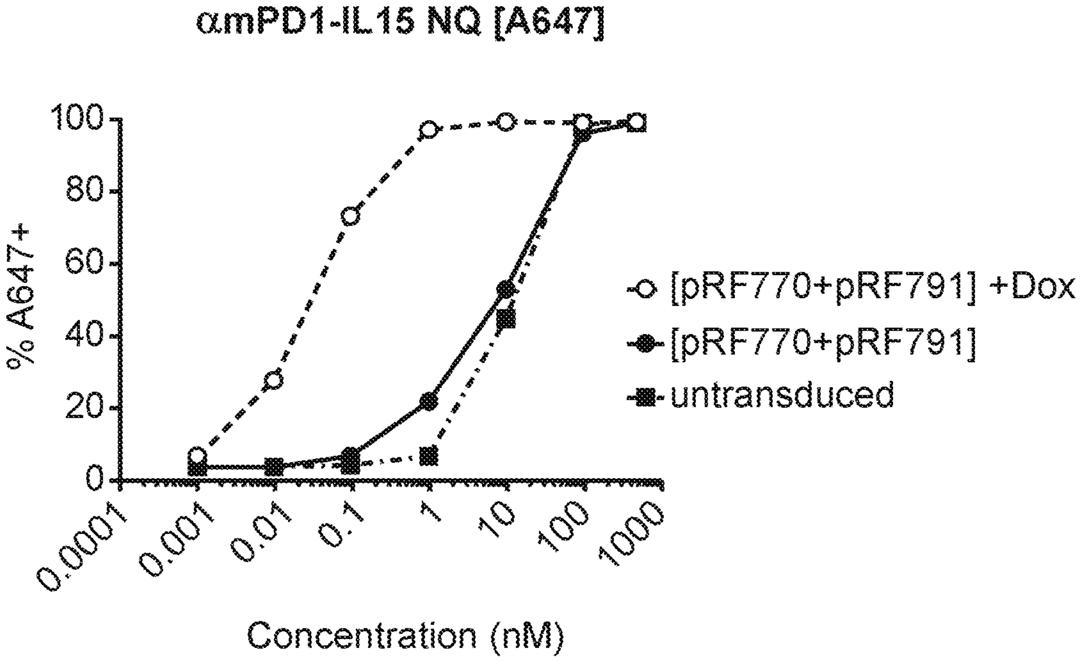

Each labeled molecule that featured an anti-mouse PD-1 moiety was able to bind to PD-1 expressing cells ("[pRF770+pRF791]+Dox") in a concentration-dependent manner, even at low picomolar final concentrations. The xmPD1-IL15RaSu-IL-15 fusion molecule (FIG. 2C) also exhibited more modest binding to cells expressing only CD122 plus CD132 ("[pRF770+pRF791]"); in contrast, the anti-mouse PD1-IL15 NQ variant showed reduced binding to these same type of cells (FIG. 2D). The isotype control antibody version (Ab8.8-IL15RaSu-IL15) only exhibited binding to any of the cells at the highest tested final protein concentrations (FIG. 2B). All four recombinant proteins tested showed background levels of binding to the 32D parent line at relatively high concentrations (>=10 nM of each compound) as well.

This example demonstrates that the anti-PD-1 antibody portion of the antibody-IL-15 chimeric proteins is a key determinant of directing protein binding to cells. The assay also reveals a difference between wildtype IL-15 and the NQ mutein in the ability of each to bind to cells expressing CD122 plus CD132 (in an antibody or PD-1-independent manner).

Example 5: In Vitro Functional Assay of Anti-Mouse PD-1-IL15 Chimeric Molecules Using a Reporter Cell Line This example describes a functional activity assay of an antibody-cytokine fusion molecule to cells expressing the IL-15 receptor (CD122 plus CD132), either with or without expression of the antibody binding target.

In this example, the ability of anti-mouse PD-1-IL15 chimeric fusion proteins to trigger downstream intracellular signaling in a reporter cell line 32D[pRF770+pRF791] was measured. The cell line 32D[pRF770+pRF791] expresses human CD122 along with endogenous mouse CD132 (common gamma chain), and can express doxycycline-inducible mouse PD-1. The activation of CD122/CD132 downstream signaling was measured by monitoring relative changes in phosphorylated STAT5 (pSTAT5), which is known to be a downstream consequence of IL-15 signaling (see for example: Steel J C, Waldmann T A, Morris J C. Trends Pharmacol Sci. 2012 January; 33(1):35-41.) The 32D [pRF770+pRF791] cells were resuspended to a concentration of 0.4-0.8*10e6 cells/mL in growth medium and grown overnight (12-16 hrs) either in the presence or absence of 1 μg/mL final concentration of doxycycline. Cells were collected by centrifugation (230×g, 5 min), washed once into growth medium lacking IL-3 and calf serum, and then resuspended at a final concentration of 1.0*10"6 cells/mL and incubated at 37° C. for 4 hours. Of the single-cell cloned lines, approximately 40,000-50,000 of the doxycycline-induced cells and 150,000-160,000 of the non-doxycycline cells were combined and added to each well. For non-single-cell-sorted lines, we routinely utilized cell populations which, upon doxycycline induction, demonstrated approximately 20-30% detectable mCherry expression by flow cytometric analysis. Recombinant protein compounds of interest were added to each well such that the final concentration of each was between 500 nM and 0.1 pM. Triplicate wells for each condition were set up identically. Plates were incubated in a cell culture incubator at 37° C. for 30', and cells were then pelleted by centrifugation (230×g, 5'). Paraformaldehyde was then immediately added to each well (4% final concentration, in PBS), the cells were mixed gently by pipetting up and down once to prevent clumping, and then incubated at 37° C. for 15 min. Cells were then pelleted by centrifugation (230×g, 5') and washed with Phosphate Buffered Saline (PBS) solution. This step was repeated two additional times. Residual PBS was carefully aspirated and 0.1 mL of cold (−20° C.) methanol was added, followed by gentle pipetting once to prevent clumping. Plates were sealed with foil and immediately placed in a −20° C. freezer for at least 1 hr and up to several days (generally, for 12-16 hours). On the day of analysis, cells were washed cells three times with PBS or FACS buffer (cells were spun at 300×g RCF to ensure pellet). The final cell pellet was resuspended in 50 ul of a 1:50 dilution of anti-pSTAT5 antibody (anti-Stat5 (pY694)-A647 (BD Biosciences, Clone: 47/Stat5(pY694)). The cells were incubated for 1 hr at room temperature in the dark. The plate was then centrifuged and washed three times with FACS buffer as described above. Cells were resuspended in 125-150 μl FACS buffer per well and the cells were analyzed on an LSRII flow cytometer. Data were analyzed using FlowJo version 10.

Because plasmid pRF770 contains a cassette for the doxycycline-inducible expression of mCherry followed by mouse PD-1 (separated by a viral 2A cleavage sequence, which results in two independent polypeptides), cells expressing mCherry (as detected on an appropriate equipped flow cytometer using the PE-Texas Red channel) are reliably scored as "PD-1+"; cells that do not fluoresce in this channel above background were considered "PD-1−" or "PD-1(low) ". Analysis of pSTAT5 positive cells was therefore gated on PD-1+ or PD-1− (or PD-1(low)) cells, as present within the same experimental reaction.

Figure 3A:
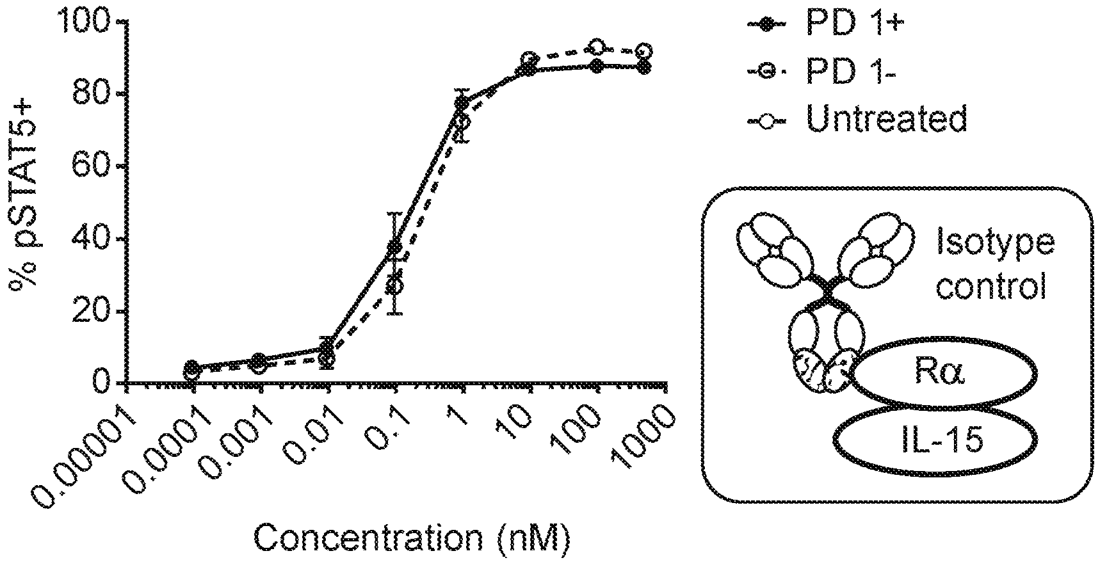
Figure 3B:
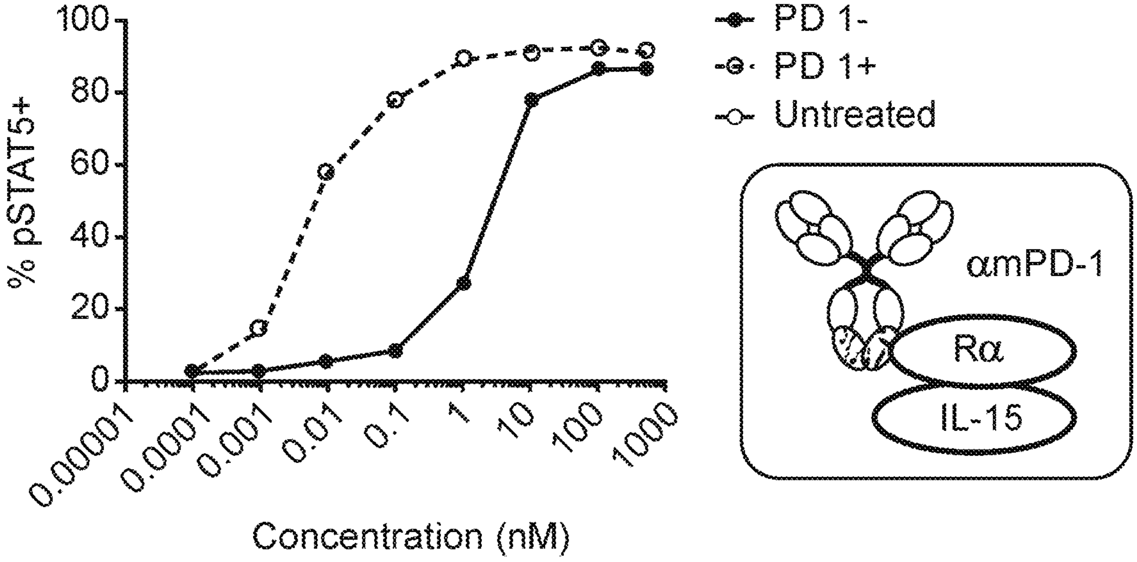
Figure 3C:
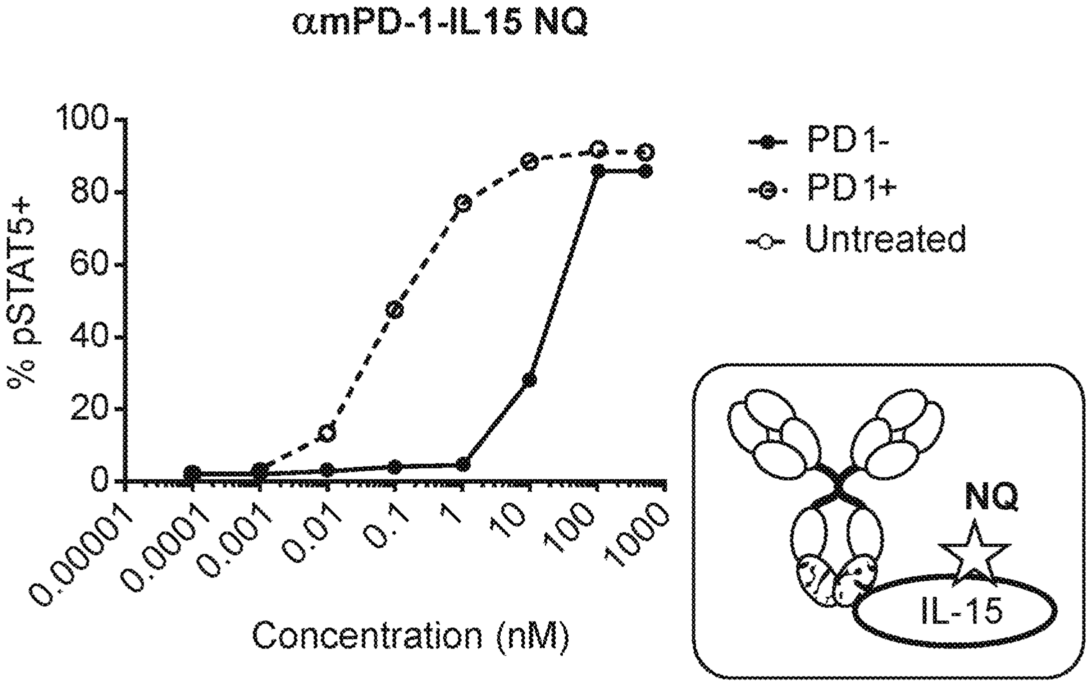
Figure 4A:
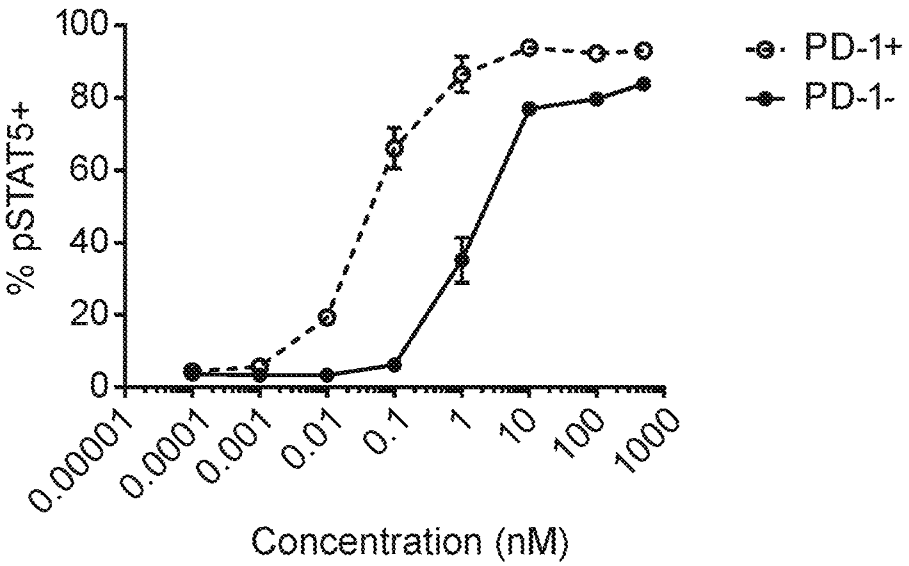
Figure 4B:
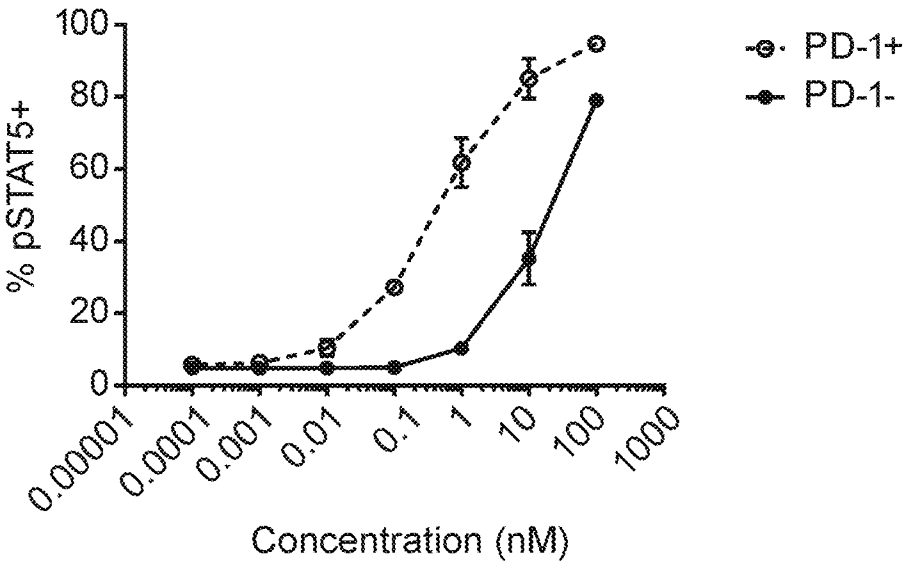
Figure 4C:
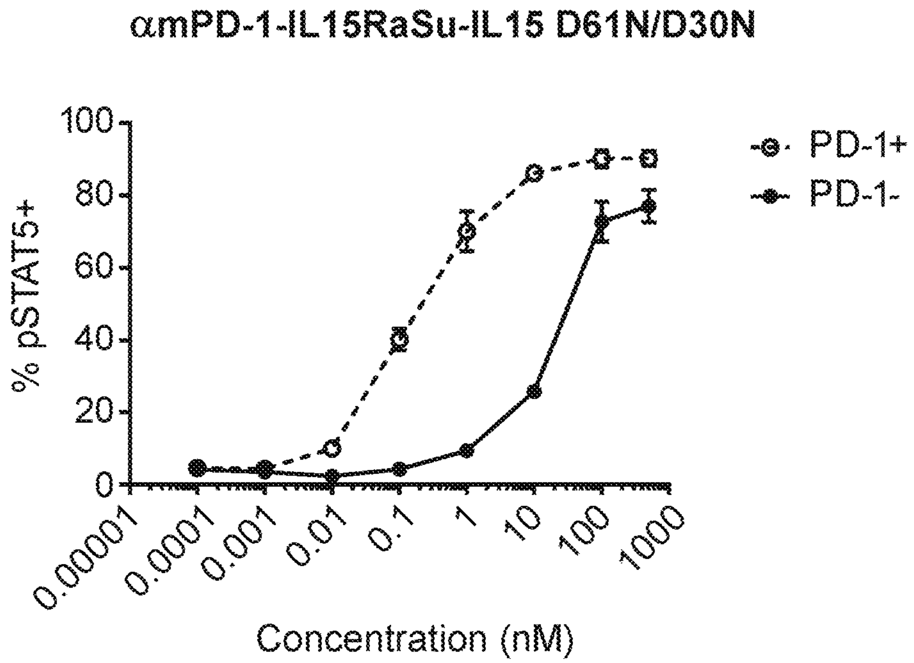
Figure 4D:
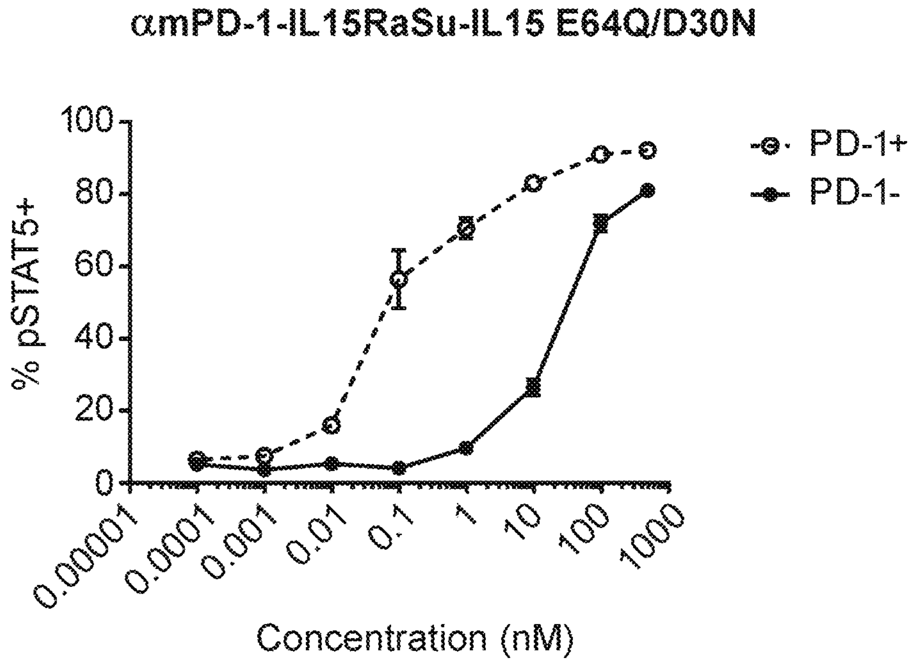
Figure 4E:
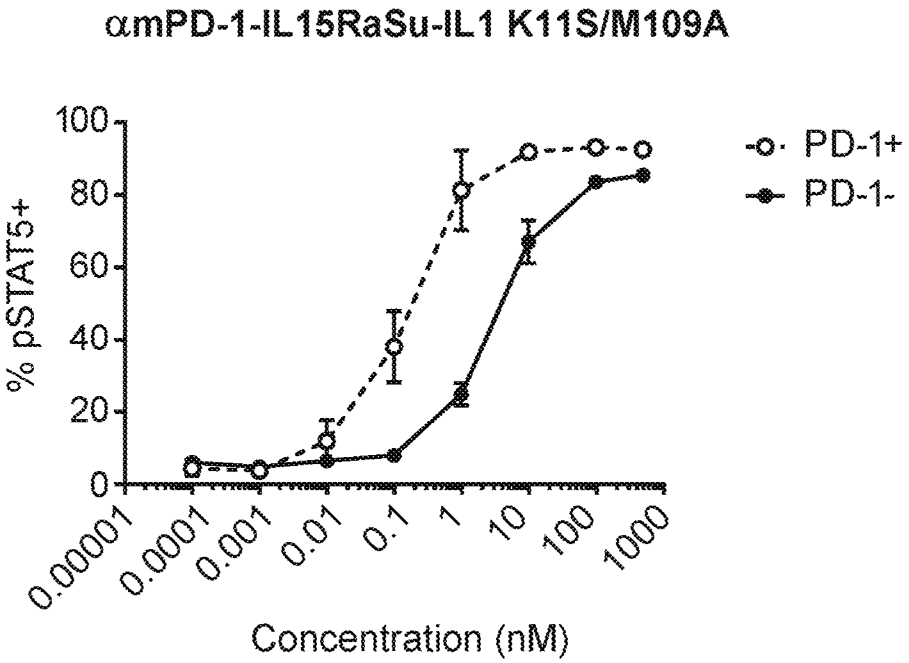
Figure 4F:
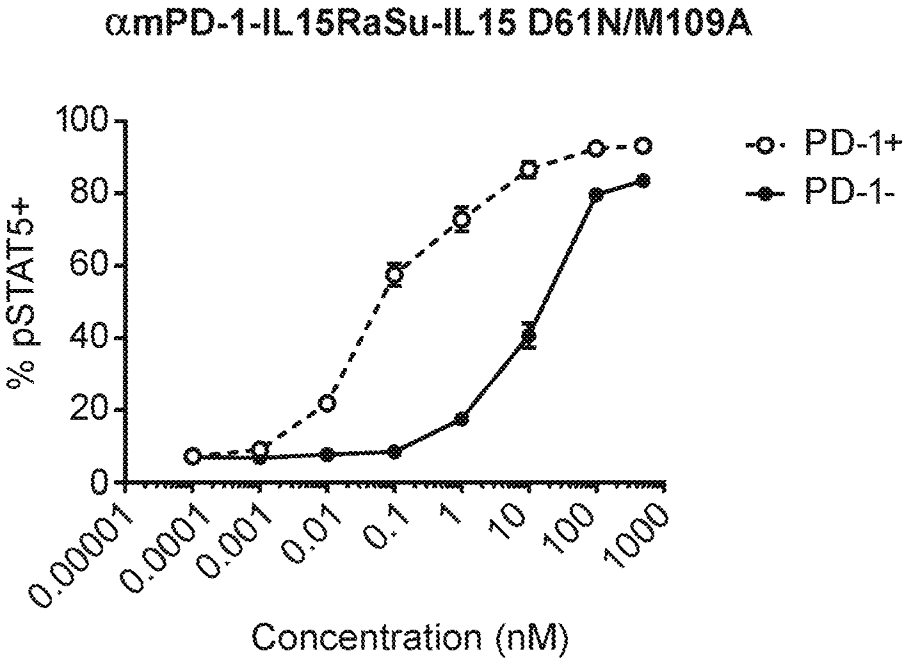
Figure 4G:
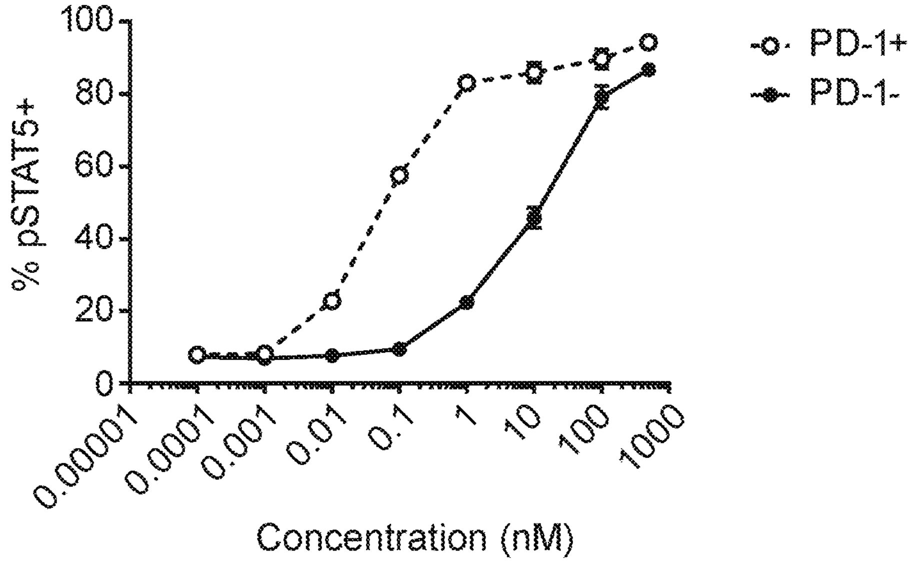
Figure 4H:
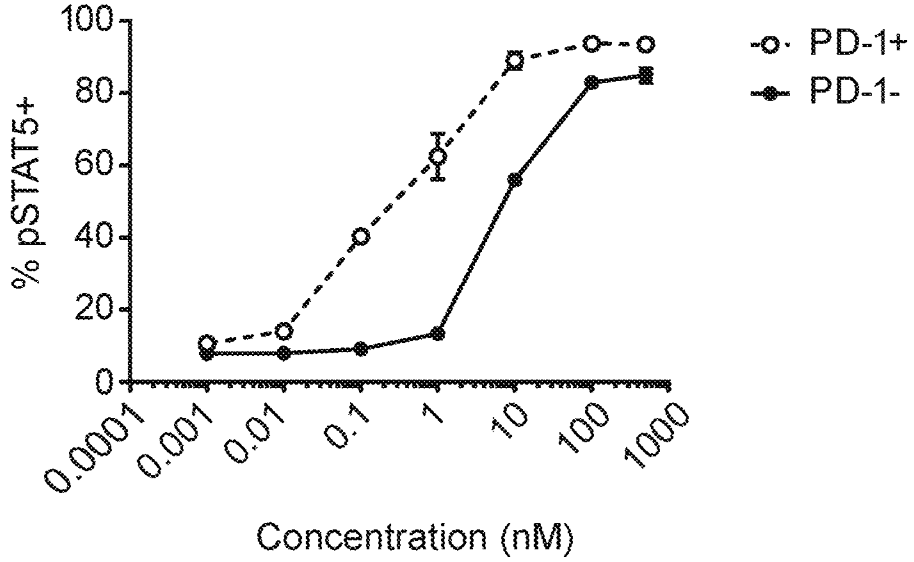
Figure 5A:
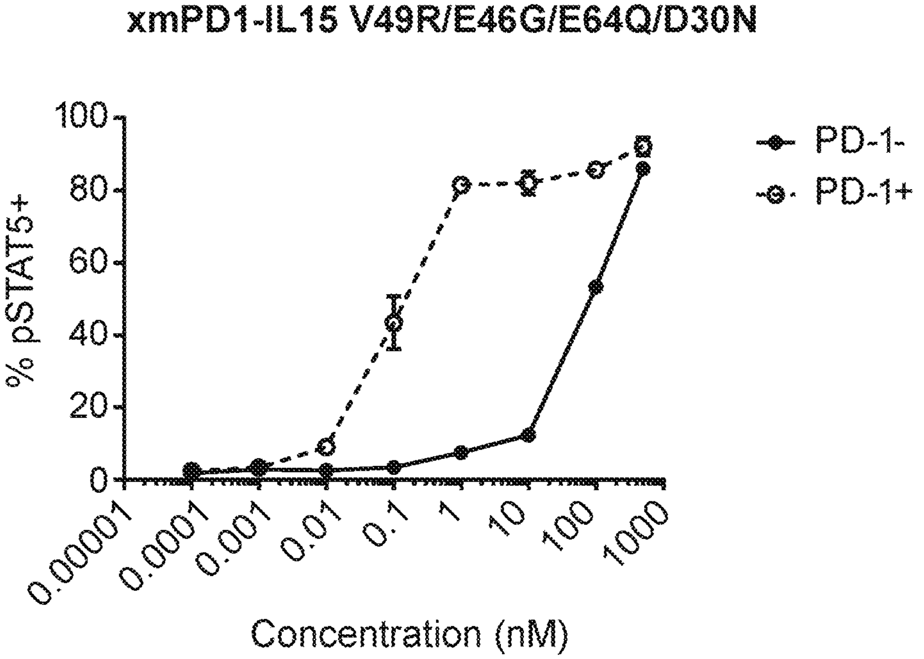
Figure 5B:
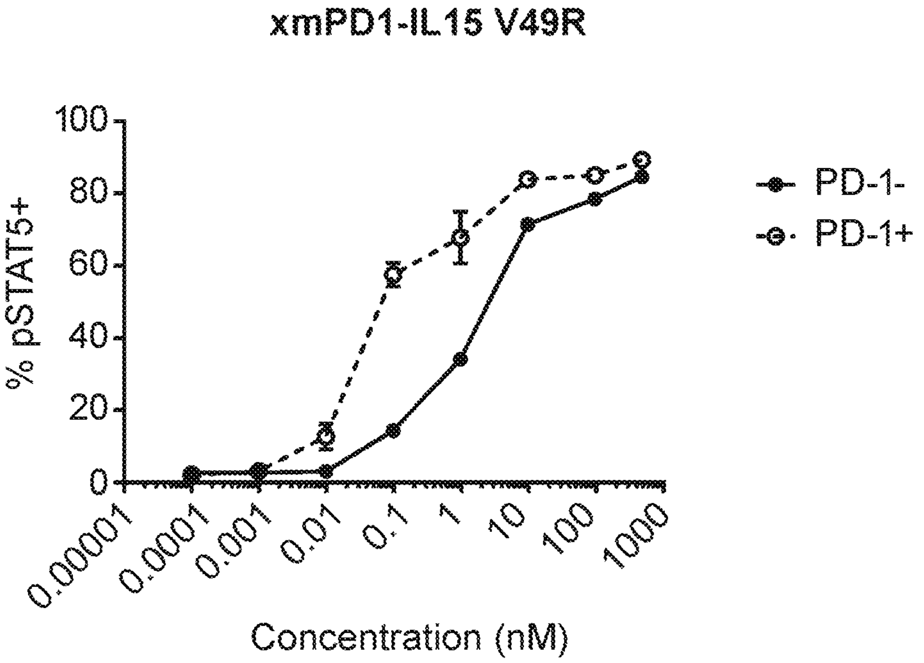
Figure 5C:
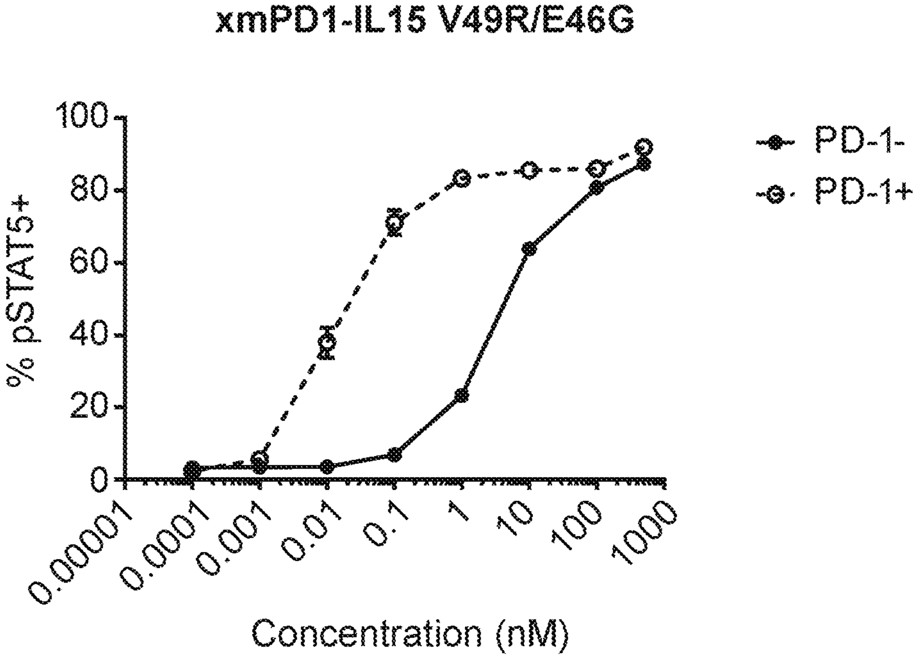
Figure 5D:
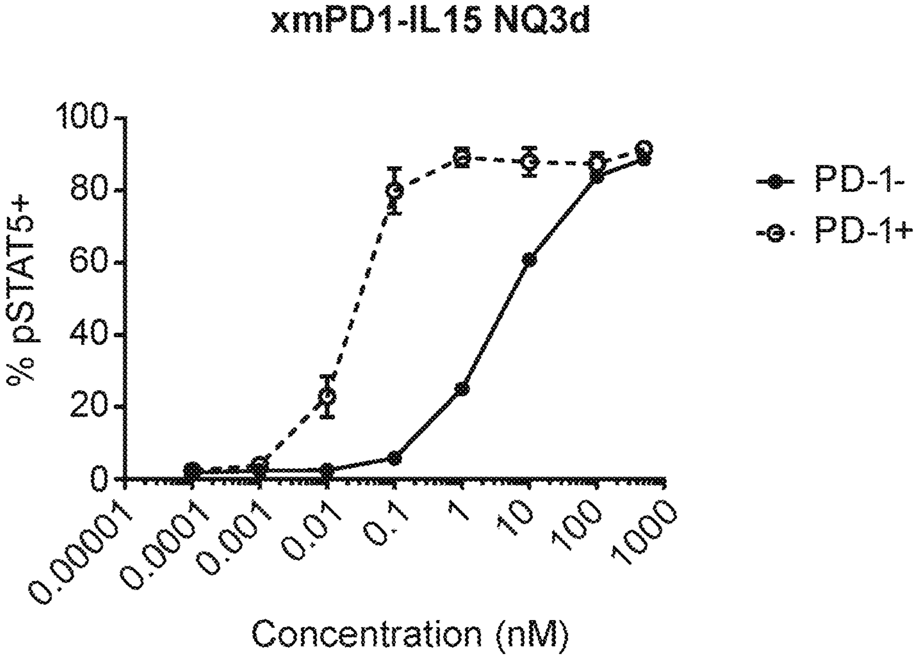
Figure 5E:
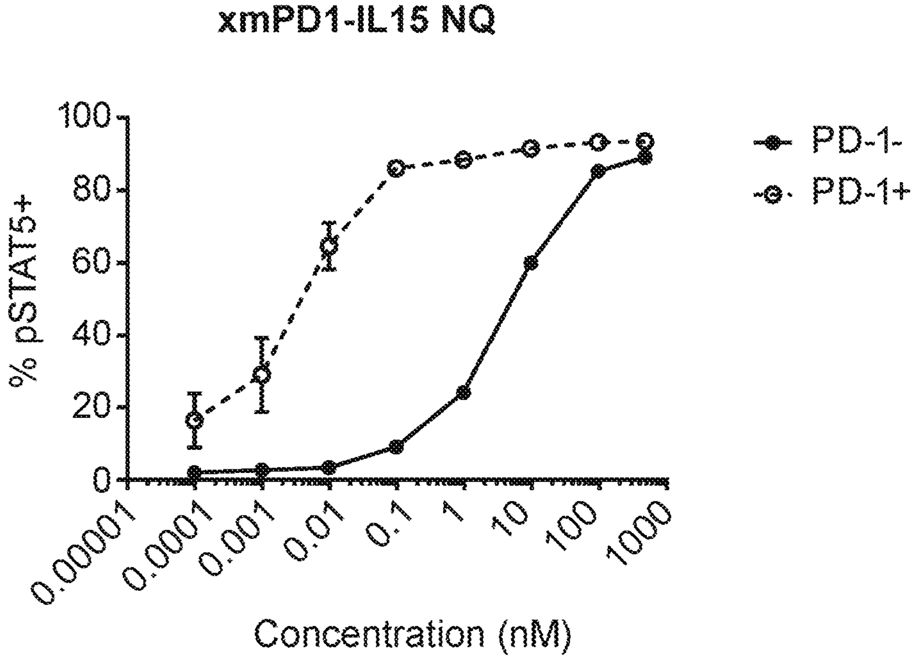
Figure 5F:
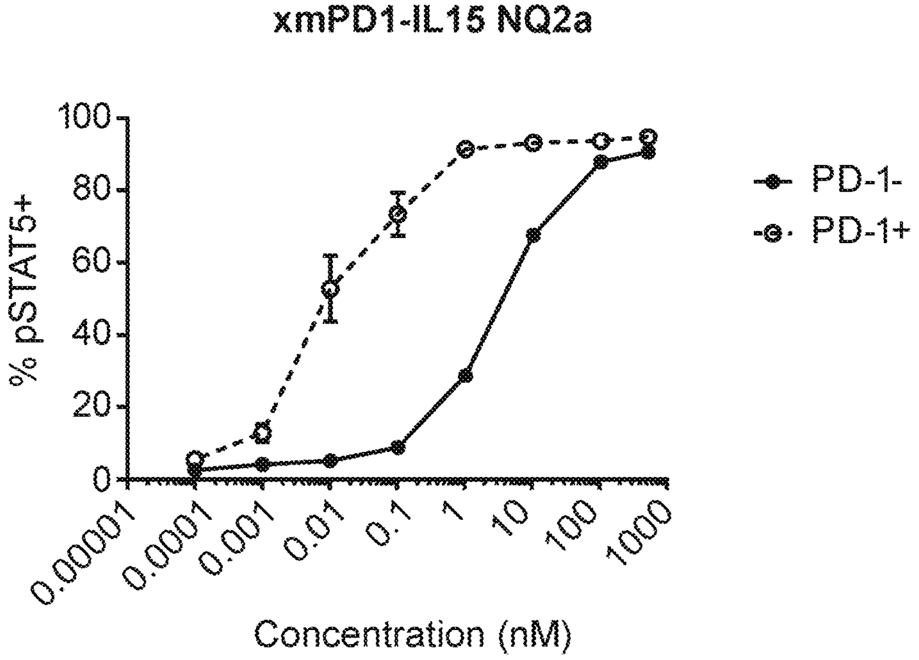
Figure 5G:
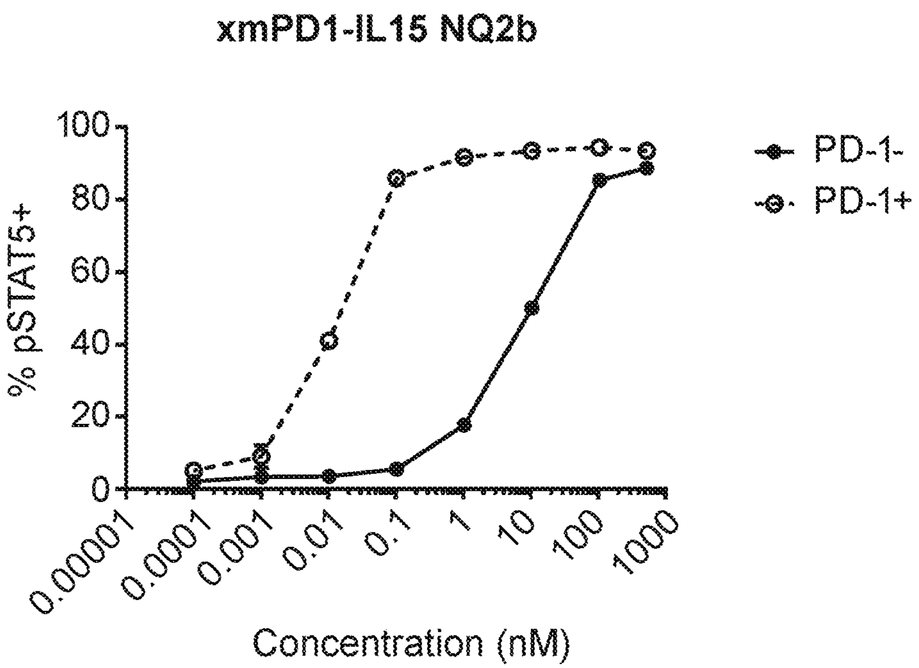
Figure 6A:
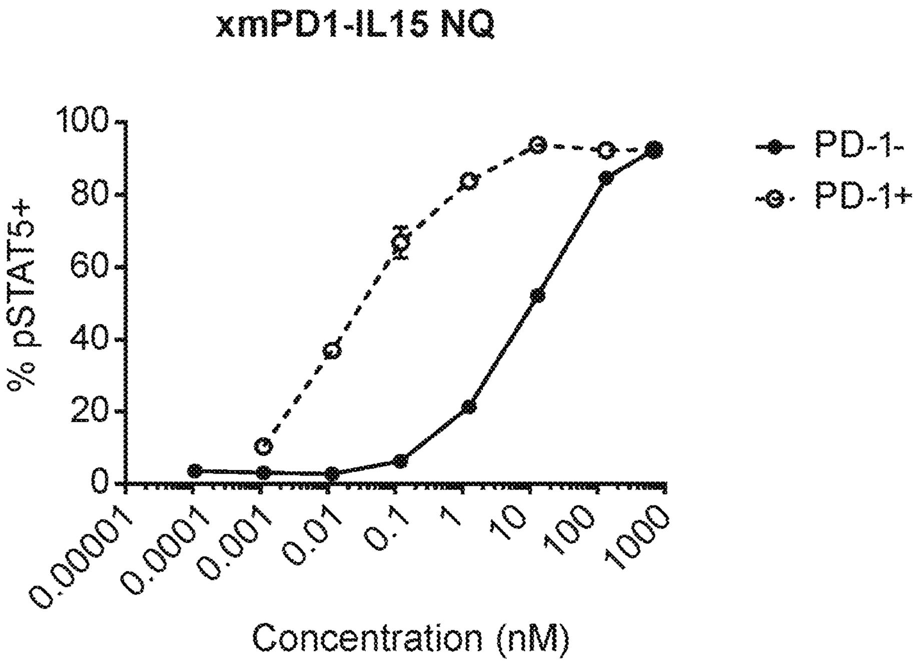
Figure 6B:
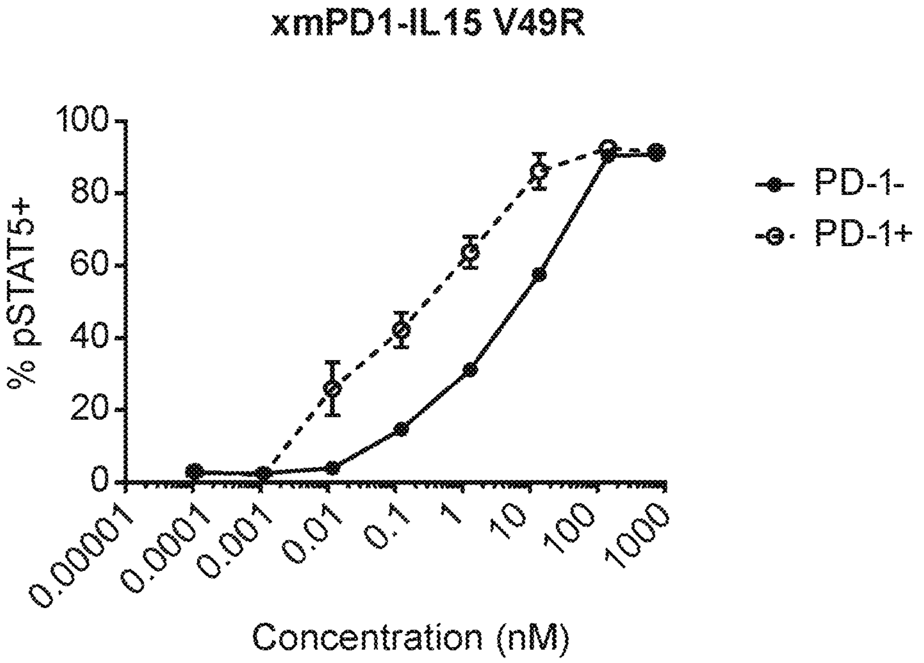
Figure 6C:
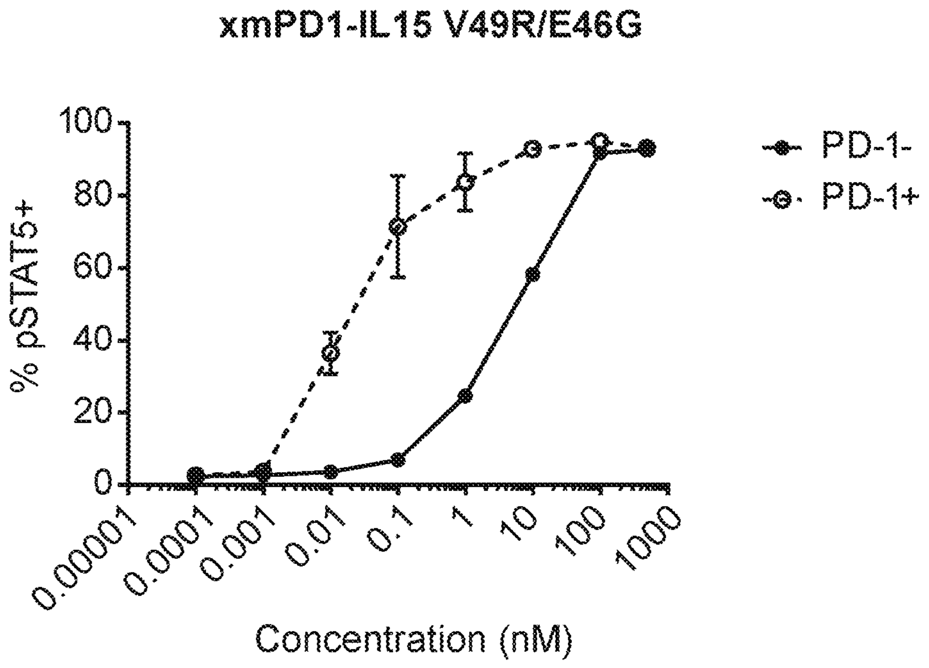
Figure 6D:
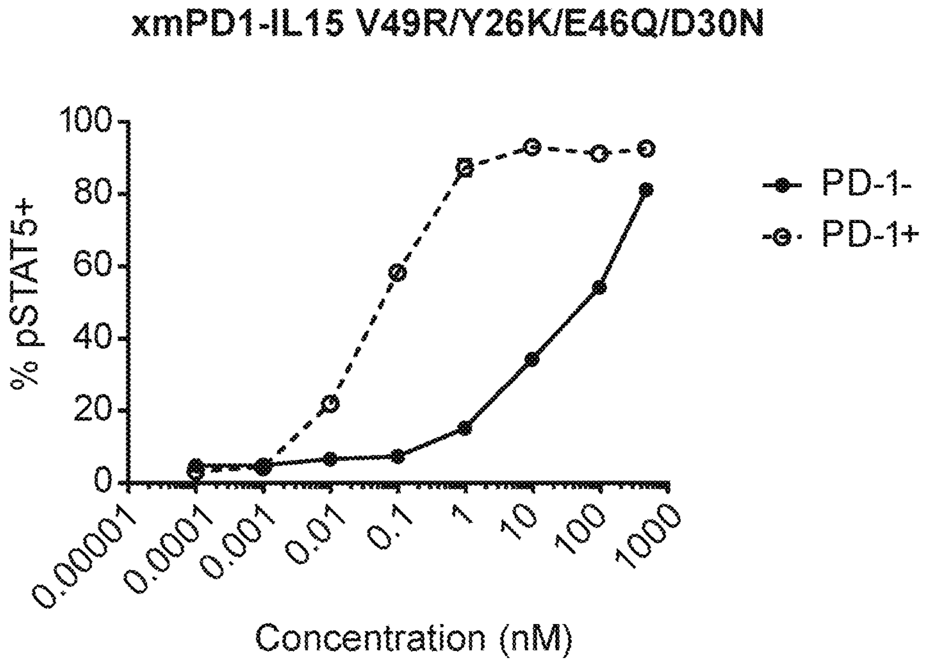
Figure 6E:
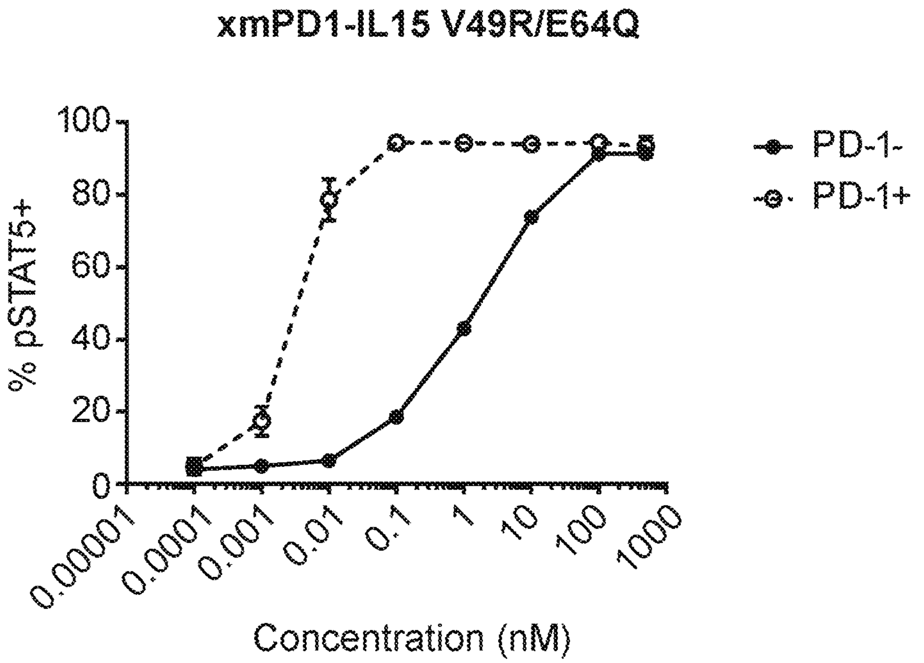
Figure 6F:
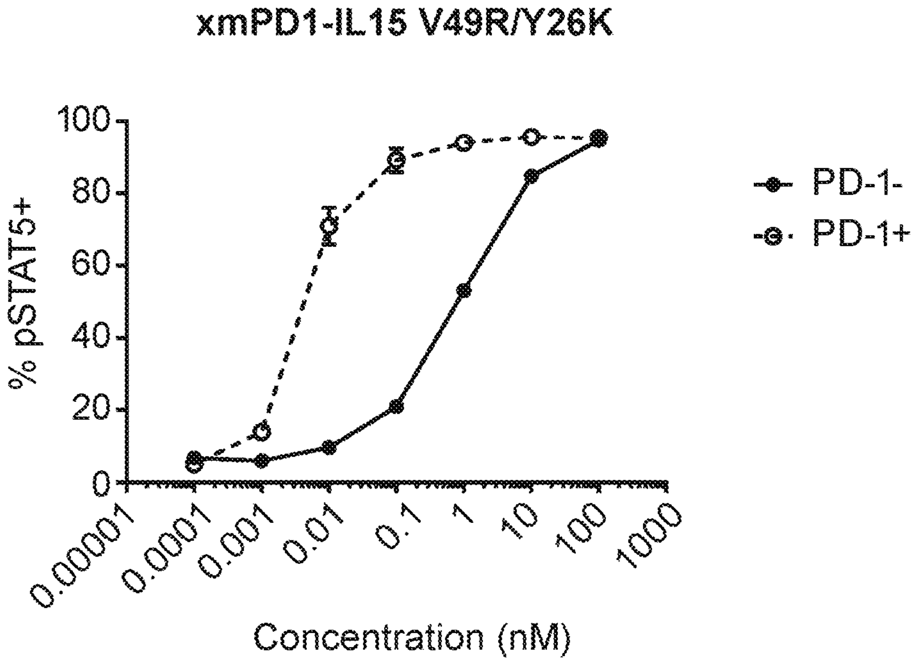
Figure 6G:
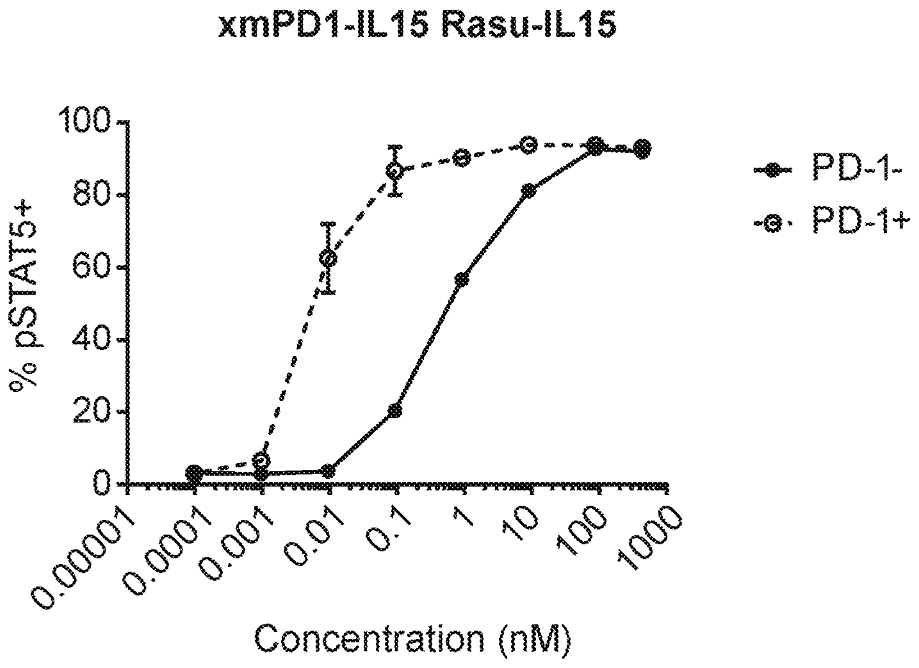

FIG. 3 depicts the use of the 32D [pRF770+791] reporter cell line to assay several IL-15-containing molecules, according to the method described above. FIG. 3A shows the effects of adding Ab8.8-IL15RaSu-IL15 to the mixed population of 32D[pRF770+791] PD-1+ and PD-1(low) reporter cells, where it causes equivalent pSTAT5 activation of both PD-1+ and PD-1(low) cells. FIG. 3B depicts the effects of adding xmPD-1-IL15RaSu-IL15 to the mixed population of 32D[pRF770+791] PD-1+ and PD-1(low) reporter cells. In this case, PD-1+ cells exhibit a much greater sensitivity, and lower EC50, to xmPD-1-IL15RaSu-IL15 as compared to PD-1(low) cells, as measured by pSTAT5 levels. FIG. 3C depicts the effects of adding xmPD-1-IL15 NQ to the mixed population of 32D[pRF770+791] PD-1+(i.e., doxycycline-induced) and PD-1(low) (i.e., non-doxycycline induced) reporter cells. PD-1+ cells exhibit a much greater sensitivity, and lower EC50, to xmPD-1-IL15 NQ as compared to PD-1(low) cells, as measured by pSTAT5 levels. Additionally, the EC50 values for anti-mouse PD-1-IL15 NQ are approximately 10-fold greater as compared to those for xmPD-1-IL15RaSu-IL15, on both PD-1+ and PD-1(low) cells, indicating that xmPD-1-IL15 NQ represents a mutein variant with reduced activity (as measured by CD122/CD132-dependent pSTAT5 activation), in addition to having the property of eliminating detectable binding to CD215 (IL-15 receptor alpha). Table 7, below, summarizes the calculated EC50 values for the aforementioned molecules, and also displays the fold change as the ratio of EC50 between PD-1+ and PD-1(low) cells.

TABLE 7

| Molecule | EC50 (nM) PD-1+ | PD-1(low) | Fold change* |
|---|---|---|---|
| Ab8.8-IL15RaSu-IL15 | 0.3 | 0.15 | 0.51 |
| xmPD1-IL15RaSu-IL15 | 0.01 | 2.19 | 365.32 |
| xmPD1-IL15 NQ | 0.09 | 21.14 | 223.07 |

*Fold change = EC50 (PD-1(low))/EC50 (PD-1+)

To identify additional variants of an antibody-targeted IL-15, wherein the IL-15 moiety contains mutations that confer a range of functional activities or binding to CD122 and/or CD132, the following experiment was conducted:

As listed in Table 8 (below) and as displayed in FIG. 4, various IL-15 mutein forms of xmPD1-IL15RaSu-IL15 were generated and assayed using the 32D[pRF770+pRF791] reporter cell line as detailed, above. Note that for each mutein, the mutations present relative to wildtype mature human IL-15 protein sequence are denoted (in the format of original amino acid, amino acid reside number as present in SEQ ID #1, new amino acid at that position). Percentages of PD-1+ or PD-1(low) cells that were positive for pSTAT5 (by flow cytometric analysis) are plotted in FIG. 4A-H, and the resulting plots used to calculate EC50 values, as shown below in Table 8.

TABLE 8

| Molecule | EC50 (nM) PD-1+ | PD-1(low) | Fold change* |
|---|---|---|---|
| xmPD1-hIL15Rasu-hIL-15 | 0.05 | 5.42 | 108 |
| xmPD1-hIL15Rasu-hIL-15 K11S/D30N | 0.42 | 18.76 | 44 |
| xmPD1-hIL15Rasu-hIL-15 D61N/D30N | 0.16 | 22.04 | 139 |
| xmPD1-hIL15Rasu-hIL-15 E64Q/D30N | 0.069 | 24.89 | 360 |
| xmPD1-hIL15Rasu-hIL-15 K11S/M109A | 0.16 | 3.13 | 19 |
| xmPD1-hIL15Rasu-hIL-15 D61N/M109A | 0.07 | 12.88 | 193 |
| xmPD1-hIL15Rasu-hIL-15 E64Q/M109A | 0.06 | 10.05 | 163 |
| xmPD1-hIL15Rasu-hIL-15 D61N | 0.38 | 6.91 | 18 |

*Fold change = EC50 (PD-1(low))/EC50 (PD-1+)

Thus, the present in vitro assay method can identify those mutants with either non-target-driven or antibody target-driven activities that differ from a corresponding chimeric protein containing a wildtype IL-15 sequence.

FIG. 5 depicts the result of an experiment wherein the 32D [pRF770+791] reporter cell line was used to assay several additional antibody-IL-15 molecules, according to the method described above in this Example. In this instance, none of the molecules included the IL-15 receptor alpha Sushi domain (IL-15RaSu). Percentages of PD-1+ or PD-1(low) cells that were positive for pSTAT5 are plotted in FIG. 5A-G, and the resulting plots used to calculate EC50 values, as shown below in Table 9.

TABLE 9

| Molecule (relevant mutation(s) listed) | EC50 (nM) PD-1+ | PD-1(low) | Fold change* |
|---|---|---|---|
| xmPD-IL15 NQ | 0.00574 | 1.724 | 300.3484 |
| xmPD-IL15 NQ2a | 0.009495 | 2.939 | 309.5313 |
| xmPD-IL15 NQ2b | 0.01349 | 8.001 | 593.106 |
| xmPD-IL15 NQ3d | 0.02294 | 3.731 | 162.6417 |
| xmPD-IL15 V49R | 0.05476 | 1.511 | 27.59313 |
| xmPD-IL15 V49R/E46G | 0.01491 | 3.432 | 230.1811 |
| xmPD-IL15 V49R/E46G/ E64Q/D30N | 0.1371 | 97.98 | 714.6608 |

*Fold change = EC50 (PD-1(low))/EC50 (PD-1+)

Thus, the in vitro assay method was used to identify those mutants which lack IL-15RaSu and possess either non-target-driven or antibody target-driven activities that differ from the comparator xmPD1-IL15 NQ.

FIG. 6 depicts the result of an additional experiment wherein the 32D [pRF770+791] reporter cell line was used to assay several additional antibody-IL-15 molecules, according to the method described above in this Example. In this instance, most of the molecules lacked the IL-15 receptor alpha Sushi domain (IL-15RaSu); xmPD-1-IL15RaSu-IL15 was included as an IL15RsSu-containing control comparator. Percentages of PD-1+ or PD-1(low) cells that were positive for pSTAT5 are plotted in FIG. 6A-G, and the resulting plots used to calculate EC50 values, as shown below in Table 10.

TABLE 10

| Molecule | EC50 (nM) | | |
|---|---|---|---|
| (relevant mutation(s) listed) | PD-1+ | PD-1(low) | Fold change* |
| xmPD-IL15 NQ | 0.03026 | 7.29 | 240.91 |
| xmPD1-V49R | 0.1634 | 4.378 | 26.79 |
| xmPD1-V49R/E64G | 0.0188 | 5.45 | 289.75 |
| xmPD1-V49R/Y26K/E64Q/D30N | 0.05614 | 21.43 | 381.72 |
| xmPD1-IL15 V49R/E46Q | 0.002937 | 1.335 | 454.55 |
| xmPD1-IL15 V49R/Y26K | 0.00412 | 0.8539 | 207.21 |
| xmPD1-IL15Rasu-IL15 | 0.0054 | 0.602 | 110.9 |

*Fold change = EC50 (PD-1(low))/EC50 (PD-1+)

FIG. 7 depicts the result of an additional experiment wherein the 32D [pRF770+791] reporter cell line was used to assay several additional antibody-IL-15 molecules, according to the method described above in this Example. In this instance, most of the molecules contained a mutation at position V49 which modulated the interaction between IL-15 and IL-15Ralpha. Percentages of PD-1+ or PD-1(low) cells that were positive for pSTAT5 are plotted in FIG. 7A-7E, and the resulting plots used to calculate EC50 values, as shown below in Table 11.

TABLE 11

| Molecule | EC50 (nM) | | |
|---|---|---|---|
| (relevant mutation(s) listed) | PD-1+ | PD-1(low) | Fold change* |
| xmPD1-IL15 V49R | 0.05573 | 0.3284 | 5.89 |
| xmPD1-IL15 V49R E46G | 0.01182 | 4.535 | 383.67 |
| xmPD1-IL15 V49K E46G | 0.007902 | 3.977 | 503.29 |
| xmPD1-IL15 V49K Y26K | 0.01751 | 3.975 | 227.01 |
| xmPD1-IL15 V49NAT | 0.04394 | 3.047 | 69.34 |

*Fold change = EC50 (PD-1(low))/EC50 (PD-1+)

Figure 7A:
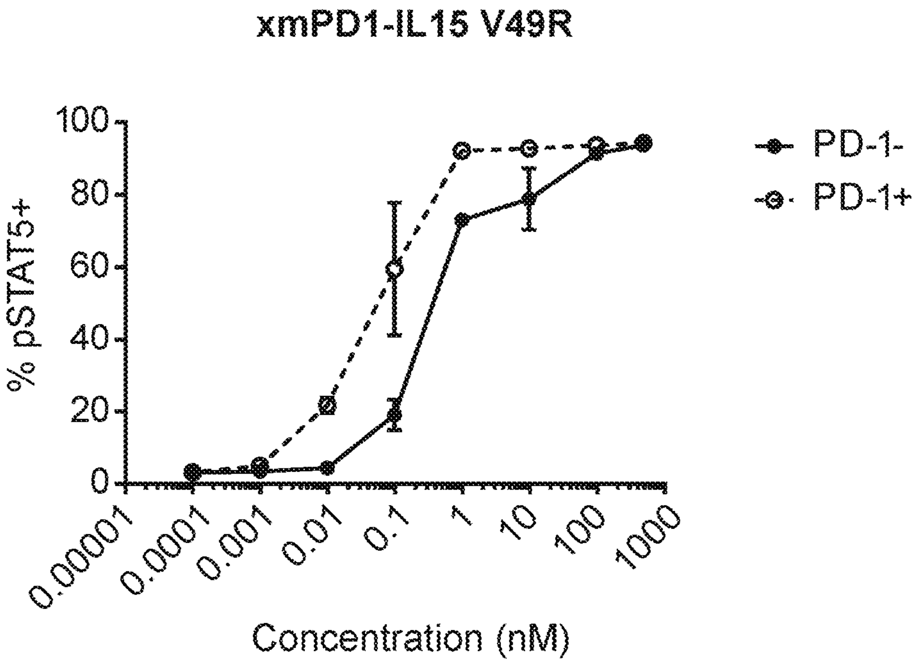
Figure 7B:
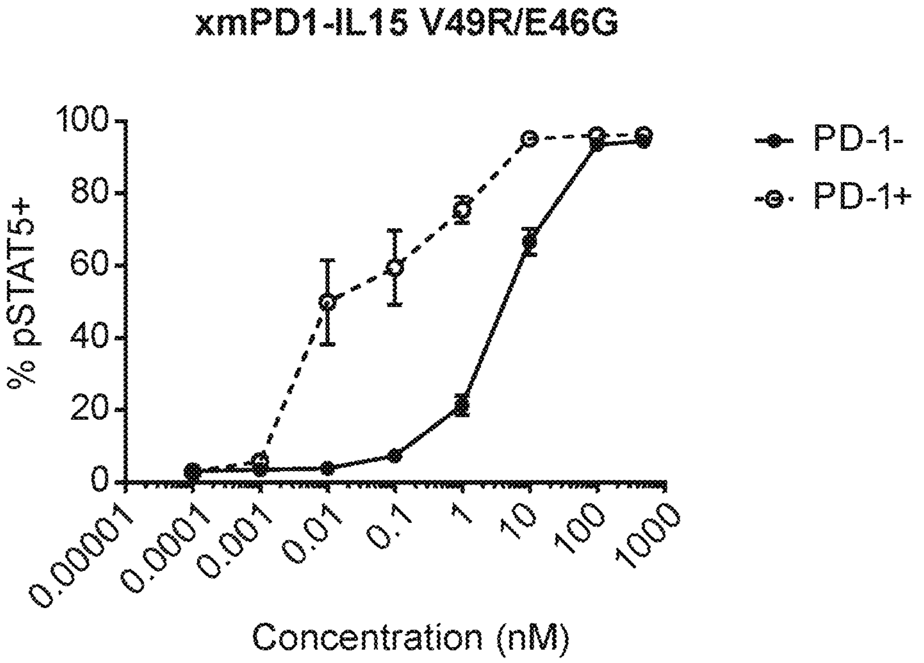
Figure 7C:
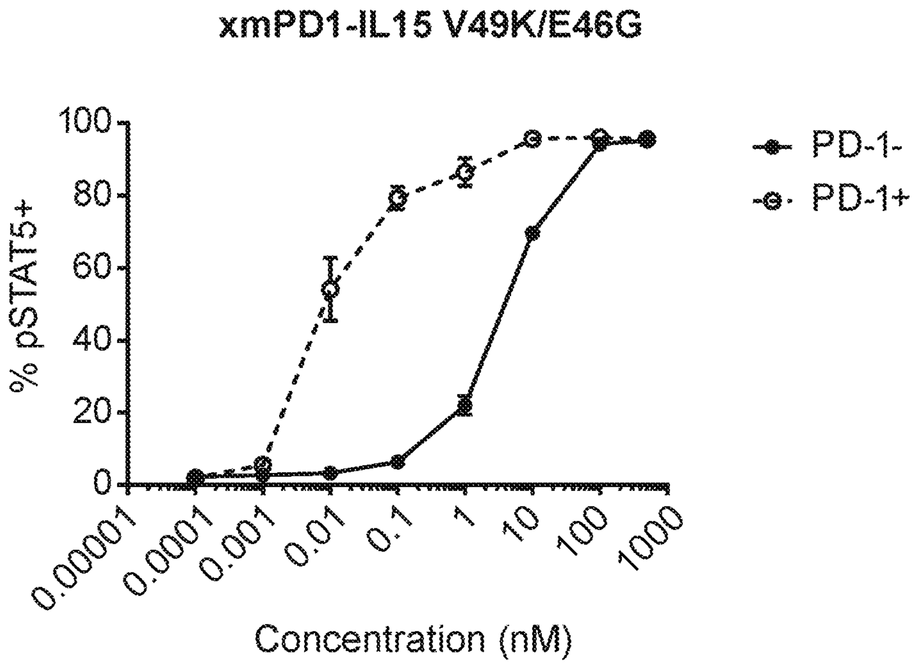
Figure 7D:
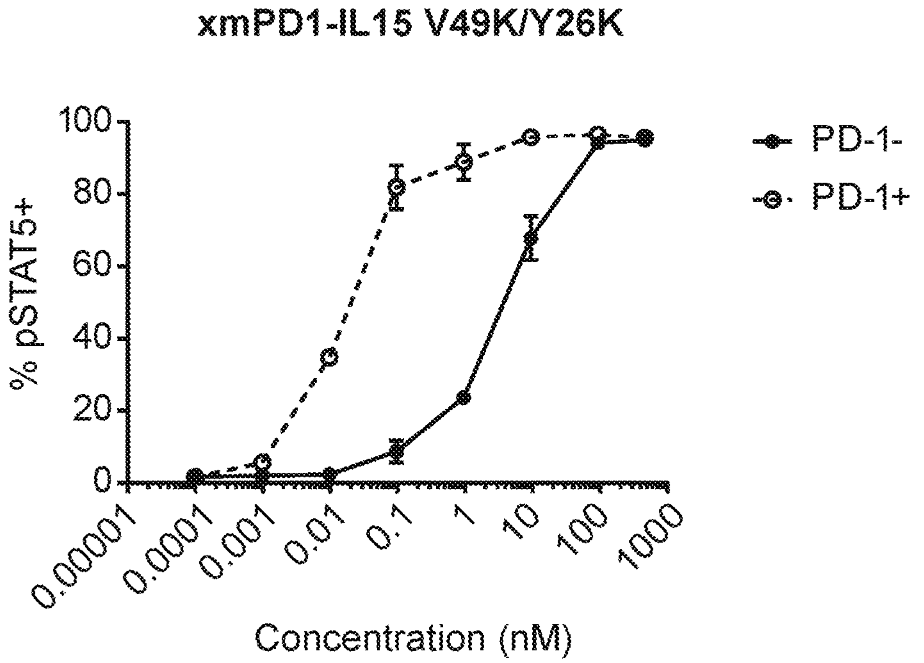
Figure 7E:
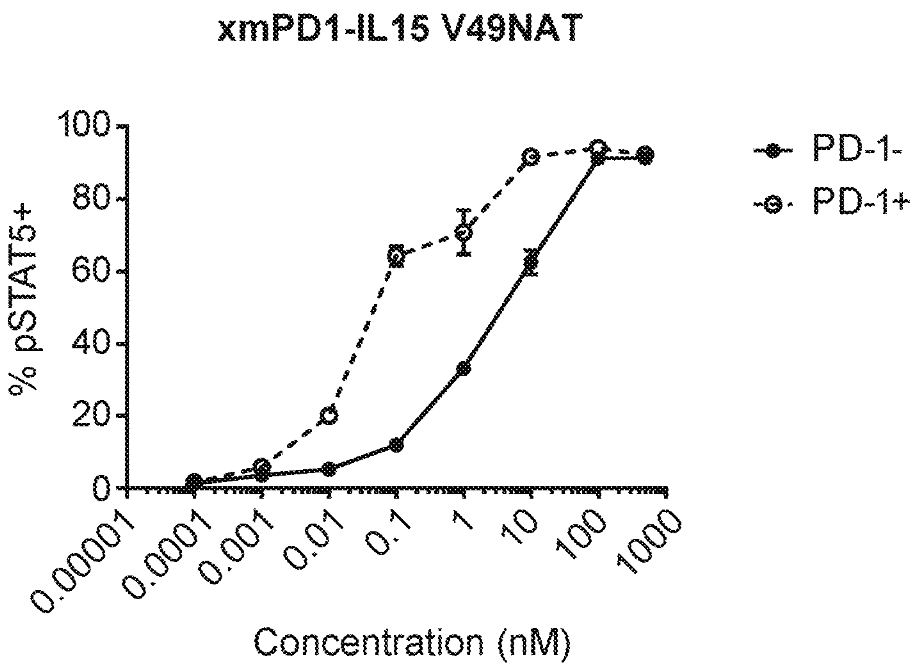
Figure 7F:
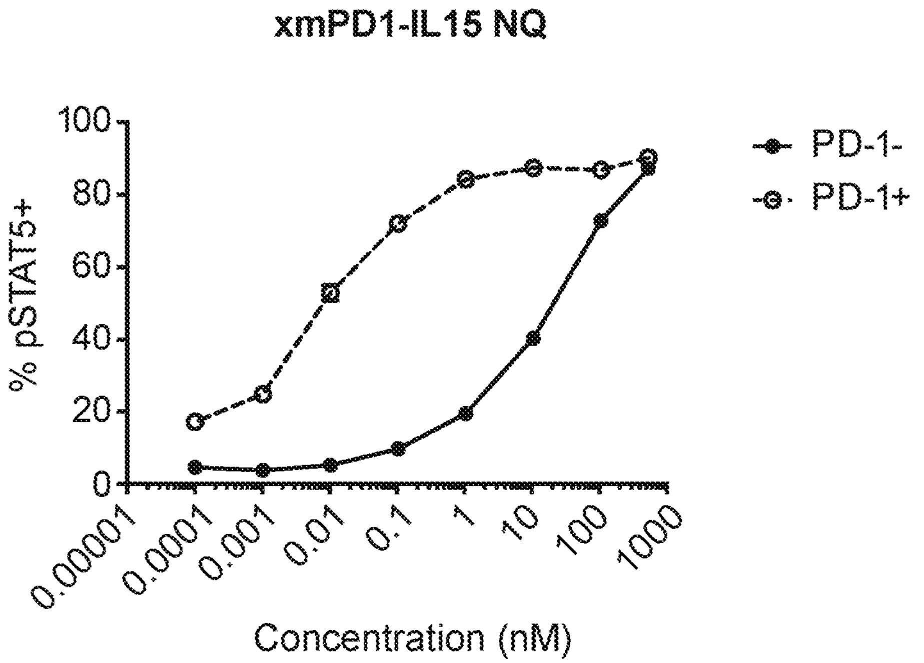
Figure 7G:
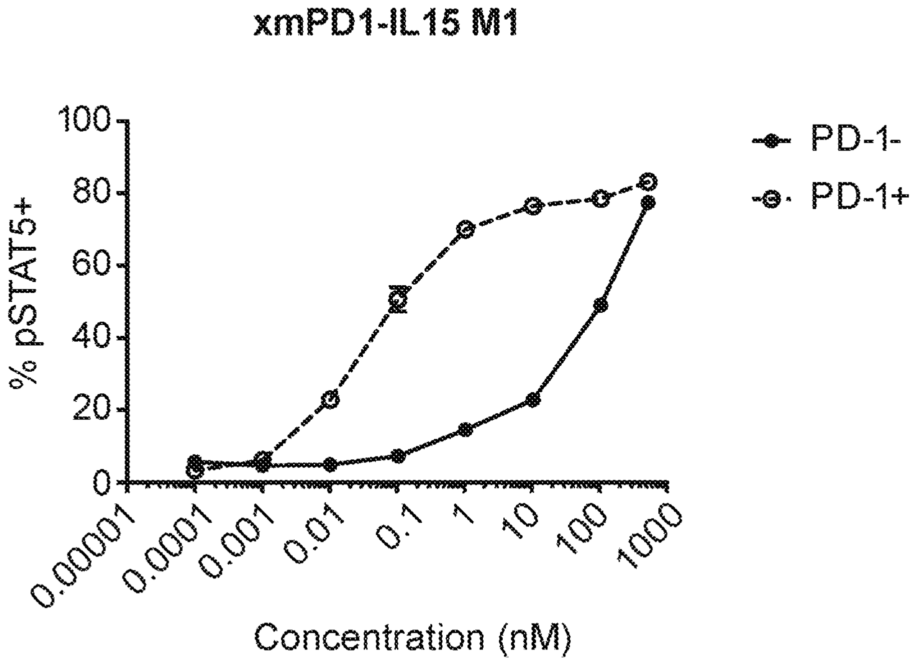
Figure 7H:
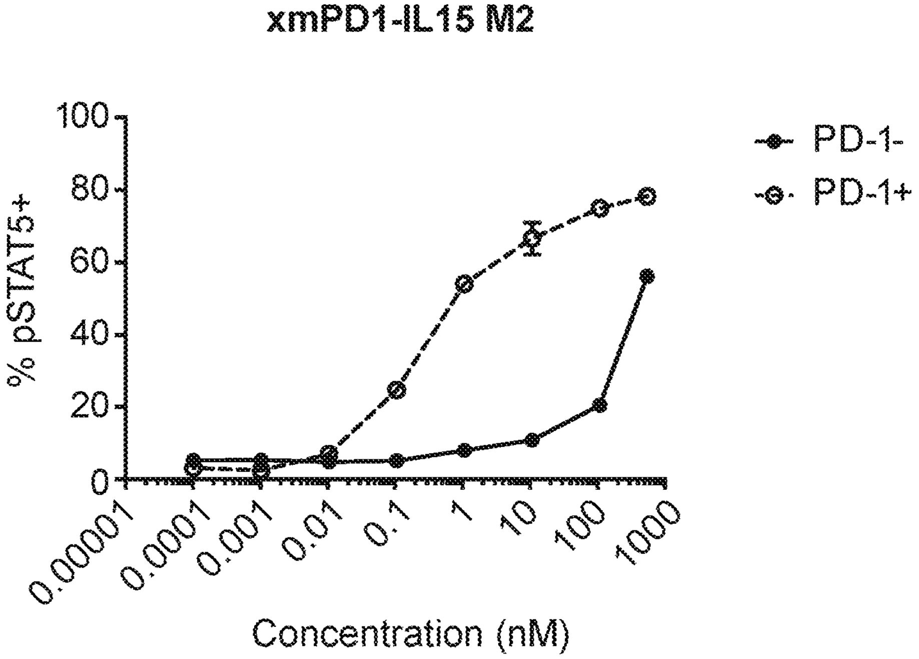

FIG. 7F-7H further depict the result of an additional experiment wherein the 32D [pRF770+791] reporter cell line was used to assay several additional antibody-IL-15 molecules, including the molecules contained the mutations at positions N1, D30 and E64 which modulated the interaction between IL-15 and IL-2Rbeta-gamma, in comparison to IL-15 NQ. Percentages of PD-1+ or PD-1(low) cells that were positive for pSTAT5 are plotted in FIG. 7F-7H, and the resulting plots used to calculate EC50 values, as shown below in Table 11A.

TABLE 11A

| Molecule (relevant | EC50 (nM) | | |
|---|---|---|---|
| mutation(s) listed) | PD-1+ | PD-1(low) | Fold change* |
| xmPD1-IL15 NQ | 0.01088 | 13.35 | 1227.02 |
| xmPD1-IL15 M1 (V49R E46G N1A D30N) | 0.05314 | 76.91 | 1447.31 |
| xmPD1-IL15 M2 (V49K E46G N1G E64Q D30N) | 0.3097 | 734.3 | 2371 |

*Fold change = EC50 (PD-1(low))/EC50 (PD-1+)

Example 6: Determination of Maximum Tolerated Dose (MTD) in Non-Tumor-Bearing Mice This Example describes the determination of the in vivo maximum tolerated dose of an antibody-IL-15 fusion protein as described herein.

Figure 8A:
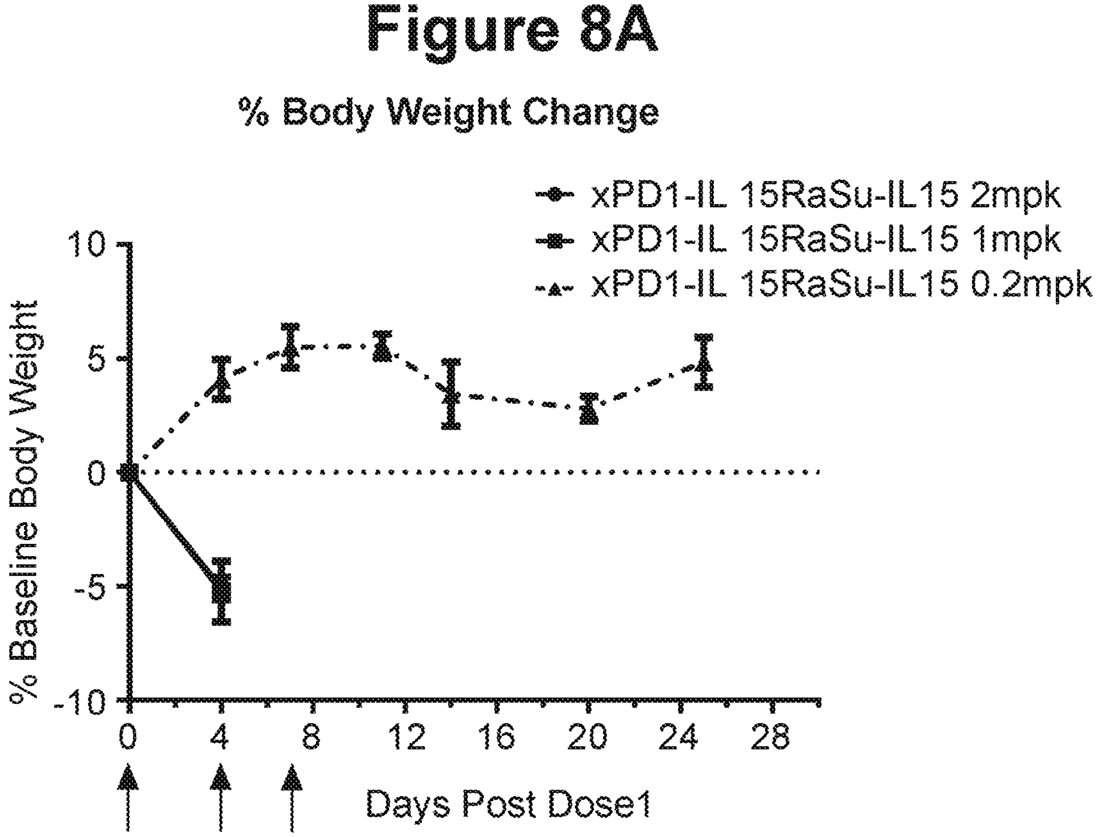
Figure 8B:
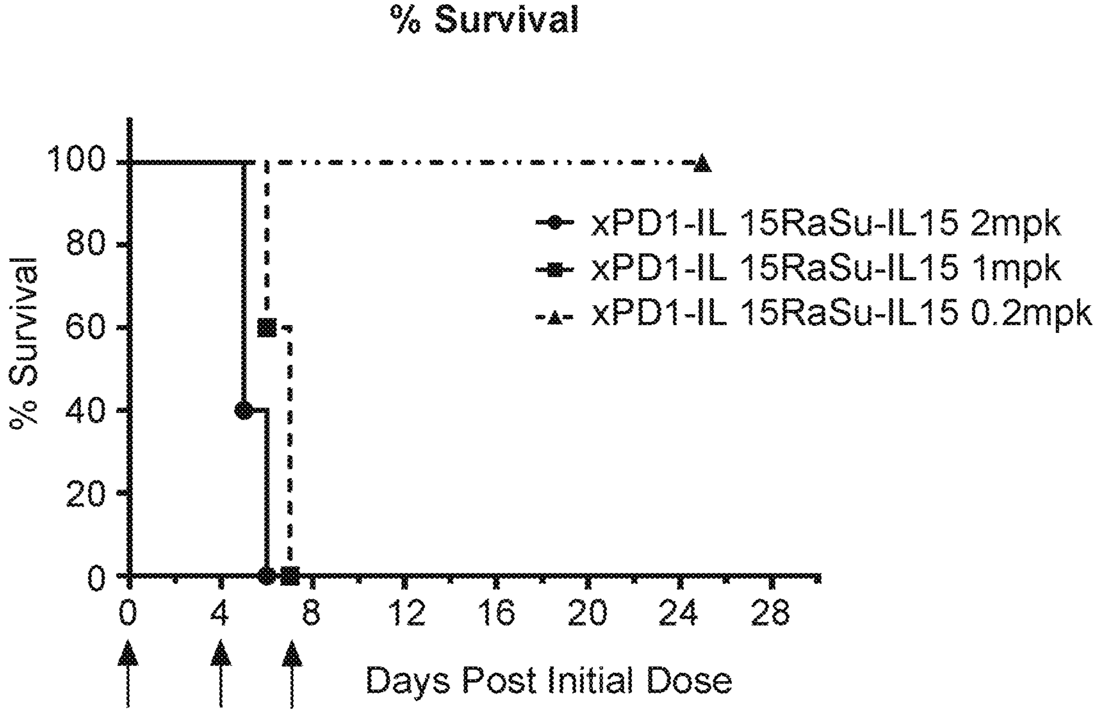
Figure 8C:
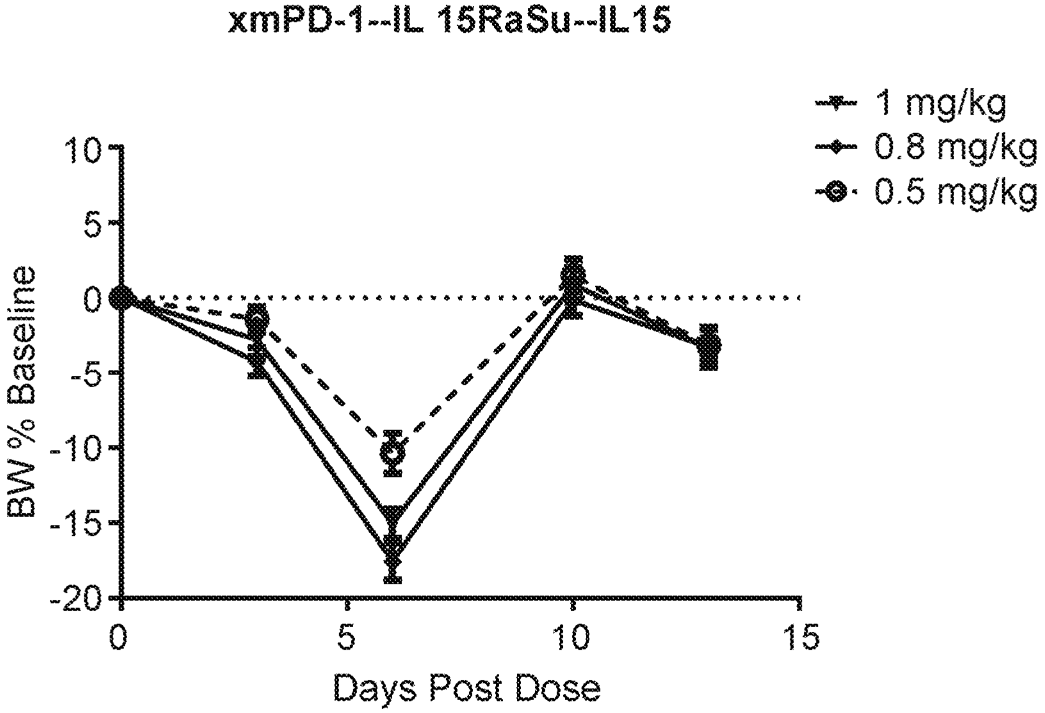
Figure 8D:
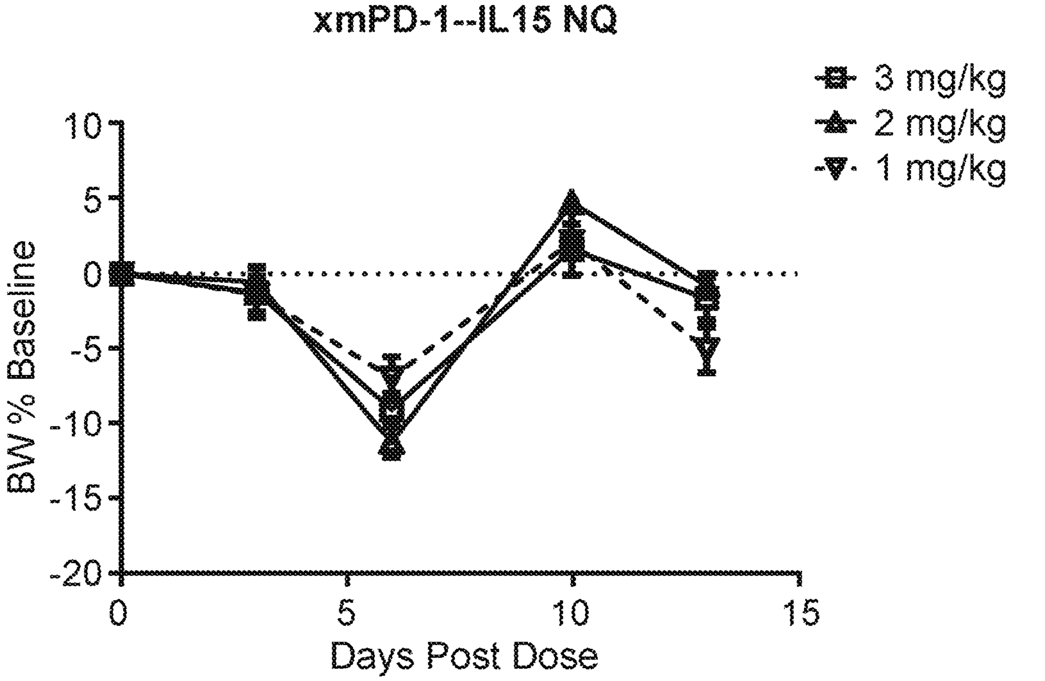

Healthy female 6-8 week-old C56/B16 mice were treated with 3 doses each of either xmPD-1-IL-15RaSu-IL15, or xmPD-1-IL-15 NQ, as indicated. On days 0, 3 and 6 of the experiment, mice were injected subcutaneously (into the neck scruff) with sufficient recombinant protein to yield the indicated concentration of each molecule, based on each animal's body weight. Each compound was administered to a cohort of 10 animals. Each animal's changes in body weight (compared to its weight at study start) were measured and the average values for each group were recorded. FIGS. 8A and 8B plot the changes in body weight and total survival, respectively, of animals in the xmPD1-IL15RaSu-IL15 groups dosed at 2 mg/kg, 1 mg/kg, or 0.2 mg/kg. Mice that received 2 mg/kg or 1 mg/kg experienced abrupt weight loss and ensuing mortality, such that by day 8 of the study, all animals in these groups had died or needed to be sacrificed. In an additional study, shown in FIG. 8C, mice were treated with xmPD1-IL15RaSu-IL15 at a final dosing concentration 1 mg/kg, 0.8 mg/kg, or 0.5 mg/kg. Mice in the 1 mg/kg and 0.8 mg/kg groups lost 15-18% of their starting body weight and appeared hunched and distressed; animals in the 0.5 mg/kg dosing group experienced more modest, transient weight loss. The MTD for xmPD1-IL15RaSu-IL15 was established as at or below 0.5 mg/kg. FIG. 8D depicts the changes in body weight following administration of xmPD1-IL15 NQ at a final concentration of 3 mg/kg, 2 mg/kg, or 1 mg/kg. Animals in all groups experienced transient weight loss (which rebounded following cessation of dosing) which was more modest than see with lower doses of xmPD1-IL15RaSu-IL15, and without any apparent signs of distress. The MTD for xmPD1-IL15 NQ was thus established as at or below 3 mg/kg, indicating that it was better tolerated than xmPD1-IL15RaSu-IL15.

Example 7: Characterization of the B16F10 Murine Syngeneic Tumor Model

Various mouse tumor cell lines are commonly available (for example, from the American Type Culture Collection, ATCC) and the immune cell infiltrate profiles have been evaluated for many of these (for example, see Mosley, S. I., et al., Cancer Immunol Res. 2017 January; 5(1):29-41). Mosley et al. and others have shown that the tumor cell line B16F10, when implanted subcutaneously into C57/B16 mice, develops a tumor that contains a relatively low abundance of T cells (as a fraction of total immune cell infiltrate) and is also poorly responsive to anti-PD-1 antibody therapy. To evaluate the expression of PD-1 on tumor-infiltrating lymphocytes (TILs) as well as peripheral immune cells, the following experiment was carried out:

Female C57/B16 mice were subcutaneously implanted in the upper thigh with approximately 500,000 B16F10 cells, which had been freshly thawed from a single, low-passage vial (of 1*10^7 cells) and cultured for the minimum time required to establish sufficient cells for implantation. When a cohort of animals with visible tumor masses of 300-400 $mm^3$ (as defined by (length×width$^2$)/2) was obtained, mice were euthanized and sacrificed, and the spleen and primary tumor mass of each animal were obtained. Splenocytes were obtained by mashing the spleens through a 40 uM mesh filter, followed by addition of 10 mL of PBS and collection by centrifugation (250×g, 5'). Cells were resuspended in 2 mL of ACK buffer for 5 min followed by addition of 10 mL of PBS and collected by centrifugation as above. The cell pellet was resuspended in 2 mL of PBS, passed through a 40 uM mesh filter, and the total cells counted. Tumor cell suspensions were obtained using the Miltenyi mouse tumor dissociation kit and the Octomax dissociator according to the manufacturer's protocol, except 1/10th of the amount of enzyme "R" was utilized. Following dissociation, cells were washed in PBS and collected by centrifugation, and then counted as above. Approximately 5 million splenocytes and the entire collected amount of tumor cells (typically, 1-5 million) from each mouse were then stained using the cocktail of antibodies as described in Table 12, below:

TABLE 12

Antibodies used for staining splenocytes and tumor cell suspensions for flow cytometry.

| Target | Label | Clone | Vendor |
|---|---|---|---|
| CD8a | APC-Cy7 | 53-6.7 | Biolegend |
| PD1 | BV421 | 29F.1A12 | Biolegend |
| CD4 | FITC | GK1.5 | Biolegend |
| NKp46 | PerCP-Cy5.5 | 29A1.4 | BD |
| CD45 | BV786 | 30-F11 | Biolegend |

Figure 9A:
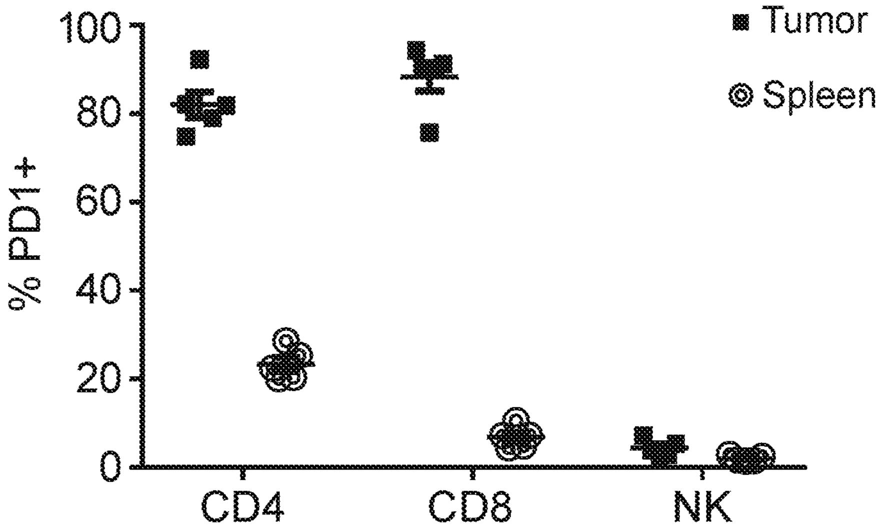
Figure 9B:
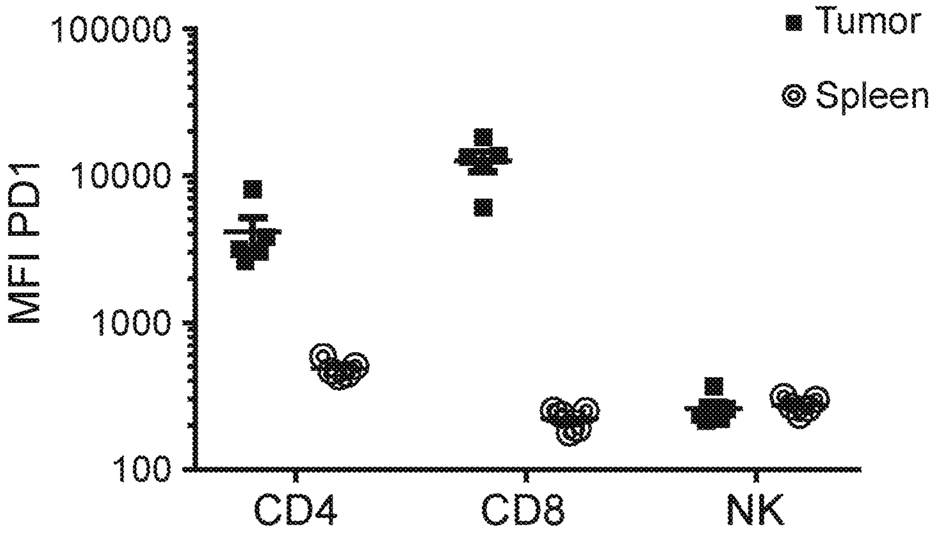

For flow cytometric analysis, after defining cells as live, singlet, CD45+ lymphocytes, T cells were gated as either CD4+ or CD8+; NK cells were defined as NKp46+ cells. FIG. 9A shows the mean fluorescence intensity (MFI) of anti-PD-1 staining on each of the aforementioned cell populations; FIG. 9B shows the percent of each population that stained positive (as defined by gating on an FMO control sample).

Thus, despite the reported low abundance of T cells amongst B16F10 TILs, the PD-1 expression pattern on TIL and peripheral T cells presented an opportunity to evaluate the effects of PD-1-driven targeting of an IL-15 moiety.

Example 8: Anti-Tumor Efficacy of Targeted IL-15 Molecules in the Murine Syngeneic B16F10 Melanoma Tumor Model This Example demonstrates the effects of various compounds, including 3 PD-1-targeted IL-15 muteins, on tumor growth, body weight changes, and overall survival of mice in the murine syngeneic B16F10 melanoma tumor model. To evaluate the effects of PD-1-targeted IL-15 muteins in this tumor model, the following experiment was carried out:

Female C57/B16 mice were subcutaneously implanted in the upper thigh with approximately 500,000 B16F10 cells, which had been freshly thawed from a single, low-passage vial (of 1*10^7 cells) and cultured for the minimum time required to establish sufficient cells for implantation. When sufficient animals with visible tumor masses of 60-100 $mm^3$ (as defined by (length×width$^2$)/2) was obtained, mice were randomized into groups (of n=10 animals) immediately prior to dosing. Each compound of interest was injected subcutaneously (neck scruff), every 3-4 days, for a total of 3 doses (day 0, defined as the day of first dosing), into each animal of a given group. Tumor volumes, body weight, and animal survival were tracked throughout the course of the experiment. Animals were sacrificed once their tumor volume measured at least 2000 $mm^3$. Overall survival of mice in each treatment group, as well as the body weight of animals within each treatment group, were recorded.

Figure 10A:
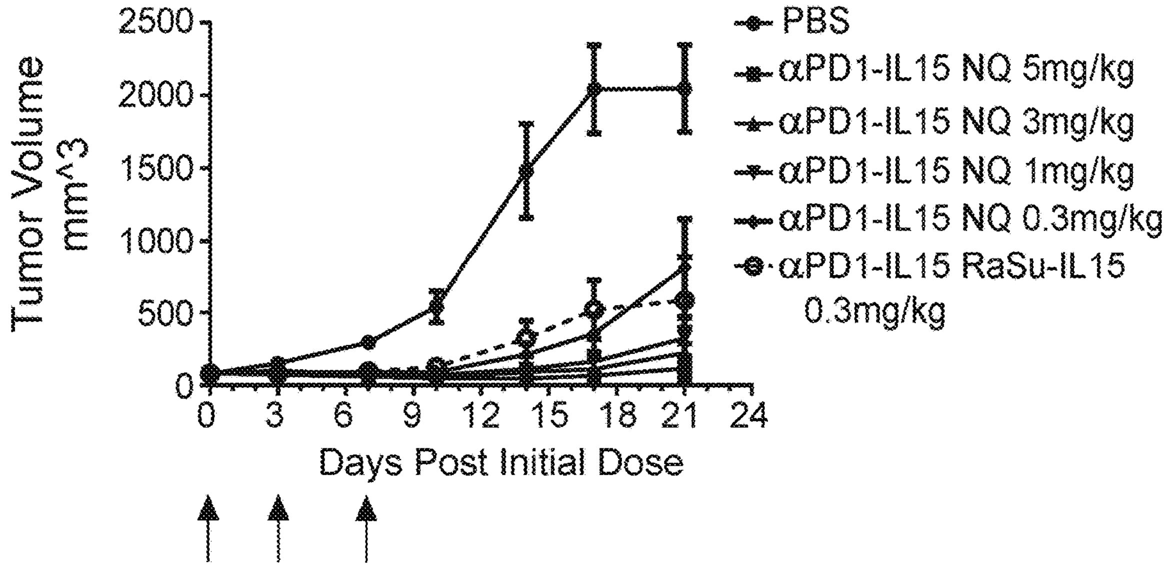

FIG. 10 depicts the results of a study wherein tumor-bearing mice were dosed with xmPD1-IL15 NQ at concentrations of 5, 3, 1, or 0.3 mg/kg; or, with xmPD1-IL15RaSu-IL15 at 0.3 mg/kg; or, with PBS as a vehicle control. FIG. 10A plots the size of implanted tumors starting at day 0 (first day of drug injection). Animals in groups receiving 5, 3, 1, or 0.3 mg/kg of anti-mouse PD-1-IL15 NQ experienced a dose-dependent inhibition in average tumor volume and in tumor volume per individual animal. Furthermore, animals in various groups experienced durable tumor regression (no tumor mass detectable more than 45 days from completion of drug administration), with long-term survival as indicated in Table 13, below:

TABLE 13

Long-term survival from animals treated with anti-PD-1-IL15 compounds.

| Treatment group* | Long-term surviving animals* |
|---|---|
| PBS | 0/10 |
| xmPD-1-IL15 NQ, 5 mg/kg | 5/6 |
| xmPD-1-IL15 NQ, 3 mg/kg | 8/10 |
| xmPD-1-IL15 NQ, 1 mg/kg | 6/10 |
| xmPD-1-IL15 NQ, 0.3 mg/kg | 5/9 |
| xmPD-1-IL15RaSu-IL15, 0.3 mg/kg | 3/8 |

*Mice in each treatment group were scored for long-term survival (more than 45 days tumor-free beyond the cessation of drug treatment).

Animals that experienced long-term survival following xmPD-1-IL15 NQ treatment were re-challenged with B16F10 tumor cells as described in this Example. No detectable tumors grew in any of the long-term surviving animals (in contrast to tumor growth in 100% of naïve mice implanted with B16F10 cells in parallel).

Figure 10B:
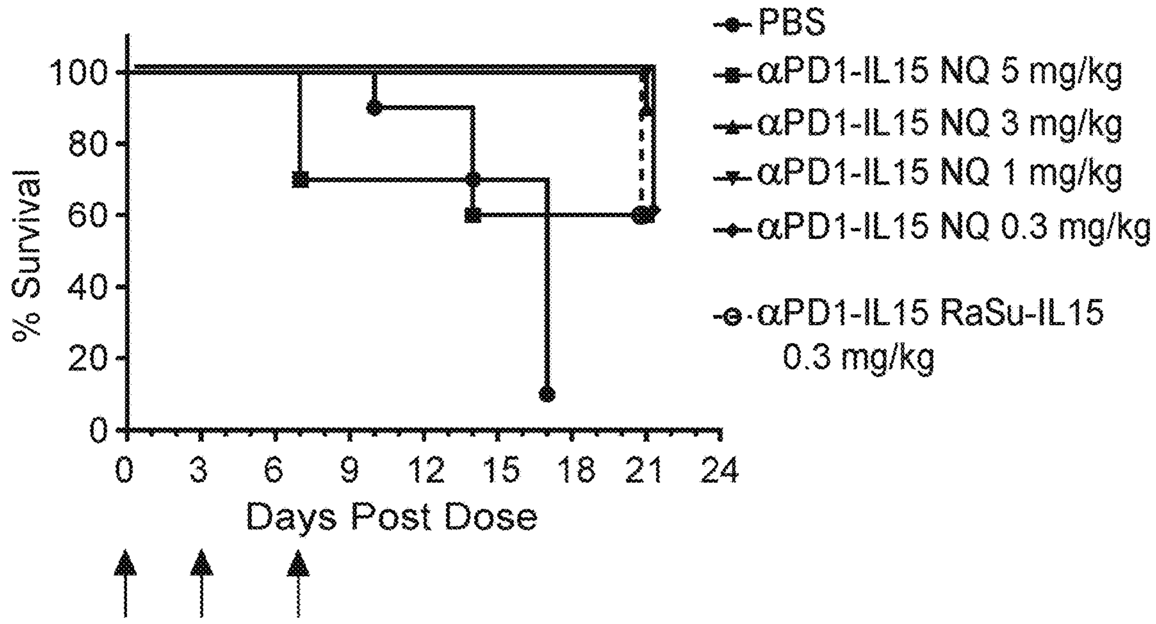
Figure 10C:
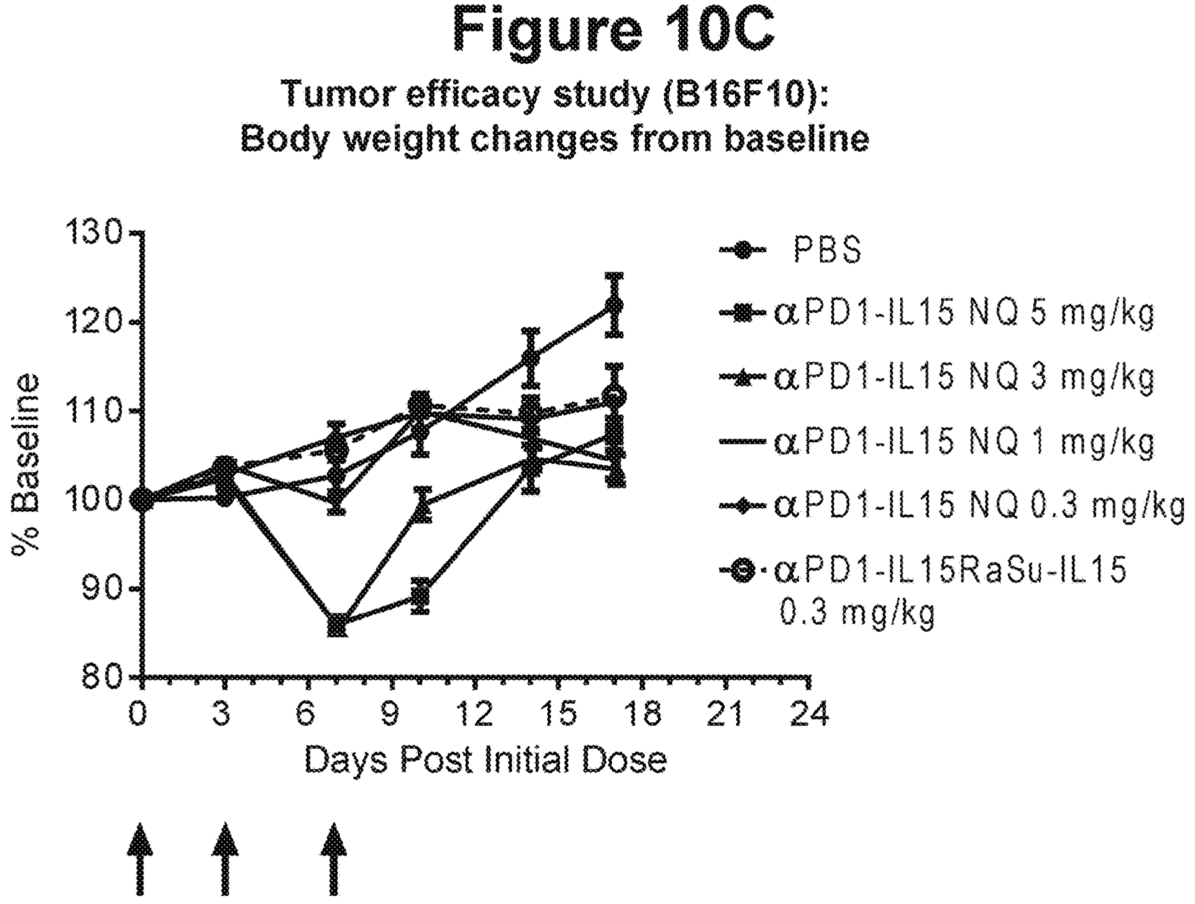

FIG. 10B plots the proportion of viable animals throughout the study. In the 5 mg/kg xmPD-1-IL15 NQ treatment group, 4 of 10 animals died in-study with tumor volumes less than 500 $mm^3$. FIG. 10C plots the averaged weight changes (from baseline, at day 0) of animals in each treatment group throughout the study. Animals in the 5 mg/kg and 3 mg/kg treatment groups experienced transient weight loss (maximum, 15% drop relative to day 0) which returned to baseline upon completion of dosing (FIG. 9C). The maximum tolerated dose of xmPD-1-IL15 NQ was defined as at or below 3 mg/kg (consistent with observations described in Example 6).

To compare and contrast the effects on tumor-bearing mice of: an anti-PD-1 antibody; an untargeted IL-15 NQ compound; and a PD-1-targeted IL-15 NQ, the following experiment was conducted:

A B16F10 tumor model study was established as previously described herein. The study included groups of n=10 animals, as summarized in Table 14, below:

TABLE 14

Treatment groups for B16 tumor efficacy study.

| Group | Treatment |
|---|---|
| 1 | PBS |
| 2 | xmPD1-IL15 NQ, 1 mg/kg |
| 3 | xmPD1-IL15 NQ, 0.3 mg/kg |
| 4 | xmPD1, 1 mg/kg |
| 5 | xmPD1, 0.3 mg/kg |
| 6 | Ab8.8-IL15 NQ, 1 mg/kg |
| 7 | Ab8.8-IL15 NQ, 0.3 mg/kg |

FIG. 11 depicts the results of a study wherein tumor-bearing mice were dosed with the compounds listed in Table 14. FIG. 11A plots the size of implanted tumors starting at day 0 (first day of drug injection). Treatment with either anti-PD-1 antibody, or with untargeted IL-15 NQ (Ab8.8-IL15 NQ) did not significantly alter the tumor growth characteristics compared to PBS treated animals. In contrast, mice treated with xmPD1-IL15 NQ exhibited significant tumor growth inhibition, in a dose-dependent manner. FIG.

11B plots the averaged body weight changes (from baseline, at day 0) of animals in each treatment group throughout the study. Mice treated with xmPD1-IL15 NQ or Ab8.8-IL15 NQ at 1 mg/kg exhibited modest body weight loss (less than 10% from baseline) at day 6, immediately prior to receiving the third dose. This weight loss was transient, with animals returning to baseline weight upon cessation of treatment.

Thus, at equivalent doses, xmPD1-IL15 NQ provided superior tumor growth inhibition versus xPD-1 or Ab8.8-IL15 NQ, and was well tolerated.

To determine the effects of a single dose of the xmPD1-IL-15 M1, the following experiment was conducted. A B16F10 tumor model study was established as previously described herein, with the exception that instead of previously giving 3 doses of each compound, only a single dose was administered in the experiment described below. The study included groups of n=10 animals, as summarized in Table 15, below.

TABLE 15

Treatment groups for B16 tumor efficacy study.

| Group | Treatment |
|---|---|
| 1 | PBS |
| 2 | xmPD1-IL15 M1 5 mg/kg |
| 3 | xmPD1-IL15 M1 1 mg/kg |
| 4 | xmPD1-IL15 M1 0.3 mg/kg |
| 5 | xmPD1-IL15 M1 0.1 mg/kg |

Figure 11A:
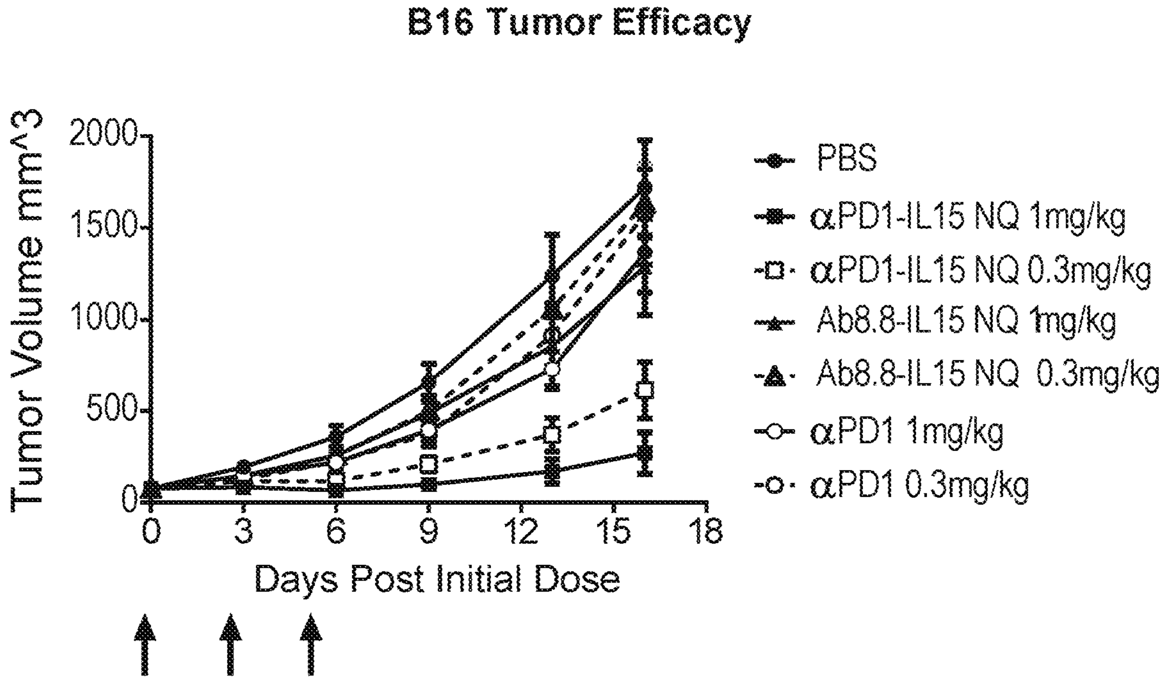
FIGS. 11A and 11B show data from an in vivo B16F10 tumor efficacy study, with mice treated with either anti-PD-1 antibody, xmPD1-IL15 NQ, or isotype control (Ab8.8)-IL15 NQ, each at either 1 or 0.3 mg/kg.
Figure 11B:
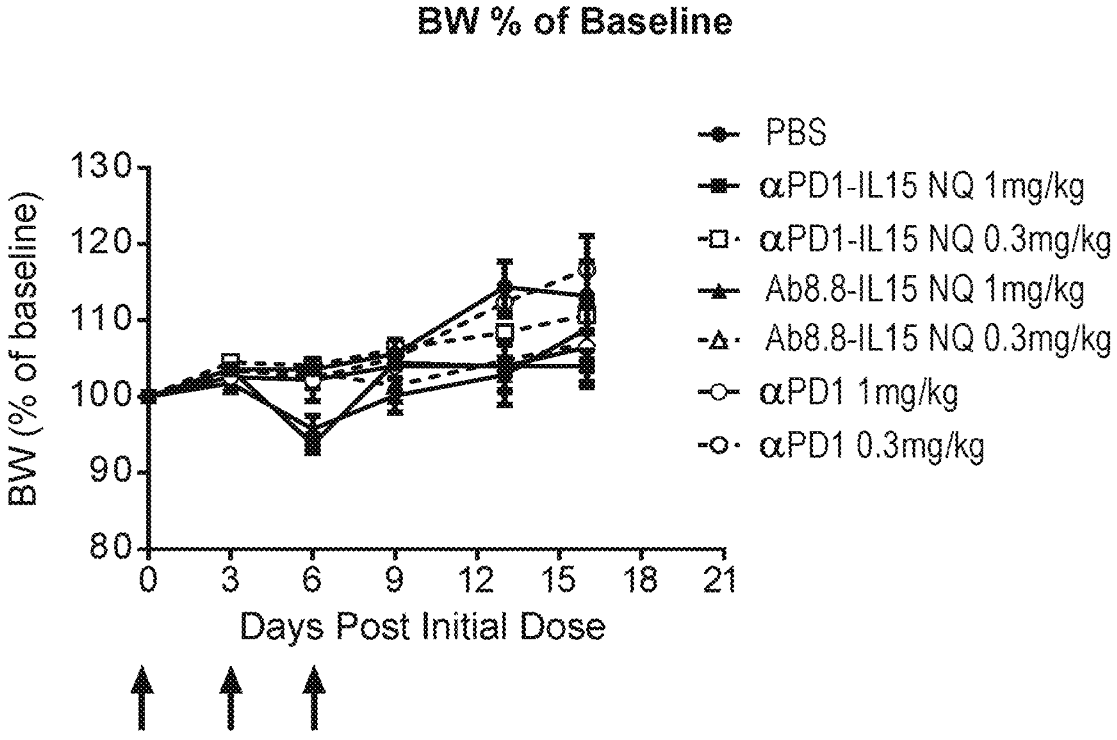
Figure 11C:
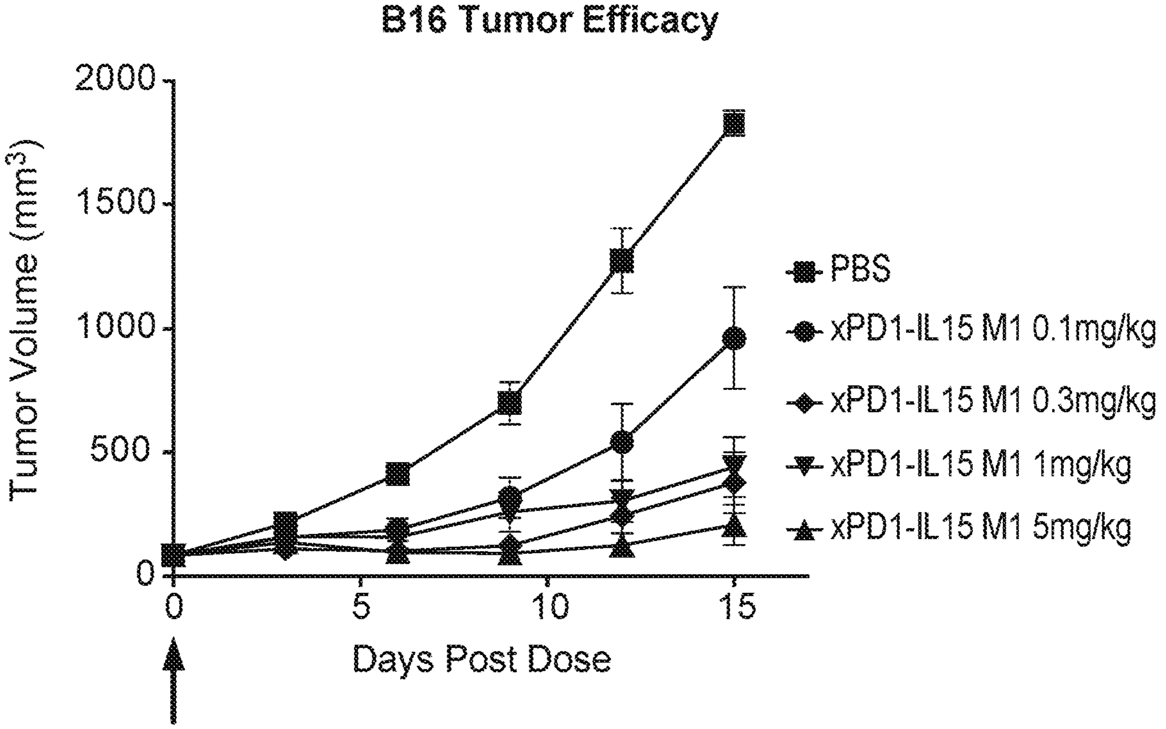
FIGS. 11C, 11D, 11E and 11F show data from an in vivo B16F10 tumor efficacy study, with mice treated with either anti-PD1-IL15 M1 or M2 (as depicted in FIGS. 1D and 1C, respectively), each at either 0.1, 0.3, 1 or 5 mg/kg.
Figure 11D:
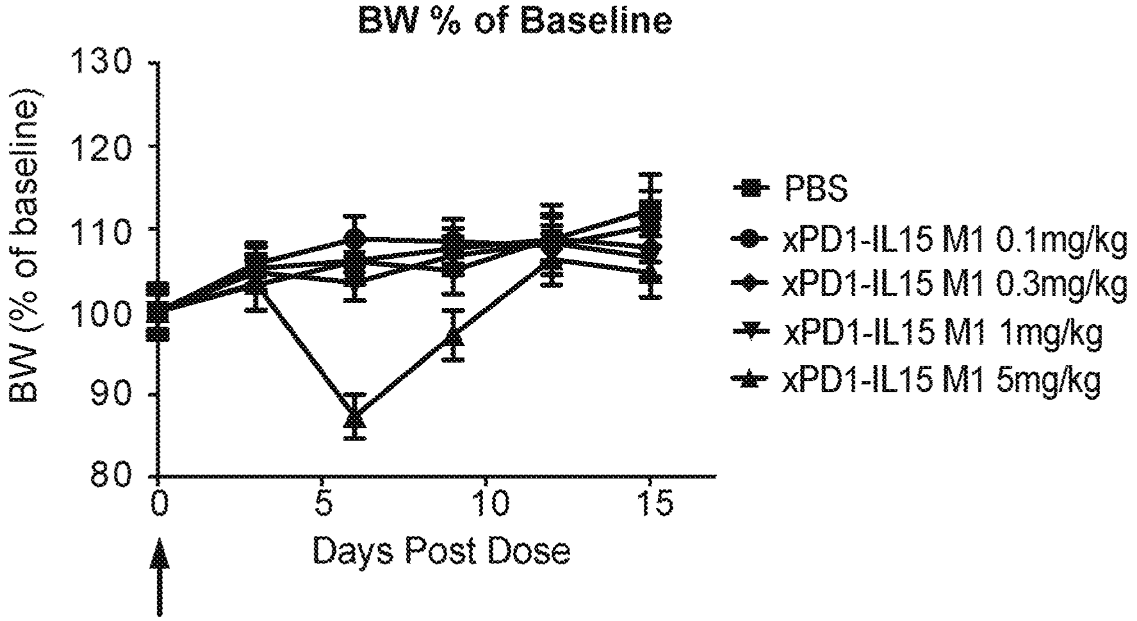

FIGS. 11C and 11D depict the results of a study wherein tumor-bearing mice were singly-dosed with either concentrations of xmPD1-IL-15 M1 listed in table 15, or PBS as a vehicle control. FIG. 11C demonstrates xPD1-IL15 M1 reduces B16F10 tumor growth in a dose-dependent manner. All xmPD1-IL15 M1 doses tested (0.1-5 mg/kg) demonstrated significant inhibition of tumor growth relative to control. Table 15 below, summarizes the number of mice at the end of the study that were determined to be tumor-free relative to each treatment. 5 mg/kg of xmPD1-IL15 M1 yielded the highest number of tumor free mice (6/10) by the end of the study. FIG. 11D plots the averaged body weight changes (from baseline, at day 0) of animals in each treatment group throughout the study. Mice treated with a single dose of xmPD1-IL15 M1 at 5 mg/kg exhibited average body weight loss of 13.5% from baseline at day 6. This weight loss was transient, with body weights rising by the next measurement (3 days later) and back to baseline upon cessation of treatment. No other treatment groups exhibited any weight loss for the duration of the study.

TABLE 16

Number of Tumor-free mice at the end of study.

| Treatment group | Tumor-free mice* |
|---|---|
| PBS | 0/10 |
| xmPD1-IL15 M1 5 mg/kg | 2/10 |
| xmPD1-IL15 M1 1 mg/kg | 3/10 |
| xmPD1-IL15 M1 0.3 mg/kg | 3/10 |
| xmPD1-IL15 M1 0.1 mg/kg | 6/10 |

*Tumor-free mice were determined based upon mice with tumor sizes at the end of study being either non-palpable or measuring less than D0 (start of dosing) tumor volume.

To determine the effects of a single dose of the xmPD1-IL-15 M2, the following experiment was conducted. A B16F10 tumor model study was established as previously described herein, with the exception that instead of previously giving 3 doses of each compound, only a single dose was administered in the experiment described below. This study included groups of n=10 animals, as summarized in Table 17 below.

TABLE 17

Treatment groups for B16 tumor efficacy study.

| Group | Treatment |
|---|---|
| 1 | PBS |
| 2 | xmPD1-IL15 M2 5 mg/kg |
| 3 | xmPD1-IL15 M2 1 mg/kg |
| 4 | xmPD1-IL15 M2 0.3 mg/kg |
| 5 | xmPD1-IL15 M2 0.1 mg/kg |

Figure 11E:
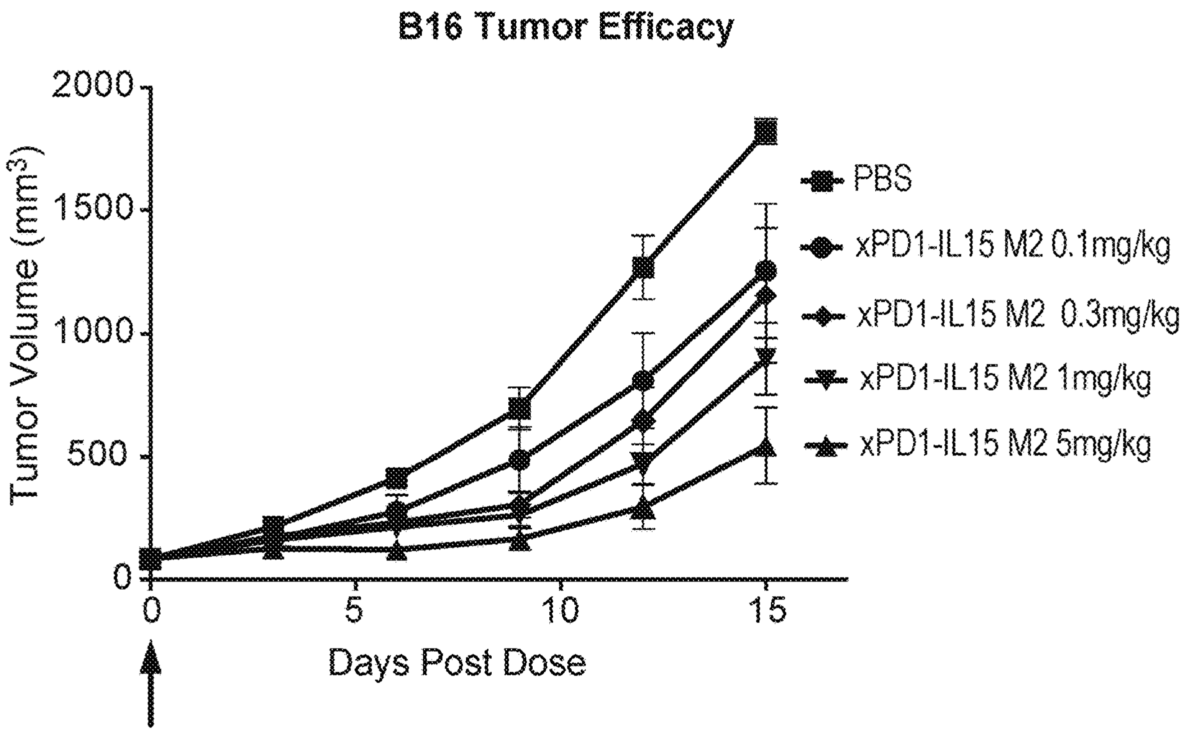
Figure 11F:
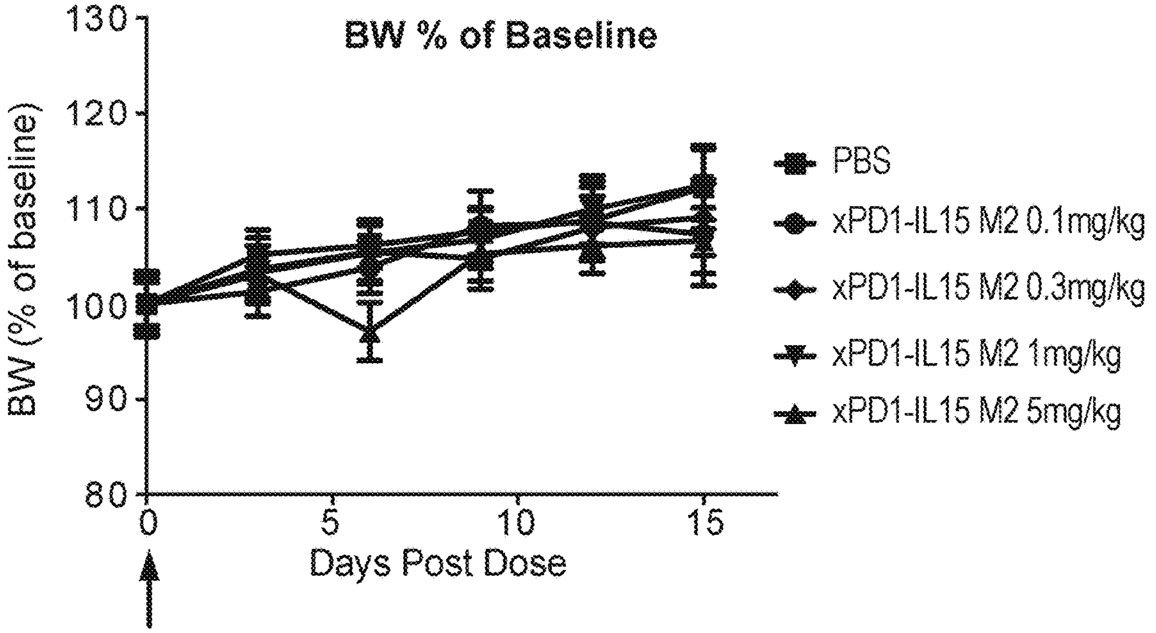

FIGS. 11E and 11F depict the results of a study wherein tumor-bearing mice were singly-dosed with either concentrations of xmPD1-IL-15 M2 listed in table 17, or PBS as a vehicle control. FIG. 11E demonstrates xPD1-IL15 M2 reduces B16F10 tumor growth in a dose-dependent manner. All xmPD1-IL15 M2 doses tested (0.1-5 mg/kg) demonstrated significant inhibition of tumor growth relative to control. Table 18 below, summarizes the number of mice at the end of the study that were determined to be tumor-free relative to each treatment. 5 mg/kg of xmPD1-IL15 M2 yielded the highest number of tumor free mice (4/10) by the end of the study. FIG. 11F plots the averaged body weight changes (from baseline, at day 0) of animals in each treatment group throughout the study. Mice treated with a single dose of xmPD1-IL15 M2 at 5 mg/kg exhibited average body weight loss of 2.9% from baseline at day 6. This weight loss was transient, with body weights returning back to baseline by the next measurement 3 days later. No other treatment groups exhibited any weight loss for the duration of the study.

TABLE 18

Number of Tumor-free mice at the end of study.

| Treatment group | Tumor-free mice* |
|---|---|
| PBS | 0/10 |
| xmPD1-IL15 M2 5 mg/kg | 1/10 |
| xmPD1-IL15 M2 1 mg/kg | 1/10 |
| xmPD1-IL15 M2 0.3 mg/kg | 3/10 |
| xmPD1-IL15 M2 0.1 mg/kg | 4/10 |

*Tumor-free mice were determined based upon mice with tumor sizes at the end of study being either non-palpable or measuring less than D0 (start of dosing) tumor volume.

To compare the effects of a single dose of the xmPD1-IL-15 M1 to xmPD1 alone, the following experiment was conducted. A B16F10 tumor model study was established as previously described herein, with the exception that instead of previously giving 3 doses of each compound, only a single dose was administered in the experiment described below. The study included groups of n=10 animals, as summarized in Table 19, below.

TABLE 19

Treatment groups for B16 tumor efficacy study.

| Group | Treatment |
|---|---|
| 1 | PBS |
| 2 | xmPD1 1 mg/kg |
| 3 | xmPD1-IL15 M1 1 mg/kg |

Figure 11G:
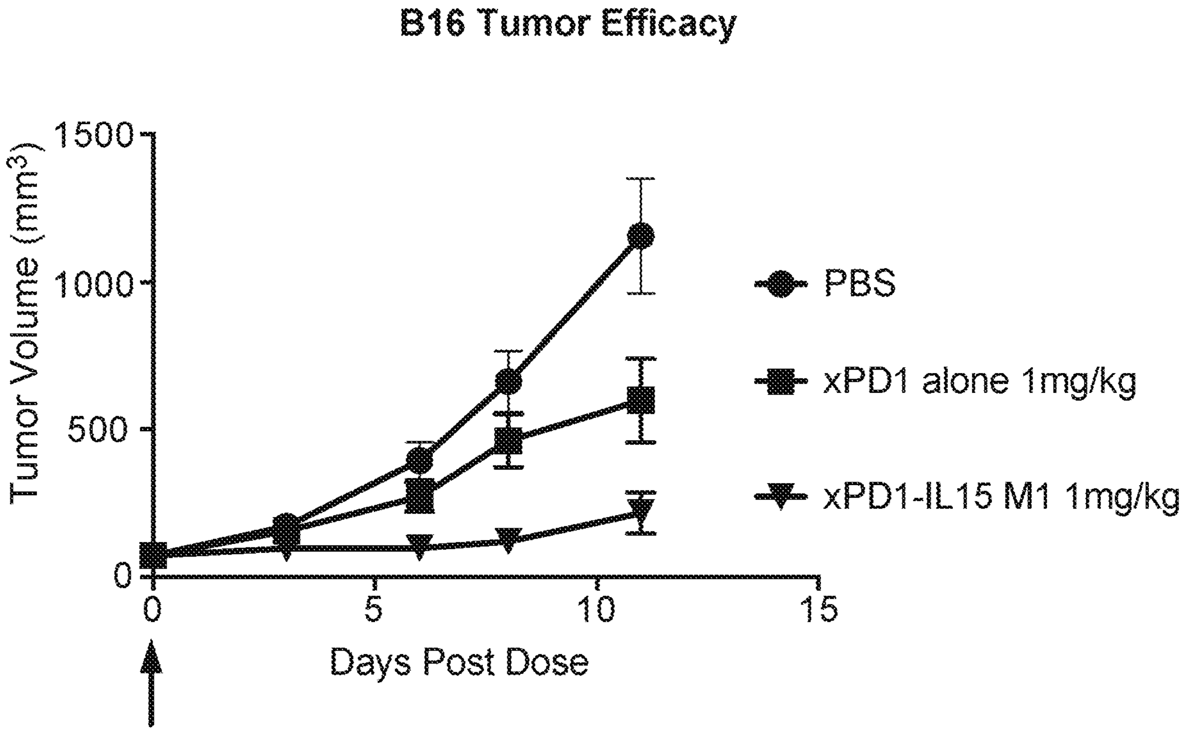
FIGS. 11G and 11H show data from an in vivo B16F10 tumor efficacy study, with mice treated with either anti-PD-1 antibody or anti-PD1-IL15 M1, each at 1 mg/kg.
Figure 11H:
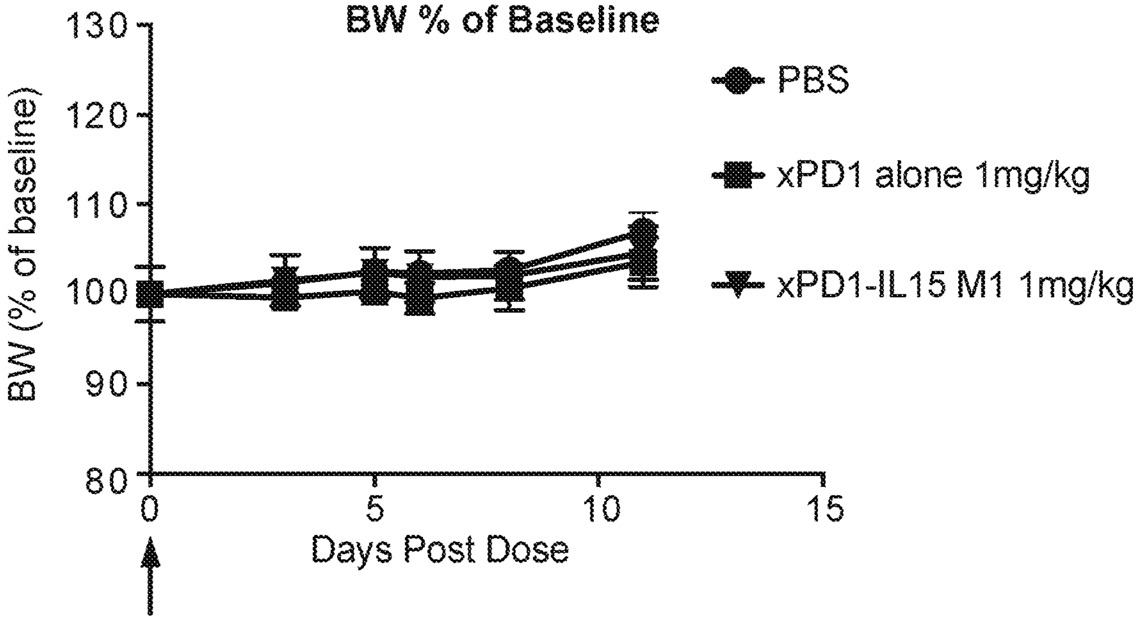

As demonstrated previously, 1 mg/kg of xmPD1-IL15 M1 given as a single dose to B16F10 tumor-bearing mice demonstrated significant tumor inhibition without any body weight loss. FIG. 11G demonstrates that while a single dose of 1 mg/kg of xmPD1 can impair B16F10 tumor growth, xmPD1-IL15 M1, demonstrates a significant improvement greater to that of xmPD1 alone. FIG. 11H plots the averaged body weight changes (from baseline, at day 0) of animals in each treatment group throughout the study. Neither, mice treated with a single dose of xmPD1-IL15 M1 at 1 mg/kg, nor 1 mg/kg of xmPD1 exhibited any body weight loss from baseline.

Example 9. Anti-Tumor Efficacy of Targeted IL-15 Molecules in the Murine Syngeneic MC38 Colon Adenocarcinoma Tumor Model This Example demonstrates the effects of various compounds, including 2 PD-1-targeted IL-15 muteins, on tumor growth and body weight changes of mice in the murine syngeneic MC38 colon adenocarcinoma tumor model. To evaluate the effects of PD-1-targeted IL-15 muteins in this tumor model, the following experiment was carried out.

Female C57/B16 mice were subcutaneously implanted in the upper thigh with approximately 500,000 MC38 cells, which had been freshly thawed from a single, low-passage vial (of 1*10^7 cells) and cultured for the minimum time required to establish sufficient cells for implantation. When sufficient animals with visible tumor masses of 60-90 $mm^3$ (as defined by (length×$width^2$)/2) was obtained, mice were randomized into groups (of n=10 animals) immediately prior to dosing. Each compound of interest was injected subcutaneously (neck scruff), once (day 0, defined as the day of first dosing), into each animal of a given group. Tumor volumes and body weight were tracked throughout the course of the experiment. Animals were sacrificed once their tumor volume measured at least 2000 $mm^3$.

Figure 11I:
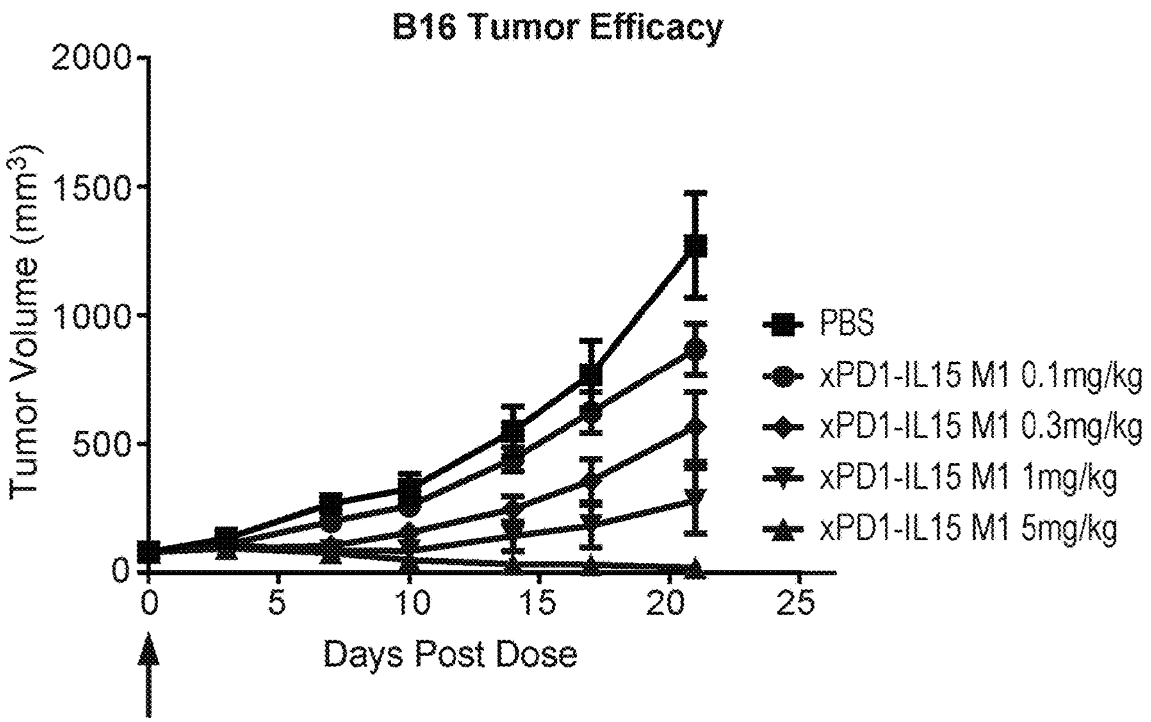
Figure 11J:
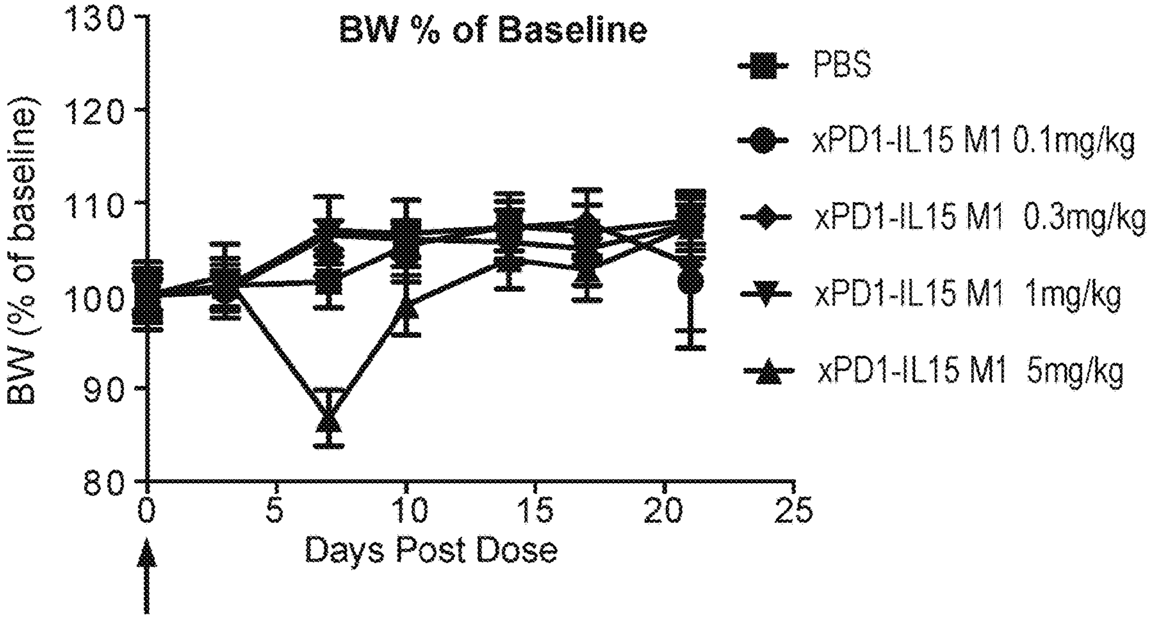

FIGS. 11I and 11J depict the results of a study wherein tumor-bearing mice were dosed with xmPD1-IL15 M1 at concentrations of 5, 1, 0.3, or 0.1 mg/kg; or, with PBS as a vehicle control. FIG. 11I plots the size of implanted tumors starting at day 0 (first day of drug injection). Animals in groups receiving 5, 1 and 0.3 mg/kg of anti-mouse PD-1-IL15 M1 experienced a dose-dependent inhibition in average tumor volume and in tumor volume per individual animal. Table 20 below, summarizes the number of mice at the end of the study that were determined to be tumor-free relative to each treatment. 5 mg/kg of xmPD1-IL15 M1 yielded the highest number of tumor free mice (9/10) by the end of the study. FIG. 11J plots the averaged body weight changes (from baseline, at day 0) of animals in each treatment group throughout the study. Animals receiving 5 mg/kg of xmPD1-IL15 M1 yielded a transient 13.2% body weight loss from D0, that returned to baseline levels by the end of study.

TABLE 20

Number of Tumor-free mice at the end of study.

| Treatment group | Tumor-free mice* |
|---|---|
| PBS | 0/10 |
| xmPD1-IL15 M1 0.1 mg/kg | 0/10 |
| xmPD1-IL15 M1 0.3 mg/kg | 2/10 |
| xmPD1-IL15 M1 1 mg/kg | 4/10 |
| xmPD1-IL15 M1 5 mg/kg | 9/10 |

*Tumor-free mice were determined based upon mice with tumor sizes at the end of study being either non-palpable or measuring less than D0 (start of dosing) tumor volume.

Figure 11K:
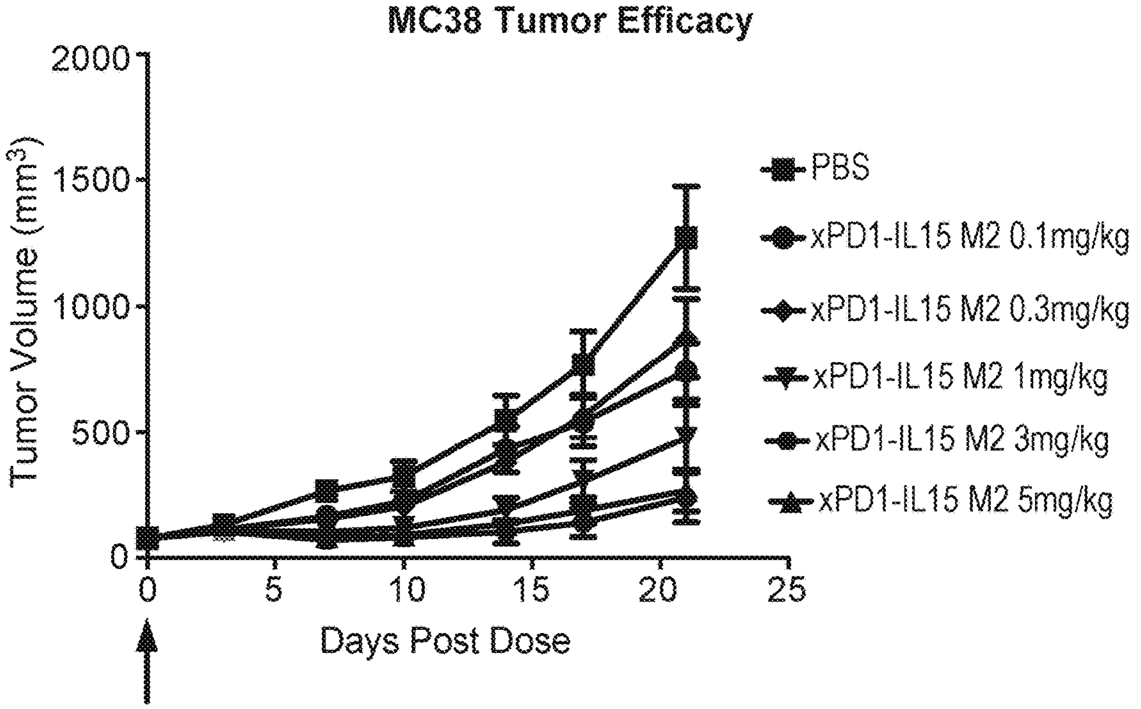
Figure 11L:
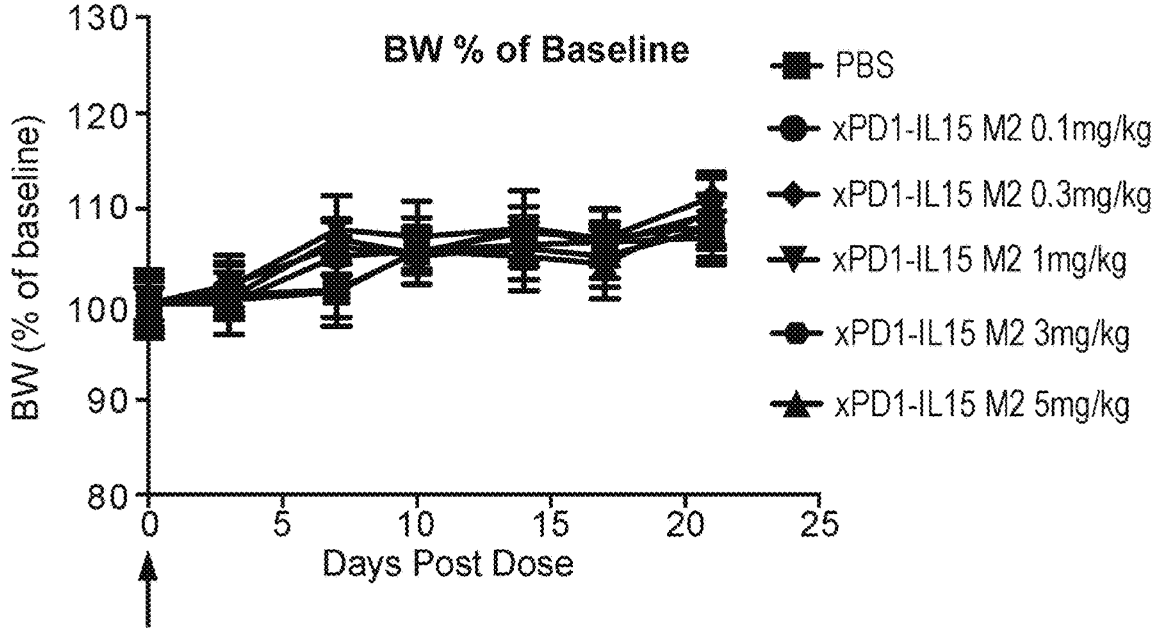

FIGS. 11K and 11L depict the results of a study wherein tumor-bearing mice were dosed with xmPD1-IL15 M2 at concentrations of 5, 1, 0.3, or 0.1 mg/kg; or, with PBS as a vehicle control. FIG. 11K plots the size of implanted tumors starting at day 0 (first day of drug injection). Animals in groups receiving 5, 1, and 0.3 mg/kg of anti-mouse PD-1-IL15 M2 experienced a dose-dependent inhibition in average tumor volume and in tumor volume per individual animal. Table 21 below, summarizes the number of mice at the end of the study that were determined to be tumor-free relative to each treatment. 5 mg/kg of xmPD1-IL15 M2 yielded the highest number of tumor free mice (4/10) by the end of the study. FIG. 11L plots the averaged body weight changes (from baseline, at day 0) of animals in each treatment group throughout the study. xmPD1-IL15 M2 at doses described above, did not yield any body weight loss throughout the study.

TABLE 21

Number of Tumor-free mice at the end of study.

| Treatment group | Tumor-free mice* |
|---|---|
| PBS | 0/10 |
| xmPD1-IL15 M2 0.1 mg/kg | 0/10 |
| xmPD1-IL15 M2 0.3 mg/kg | 0/10 |
| xmPD1-IL15 M2 1 mg/kg | 3/10 |
| xmPD1-IL15 M2 5 mg/kg | 4/10 |

*Tumor-free mice were determined based upon mice with tumor sizes at the end of study being either non-palpable or measuring less than D0 (start of dosing) tumor volume.

Example 10. Characterizing the Effects of Targeted IL-15 on Murine Immune Cell Populations This Example describes a method to assess the functional consequences of administering a PD-1-targeted IL-15 mutein to a mouse, using immune cell phenotyping of splenic and tumor-infiltrating lymphocytes.

B16F10 tumor-bearing mice were established essentially as described in Example 8, Table 14, with n=4 or 5 mice per treatment group. When Table 22 lists the compounds received by each group and the number of animals per group:

TABLE 22

Treatment groups for immune cell profiling study.

| Group | Treatment |
|---|---|
| 1 | PBS, n = 5 |
| 2 | xmPD1-IL15 NQ, 0.3 mg/kg, n = 4 |
| 3 | xmPD1, 0.3 mg/kg, n = 5 |
| 4 | Ab8.8-IL15 NQ, 0.3 mg/kg, n = 5 |

Splenocytes and tumor cell suspensions were obtained from each animal as described in Example 7. The resulting cell suspensions were then stained with the following cocktail of fluorescently-labeled antibodies or viability dyes, as indicated below in Table 23:

TABLE 23

| Antibody and live/dead dye staining panel for immune cell profiling study. | | | | |
|---|---|---|---|---|
| Target | Label | Clone | Manufacturer | Dilution |
| L/D Blue | | | Life Tech | 1:100 |
| CD45 | A700 | 30-F11 | Biolegend | 1:100 |
| CD90.2 | BUV395 | 30-H12 | Biolegend | 1:100 |
| CD4 | PerCPCy5.5 | GK1.5 | Biolegend | 1:100 |
| CD8 | BV785 | 53-6.7 | Biolegend | 1:100 |
| FoxP3 | Pac Blue | FJK-16s | eBiosciences | 1:50 |
| xhFc | APC | H2 | Southern Biotech | 1:500 |

TABLE 23-continued

| Antibody and live/dead dye staining panel for immune cell profiling study. | | | | |
|---|---|---|---|---|
| Target | Label | Clone | Manufacturer | Dilution |
| CD16 | APCe780 | ebioCB16 | Invitrogen | |
| Perforin | PE | dG9 | Biolegend | |

Staining, washing, and analysis of cells by flow cytometry were carried out as described in Example 7.

FIG. 12A shows the results from an experiment designed to detect either Ab8.8-IL15 NQ, xmPD1-IL15 NQ, or xPD-1, on isolated splenocytes or tumor-infiltrating lymphocytes. T cells (viable, singlet, CD90.2+) from either tumor (histograms, shown on top row) or spleen (shown on bottom row) were further subdivided into CD8+ (left column) or CD4+ (right column). Overlaid histograms for each cell population show the results of staining those cells with anti-human Fc (to detect the common human IgG Fc portion present in each of the recombinant molecules) from animals treated with the compounds as listed next to each plot. The xmPD1-NQ molecule was detected on CD8+ TILs and to a lesser extent on CD4+ TILs, mirroring the detection of xmPD1 molecule, albeit with a lower intensity. Ab8.8-IL15 NQ molecule was not detected above background levels on CD8+ TILs. Very little signal above background staining was observed for all molecules from CD4+ or CD8+ splenocytes at the time of analysis. Table 24 summarizes the results obtained from staining splenocytes and TILs from all animals including in this experiment.

TABLE 24

Summary of anti-human Fc+ splenocytes or TILs from mice of various treatment groups.

| Tumor | | | | Spleen | | | |
|---|---|---|---|---|---|---|---|
| Sample # | Treatment group | % xFc+ of CD8+ | % xFc+ of CD4+ | Sample # | Treatment group | % xFc+ of CD8+ | % xFc+ of CD4+ |
| T1 | xPD1 | 85.9 | 70.3 | S1 | xPD1 | 3.84 | 4.75 |
| T2 | xPD1 | 68.6 | 87.1 | S2 | xPD1 | 1.64 | 15.5 |
| T3 | xPD1 | 87.4 | 57.4 | S3 | xPD1 | 1.98 | 7.64 |
| T4 | xPD1 | 81.1 | 69.7 | S7 | xPD1-IL15 NQ | 0.25 | 1.39 |
| T5 | xPD1 | 88 | 66.7 | S8 | xPD1-IL15 NQ | 0.48 | 0.91 |
| T7 | xPD1-IL15 NQ | 63.2 | 22.5 | S9 | xPD1-IL15 NQ | 0.27 | 0.84 |
| T8 | xPD1-IL15 NQ | 39.8 | 12.8 | S10 | xPD1-IL15 NQ | 0.23 | 2.17 |
| T9 | xPD1-IL15 NQ | 51.7 | 22.5 | S11 | Ab8.8-IL15 NQ | 0.049 | 0.28 |
| T10 | xPD1-IL15 NQ | 23.8 | 12.9 | S12 | Ab8.8-IL15 NQ | 0.074 | 0.2 |
| T11 | Ab8.8-IL15 NQ | 0.68 | 1 | S13 | Ab8.8-IL15 NQ | 0.44 | 0.32 |
| T12 | Ab8.8-IL15 NQ | 2.06 | 5.88 | S14 | Ab8.8-IL15 NQ | 13.1 | 0.23 |
| T13 | Ab8.8-IL15 NQ | 1.1 | 3.5 | S15 | Ab8.8-IL15 NQ | 0.84 | 0.14 |
| T14 | Ab8.8-IL15 NQ | 2.09 | 3.56 | S16 | PBS | 0.17 | 0.096 |
| T15 | Ab8.8-IL15 NQ | 1.72 | 6.18 | S17 | PBS | 0.07 | 0.089 |
| T16 | PBS | 0.56 | 0.93 | S18 | PBS | 0.092 | 0.14 |
| T17 | PBS | 0.38 | 0.44 | S19 | PBS | 0.089 | 0.14 |
| T18 | PBS | 0.33 | 0.44 | S20 | PBS | 0.031 | 0.12 |
| T19 | PBS | 2.2 | 1.02 | | | | |
| T20 | PBS | 0.25 | 0.21 | | | | |

In summary, anti-PD1 and xmPD1-IL15 NQ show similar patterns of targeting: specifically, they are enriched on tumor-resident CD8+ T cells.

In addition, these same stained splenocytes and TILs were analyzed to assess changes in immune cell frequencies due to the aforementioned treatments. FIG. 12B and FIG. 12C depict the changes in immune cell subsets due to various treatments in splenocytes or TILs, respectively. FIG. 12D plots the CD8:CD4 ratios of T cells in the spleen and the tumor. Of note, the CD8:CD4 T cell ratio in the tumor increased with xmPD1-IL15 NQ treatment, but not with Ab8.8-IL15 NQ or xmPD1 treatments. There were no changes in splenic CD8:CD4 ratios in any of the treatment groups. Thus, using a PD-1-targeted version of the IL-15 NQ mutein resulted in significant changes in the CD8:CD4 ratio, as well as significant differences in anti-tumor efficacy (FIG. 10A).

FIG. 13 describes a method to assess the pharmacodynamic effect of administering a PD-1-targeted IL-15 muteins M1 and M2 to a mouse, using immune cell phenotyping of peripheral blood and tumor-infiltrating lymphocytes.

B16F10 tumor-bearing mice were established essentially as described in Example 8 Table 15, with n=5 mice per treatment group. When Table 25 lists the compounds received by each group and the number of animals per group:

TABLE 25

Treatment groups for immune cell profiling study.

| Group | Treatment |
|---|---|
| 1 | PBS, n = 5 |
| 2 | xmPD1-IL15 M1, 0.3 mg/kg, n = 5 |
| 3 | xmPD1-IL15 M1, 1 mg/kg, n = 5 |
| 4 | xmPD1-IL15 M2, 1 mg/kg, n = 5 |
| 5 | xmPD1-IL15 M2, 3 mg/kg, n = 5 |

Peripheral blood and tumor cell suspensions were obtained from each animal on Day 3, 6 or 9 post-xmPD1-IL15 treatment as described in Example 7. The resulting cell suspensions were then stained with a cocktail of fluorescently-labeled antibodies or viability dyes, as indicated in Table 23. Staining, washing, and analysis of cells by flow cytometry were carried out as described in Example 7.

FIGS. 13A and 13B show the absolute counts of NK, CD8+ T and Treg cells in peripheral blood or tumor-infiltrating lymphocytes at Day 6, which showed to have the maximum effect by xmPD1-IL15 M1 and xmPD1-IL15 m2, respectively. Both xmPD1-IL15 muteins did not expand Treg cells in peripheral blood and tumor. NK cells expanded more than CD8+ T cells in peripheral blood, especially at the higher dose. This is due to the fact that NK cells have higher expression level of IL-2 receptors, while CD8+ T cells have no or low expression of PD-1. But CD8+ T cells expanded more than NK cells in the tumor, suggesting that both xmPD1-IL15 muteins are targeted to the tumor via PD-1 on CD8+ TILs over NK cells.

Three studies were performed to determine which immune cell type is required for anti-tumor efficacy of of xmPD1-M1, and whether T cell migration was required for efficacy: NK1.1+ depletion, CD8 T cell depletion, and treatment with FTY720, an inhibitor of T cell migration (shown in FIGS. 13C, 13D and 13E). CD8 T cells were depleted with aCD8b antibody (clone 53-5.8, 350 mg dosed i.p., 3 and 1 day prior to M1 injection and weekly thereafter). NK cells were depleted with aNK1.1 antibody (clone PK136, 200 □g i.p., 2 days prior to 1 mg/kg M1 injection and weekly thereafter). Control groups included IgG2a isotype (clone C1.18.4) and IgG1 isotype (clone TNP6A7). FTY720 compound was dosed i.p. 1 mg/kg 3 and 1 days prior to 1 mg/kg M1 injection and every 3 days thereafter.

FIGS. 13C and 13D show the respective effects of depleting CD8 T and NK1.1+ cells on anti-tumor efficacy in B16 model after treatment of 1 mg/kg xmPD1-IL15 M1. NK1.1+ cells contain both NK and NK T cells. These studies suggested that efficacy of xmPD1-M1 was lost in the absence of CD8 T cells but not NK1.1+ cells.

FIG. 13E shows the effect of FTY420 treatment, which inhibits T cell egress, on anti-tumor efficacy in B16 model after treatment of 1 mg/kg xmPD1-IL15 M1. Results show that T cell migration was not required for efficacy.

Example 11. Characterizing the Effects of Targeted IL-15 on Cytokine Production In Vivo This Example describes a method to assess the functional consequences of administering a PD-1-targeted IL-15 mutein to a mouse, by assessing the cytokines present in peripheral blood.

Female (8 week old) C57B6/6J mice (Jackson Laboratories, Sacramento, Calif.) were dosed subcutaneously with the compounds and doses as listed in Table 26, below:

TABLE 26

Treatment groups for in vivo cytokine study.

| Group | Treatment |
|---|---|
| 1 | xmPD1-IL15 NQ, 1 mg/kg |
| 2 | xmPD1-IL15 NQ, 0.3 mg/kg |
| 3 | xmPD1-IL15RaSu, 1 mg/kg |
| 4 | xmPD1-IL15RaSu, 0.3 mg/kg |
| 5 | Ab8.8-IL15 NQ, 1 mg/kg |
| 6 | Ab8.8-IL15 NQ, 0.3 mg/kg |

Blood was collected at 0 hr, 2 hr, 4 hr, 6 hr, 24 hr, 48 hr, 72 hr, 96 hr and 120 hr post-dose (n=3 mice per time point) by submandibular vein puncture (in-life) or by cardiac puncture immediately (after euthanasia with $CO_2$) and processed for serum in micro 1.1m1Z-gel tubes (Sarstedt, Numbrecht, Germany). Appropriate volumes for blood draws in each mouse was followed according to the NIH Guidelines for Survival Bleeding of Mice and Rats http://oacu.od.nih.gov/ARAC/survival.pdf. All animals were maintained in an AAALAC-accredited facility and used in accordance with recommendations as described in the Guide for the Care and Use of Laboratory Animals (Institute on Laboratory Animal Resources, Rockville, Md.).

Multiple serum cytokines including IFNgamma and IL-6 were measured using the multi-spot electrochemiluminescence U-plex assay (Meso Scale Discovery, Rockville, Md.). A 1:5 dilution of total serum from each mouse sample was made in assay buffer and added to plates for an overnight incubation at 4° C. The remaining steps were followed as described by the manufacturer. Data were plotted as groups with SEM and statistics were done by t-tests when comparing 2 groups or 2-way ANOVA followed by Tukey's multiple comparison tests (GraphPad Prism, La Jolla, Calif.).

FIG. 14 shows the results obtained from analyzing serum cytokine levels in the various treatment group animals. FIG. 14A shows the measured levels of IFNγ. Of note, xmPD1-IL15RaSu-IL15 treatment group animals had significantly higher IFNγ than did animals from the other treatment groups, through 48 hrs post-dose. At 72 hrs, the xmPD1-IL15 NQ treated animals exhibited slightly higher IFNγ than animals from the xmPD1-IL15RaSu-IL15 0.3 mg/kg group; and, at 96 hrs, animals from both xmPD1-IL15 NQ groups had slightly higher IFNγ than mice from any other group. This difference persisted through the end of the study (120 hrs post-dose). In contrast, animals receiving untargeted, NQ-mutant IL15 (i.e., Ab8.8-IL15 NQ animals) produced significantly lower IFNg at the 48 and 72 hr time points. Thus, the kinetics and maximal response of IFNγ generation differ between the tested molecules, with NQ variants generating reduced levels of IFNg compared to wildtype IL-15-containing molecules at equivalent doses. Furthermore, the presence of an anti-PD-1 targeting arm led to significant differences in IFNg production, highlighting the value of using a target-driven cytokine modality.

FIG. 14B shows the levels of the cytokine IL-6 as measured in the various treatment groups. In comparing all three tested groups at 1 mg/kg, mPD1-IL15RaSu-IL15 treatment group animals had significantly higher IL-6 than did animals from the other treatment groups, through 48 hrs post-dose. In the 72-120 hour time point samples, group xmPD1-IL15 NQ generated IL-6 levels that were comparable to those from the xmPD1-IL15RaSu-IL15 1 mg/kg treatment group. In contrast, animals from the Ab8.8-IL15 NQ group generated a consistent amount of IL-6 which was always equivalent to or below the levels generated by the PD-1 targeted versions. A similar pattern of IL-6 production was seen in the 0.3 mg/kg groups, with xmPD1-IL15RaSu-IL15 producing an earlier, higher peak, followed by xmPD1-IL15 NQ producing a later-emerging and longer-lasting peak. Thus, the NQ variant differs from its wildtype IL-15 moiety counterpart in the kinetics and maximal output of two inflammatory cytokines produced in vivo at comparable doses; and, targeted NQ produced more IFNγ and IL-6 across multiple time points than did untargeted.

Example 12: In Vitro Functional Assay of Anti-Human PD-1-IL15 M1 and M2 Molecules Using Human Peripheral Blood Mononuclear Cells (hPBMCs)

In this example, the effects of the targeted anti-human PD-1-IL15 on the induction of pSTAT5 is compared to that of the untargeted isotype control-antibody-IL15 chimeric molecules on human NK cells, CD8+ effector memory (em) T cells and CD8+ central memory (cm) T cells from hPBMCs.

Blood from healthy volunteers was taken and hPBMCs were isolated using a ficoll-paque (GE Healthcare) gradient, washed with PBS to remove platelets, and cleared of red blood cells using ACK lysis buffer (Gibco). Cells were then plated at 2*10e6 cells/well in 50 ul serum free RPMI 1640 media (Gibco), and allowed to rest for 2-4 hours at 37° C. After resting, cells were treated with the listed molecules (Table 18) at the given concentrations for 30 min at 37° C. Cells were then immediately fixed with 2% PFA (Electron Microscopy Sciences) for 10 min at room temperature, after which they were stained for surface markers for 30 min at 4° C. Cells were then fixed again with 2% PFA for 10 min at room temperature, then resuspended in cold Perm Buffer III (BD), and stored at −20° C. overnight. The following day, cells were stained for intracellular markers using the antibodies (as described in Table 27, below) in permeabilization buffer (ebioscience) for 45 min, then analyzed by flow cytometry.

TABLE 27

Antibodies used for staining different lymphocytes in hPBMC and pSTAT5 activity for flow cytometry.

| Target | Label | Clone | Vendor |
|---|---|---|---|
| CD45 | BV605 | HI30 | Biolegend |
| CD3 | BUV395 | SK7 | BD |
| CD4 | BV711 | RPA-T4 | Biolegend |
| CD8 | BV510 | SK1 | Biolegend |
| CD25 | BV421 | BC96 | Biolegend |
| CD62L | BV786 | DREG-56 | Biolegend |
| CD45RO | FITC | UCHL1 | Biolegend |
| CD16 | APCe780 | ebioCB16 | Invitrogen |
| Perforin | PE | dG9 | Biolegend |
| pSTAT5 | A647 | 47/STAT5(p694) | BD |

FIGS. 15A-15F depict the effects of adding targeted anti-human PD-1 (xhPD1)-IL15 and untargeted isotype control-antibody-IL15 chimeric molecules to the hPBMCs, where they cause different pSTAT5 activation on human NK cells, $CD8^+$ em T cells and $CD8^+$ cm T cells. In NK cells, there is no significant targeting activity for xhPD1-IL15 compared to that of the isotype control-IL15 (M1 in FIGS. 15A and M2 in FIG. 15D), as NK cells have no or low PD-1 expression (Table 28). In $CD8^+$ em T cells and $CD8^+$ cm T cells, there are significant targeting activities for xhPD1-IL15 compared to that of the isotype control-IL15 (M1 in FIGS. 15B-15C and M2 in FIG. 15E-15F), as $CD8^+$ em T cells and $CD8^+$ cm T cells have PD-1 expression (Table 28). The EC50 values for the isotype control-IL15 on NK cells are 3-4-fold lower as compared to that on $CD8^+$ em T cells and CD8+cm T cells, confirming that NK cells are more sensitive to IL15 activation in general due to the fact that they have higher level of CD122/CD132 expression. However, the $CD8^+$ cm T cells and $CD8^+$ cm T cells are more sensitive to the xPD1-IL15 activation because of the targeting activity driven by the PD-1 expression on those cell types. This example shows that xPD1-IL15 can also preferentially activates PD-1+ cells over PD-1(low) cells in a human system as well as the mouse system as shown in the previous Examples. Table 28, below, summarizes the calculated EC50 values for the aforementioned molecules, and also displays the fold change as the ratio of EC50 between isotype control-IL15 and xhPD1-IL15.

TABLE 28

| | Average of 3 healthy donors | | | | | | | |
|---|---|---|---|---|---|---|---|---|
| | | | EC50 (nM) | | | | | |
| | FMO/ | FMO/ | Isotype control-- | xhPD1-- | Isotype control-- | xhPD1-- | Fold change* | |
| | % PD-1 | MFI PD-1 | IL15 M1 | IL15 M1 | IL15 M2 | IL15 M2 | M1 | M2 |
| NK cells | 1.4/6.55 | 495/491 | 0.9455 | 0.4746 | 11.22 | 8.266 | 1.99 | 1.36 |
| $CD8^+$em T cells | 2.53/70.4 | −3.76/897 | | | | | | |
| $CD8^+$cm T cells | 2.89/61.3 | −10.1/742 | 3.665 | 0.07804 | 37.63 | 0.4916 | 46.96 | 76.55 |

*Fold change = EC50 (Isotype control--IL15)/EC50 (xhPD1--IL15)

Example 13: In Vivo Efficacy Study of Anti-Mouse PD-1-IL15 M1 and Anti-EDA-IL-10 Fusion Protein in MC38 Model This Example describes a method to assess the anti-tumor efficacy of administering a PD-1-targeted IL-15 molecule (xPD1-IL15 M1) in combination with an anti-EDA-IL-10 fusion protein (xEDA-IL 10). Mice were dosed as follows: xPD1-IL15 M1 was dosed on day 0 at 0.3 mg/kg or 1 mg/kg and anti-EDA-IL-10 fusion protein (xEDA-IL 10) was dosed on day 0 and 2 times/week thereafter for a total of 5 doses at 5 mg/kg each dose. As shown in FIGS. 16A and 16B, a synergistic effect was observed in both doses of xPD1-IL15 M1 administered in combination with anti-EDA-IL-10 fusion protein (xEDA-IL 10), and in particular, the lower dose (0.3 mg/kg) xPD1-IL15 M1.

FIG. 16C plots the averaged body weight changes (from baseline, at day 0) of animals in each treatment group throughout the study. Mice treated with a single dose of xPD1-IL15 M1 at 1 mg/kg in combination with 5 mg/kg of anti-EDA-IL-10 fusion protein (xEDA-IL 10) exhibited average body weight loss of 12% from baseline at day 6. This weight loss was transient, with body weights returning back to baseline by the next measurement 3 days later. No other treatment groups exhibited any weight loss for the duration of the study.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated human interleukin 15 (IL-15) variant comprising amino acid substitutions at positions a) V49 and S51 or b) V49, I50, and S51 of SEQ ID NO: 1, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant has decreased or no binding to the human IL-15 receptor alpha (IL-15Rα) and the human IL-2 receptor beta/gamma (IL-2Rβγ) as compared to the wild-type human IL-15 polypeptide or a wild-type IL-15 receptor alpha-IL-15 fusion polypeptide, and wherein the amino acid substitution at position V49 is glycosylated.

2. The isolated IL-15 variant of claim 1, wherein the IL-15 variant comprises amino acid substitutions at positions selected from the group consisting of:

a) V49, I50, S51, N4, D30, and E64;
b) V49, I50, S51, N4, D30, E64, and I68;
c) V49, I50, S51, N4, D30, E64, M109;
d) V49, I50, S51, N4, D30, E64, I68, and M109;
e) V49, I50, S51, D30, E64, and I68;
f) V49, I50, S51, D30, E64, M109;
g) V49, I50, S51, D30, E64, I68, and M109;
h) N1, V49, I50, and S51;
i) N4, V49, I50, and S51;
j) S7, V49, I50, and S51;
k) K10, V49, I50, and S51;
l) K11, V49, I50, and S51;
m) S29, V49, I50, and S51;
n) V31, V49, I50, and S51;
o) H32, V49, I50, and S51;
p) V49, I50, S51, and E64;
q) V49, I50, S51, and I68;
r) V49, I50, S51, and L69;
s) V49, I50, S51, and I111;
t) N4, V49, I50, S51, and E64;
u) N1, D30, V49, I50, and S51;
v) N4, D30, V49, I50, and S51;
w) S7 D30, V49, I50, and S51;
x) K10, D30, V49, I50, and S51;
y) K11, D30, V49, I50, and S51;
z) S29, D30, V49, I50, and S51;
aa) D30, V49, I50, S51, and E64;
bb) D30, V49, I50, S51, and I68;
cc) D30, V49, I50, S51, and L69; and
dd) D30, V49, I50, S51, and I111.

3. The isolated IL-15 variant of claim 1, wherein the amino acid substitutions comprise one or more specific substitutions at:

a) V49N;
b) I50A or I50G;
c) S51T;
d) N1K, N1G, N1Q, N1R, N1E, N1A, or N1D;
e) N4K, N4G, N4A, N4S, N4D, N4E, N4I, N4L, N4R, N4T, N4W, or N4Q;
f) S7E, S7G, S7D, S7K, S7N, S7R, S7H, or S7T;
g) K10A, K10S, K10E, K10L, K10M, K10D, or K10G;
h) K11D, K11S, or K11W;
i) D30N;
j) E64Q, E64K, E64A, E64S, E64N, E64H, E64T, or E64R;
k) E53N;
l) G55S or G55T;
m) E89N;
n) L91S or L91T;
o) Y26K, Y26R, or Y26H;
p) S29N;
q) V31S, V31D, or V31K;
r) H32G;
s) I68S, I68A, I68R, I68T, I68K, I68N, I68M, I68F, I68Y, I68E, or I68H;
t) L69A, L69S, L69D, L69T, L69M, L69G, L69Q, L69I, L69E, or L69V;
u) M109A, M109S, M109D, or M109K; and/or
v) I111A, I111K, I111S, or I111D.

4. The isolated IL-15 variant of claim 1, wherein the IL-15 variant comprises amino acid substitutions at positions selected from the group consisting of:

a) N4K, D30N, V49N, I50A, S51T, and E64Q;
b) N4Q, D30N, V49N, I50A, and S51T;
c) D30N, V49N, I50A, S51T, and E64Q;
d) N4Q, D30N, V49N, I50A, S51T, and E64Q;
e) N4Q, V49N, I50A, and S51T;
f) V49N, I50A, S51T, and E64Q; and
g) N4Q, V49N, I50A, S51T, and E64Q.

5. An isolated human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant has no binding to the human IL-15 receptor alpha (IL-15Rα) and decreased binding to the human IL-2 receptor beta/gamma (IL-2Rβγ) as compared to the wild-type human IL-15 polypeptide or a wild-type IL-15 receptor alpha-IL-15 fusion polypeptide.

6. The isolated IL-15 variant of claim 5, wherein the IL-15 variant comprises amino acid substitutions at positions selected from the group consisting of:
a) N1, E46, and V49;
b) N4, E46, and V49;
c) S7, E46, and V49;
d) K10, E46, and V49;
e) K11, E46, and V49;
f) S29, E46, and V49;
g) V31, E46, and V49;
h) H32, E46, and V49;
i) E46, V49, and E64;
j) E46, V49, and I68;
k) E46, V49, and L69;
l) E46, V49, and I111;
m) N4, E46, V49, and E64;
n) E46, V49, N4, D30, and E64;
o) E46, V49, N4, D30, E64, and I68;
p) E46, V49, N4, D30, E64, and M109;
q) E46, V49, N4, D30, E64, I68, and M109;
r) N1, D30, E46, and V49;
s) N4, D30, E46, and V49;
t) S7, D30, E46, and V49;
u) K10, D30, E46, and V49;
v) K11, D30, E46, and V49;
w) S29, D30, E46, and V49;
x) D30, E46, V49, and E64;
y) D30, E46, V49R, and I68;
z) D30, E46, V49R, and L69;
aa) D30, E46, V49R, and I111;
bb) N1, D30, E46, V49, and M109;
cc) N4, D30, E46, V49, and M109;
dd) S7, D30, E46, V49, and M109;
ee) K10, D30, E46, V49, and M109;
ff) K11, D30, E46, V49, and M109;
gg) D30, E46, V49, E64, and M109;
hh) D30, E46, V49, I68, and M109;
ii) D30, E46, V49, L69 and M109;
jj) D30, E46, V49, M109, and I111;
kk) D30, E46, V49, E64, I68, and M109;
ll) E46, V49, D30, E64, and I68;
mm) E46, V49, E64, and M109;
nn) E46, V49, D30, E64, I68, and M109;
oo) D22, Y26, V49, E46, E53, E89, and E93; and
pp) N1, D30, E46, V49, and E64.

7. The isolated IL-15 variant of claim 5, wherein the amino acid substitutions comprise one or more specific substitutions at:
a) N1Q, N1K, N1R, N1E, N1A, N1D, or N1G;
b) N4K, N4G, N4A, N4S, N4D, N4E, N4R, N4T, N4I, N4L, N4W, or N4Q;
c) S7E, S7G, S7D, S7K, S7N, S7R, S7H, or S7T;
d) K10D, K10A, K10S, K10E, K10L, K10M, K10D, or K10G;
e) K11D, K11S, or K11W;
f) D22N;
g) Y26K, Y26R, or Y26H;
h) S29N;
i) D30N;
j) V31S, V31D, or V31K;
k) H32G;
l) E46G or E46Q;
m) V49N, V49K, V49R, V49E, V49H, or V49Q;
n) E53Q;
o) G55S or G55T
p) E64Q, E64K, E64A, E64S, E64N, E64H, E64T, or E64R;
q) I68S, I68A, I68R, I68T, I68K, I68N, I68M, I68F, I68Y, I68E, or I68H;
r) L69S, L69A, L69D, L69T, L69M, L69G, L69Q, L69I, L69E, or L69V;
s) E89Q;
t) E93Q;
u) M109A, M109S, M109D, or M109K; and/or
v) I111A, I111K, I111S, or I111D.

8. The isolated IL-15 variant of claim 5, wherein the IL-15 variant comprises amino acid substitutions at positions selected from the group consisting of:
a) N1K, E46G, and V49R;
b) N4K, E46G, and V49R;
c) N4Q, E46G, and V49R;
d) S7T, E46G, and V49R;
e) V31S, E46G, and V49R;
f) V31K, E46G, and V49R;
g) E46G, V49R, and E64Q;
h) E46G, V49R, and E64K;
i) N4Q, E46G, V49R, and E64Q;
j) N1G, D30N, E46G, and V49R;
k) N1K, D30N, E46G, and V49R;
l) N1Q, D30N, E46G, and V49R;
m) N4G, D30N, E46G, and V49R;
n) N4K, D30N, E46G, and V49R;
o) N4Q, D30N, E46G, and V49R;
p) S7E, D30N, E46G, and V49R;
q) S7G, D30N, E46G, and V49R;
r) S7T, D30N, E46G, and V49R;
s) K10D, D30N, E46G, and V49R;
t) D30N, E46G, V49R, and E64A;
u) D30N, E46G, V49R, and E64Q;
v) D30N, E46G, V49R, and E64K;
w) D30N, E46G, V49R, and I68S;
x) D30N, E46G, V49R, and I68K;
y) N4K, D30N, E46G, V49R, and E64K;
z) N4Q, D30N, E46G, V49R, and E64K;
aa) N4K, D30N, E46G, V49R, and E64Q;
bb) N4Q, D30N, E46G, V49R, and E64Q;
cc) N4K, D30N, E46G, V49R, and I68S;
dd) D30N, E46G, V49R, E64Q, and I68S;
ee) N1A, D30N, E46G, and V49R; and
ff) N1G, D30N, E46G, V49R, and E64Q.

9. An isolated fusion protein comprising: 1) an antibody comprising a Fc domain; and b) a human interleukin 15 (IL-15) variant comprising amino acid substitutions at positions a) V49 and S51 or b) V49, I50, and S51 of SEQ ID NO: 1, wherein the amino acid substitution at position V49 of SEQ ID NO: 1 is glycosylated, and further comprising one or more amino acid substitutions at positions N1, N4, S7, K10, K11, Y26, S29, D30, V31, H32, E53, G55, E64, I68, L69, E89, L91, M109, and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

10. The fusion protein of claim 9, wherein the IL-15 variant comprises amino acid substitutions at positions selected from the group consisting of:

a) V49, I50, S51, N4, D30, and E64;
b) V49, I50, S51, N4, D30, E64, and I68;
c) V49, I50, S51, N4, D30, E64, M109;
d) V49, I50, S51, N4, D30, E64, I68, and M109;
e) V49, I50, S51, D30, E64, and I68;
f) V49, I50, S51, D30, E64, M109;
g) V49, I50, S51, D30, E64, I68, and M109;
h) N1, V49, I50, and S51;
i) N4, V49, I50, and S51;
j) S7, V49, I50, and S51;
k) K10, V49, I50, and S51;
l) K11, V49, I50, and S51;
m) S29, V49, I50, and S51;
n) V31, V49, I50, and S51;
o) H32, V49, I50, and S51;
p) V49, I50, S51, and E64;
q) V49, I50, S51, and I68;
r) V49, I50, S51, and L69;
s) V49, I50, S51, and I111;
t) N4, V49, I50, S51, and E64;
u) N1, D30, V49, I50, and S51;
v) N4, D30, V49, I50, and S51;
w) S7, D30, V49, I50, and S51;
x) K10, D30, V49, I50, and S51;
y) K11, D30, V49, I50, and S51;
z) S29, D30, V49, I50, and S51;
aa) D30, V49, I50, S51, and E64;
bb) D30, V49, I50, S51, and I68;
cc) D30, V49, I50, S51, and L69; and
dd) D30, V49, I50, S51, and I111.

11. The fusion protein of claim 9, wherein the amino acid substitutions comprise one or more specific substitutions at:

a) V49N;
b) I50A or I50G;
c) S51T;
d) N1K, N1G, N1Q, N1R, N1E, N1A, or N1D;
e) N4K, N4G, N4A, N4S, N4D, N4E, N4L, N4R, N4T, or N4Q;
f) S7E, S7G, S7D, S7K, S7N, S7R, S7H, or S7T;
g) K10A, K10S, K10E, K10L, K10M, K10D, or K10G;
h) K11D, K11S, or K11W;
i) D30N;
j) E64Q, E64K, E64A, E64S, E64N, E64H, E64T, or E64R;
k) E53N;
l) G55S or G55T;
m) E89N;
n) L91S or L91T;
o) Y26K, Y26R, or Y26H;
p) S29N;
q) V31S, V31D, or V31K;
r) H32G;
s) I68S, I68A, I68R, I68T, I68K, I68N, I68M, I68F, I68Y, I68E, or I68H;
t) L69S, L69A, L69D, L69T, L69M, L69G, L69Q, L69I, L69E, or L69V;
u) M109A, M109S, M109D, or M109K; and/or
v) I111A, I111K, I111S, or I111D.

12. The fusion protein of claim 9, wherein the IL-15 variant comprises amino acid substitutions at positions selected from the group consisting of:

a) N4K, D30N, V49N, I50A, S51T, and E64Q;
b) N4Q, D30N, V49N, I50A, and S51T;
c) D30N, V49N, I50A, S51T, and E64Q;
d) N4Q, D30N, V49N, I50A, S51T, and E64Q;
e) N4Q, V49N, I50A, and S51T;
f) V49N, I50A, S51T, and E64Q; and
g) N4Q, V49N, I50A, S51T, and E64Q.

13. An isolated fusion protein comprising: 1) an anti-PD-1 antibody comprising a Fc domain; and b) a human interleukin 15 (IL-15) variant comprising amino acid substitutions at positions E46 and V49 of SEQ ID NO: 1, and at least one or more amino acid substitution(s) at positions N1, N4, S7, K10, K11, D22, Y26, S29, D30, V31, H32, E53, G55, E64, I68, L69, E89, E93, M109 and/or I111 of SEQ ID NO: 1, wherein the IL-15 variant is covalently linked to the Fc domain of the antibody, and wherein the Fc domain has decreased or no antibody dependent cellular cytotoxicity (ADCC) activity compared to the wild-type Fc.

14. The fusion protein of claim 13, wherein the IL-15 variant comprises amino acid substitutions at positions selected from the group consisting of:

a) N1, E46, and V49;
b) N4, E46, and V49;
c) S7, E46, and V49;
d) K10, E46, and V49;
e) K11, E46, and V49;
f) S29, E46, and V49;
g) V31, E46, and V49;
h) H32, E46, and V49;
i) E46, V49, and E64;
j) E46, V49, and I68;
k) E46, V49, and L69;
l) E46, V49, and I111;
m) N4, E46, V49, and E64;
n) E46, V49, N4, D30, and E64;
o) E46, V49, N4, D30, E64, and I68;
p) E46, V49, N4, D30, E64, and M109;
q) E46, V49, N4, D30, E64, I68, and M109;
r) N1, D30, E46, and V49;
s) N4, D30, E46, and V49;
t) S7, D30, E46, and V49;
u) K10, D30, E46, and V49;
v) K11, D30, E46, and V49;
w) S29, D30, E46, and V49;
x) D30, E46, V49, and E64;
y) D30, E46, V49R, and I68;
z) D30, E46, V49R, and L69;
aa) D30, E46, V49R, and I111;
bb) N1, D30, E46, V49, and M109;
cc) N4, D30, E46, V49, and M109;
dd) S7, D30, E46, V49, and M109;
ee) K10, D30, E46, V49, and M109;
ff) K11, D30, E46, V49, and M109;
gg) D30, E46, V49, E64, and M109;
hh) D30, E46, V49, I68, and M109;
ii) D30, E46, V49, L69, and M109;
jj) D30, E46, V49, M109, and I111;
kk) D30, E46, V49, E64, I68, and M109;
ll) E46, V49, D30, E64, and I68;
mm) E46, V49, E64, and M109;
nn) E46, V49, D30, E64, I68, and M109;
oo) D22, Y26, V49, E46, E53, E89, and E93; and
pp) N1, D30, E46, V49, and E64.

15. The fusion protein of claim 13, wherein the IL-15 variant comprises amino acid substitutions at positions selected from the group consisting of:

a) N1Q, N1K, N1R, N1E, N1A, N1D, or N1G;

b) N4K N4G, N4A, N4S, N4D, N4E, N4L, N4R, N4T, or N4Q;

c) S7E, S7G, S7D, S7K, S7N, S7R, S7H, or S7T;

d) K10D, K10A, K10S, K10E, K10L, K10M, K10D, or K10G;

e) K11D, K11S, or K11W;

f) D22N;

g) Y26K, Y26R, or Y26H;

h) S29N;

i) D30N;

j) V31S, V31D, or V31K k) H32G;

l) E46G or E46Q;

m) V49N, V49K, V49R, V49E, V49H, or V49Q;

n) E53Q;

o) G55S or G55T;

p) E64Q, E64K, E64A, E64S, E64N, E64H, E64T, or E64R;

q) I68S, I68A, I68R, I68T, I68K, I68N, I68M, I68F, I68Y, I68E or I68H;

r) L69S, L69A, L69D, L69T, L69M, L69G, L69Q, L69I, L69E, or L69V;

s) E89Q;

t) E93Q;

u) M109A, M109S, M109D, or M109K; and v) I111A, I111K, I111S, or I111D.

16. The fusion protein of claim 13, wherein the IL-15 variant comprises amino acid substitutions at positions selected from the group consisting of:

a) N1K, E46G, and V49R;

b) N4K, E46G, and V49R;

c) N4Q, E46G, and V49R;

d) S7T, E46G, and V49R;

e) V31S, E46G, and V49R;

f) V31K, E46G, and V49R;

g) E46G, V49R, and E64Q;

h) E46G, V49R, and E64K;

i) N4Q, E46G, V49R, and E64Q;

j) N1G, D30N, E46G, and V49R;

k) N1K, D30N, E46G, and V49R;

l) N1Q, D30N, E46G, and V49R;

m) N4G, D30N, E46G, and V49R;

n) N4K, D30N, E46G, and V49R;

o) N4Q, D30N, E46G, and V49R;

p) S7E, D30N, E46G, and V49R;

q) S7G, D30N, E46G, and V49R;

r) S7T, D30N, E46G, and V49R;

s) K10D, D30N, E46G, and V49R;

t) D30N, E46G, V49R, and E64A;

u) D30N, E46G, V49R, and E64Q;

v) D30N, E46G, V49R, and E64K;

w) D30N, E46G, V49R, and I68S;

x) D30N, E46G, V49R, and I68K;

y) N4K, D30N, E46G, V49R, and E64K;

z) N4Q, D30N, E46G, V49R, and E64K;

aa) N4K, D30N, E46G, V49R, and E64Q;

bb) N4Q, D30N, E46G, V49R, and E64Q;

cc) N4K, D30N, E46G, V49R, and I68S;

dd) D30N, E46G, V49R, E64Q, and I68S;

ee) N1A, D30N, E46G, and V49R; and ff) N1G, D30N, E46G, V49R, and E64Q.

17. The fusion protein of claim 13 comprising the amino acid sequence of SEQ ID NO: 86, 87, 89, or 90.

18. The fusion protein of claim 13, wherein the antibody has an isotype that is selected from the group consisting of $IgG_1$, $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P, and $IgG_{4\Delta c}$ S228P.

19. The fusion protein of claim 18, wherein the antibody is a) an IgG2, and the antibody variable domain comprises amino acid modifications at positions 223, 225, and/or 228 in the hinge region and at position 409 and/or 368 (EU numbering scheme) in the CH3 region of the human IgG2 (SEQ ID NO: 3); b) an IgG1, and the antibody variable domain comprises amino acid modifications at positions 221 and/or 228 in the hinge region and at position 409 and/or 368 (EU numbering scheme) in the CH3 region of the human IgG1 (SEQ ID NO: 2); or c) an IgG1, and the antibody variable domain comprise amino acid modifications at positions 349, 354, 366, 368, and/or 407 (EU numbering scheme) in the CH3 region of the human IgG1 (SEQ ID NO: 2).

20. The fusion protein of claim 19, wherein the antibody further comprises an amino acid modification at a) one or more positions 265, 330, and/or 331 of the human IgG2 (SEQ ID NO: 3); or b) one or more positions 234, 235, and/or 237 of the human IgG1 (SEQ ID NO: 2).

21. The fusion protein of claim 13, wherein the antibody is an anti-PD-1 antibody comprising a heavy chain variable (VH) region comprising a VH complementarity determining region one (CDR1) comprising the amino acid sequence of SEQ ID NO: 14, 15, 80, 81, 91, or 92, a VH CDR2 comprising the amino acid sequence of SEQ ID NO: 16, 17, 82, or 83, and a VH CDR3 comprising the amino acid sequence shown in SEQ ID NO: 18 or 62; and a VL CDR1 comprising the amino acid sequence shown in SEQ ID NO: 19 or 31, a VL CDR2 comprising the amino acid sequence shown in SEQ ID NO: 20 or 32, and a VL CDR3 comprising the amino acid sequence shown in SEQ ID NO: 21 or 33.

22. The fusion protein of claim 13, wherein the antibody is an anti-PD-1 antibody comprising a VH region comprising a CDR1, CDR2, and CDR3 of the VH having the amino acid sequence of SEQ ID NO: 12, 34, 78, or 36, and a VL region comprising a CDR1, CDR2, and CDR3 of the VL having the amino acid sequence of SEQ ID NO: 13, 35, 79, or 37.

23. The fusion protein of claim 13, wherein the IL-15 variant is covalently linked to the antibody by a polypeptide linker and/or a polypeptide tag.

24. A pharmaceutical composition comprising the IL-15 variant of claim 5 or the fusion protein of claim 13, and a pharmaceutically acceptable carrier.

25. A kit for the treatment of cancer comprising the pharmaceutical composition of claim 24.

26. The pharmaceutical composition of claim 24 for the treatment of cancer, optionally wherein the cancer is a solid cancer or a liquid cancer and/or the cancer is relapsed, refractory, or metastatic.

27. The pharmaceutical composition of claim 26, wherein the pharmaceutical composition is in combination with a second therapeutic agent.

28. An isolated fusion protein comprising: 1) an antibody comprising a Fc domain; and b) a human interleukin 15 (IL-15) variant comprising amino acid substitutions at positions E46, V49, N1, E64, and D30 of SEQ ID NO: 1, wherein the antibody specifically binds to PD-1, and wherein the IL-15 variant is covalently linked to the Fc domain of the antibody.

29. The isolated fusion protein of claim 28, wherein the human interleukin 15 (IL-15) variant comprises the amino acid substitutions E46G, V49R, N1G, E64Q, and D30N.

30. The fusion protein of claim 28, wherein the antibody comprises a heavy chain variable (VH) region comprising a VH complementarity determining region one (CDR1) comprising the amino acid sequence of SEQ ID NO: 80, 81, or 91, a VH CDR2 comprising the amino acid sequence of SEQ ID NO: 82, or 83, and a VH CDR3 comprising the amino acid sequence of SEQ ID NO: 62; and a VL CDR1 comprising the amino acid sequence of SEQ ID NO: 31, a VL CDR2 comprising the amino acid sequence of SEQ ID NO: 32, and a VL CDR3 comprising the amino acid sequence of SEQ ID NO: 33.

31. The fusion protein of claim 28, wherein the antibody comprises a VH region comprising a CDR1, CDR2, and CDR3 of the VH comprising the amino acid sequence of SEQ ID NO: 36, and a VL region comprising a CDR1, CDR2, and CDR3 of the VL comprising the amino acid sequence of SEQ ID NO: 37.

32. The fusion protein of claim 28, wherein the fusion protein comprises a polypeptide comprising the amino acid sequence of SEQ ID NO: 65.

33. The fusion protein of claim 32, wherein the fusion protein further comprises a polypeptide comprising the amino acid sequence of SEQ ID NO: 74.

34. The fusion protein of claim 33, wherein the fusion protein further comprises a polypeptide comprising the amino acid sequence of SEQ ID NO: 90.

35. The fusion protein of claim 28, wherein the fusion protein preferentially activates PD-1+ cells over PD-1(low) cells.

36. An isolated fusion protein comprising a human interleukin 15 (IL-15) variant, wherein the fusion protein comprises a polypeptide comprising the amino acid sequence of SEQ ID NO: 90, a polypeptide comprising the amino acid sequence of SEQ ID NO: 74, and a polypeptide comprising the amino acid sequence of SEQ ID NO: 65.

* * * * *